United States Patent
Lee et al.

(10) Patent No.: US 12,415,823 B2
(45) Date of Patent: Sep. 16, 2025

(54) HETEROCYCLIC COMPOUND AND ORGANIC LIGHT-EMITTING DEVICE COMPRISING SAME

(71) Applicant: LT MATERIALS CO., LTD., Yongin (KR)

(72) Inventors: Gi-Back Lee, Yongin-si (KR); Yu-Jin Heo, Yongin-si (KR); Won-Jang Jeong, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 931 days.

(21) Appl. No.: 17/612,703

(22) PCT Filed: Oct. 20, 2020

(86) PCT No.: PCT/KR2020/014308
§ 371 (c)(1),
(2) Date: Nov. 19, 2021

(87) PCT Pub. No.: WO2021/080282
PCT Pub. Date: Apr. 29, 2021

(65) Prior Publication Data
US 2022/0289693 A1  Sep. 15, 2022

(30) Foreign Application Priority Data
Oct. 25, 2019 (KR) .................. 10-2019-0133975

(51) Int. Cl.
*C07F 9/6521* (2006.01)
*C07D 213/16* (2006.01)
(Continued)

(52) U.S. Cl.
CPC .......... *C07F 9/6521* (2013.01); *C07D 213/16* (2013.01); *C07D 239/26* (2013.01);
(Continued)

(58) Field of Classification Search
CPC .. C07D 251/24; C07D 239/26; C07D 213/19; C07D 403/10; C07D 405/10;
(Continued)

(56) References Cited

U.S. PATENT DOCUMENTS

| 4,356,429 A | 10/1982 | Tang |
| 2016/0248020 A1 | 8/2016 | Ondari et al. |

(Continued)

FOREIGN PATENT DOCUMENTS

| CN | 110156777 A | 8/2019 |
| JP | 2008-231047 A | 10/2008 |

(Continued)

OTHER PUBLICATIONS

International Search Report (PCT/ISA/210) Issued in PCT/KR2020/014308. dated Feb. 17, 2021.
(Continued)

*Primary Examiner* — Vu A Nguyen
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

14 Claims, 3 Drawing Sheets

(51) Int. Cl.
*C07D 239/26* (2006.01)
*C07D 251/24* (2006.01)
*C07D 401/10* (2006.01)
*C07D 403/10* (2006.01)
*C07D 405/10* (2006.01)
*C07D 471/04* (2006.01)
*C07F 9/32* (2006.01)
*H10K 50/15* (2023.01)
*H10K 50/16* (2023.01)
*H10K 50/17* (2023.01)
*H10K 50/18* (2023.01)
*H10K 85/60* (2023.01)

(52) U.S. Cl.
CPC ......... *C07D 251/24* (2013.01); *C07D 401/10* (2013.01); *C07D 403/10* (2013.01); *C07D 405/10* (2013.01); *C07D 471/04* (2013.01); *C07F 9/3229* (2013.01); *H10K 85/622* (2023.02); *H10K 85/624* (2023.02); *H10K 85/654* (2023.02); *H10K 85/6572* (2023.02); *H10K 85/6574* (2023.02); *H10K 50/15* (2023.02); *H10K 50/16* (2023.02); *H10K 50/171* (2023.02); *H10K 50/18* (2023.02)

(58) Field of Classification Search
CPC .............. C07D 471/04; H01L 51/0067; H01L 51/0054; H01L 51/0072; H01L 51/0056; H01L 51/0073; H01L 51/5072; C07F 9/3229
See application file for complete search history.

(56) References Cited

U.S. PATENT DOCUMENTS

| | | |
|---|---|---|
| 2018/0175302 A1 | 6/2018 | Jang et al. |
| 2019/0207123 A1 | 7/2019 | Yoon et al. |
| 2020/0168805 A1 | 5/2020 | Park et al. |

FOREIGN PATENT DOCUMENTS

| | | | |
|---|---|---|---|
| JP | 2015-10077 A | | 1/2015 |
| KR | 10-2015-0115848 A | | 10/2015 |
| KR | 10-2017-0065317 A | | 6/2017 |
| KR | 10-2019-0009994 A | | 1/2019 |
| KR | 10-2019-0080600 A | | 7/2019 |
| KR | 10-2019-0108935 | * | 9/2019 |
| KR | 10-2019-0108935 A | | 9/2019 |
| WO | WO 2015/073343 A1 | | 5/2015 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials." Advanced Materials, vol. 6, No. 9, 1994, pp. 877-679.

* cited by examiner

【FIG. 1】
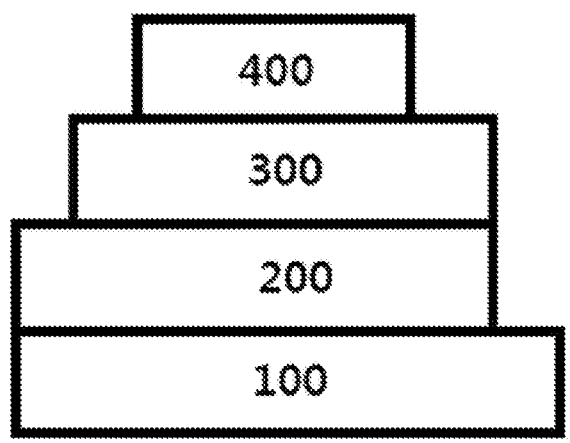
【FIG. 2】
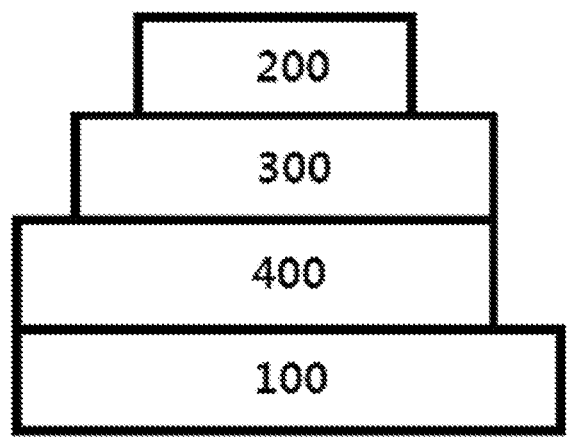

【FIG. 3】
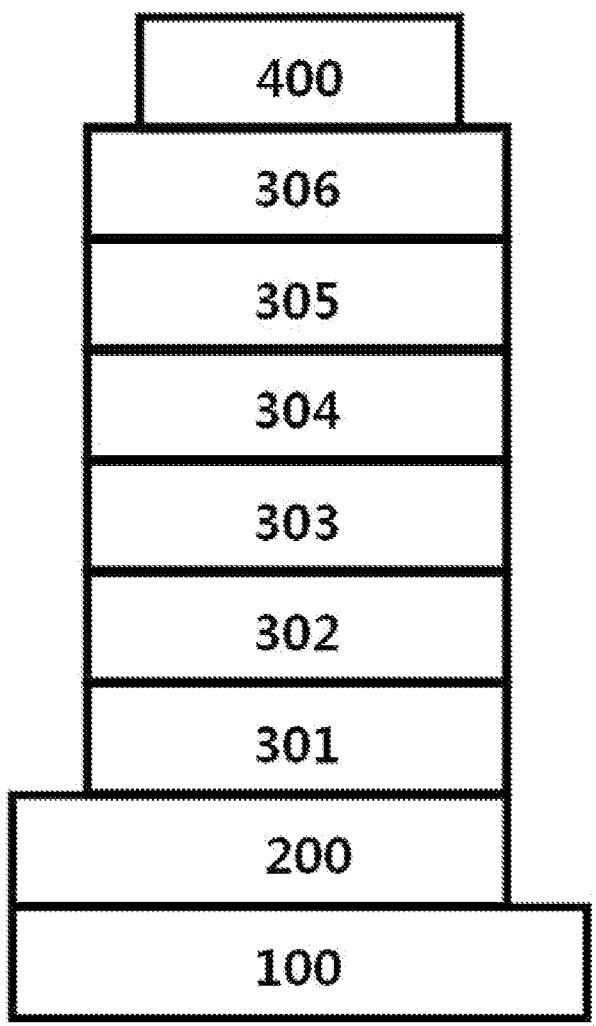

[FIG. 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2019-0133975, filed with the Korean Intellectual Property Office on Oct. 25, 2019, the entire contents of which are incorporated herein by reference.

The present specification relates to a heterocyclic compound, and an organic light emitting device comprising the same.

Background Art

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

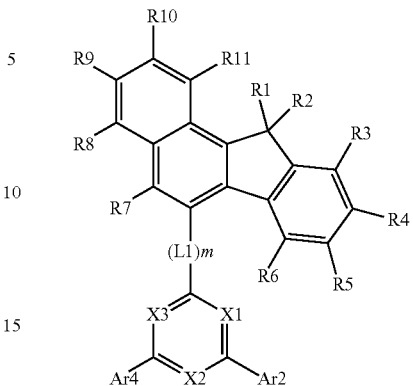

In Chemical Formula 1,

R1 and R2 are the same as or different from each other, and each independently a substituted or unsubstituted C1 to C60 alkyl group; a substituted or unsubstituted C6 to C60 aryl group; or a substituted or unsubstituted C2 to C60 heteroaryl group, or groups adjacent to each other bond to each other to form a substituted or unsubstituted C6 to C60 aromatic hydrocarbon ring or a substituted or unsubstituted C2 to C60 heteroring, L1 is a direct bond; a substituted or unsubstituted C6 to C60 arylene group; or a substituted or unsubstituted C2 to C60 heteroarylene group, X1 to X3 are the same as or different from each other, and each independently N; or CRa, and at least one thereof is N, Ra, Ar2 and Ar4 are the same as or different from each other, and each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, R3 to R11 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, R, R' and R" are the same as or different from each other, and each independently hydrogen; a substituted or unsubstituted C1 to C40 alkyl group; or a substituted or unsubstituted C6 to C40 aryl group, and m is an integer of 1 to 6, and when m is 2 or greater, substituents in the parentheses are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a hole blocking material, a light emitting material, an electron transfer material, an electron injection material, a charge generation material or the like. Particularly, the compound can be used as an electron transfer layer material or a hole blocking layer material of the organic light emitting device.

When using the compound represented by Chemical Formula 1 in the organic material layer, a driving voltage of the device can be lowered, light efficiency can be enhanced, and lifetime properties of the device can be enhanced by thermal stability of the compound.

In other words, the compound represented by Chemical Formula 1 has an azine-based substituent having excellent electron transfer properties at a specific position on the skeleton having a fluorene group, and when included in an organic light emitting device, superior efficiency and driving are obtained through adjusting band gap and T1 value by strengthening electron withdrawing properties.

Particularly, when using the azine derivative as an electron transfer layer, superior electron withdrawing properties of the azine functional group improves the flow of electrons enhancing electron transfer capability of the electron transfer layer, and by combining the azine moiety with a substituent with enhanced hole properties, planarity of the azine derivative and the glass transition temperature increase, which increases thermal stability of the compound.

In addition, electron transfer capability and hole blocking capability can be enhanced through adjusting band gap and T1 value, and molecular stability increases as well, and as a result, the device can have lowered driving voltage, enhanced light efficiency, and lifetime properties of the device can be enhanced due to thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium such as a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as $T2/T1 \times 100 = T$ % when the total number of substituents that a basic compound may have is defined as T1, and the number of specific substituents among these is defined as T2.

In other words, in one example, having a deuterium content of 20% in a phenyl group represented by

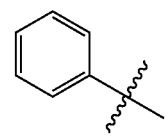 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

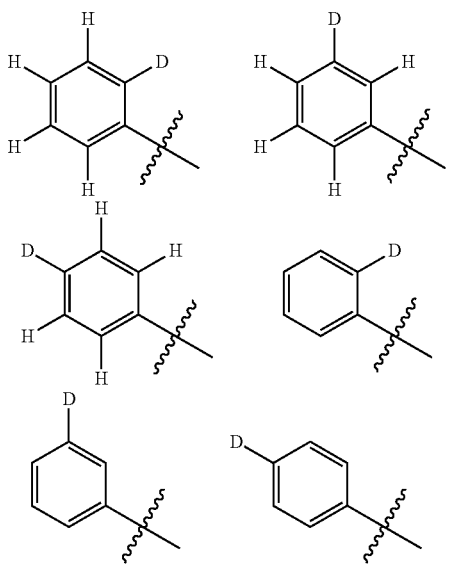

In addition, in one embodiment of the present application, "a phenyl group having a deuterium content of 0%" may mean a phenyl group that does not comprise a deuterium atom, that is, a phenyl group that has 5 hydrogen atoms.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a Spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted, any one of the following structures may be included, however, the structure is not limited thereto.

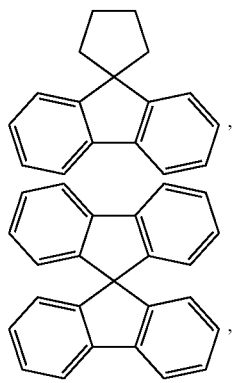

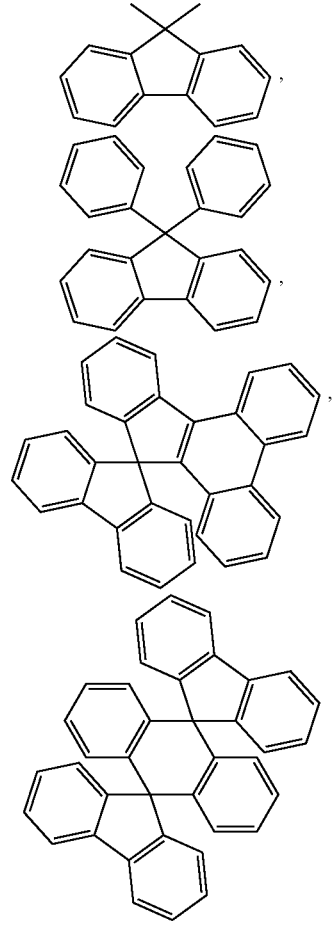

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b] carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by any one of the following Chemical Formula 2 to Chemical Formula 4.

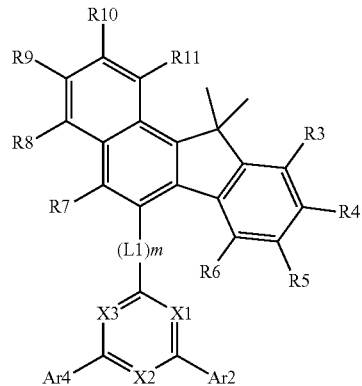

[Chemical Formula 2]

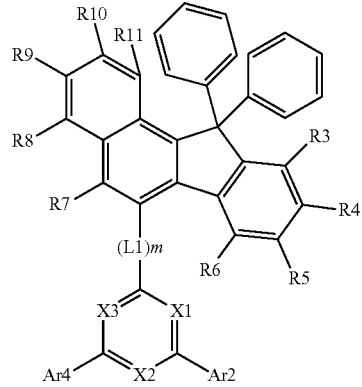

[Chemical Formula 3]

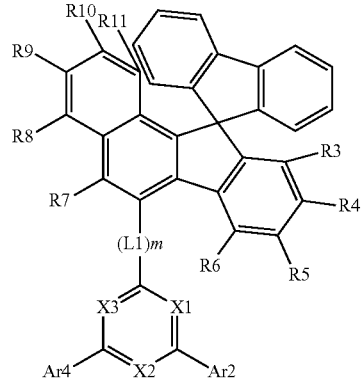

[Chemical Formula 4]

In Chemical Formulae 2 to 4,
X1 to X3, R3 to R11, L1, Ar2, Ar4 and m have the same definitions as in Chemical Formula 1.

In one embodiment of the present application, R1 and R2 are the same as or different from each other, and each independently a substituted or unsubstituted C1 to C60 alkyl group; a substituted or unsubstituted C6 to C60 aryl group; or a substituted or unsubstituted C2 to C60 heteroaryl group, or groups adjacent to each other may bond to each other to form a substituted or unsubstituted C6 to C60 aromatic hydrocarbon ring or a substituted or unsubstituted C2 to C60 heteroring.

In another embodiment, R1 and R2 are the same as or different from each other, and each independently a C1 to C60 alkyl group; or a C6 to C60 aryl group, or groups adjacent to each other may bond to each other to form a substituted or unsubstituted C6 to C60 aromatic hydrocarbon ring or a substituted or unsubstituted C2 to C60 heteroring.

In another embodiment, R1 and R2 are the same as or different from each other, and each independently a C1 to C30 alkyl group; or a C6 to C40 aryl group, or groups adjacent to each other may bond to each other to form a substituted or unsubstituted C6 to C40 aromatic hydrocarbon ring.

In another embodiment, R1 and R2 are the same as or different from each other, and each independently a linear C1 to C10 alkyl group; or a C6 to C20 monocyclic aryl group, or groups adjacent to each other may bond to each other to form a polycyclic C6 to C40 aromatic hydrocarbon ring.

In another embodiment, R1 and R2 are the same as or different from each other, and each independently a methyl group; or a phenyl group, or groups adjacent to each other may bond to each other to form a fluorenyl ring.

In one embodiment of the present application, R3 to R11 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, and R, R' and R" are the same as or different from each other, and may be each independently hydrogen; a substituted or unsubstituted C1 to C40 alkyl group; or a substituted or unsubstituted C6 to C40 aryl group.

In another embodiment, R3 to R11 are the same as or different from each other, and may be each independently selected from the group consisting of hydrogen; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, R3 to R11 are the same as or different from each other, and may be each independently hydrogen; a halogen group; —CN; a substituted or unsubstituted C6 to C60 aryl group; or a substituted or unsubstituted C2 to C60 heteroaryl group.

In another embodiment, R3 to R11 are the same as or different from each other, and may be each independently hydrogen; a halogen group; —CN; a substituted or unsubstituted C6 to C30 aryl group; or a substituted or unsubstituted C2 to C30 heteroaryl group.

In another embodiment, R3 to R11 are the same as or different from each other, and may be each independently hydrogen; a fluoro group (—F); or —CN.

In one embodiment of the present application, L1 may be a direct bond; a substituted or unsubstituted C6 to C60 arylene group; or a substituted or unsubstituted C2 to C60 heteroarylene group.

In another embodiment, L1 may be a direct bond; or a substituted or unsubstituted C6 to C60 arylene group.

In another embodiment, L1 may be a direct bond; or a substituted or unsubstituted C6 to C40 arylene group. In another embodiment, L1 may be a direct bond; or a substituted or unsubstituted C6 to C30 arylene group.

In another embodiment, L1 may be a direct bond; or a substituted or unsubstituted monocyclic or polycyclic C6 to C30 arylene group.

In another embodiment, L1 may be a direct bond; or a monocyclic or polycyclic C6 to C30 arylene group unsubstituted or substituted with one or more substituents selected from the group consisting of a C1 to C10 alkyl group, a C6 to C20 aryl group, a C2 to C20 heteroaryl group, —P(=O)RR' and —CN, or a combination of the substituents.

In another embodiment, L1 may be a direct bond; a phenylene group; a biphenylene group; a naphthalene group; a biphenyl group substituted with one or more substituents selected from the group consisting of —P(=O)RR' and —CN; a phenylene group substituted with a pyridine group unsubstituted or substituted with a methyl group, —CN, a carbazole group, a dibenzofuran group and a naphthyl group unsubstituted or substituted with —CN.

In another embodiment, L1 may be any one of the following structural formulae.

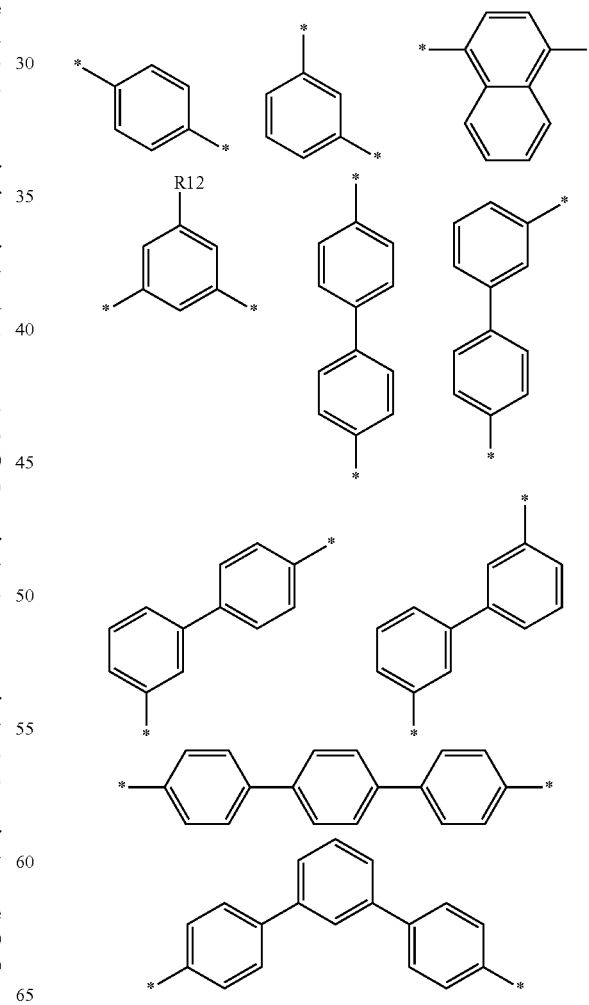

In the structural formulae, ⤳ means a position linked to the substituents of Chemical Formula 1, R12 is a substituted or unsubstituted C1 to C60 alkyl group; a substituted or unsubstituted C6 to C60 aryl group; a substituted or unsubstituted C2 to C60 heteroaryl group; —CN; or —P(=O)RR', and R and R' have the same definitions as in Chemical Formula 1.

In one embodiment of the present application, R12 may be a substituted or unsubstituted C1 to C60 alkyl group; a substituted or unsubstituted C6 to C60 aryl group; a substituted or unsubstituted C2 to C60 heteroaryl group; —CN; or —P(=O)RR'.

In another embodiment, R11 may be a substituted or unsubstituted C6 to C60 aryl group; a substituted or unsubstituted C2 to C60 heteroaryl group; or —CN.

In another embodiment, R12 may be a substituted or unsubstituted C6 to C40 aryl group; a substituted or unsubstituted C2 to C40 heteroaryl group; or —CN.

In another embodiment, R12 may be a substituted or unsubstituted C6 to C30 aryl group; a substituted or unsubstituted C2 to C30 heteroaryl group; or —CN.

In another embodiment, R12 may be a C6 to C30 aryl group unsubstituted or substituted with —CN or —P(=O)RR'; a C2 to C30 heteroaryl group unsubstituted or substituted with a C1 to C10 alkyl group; or —CN.

In another embodiment, R12 may be a phenyl group unsubstituted or substituted with —CN or —P(=O)RR'; a dibenzofuran group; a carbazole group; a naphthyl group unsubstituted or substituted with —CN; a pyridine group unsubstituted or substituted with a methyl group; or —CN.

In one embodiment of the present application, X1 to X3 are the same as or different from each other, and each independently N; or CRa, and at least one thereof may be N.

In one embodiment of the present application, X1 is N, X2 is CAr3, and X3 is CAr5, and Ar3 and Ar5 have the same definition as Ra of Chemical Formula 1.

In one embodiment of the present application, X1 is N, X2 is N, and X3 is CAr5, and Ar5 has the same definition as Ra of Chemical Formula 1.

In one embodiment of the present application, X1 is N, X3 is N, and X2 is CAr3, and Ar3 has the same definition as Ra of Chemical Formula 1.

In one embodiment of the present application, X1 to X3 are N.

In one embodiment of the present application, X2 is N, X1 is CAr1, and X3 is CAr5, and Ar1 and Ar5 have the same definition as Ra of Chemical Formula 1.

In one embodiment of the present application, Ra, Ar2 and

Ar4 are the same as or different from each other, and each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other may bond to each other to form a substituted or unsubstituted C6 to C60 aromatic hydrocarbon ring or a substituted or unsubstituted C2 to C60 heteroring.

In another embodiment, Ra, Ar2 and Ar4 are the same as or different from each other, and each independently selected from the group consisting of hydrogen; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aromatic hydrocarbon ring or a substituted or unsubstituted C2 to C60 heteroring.

In another embodiment, Ra, Ar2 and Ar4 are the same as or different from each other, and each independently selected from the group consisting of hydrogen; a substituted or unsubstituted C6 to C40 aryl group; and a substituted or unsubstituted C2 to C40 heteroaryl group, or two or more groups adjacent to each other may bond to each other to form a substituted or unsubstituted C2 to C40 heteroring.

In another embodiment, Ra, Ar2 and Ar4 are the same as or different from each other, and each independently hydrogen; or a C6 to C40 aryl group unsubstituted or substituted with one or more substituents selected from the group consisting of a C6 to C40 aryl group and a C2 to C40 heteroaryl group, or two or more groups adjacent to each other may bond to each other to form a C2 to C40 heteroring unsubstituted or substituted with a C6 to C40 aryl group.

In another embodiment, Ra, Ar2 and Ar4 are the same as or different from each other, and each independently hydrogen; a phenyl group unsubstituted or substituted with one or more substituents selected from the group consisting of a phenyl group and a carbazole group; a biphenyl group; or a terphenyl group, or two or more groups adjacent to each other may bond to each other to form a quinoline ring unsubstituted or substituted with a phenyl group.

In one embodiment of the present application,

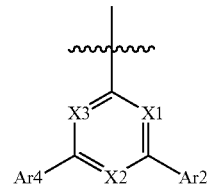

of Chemical Formula 1 may be represented by any one of the following Chemical Formulae 1-1 to 1-5.

[Chemical Formula 1-1]

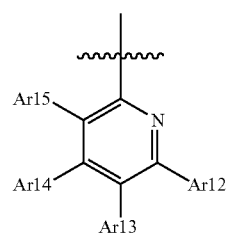

[Chemical Formula 1-2]

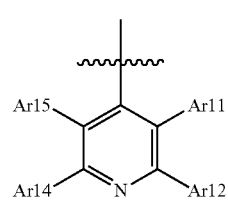

[Chemical Formula 1-3]

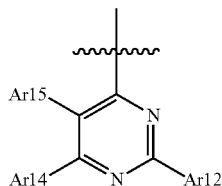

[Chemical Formula 1-6]

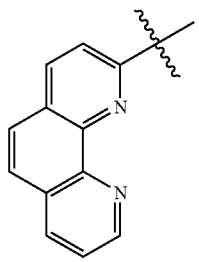

[Chemical Formula 1-4]

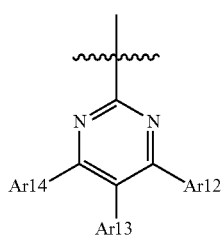

[Chemical Formula 1-7]

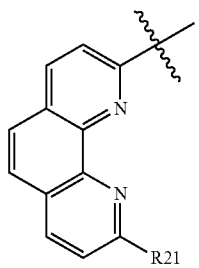

In Chemical Formulae 1-6 and 1-7,

[Chemical Formula 1-5]

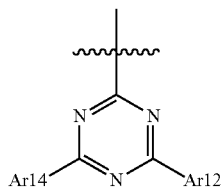

means a position linked to L1 of Chemical Formula 1,

Ar11 to Ar15 are the same as or different from each other, and each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, and R, R' and R" have the same definitions as in Chemical Formula 1.

In one embodiment of the present application,

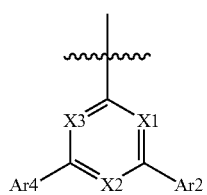

of Chemical Formula 1 may be represented by the following Chemical Formula 1-6 or 1-7.

means a position linked to L1 of Chemical Formula 1, and

R21 is hydrogen; a substituted or unsubstituted C6 to C60 aryl group; or a substituted or unsubstituted C2 to C60 heteroaryl group.

In one embodiment of the present application, Ar11 and Ar15 are the same as or different from each other, and may be each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group.

In another embodiment, Ar11 and Ar15 are the same as or different from each other, and may be each independently selected from the group consisting of hydrogen; a substituted or unsubstituted C6 to C40 aryl group; and a substituted or unsubstituted C2 to C40 heteroaryl group.

In another embodiment, Ar11 and Ar15 are the same as or different from each other, and may be each independently hydrogen; or a C6 to C40 aryl group unsubstituted or substituted with one or more substituents selected from the group consisting of a C6 to C40 aryl group and a C2 to C40 heteroaryl group.

In another embodiment, Ar11 and Ar15 are the same as or different from each other, and may be each independently hydrogen; a phenyl group unsubstituted or substituted with one or more substituents selected from the group consisting of a phenyl group and a carbazole group; a biphenyl group; or a terphenyl group.

In one embodiment of the present application, R21 is hydrogen; a substituted or unsubstituted C6 to C60 aryl group; or a substituted or unsubstituted C2 to C60 heteroaryl group.

In another embodiment, R21 is hydrogen; or a substituted or unsubstituted C6 to C60 aryl group.

In another embodiment, R21 is hydrogen; or a substituted or unsubstituted C6 to C40 aryl group.

In another embodiment, R21 is hydrogen; or monocyclic or polycyclic C6 to C40 aryl group.

In another embodiment, R21 is hydrogen; or a monocyclic C6 to C20 aryl group.

In another embodiment, R21 is hydrogen; or a phenyl group.

In one embodiment of the present application, Ar12 is represented by

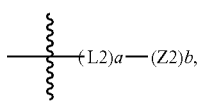

and Ar14 is a substituted or unsubstituted C6 to C60 aryl group,

L2 is a direct bond; a substituted or unsubstituted C6 to C60 arylene group; or a substituted or unsubstituted C2 to C60 heteroarylene group, Z2 is a substituted or unsubstituted C6 to C60 aryl group; or a substituted or unsubstituted C2 to C60 heteroaryl group, and a and b are the same as or different from each other and each an integer of 1 to 6, and when a and b are 2 or greater, substituents in the parentheses are the same as or different from each other.

In one embodiment of the present application, Ar12 has the same definition as Ar2 of Chemical Formula 1, and Ar14 has the same definition as Ar4 of Chemical Formula 1.

In one embodiment of the present application, Ar12 is represented by

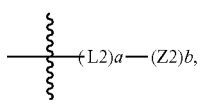

and Ar14 is a substituted or unsubstituted C6 to C60 aryl group,

L2 is a direct bond; a substituted or unsubstituted C6 to C60 arylene group; or a substituted or unsubstituted C2 to C60 heteroarylene group, Z2 is a substituted or unsubstituted C6 to C60 aryl group; or a substituted or unsubstituted C2 to C60 heteroaryl group, and a and b are the same as or different from each other and each an integer of 1 to 6, and when a and b are 2 or greater, substituents in the parentheses are the same as or different from each other.

In one embodiment of the present application, Ar12 has the same definition as Ar2 of Chemical Formula 1, and Ar14 has the same definition as Ar4 of Chemical Formula 1.

In one embodiment of the present application, Ar12 is represented by

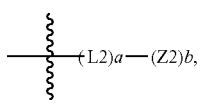

and Ar14 may be a substituted or unsubstituted C6 to C60 aryl group.

In another embodiment, Ar12 is represented by

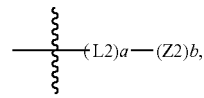

and Ar14 may be a substituted or unsubstituted C6 to C40 aryl group.

In another embodiment, Ar12 is represented by

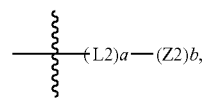

and Ar14 may be a C6 to C40 aryl group.

In another embodiment, Ar12 is represented by

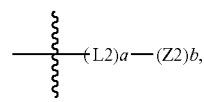

and Ar14 may be a C6 to C20 aryl group.

In another embodiment, Ar12 is represented by

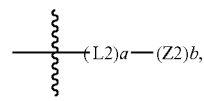

and Ar14 may be a monocyclic or polycyclic C6 to C20 aryl group.

In another embodiment, Ar12 is represented by

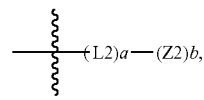

and Ar14 may be a phenyl group or a biphenyl group.

In one embodiment of the present application, L2 may be a direct bond; a substituted or unsubstituted C6 to C60 arylene group; or a substituted or unsubstituted C2 to C60 heteroarylene group.

In another embodiment, L2 may be a direct bond; or a substituted or unsubstituted C6 to C60 arylene group.

In another embodiment, L2 may be a direct bond; or a substituted or unsubstituted C6 to C40 arylene group.

In another embodiment, L2 may be a direct bond; or a C6 to C40 arylene group.

In another embodiment, L2 may be a direct bond; or a monocyclic or polycyclic C6 to C20 arylene group.

In another embodiment, L2 may be a direct bond; a phenylene group; or a biphenylene group.

In one embodiment of the present application, Z2 may be a substituted or unsubstituted C6 to C60 aryl group; or a substituted or unsubstituted C2 to C60 heteroaryl group.

In another embodiment, Z2 may be a substituted or unsubstituted C6 to C40 aryl group; or a substituted or unsubstituted C2 to C40 heteroaryl group.

In another embodiment, Z2 may be a C6 to C40 aryl group; or a C2 to C40 heteroaryl group.

In another embodiment, Z2 may be a C6 to C20 aryl group; or a C2 to C20 heteroaryl group.

In another embodiment, Z2 may be a C6 to C20 aryl group; or a C2 to C20 heteroaryl group comprising N.

In another embodiment, Z2 may be a phenyl group; a biphenyl group; or a carbazole group.

In one embodiment of the present application, R, R' and R" are the same as or different from each other, and may be each independently hydrogen; a substituted or unsubstituted C1 to C40 alkyl group; or a substituted or unsubstituted C6 to C40 aryl group.

In another embodiment, R, R' and R" are the same as or different from each other, and may be each independently a substituted or unsubstituted C1 to C20 alkyl group; or a substituted or unsubstituted C6 to C20 aryl group.

In another embodiment, R, R' and R" are the same as or different from each other, and may be each independently a C1 to C20 alkyl group; or a C6 to C20 aryl group.

In another embodiment, R, R' and R" are the same as or different from each other, and may be each independently a C1 to C20 linear alkyl group; or a C6 to C20 monocyclic aryl group.

In another embodiment, R, R' and R" may be a methyl group; or a phenyl group.

In another embodiment, R, R' and R" may be a methyl group.

In the heterocyclic compound provided in one embodiment of the present application, Chemical Formula 1 is represented by any one of the following compounds.

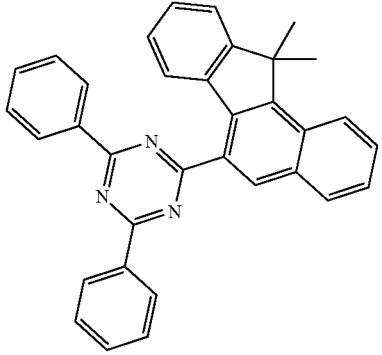

1

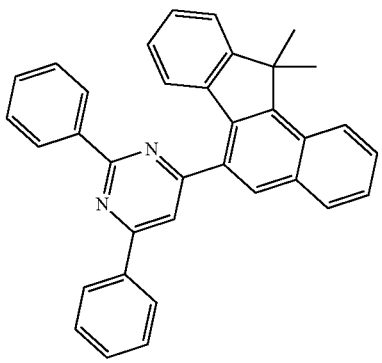

2

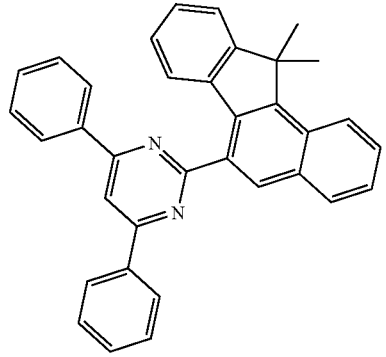

3

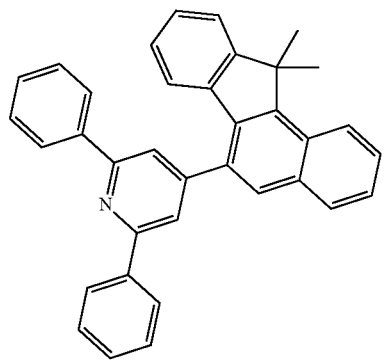

4

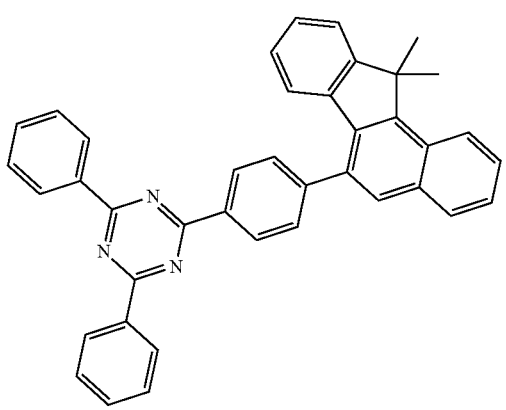

5

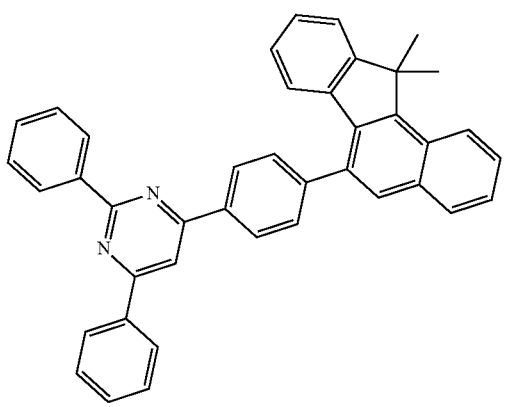

6

-continued
7
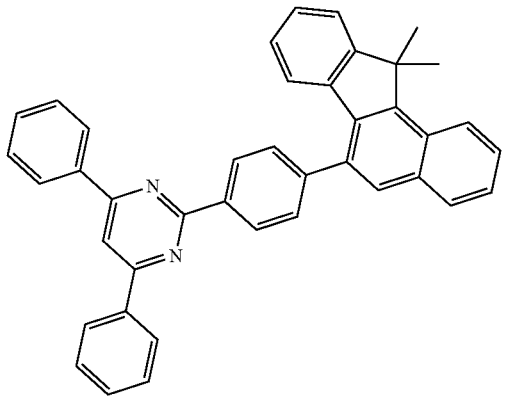
8
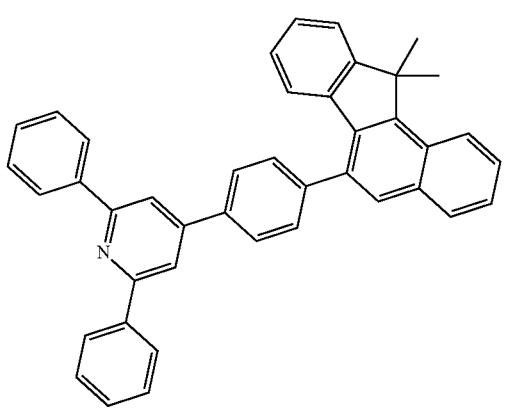
9
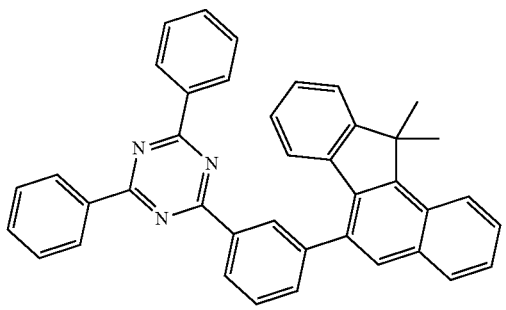
10
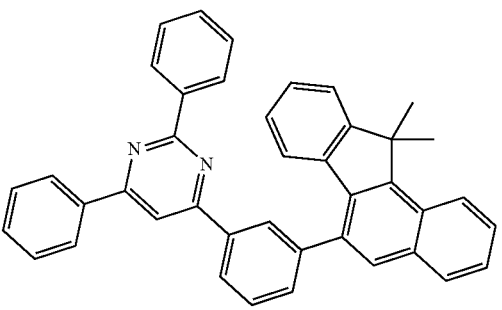
-continued
11
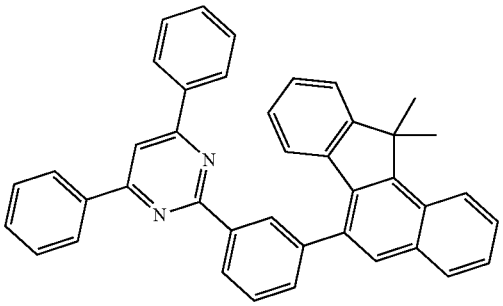
12
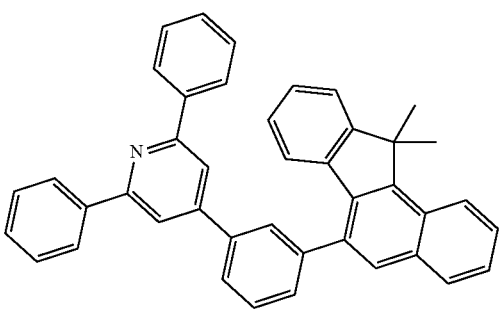
13
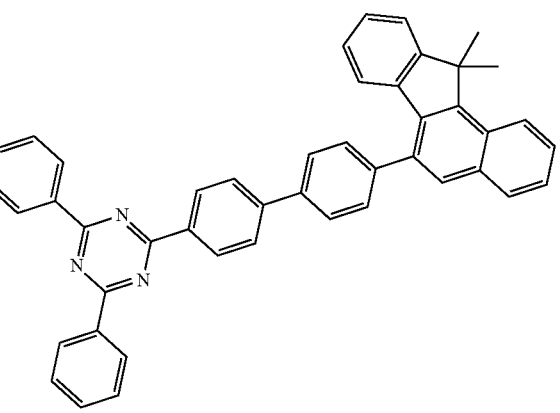
14
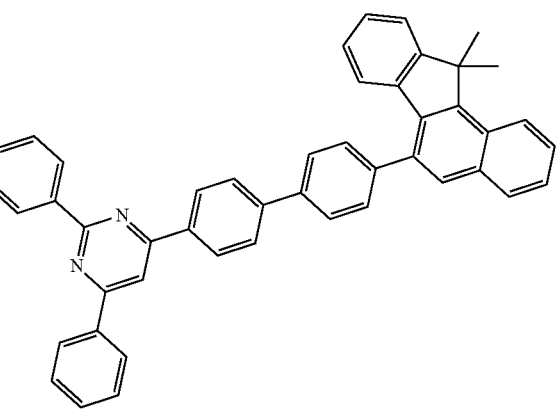

15
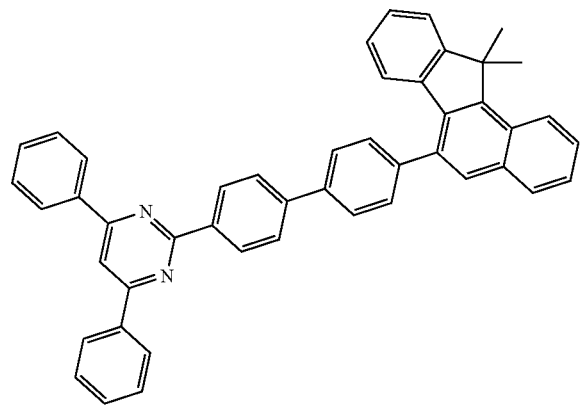
16
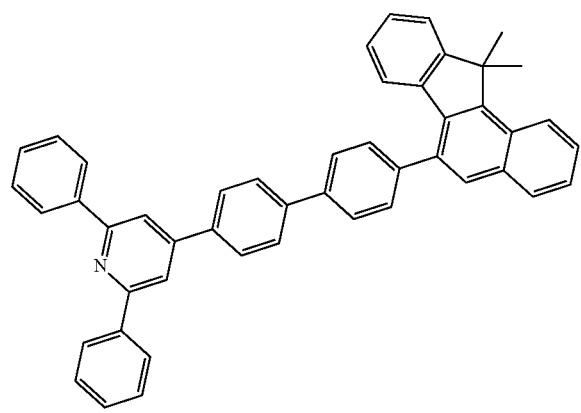
17
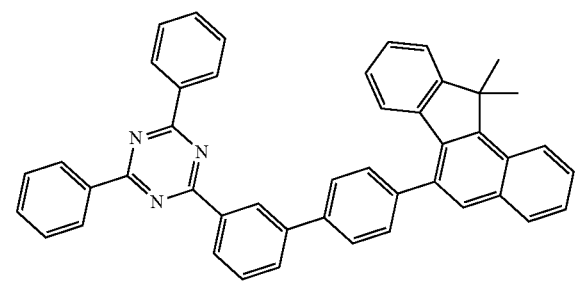
18
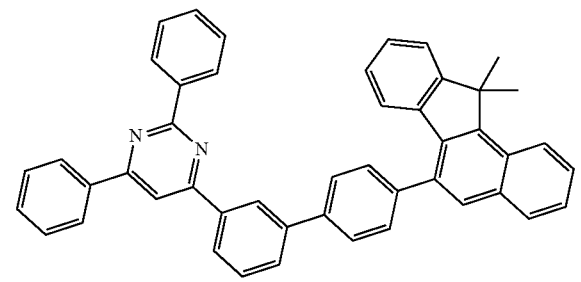
19
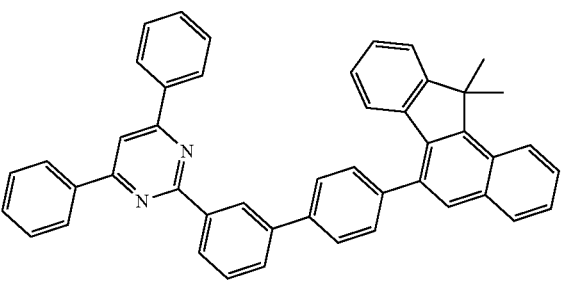
20
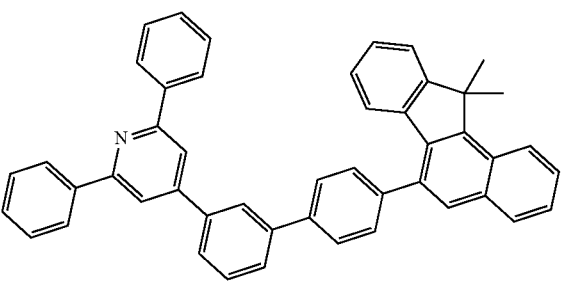
21
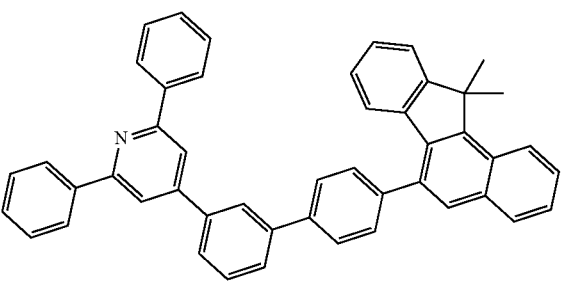
22

23
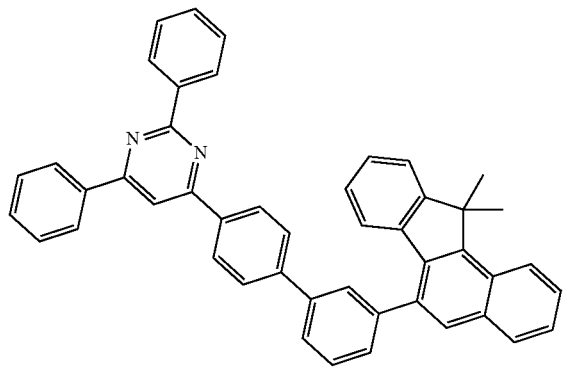
24
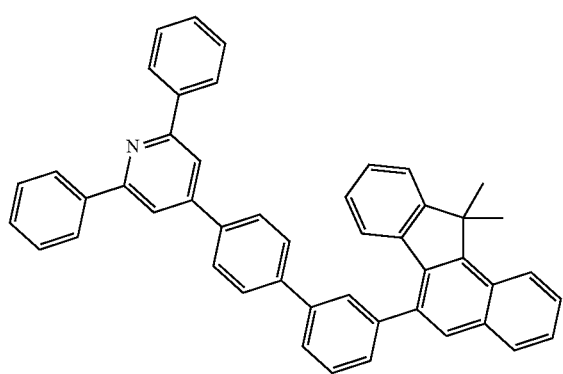
25
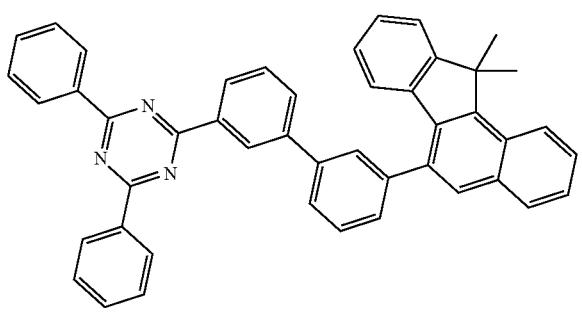
26
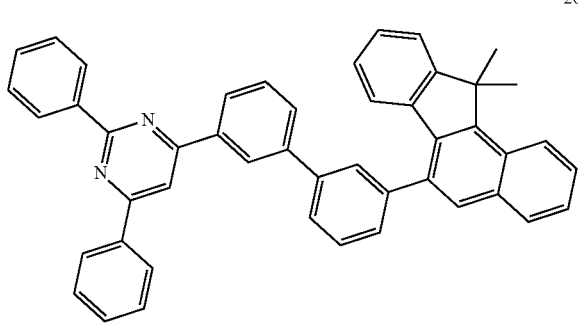
27
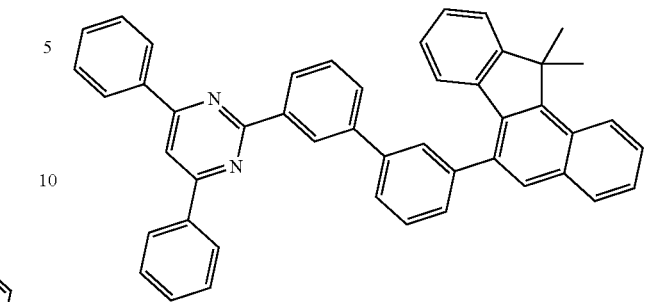
28
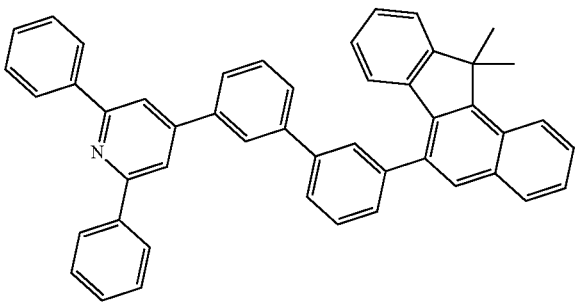
29
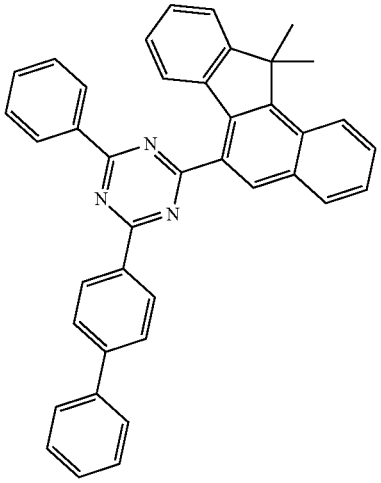
30
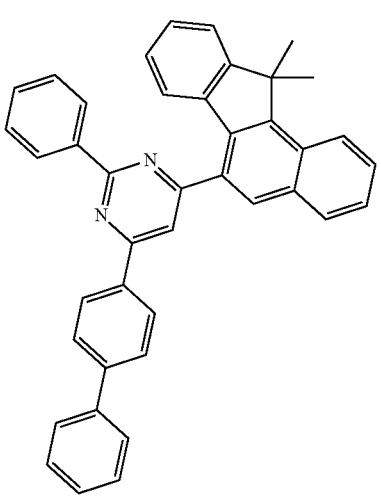

31
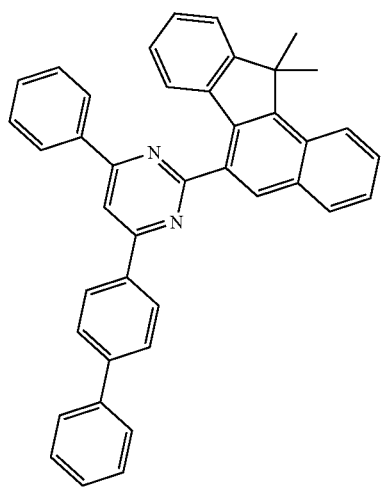
32
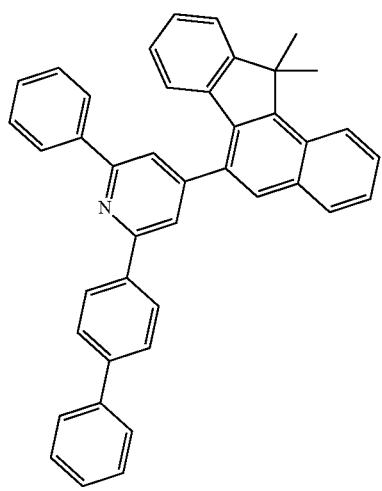
33
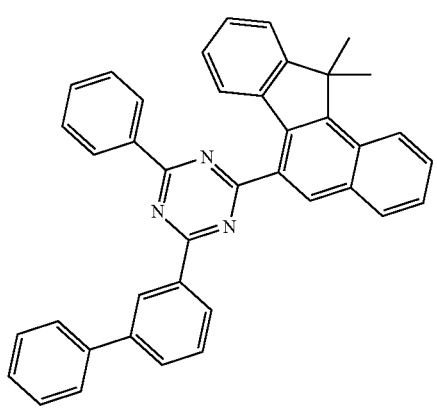
34
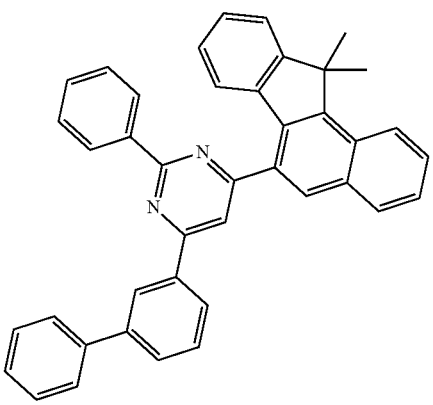
35
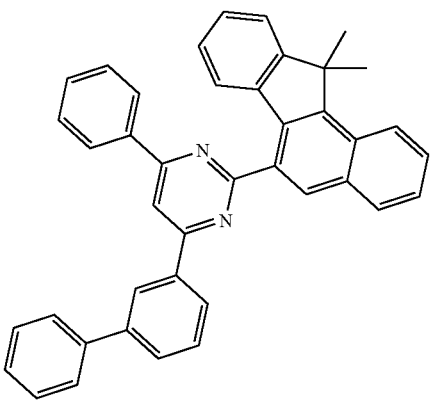
36
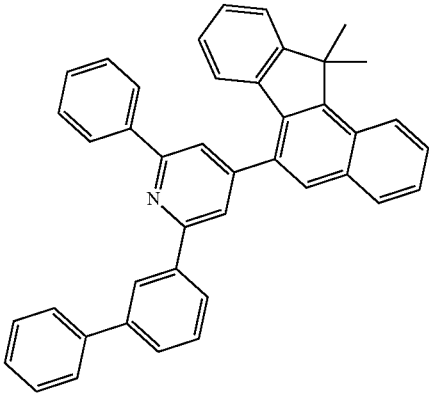

37
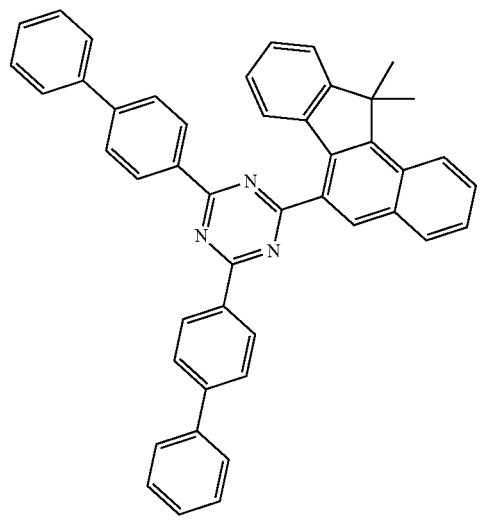
38
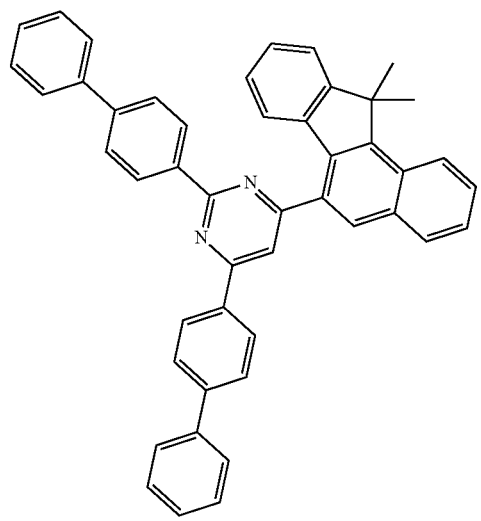
39
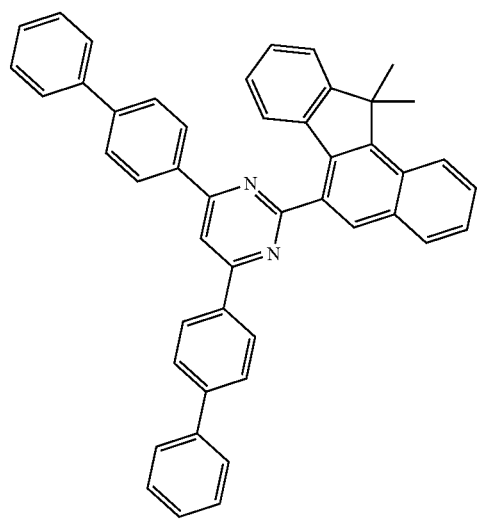
40
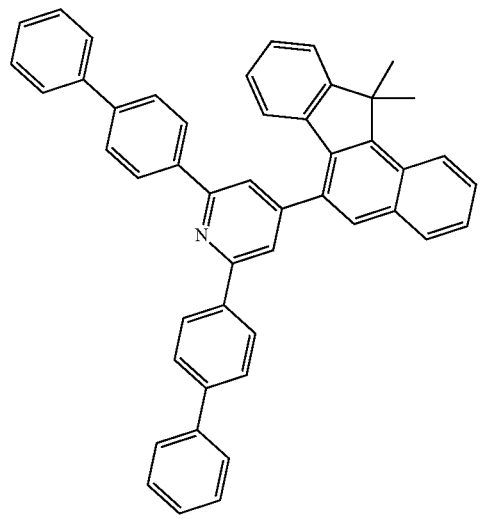
41
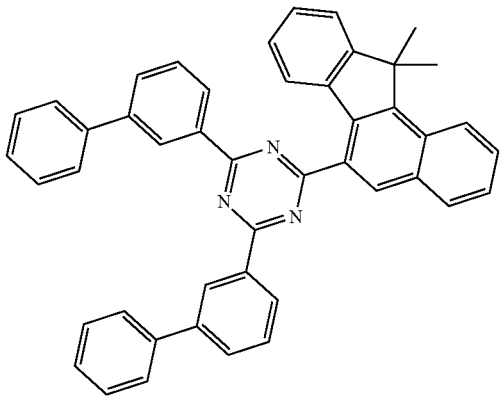
42
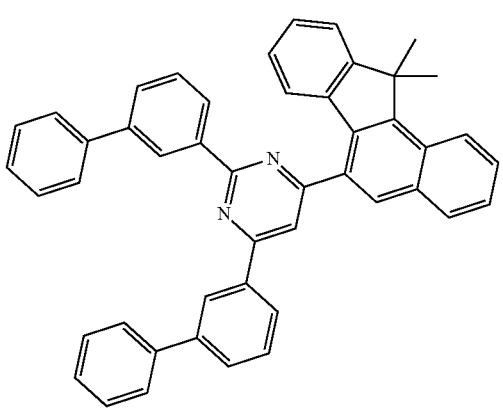

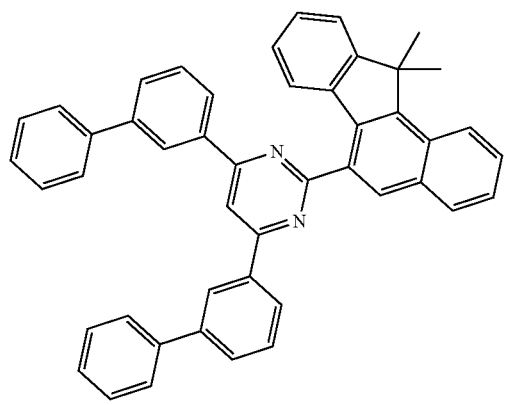
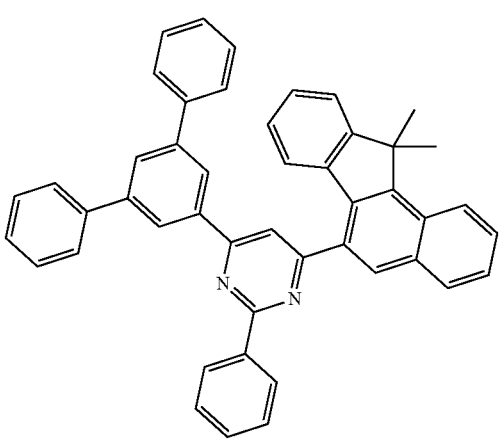
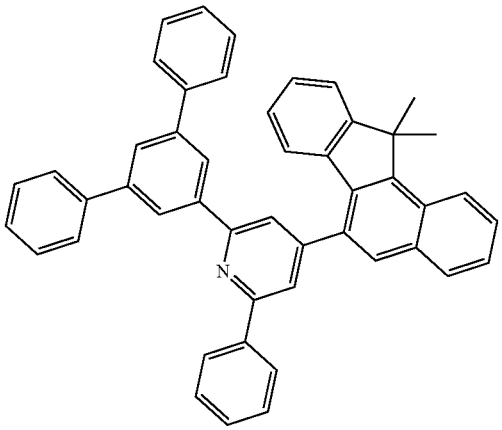

49
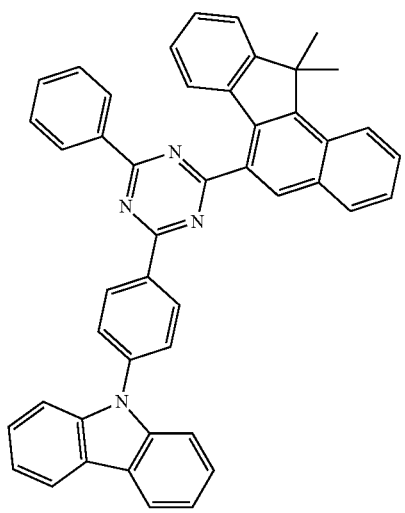
50
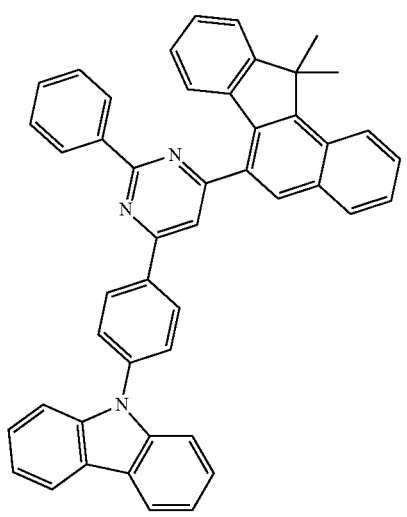
51
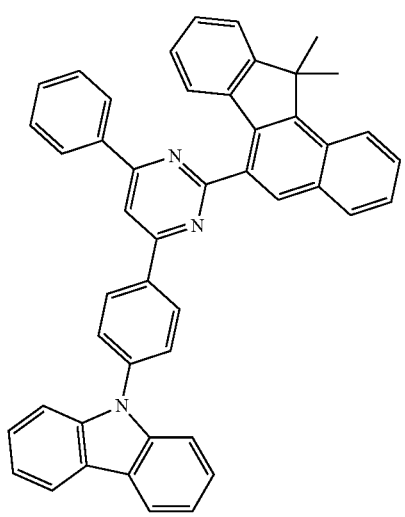
52
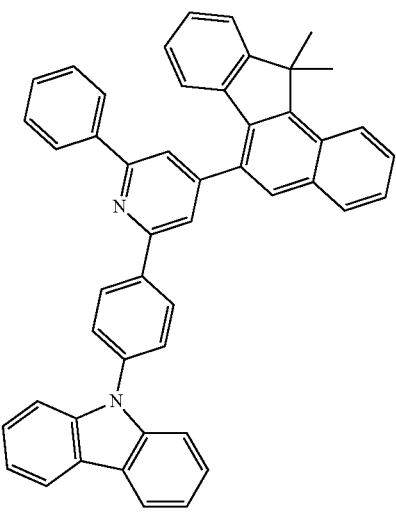
53
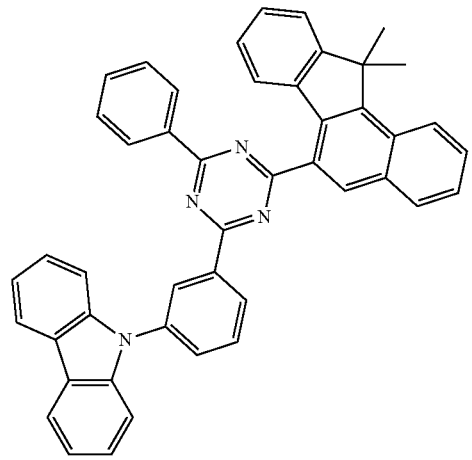
54
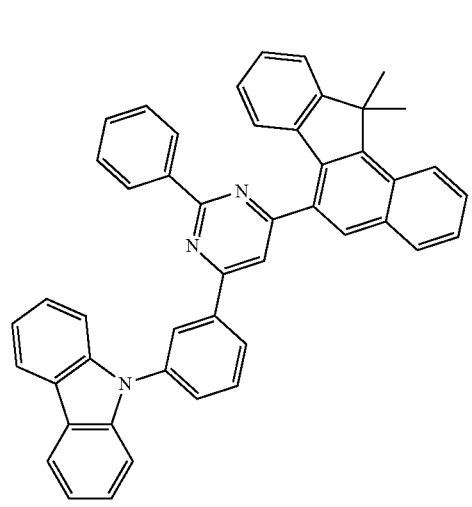

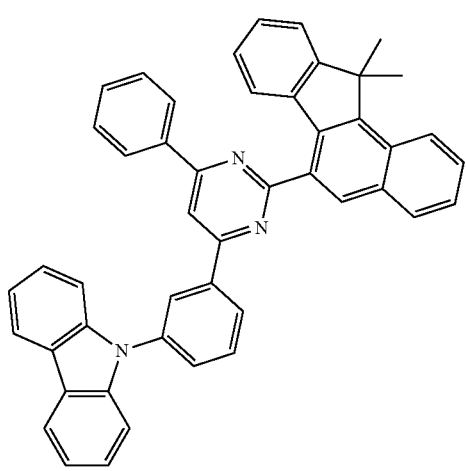
55
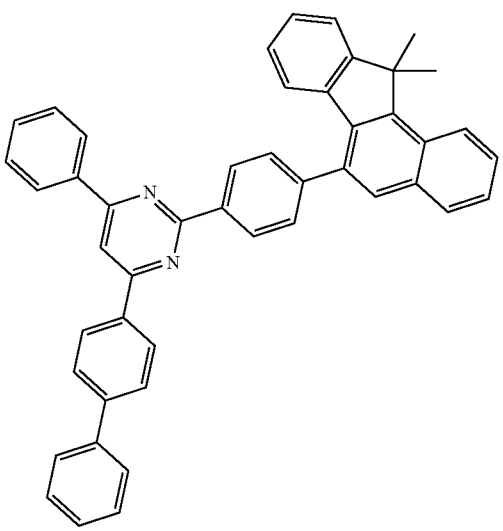
56
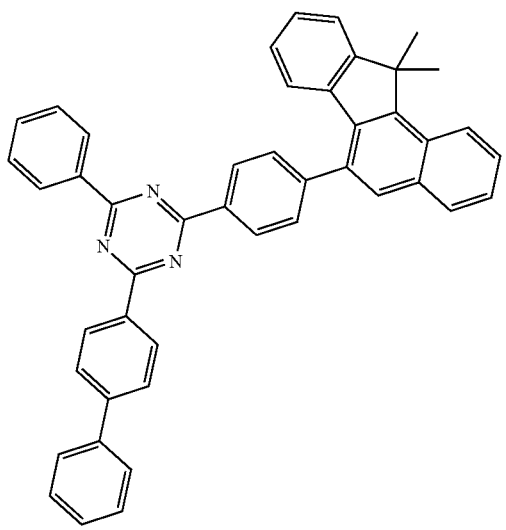
57

61
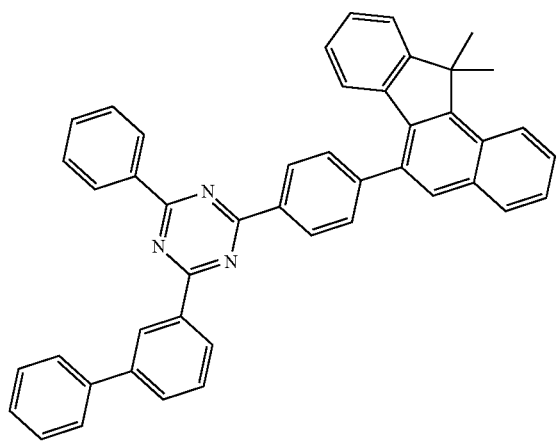
62
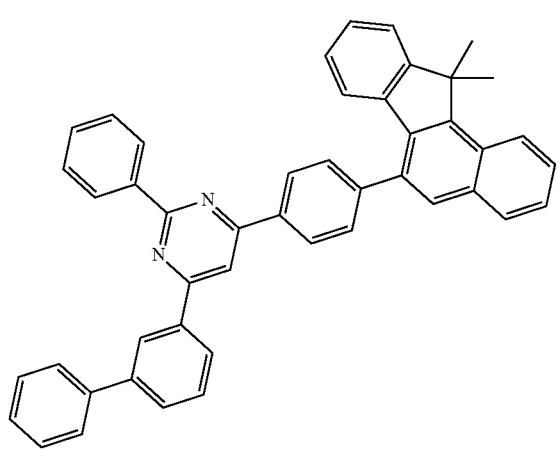
63
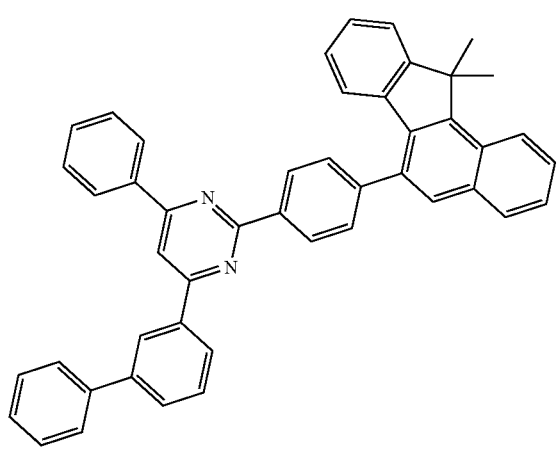
64
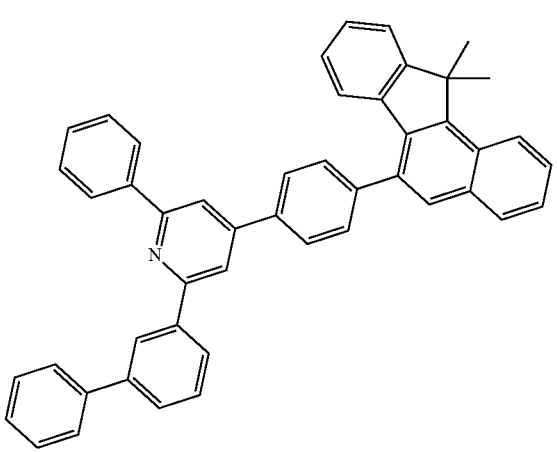
65
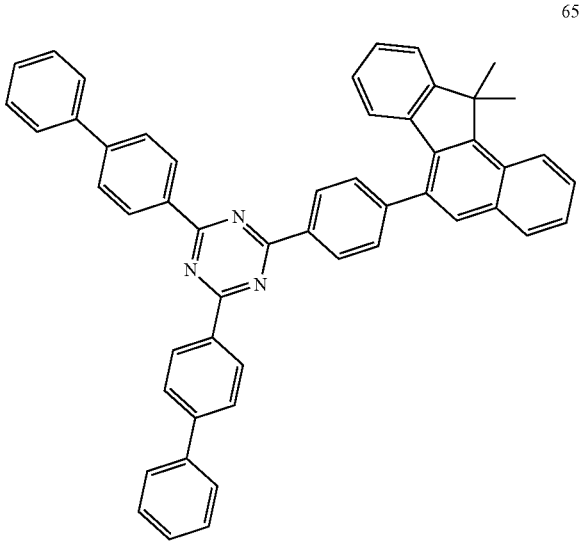
66
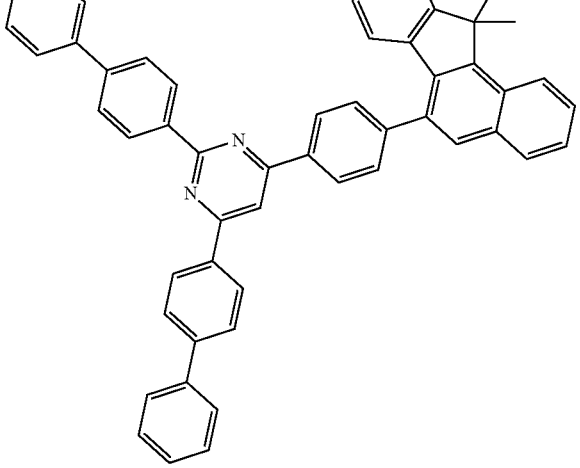

67
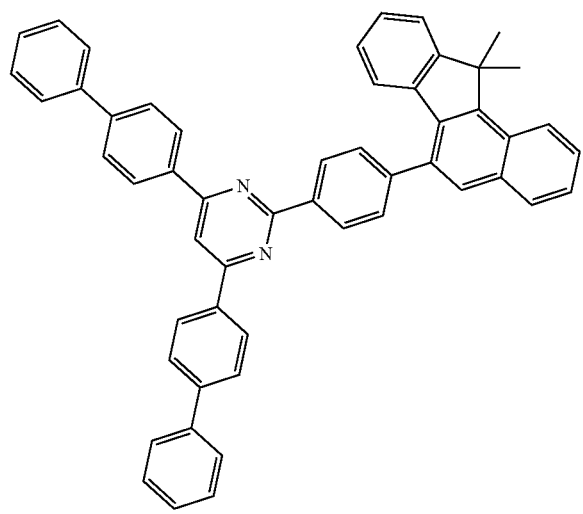
68
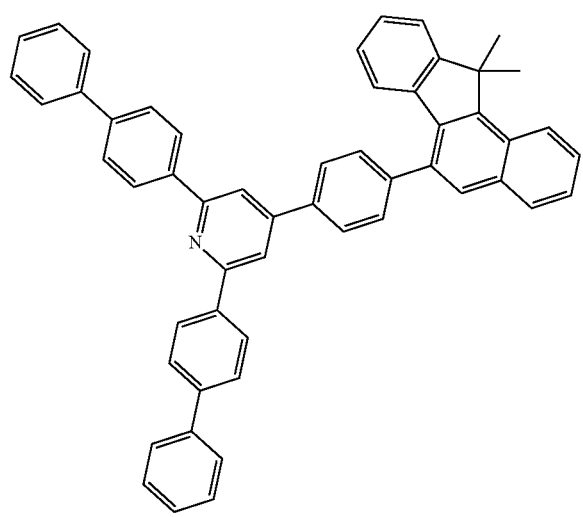
69
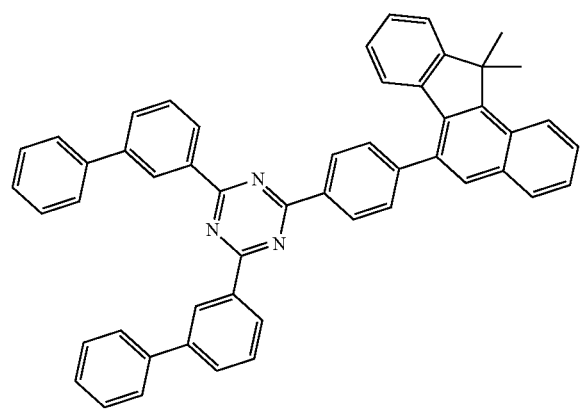
70
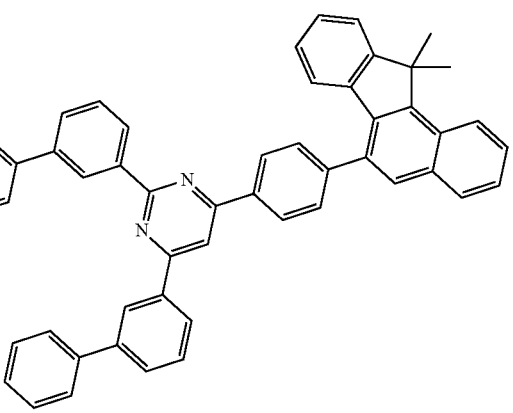
71
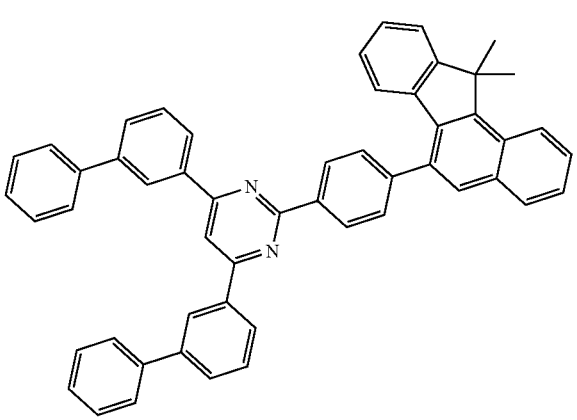
72
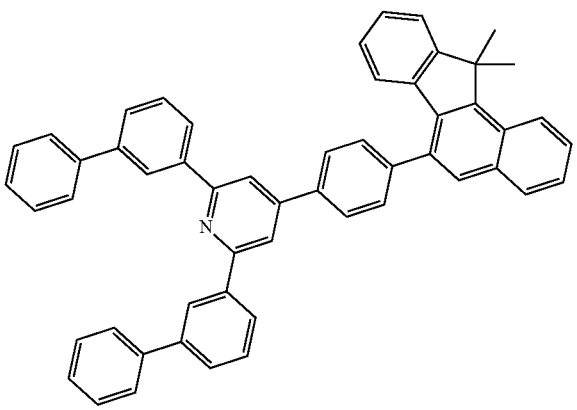

-continued
73
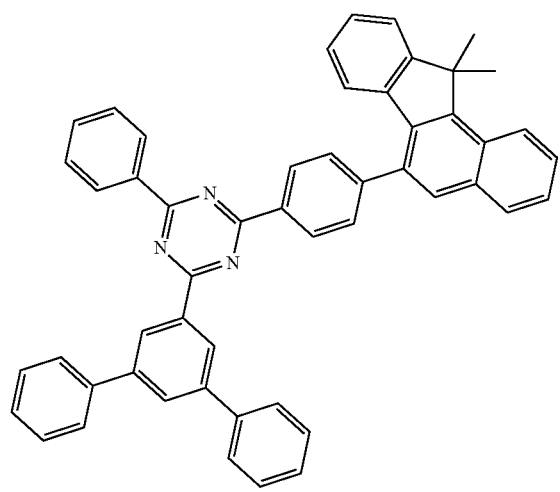
74
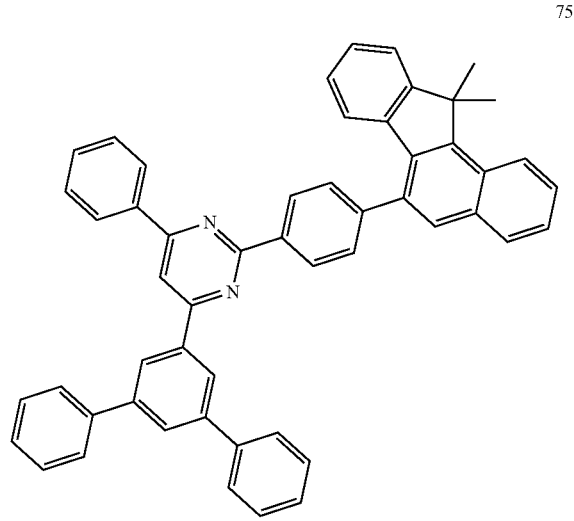
75
-continued
76
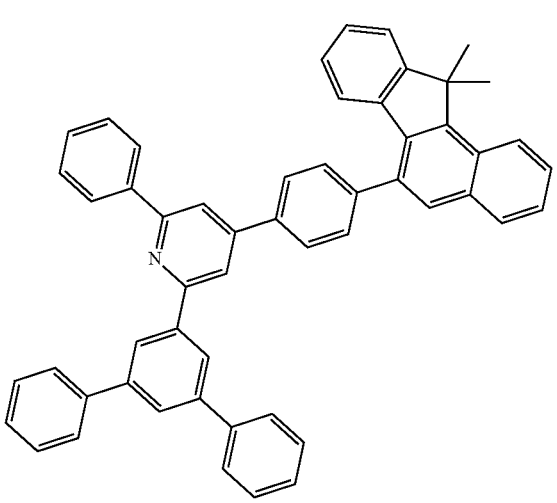
77
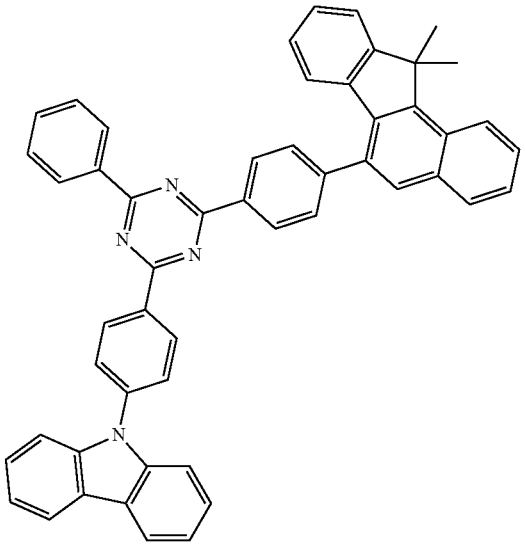
78
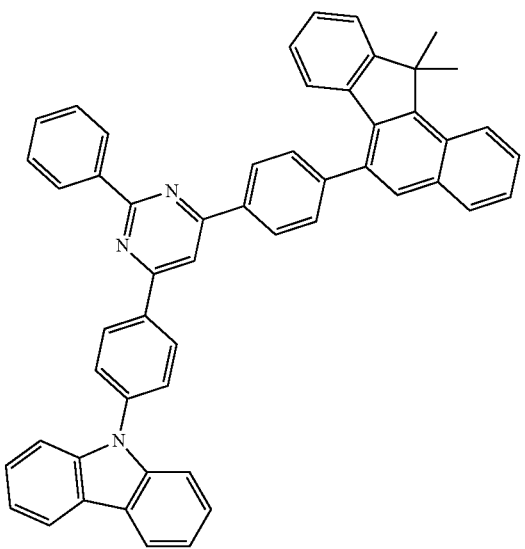

79
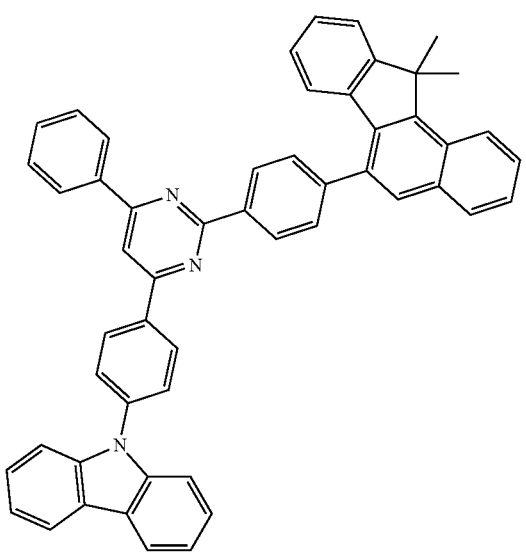
80
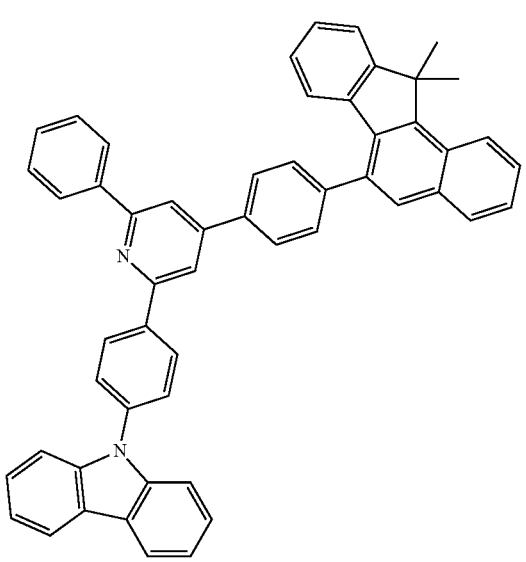
81
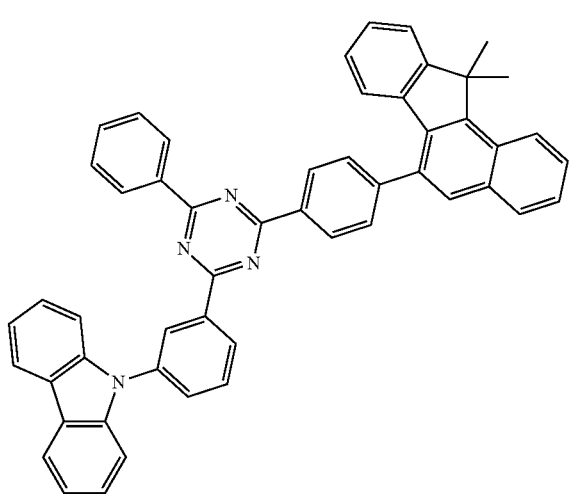
82
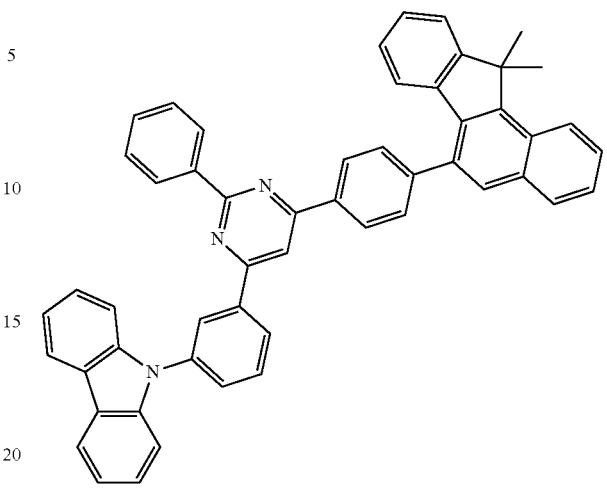
83
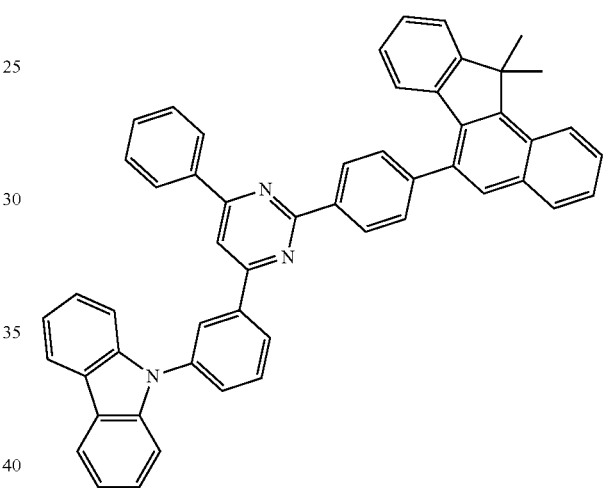
84
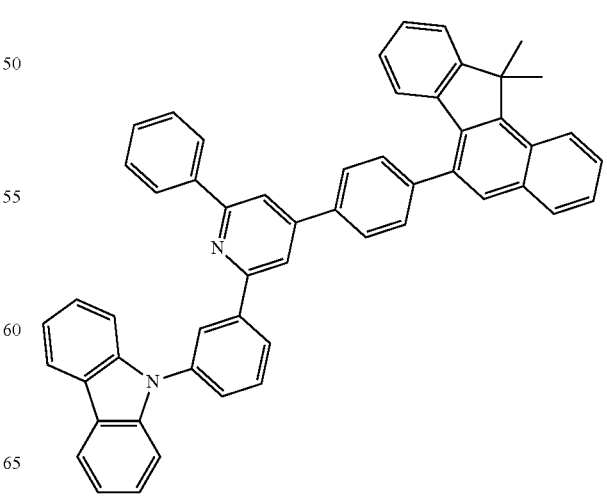

85
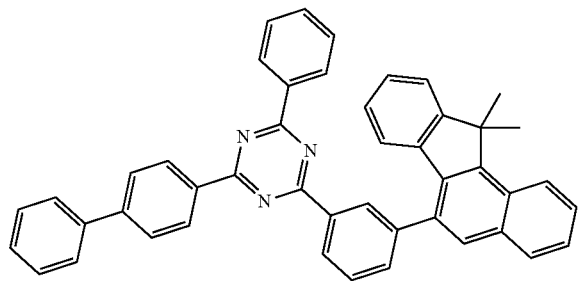
86
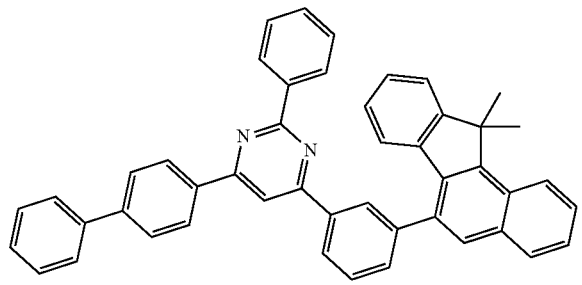
87
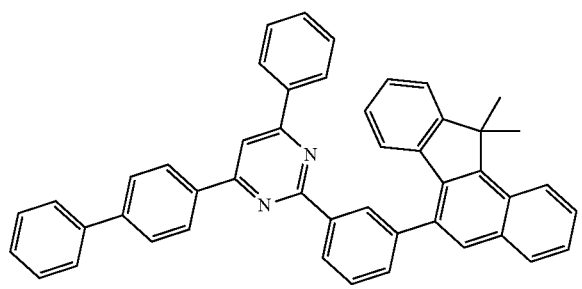
88
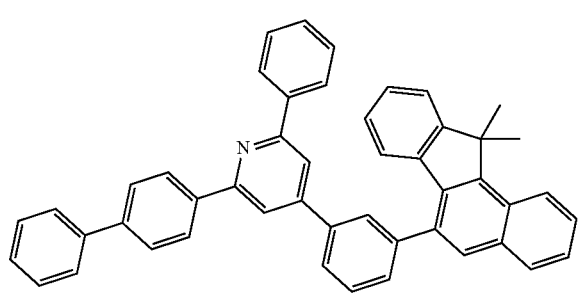
89
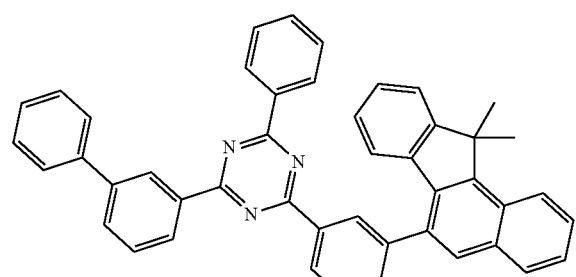
90
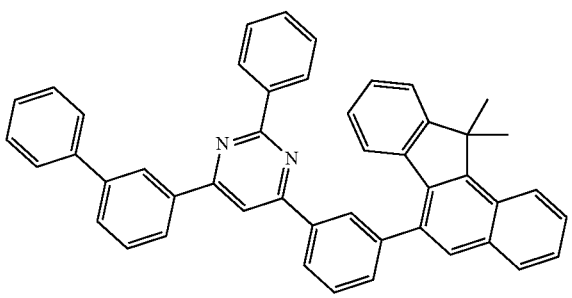
91
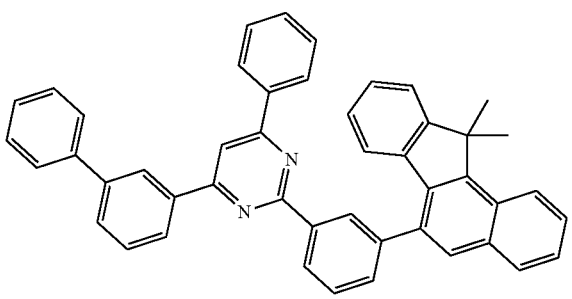
92
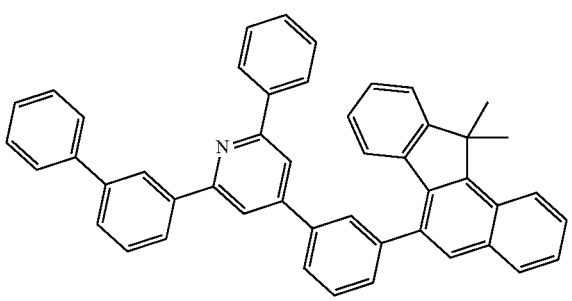
93
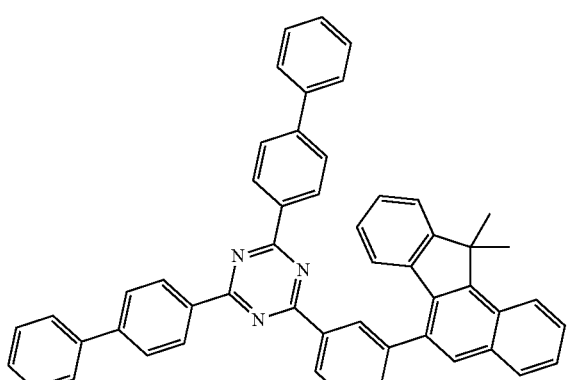

94
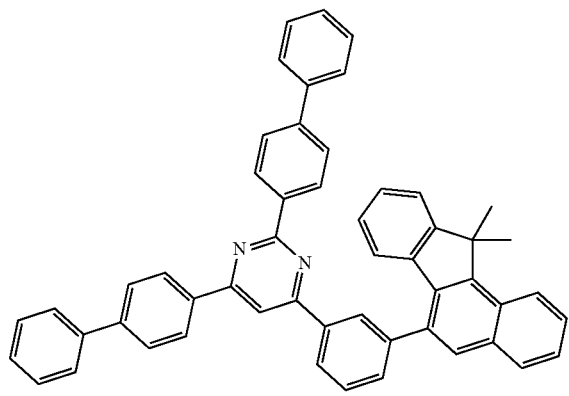
95
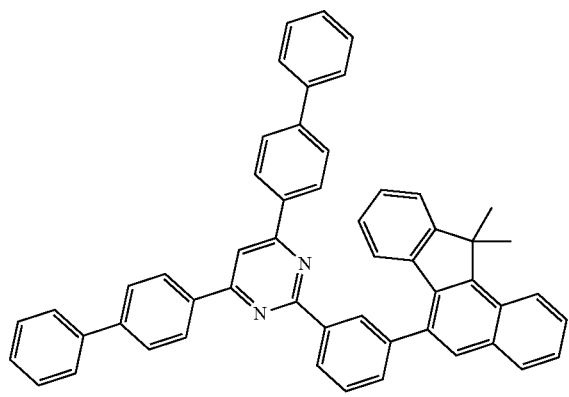
96
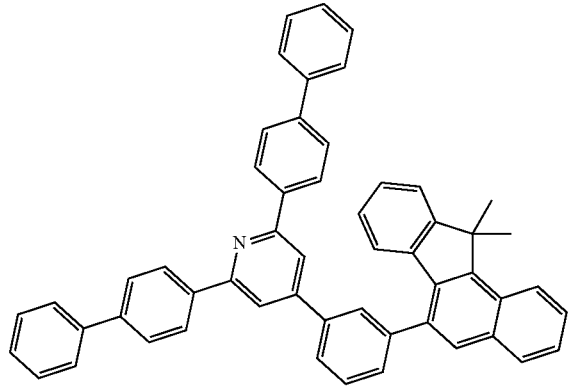
97
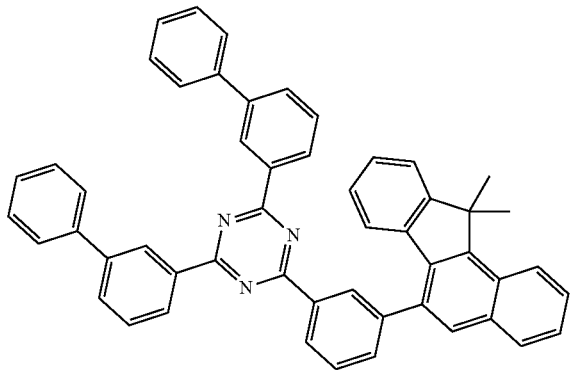
98
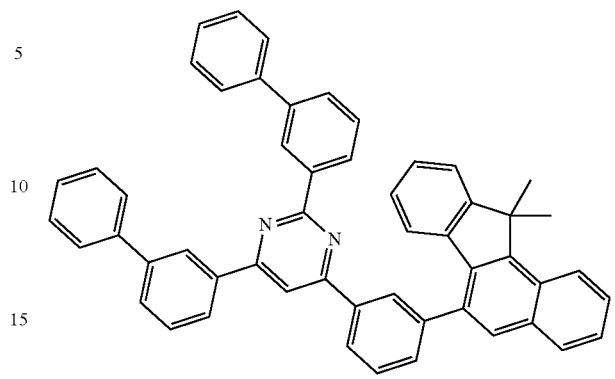
99
100
101

102
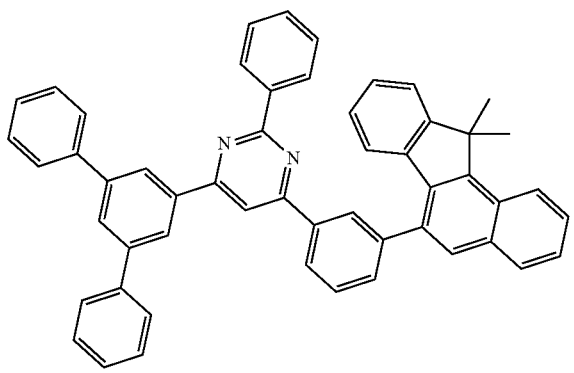
103
104
105
106
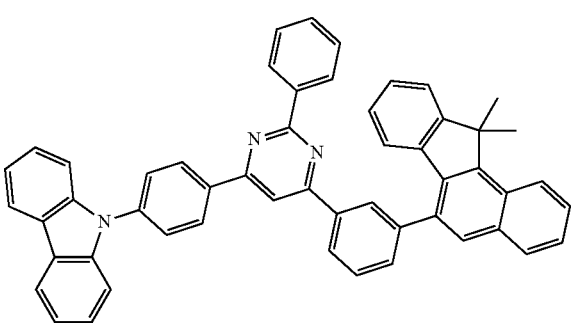
107
108
109
110
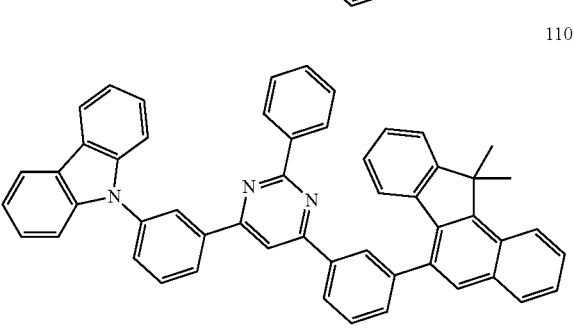

111
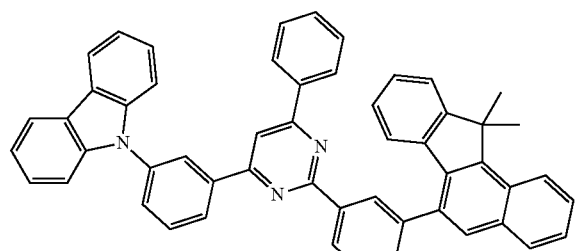
112
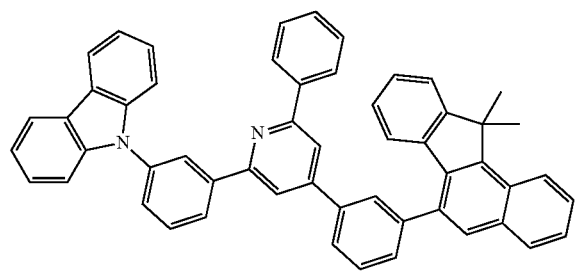
113
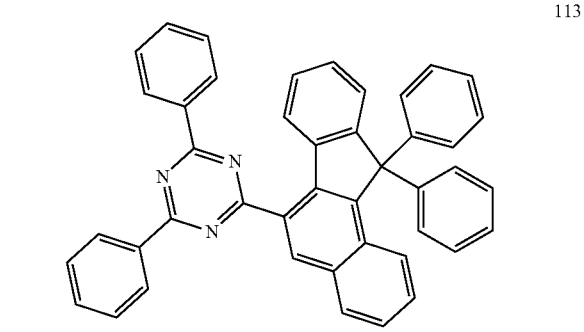
114
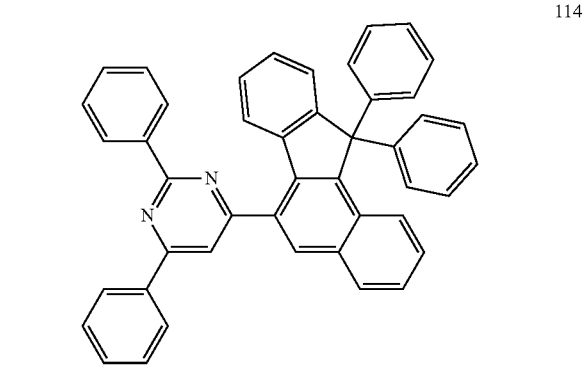
115
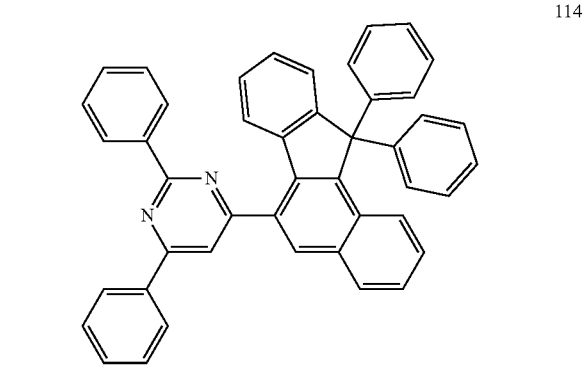
116
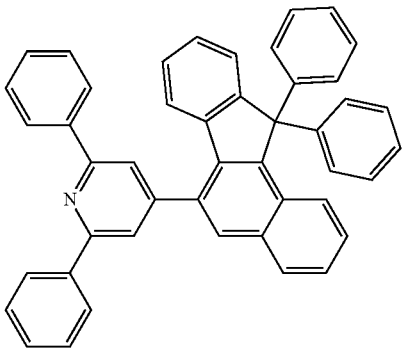
117
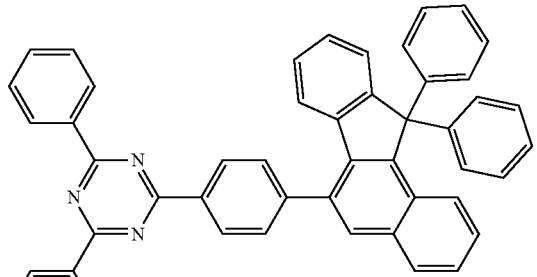
118
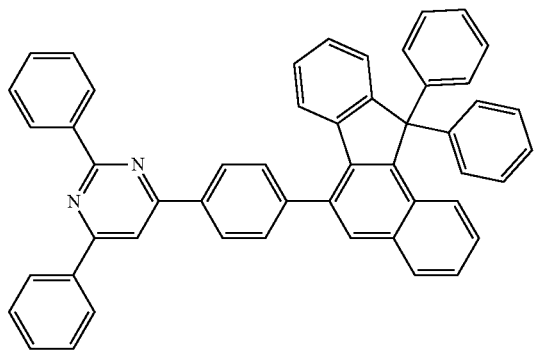
119
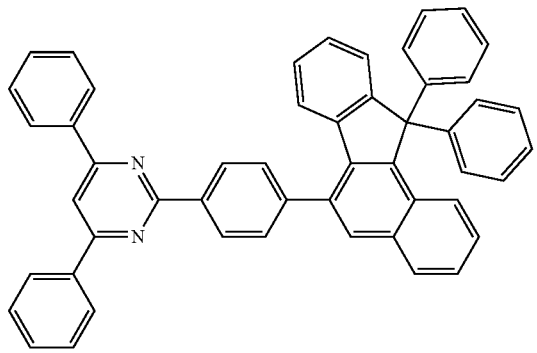

120
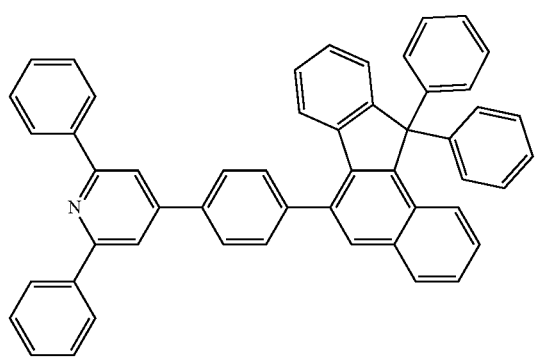
124
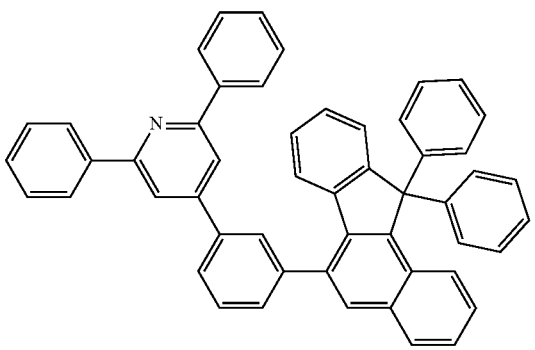
121
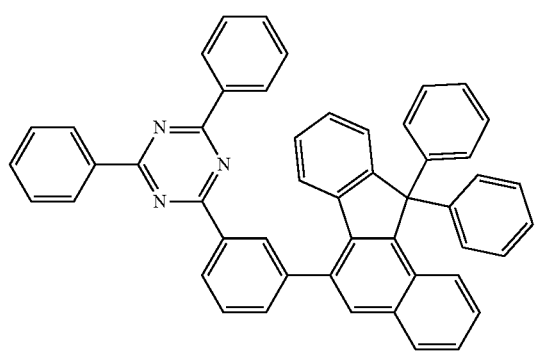
125
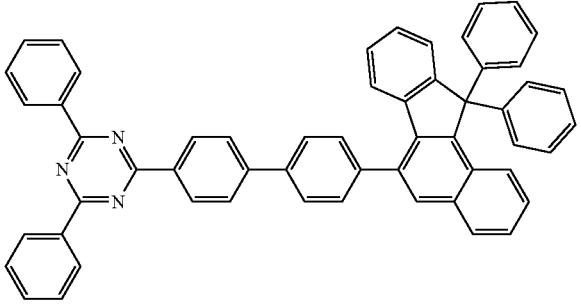
122
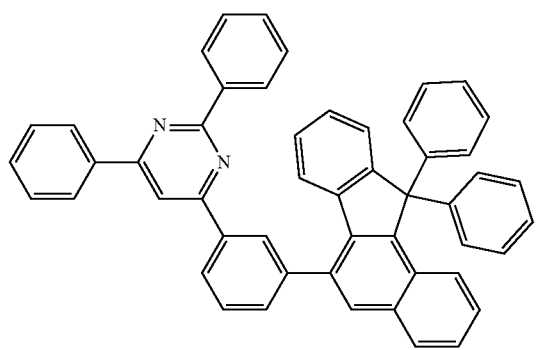
126
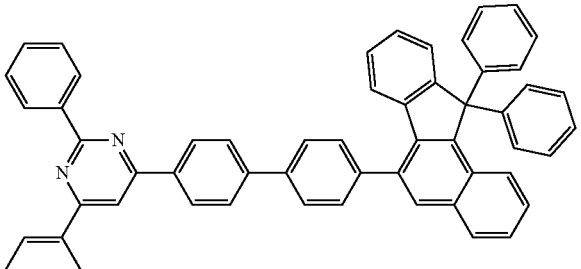
123
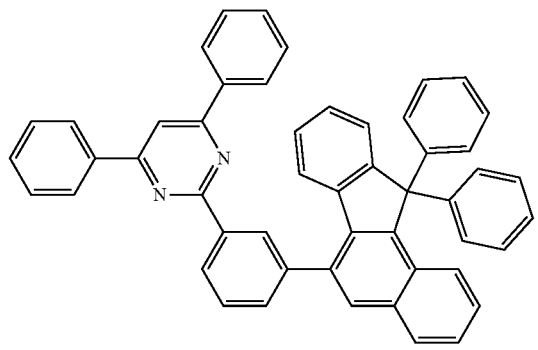
127
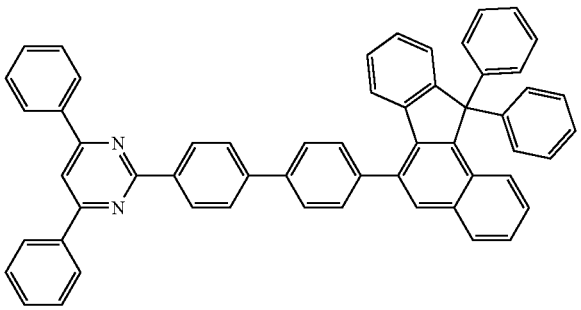

128
129
130
131
132
133
134
135

136
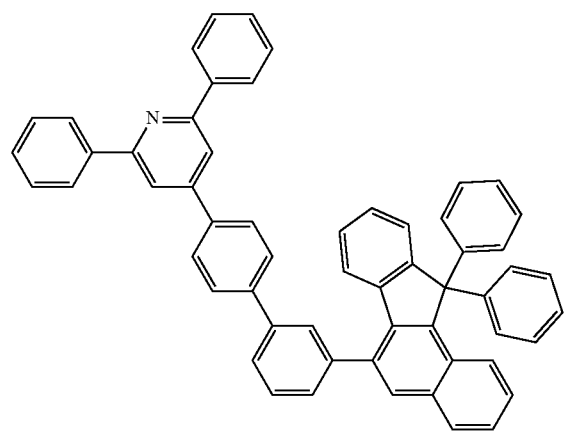
137
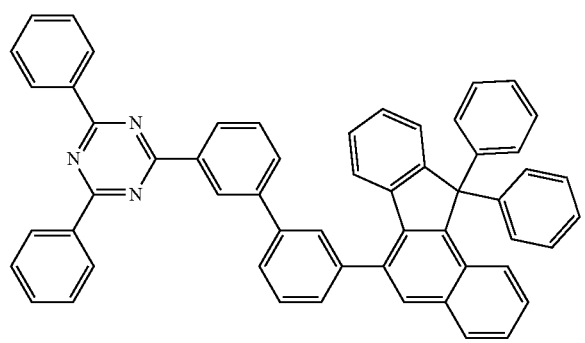
138
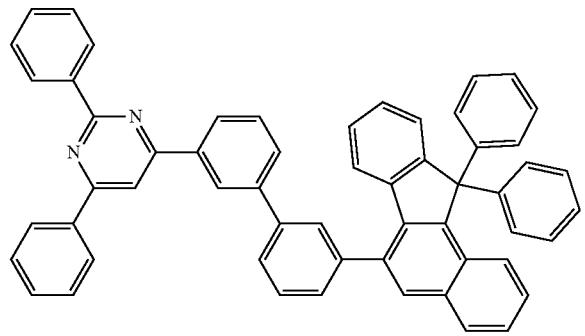
139
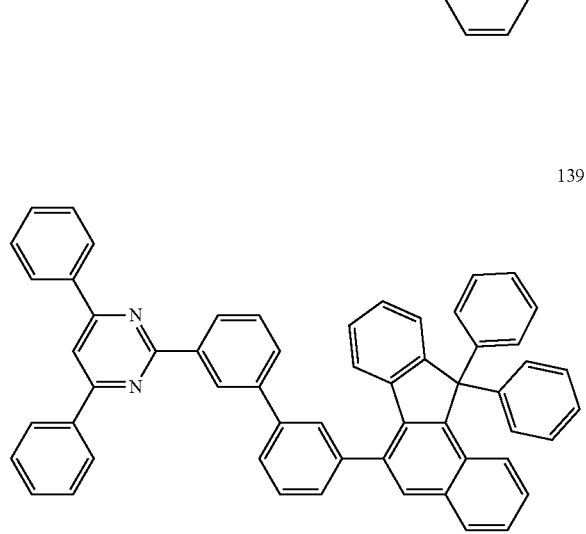
140
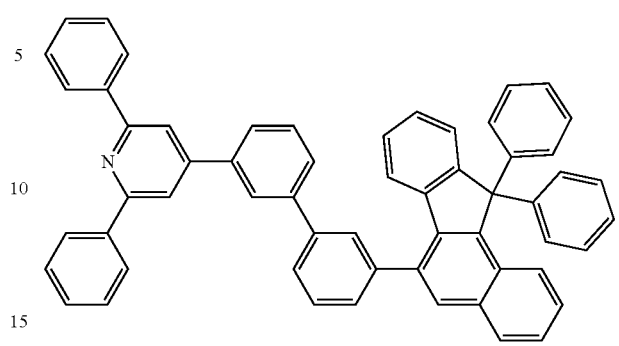
141
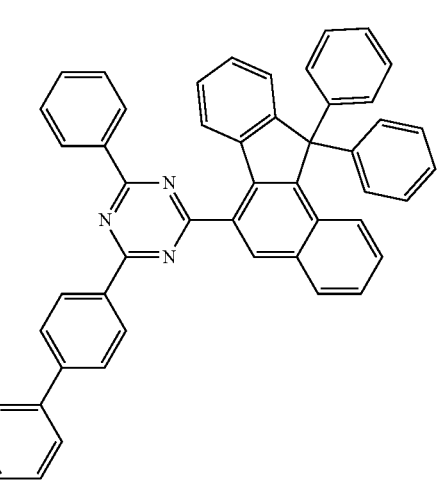
142
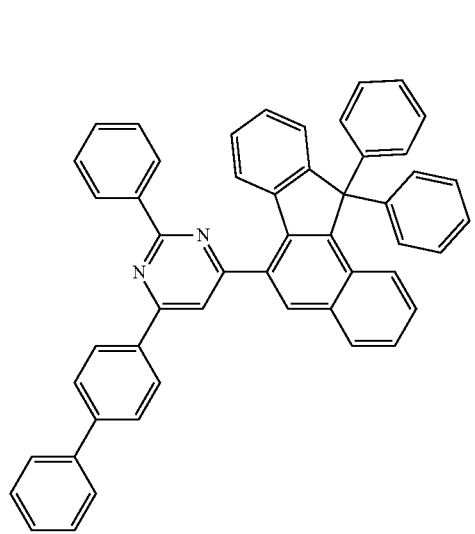

143
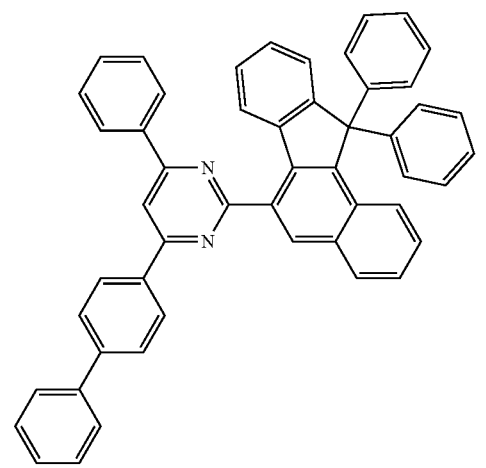
144
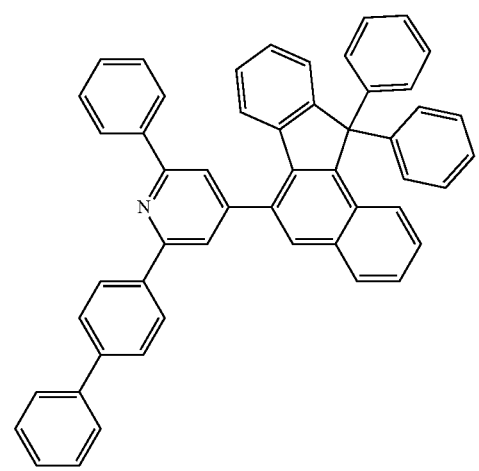
145
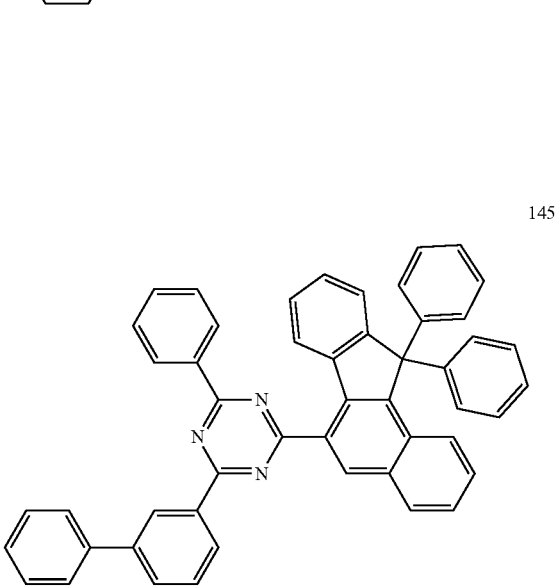
146
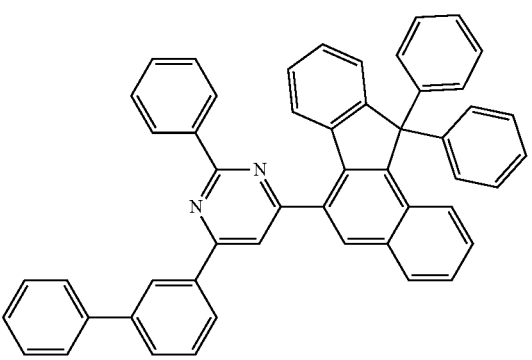
147
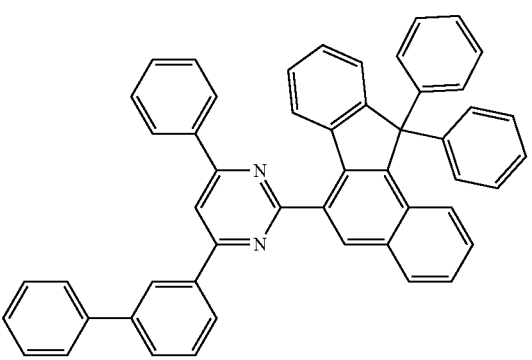
148
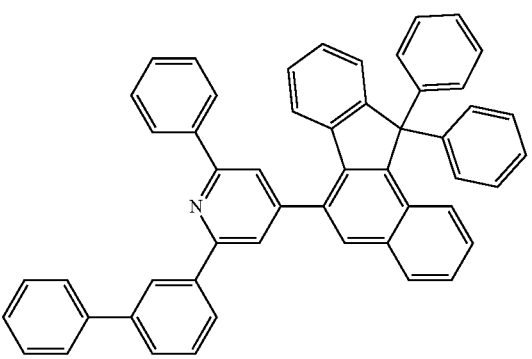
149
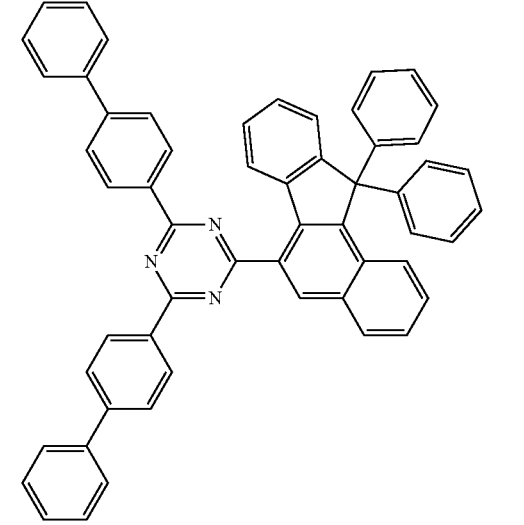

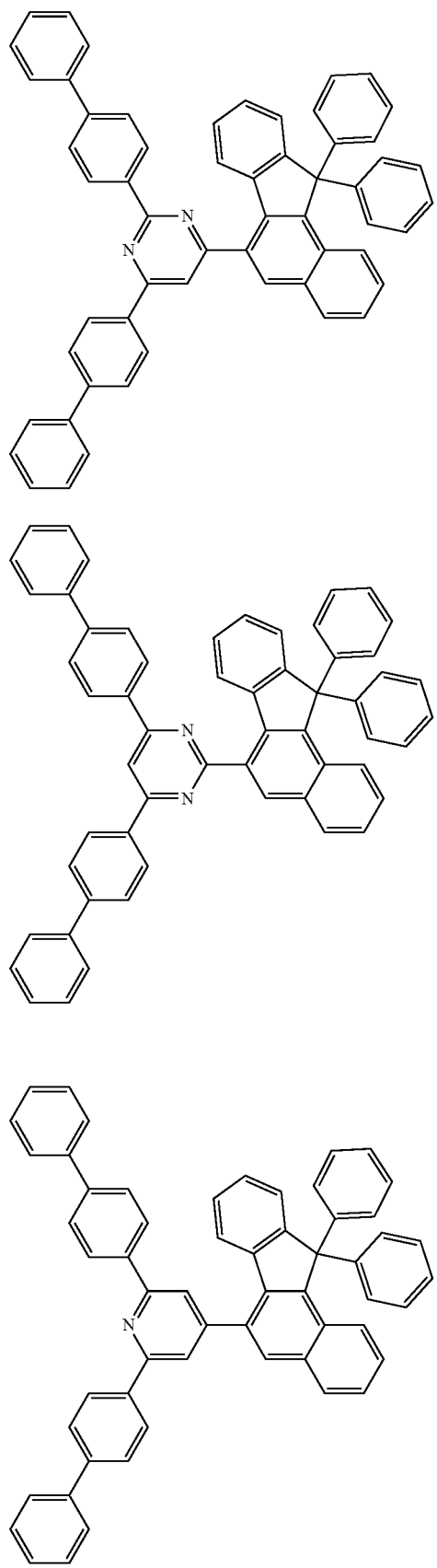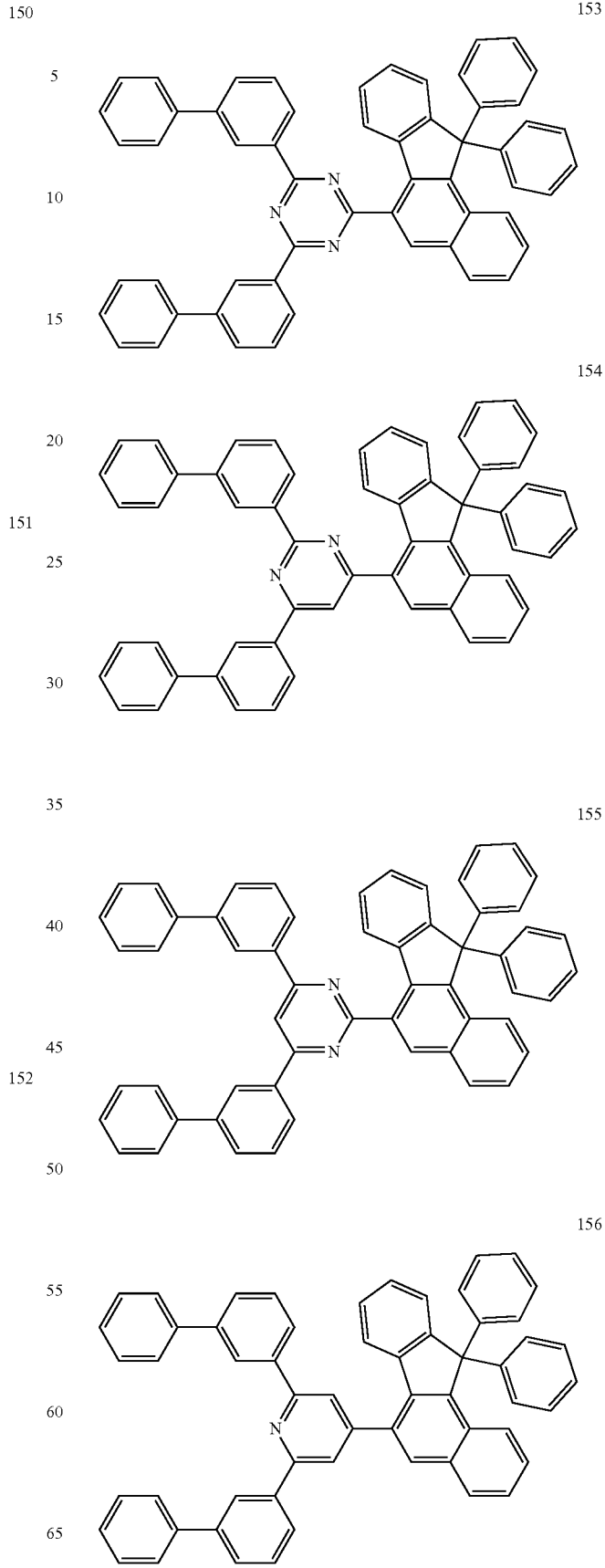

157
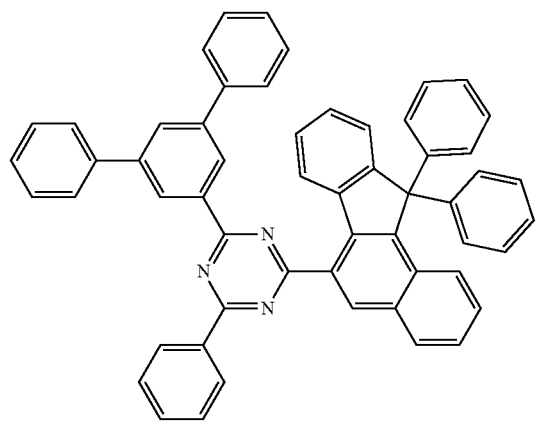
158
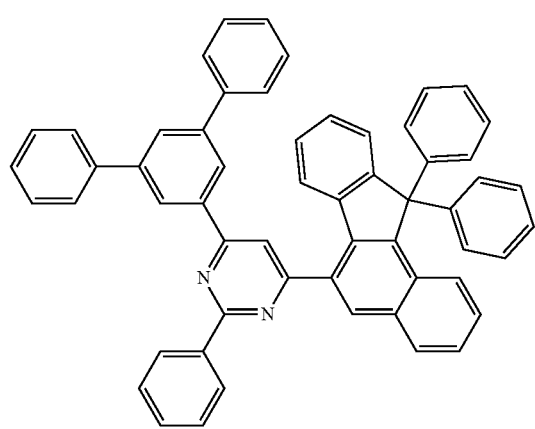
159
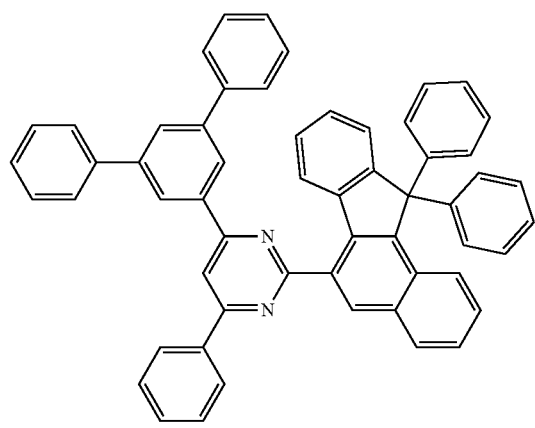
160
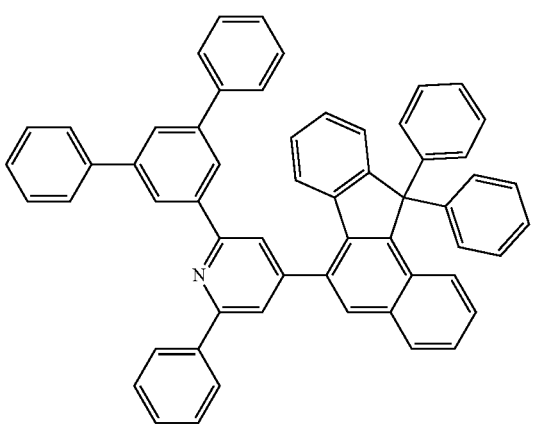
161
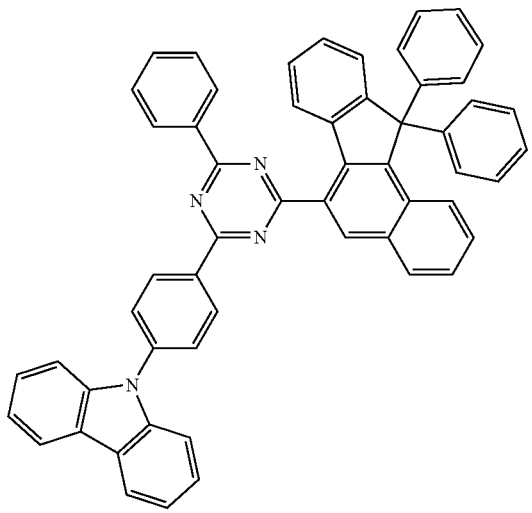
162
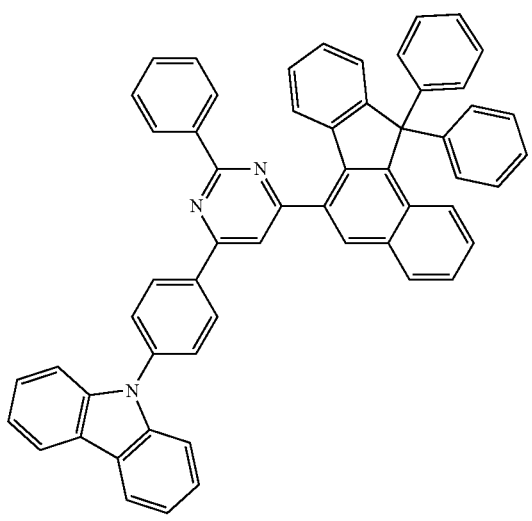

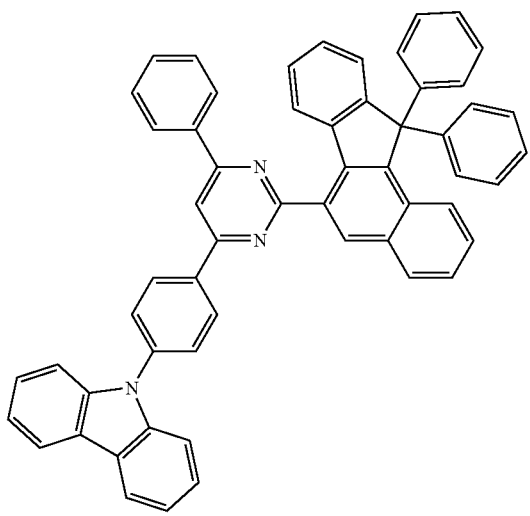
163
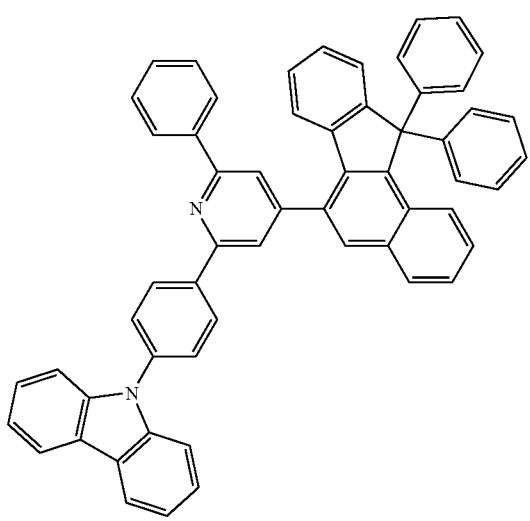
164
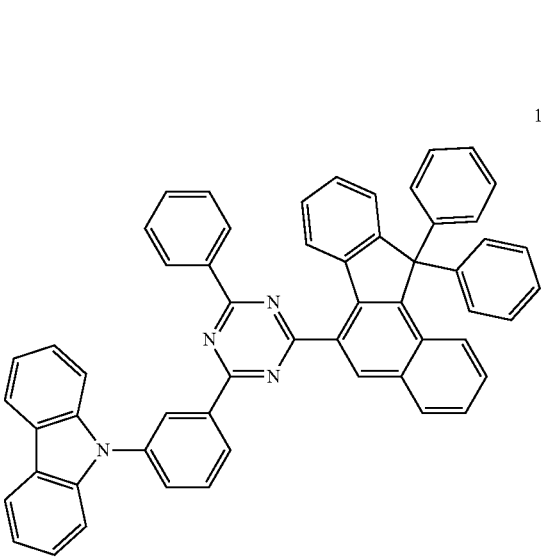
165
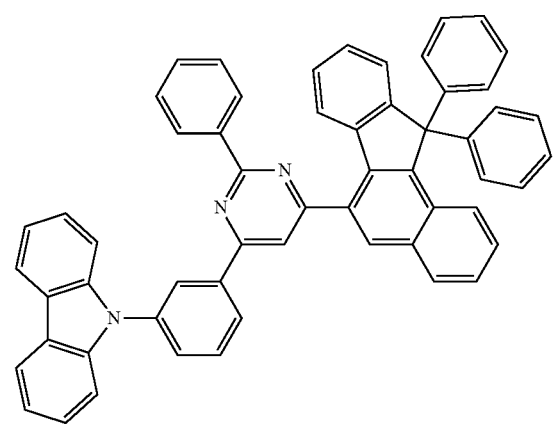
166
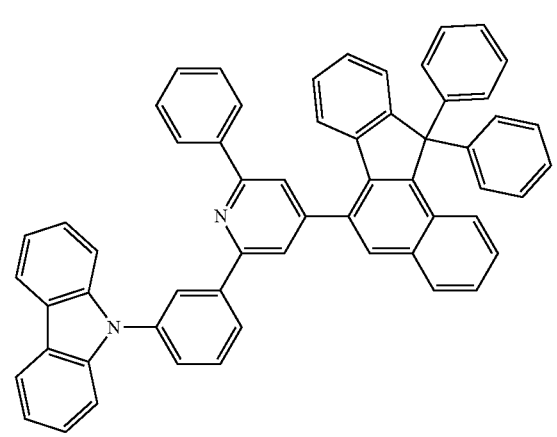
167
168

169
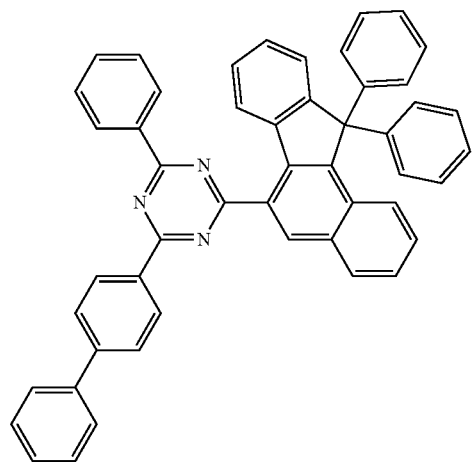
170
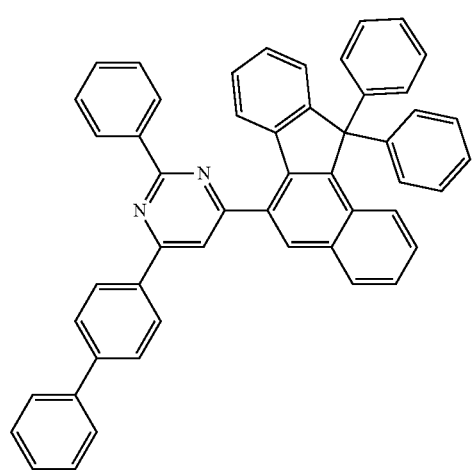
171
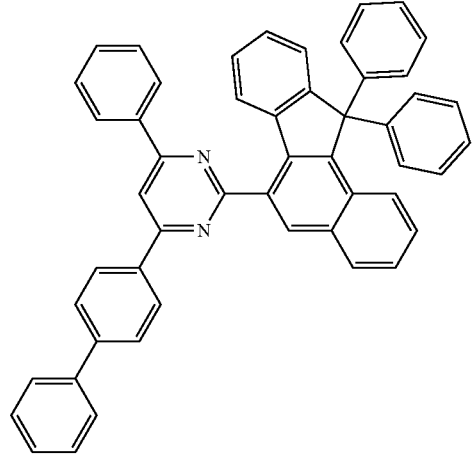
172
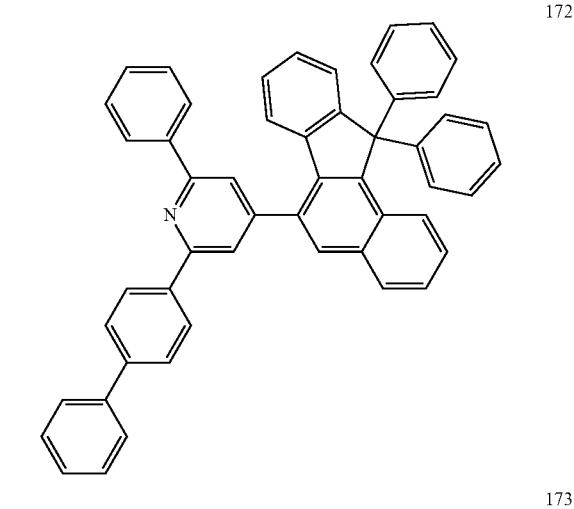
173
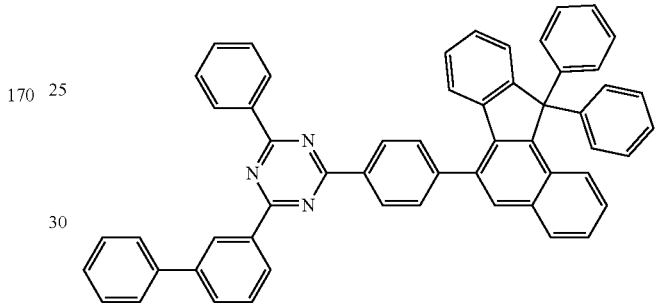
174
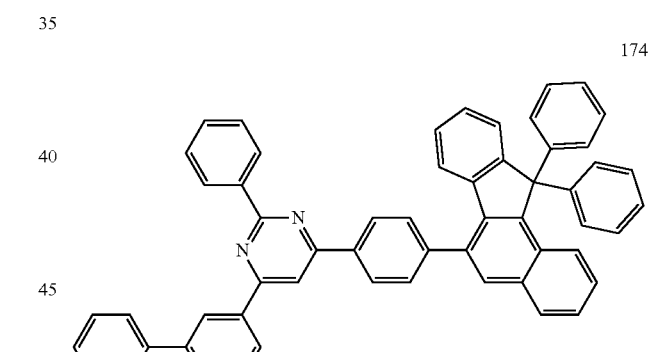
175
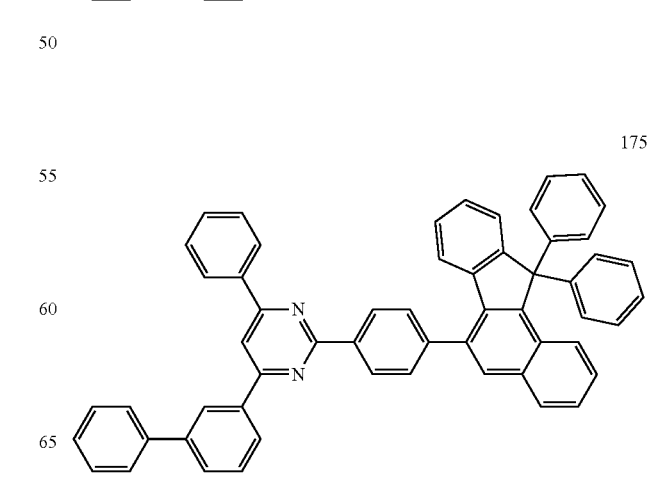

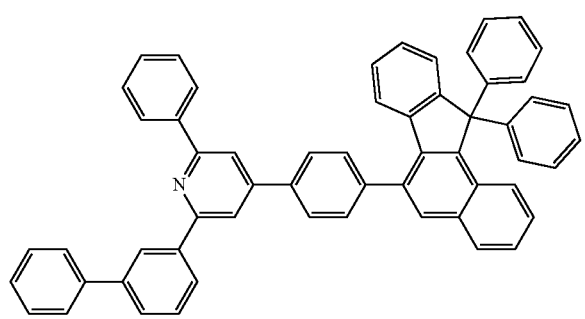
176
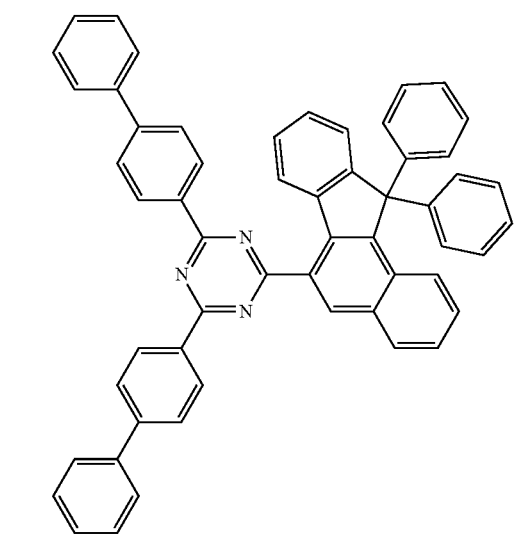
177
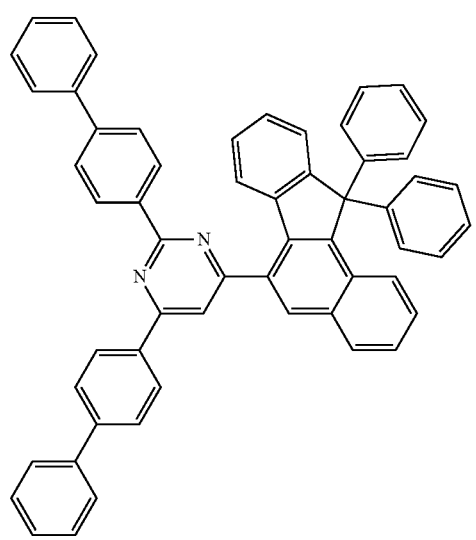
178
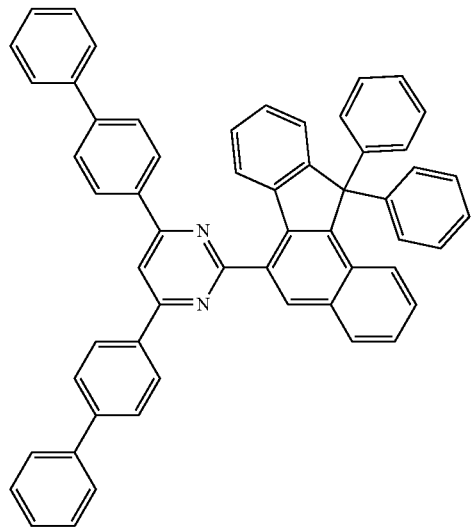
179
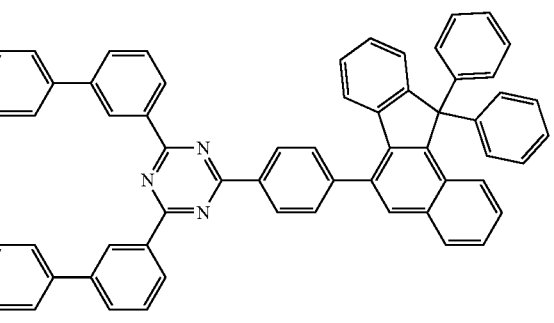
180
181

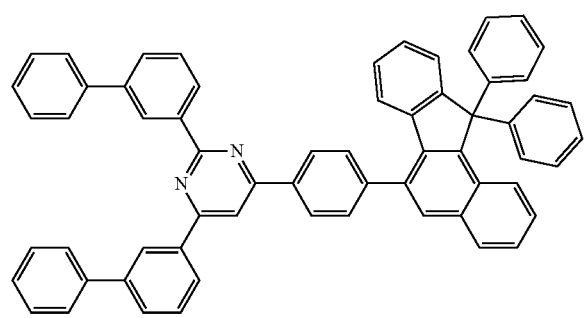
182
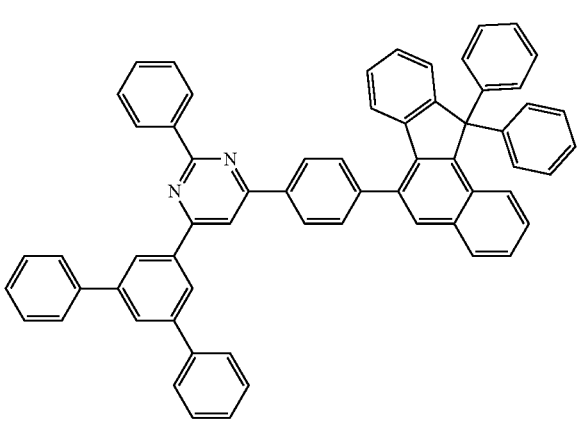
186
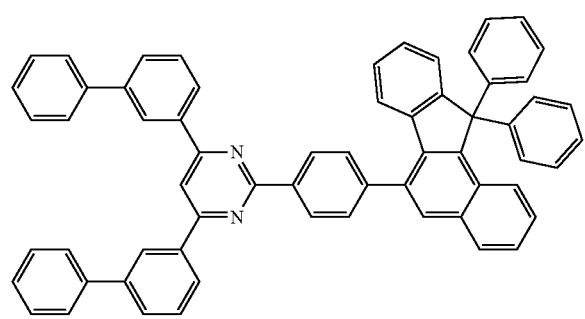
183
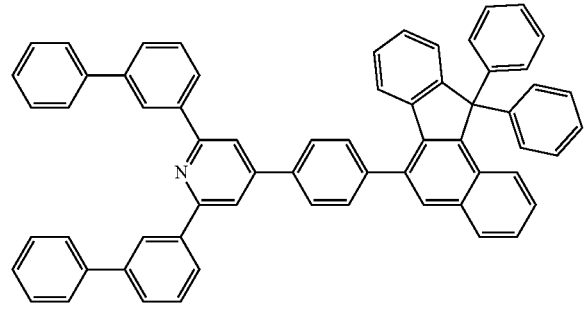
184
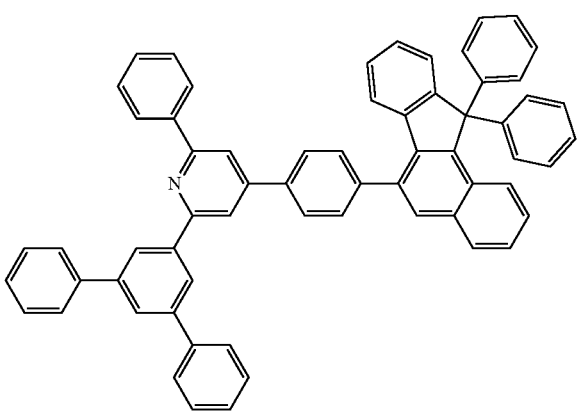
187
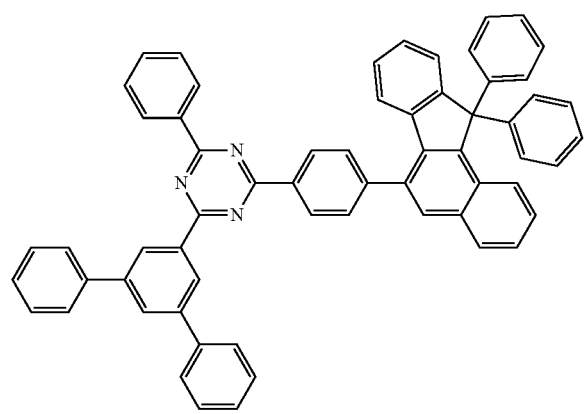
185
188

189
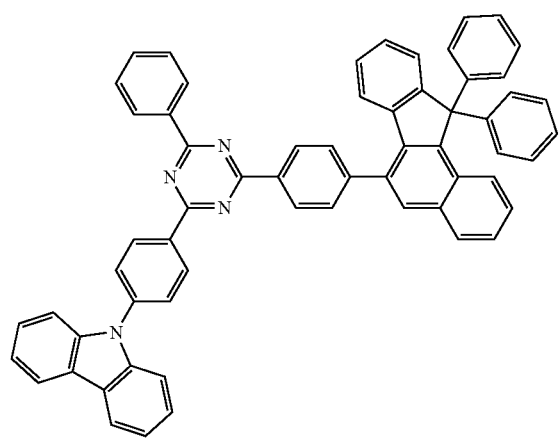
190
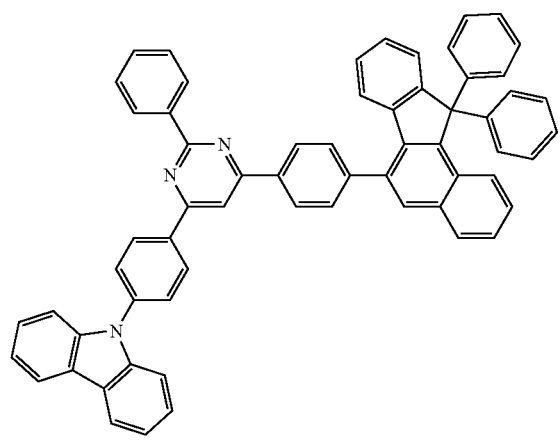
191
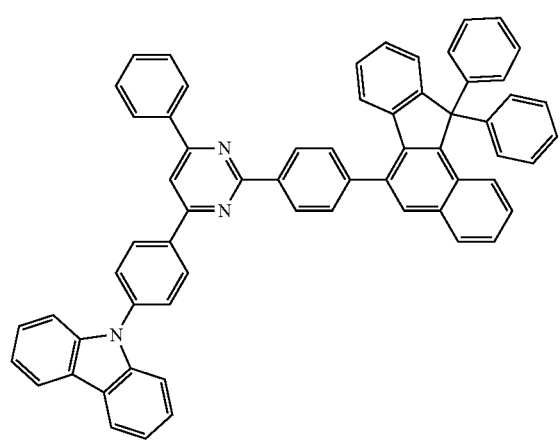
192
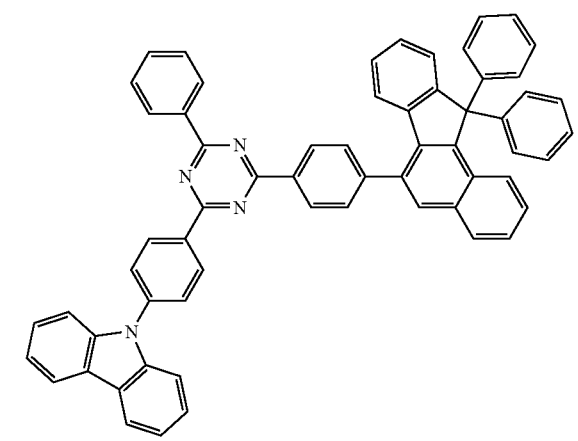
193
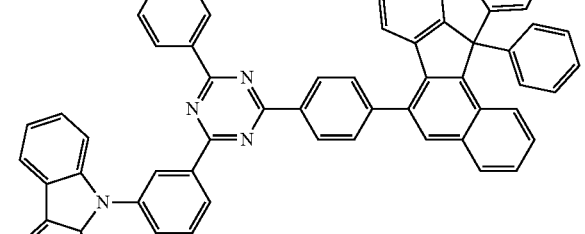
194
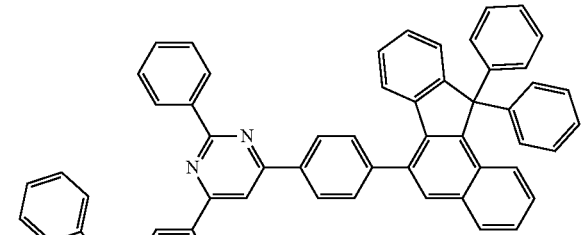
195
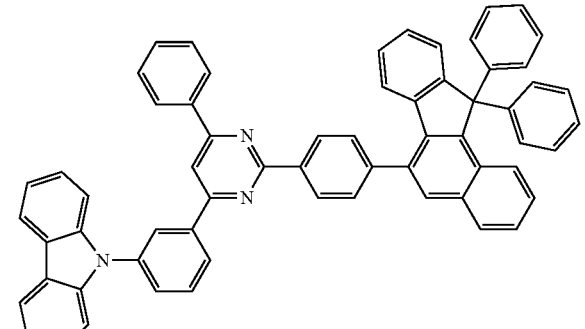

196
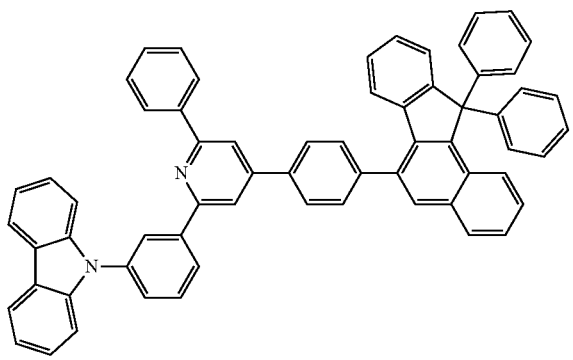
197
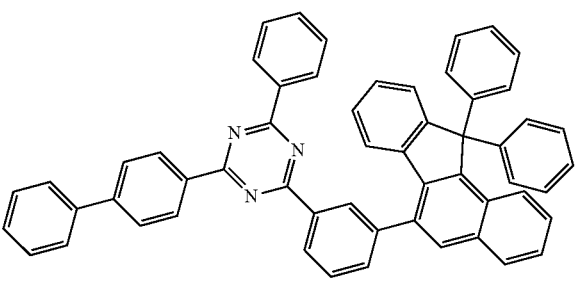
198
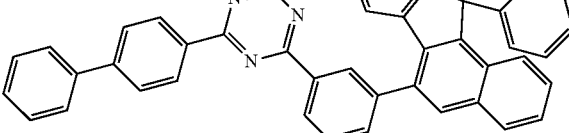
199
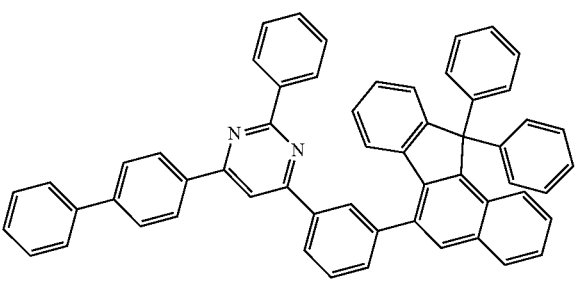
200
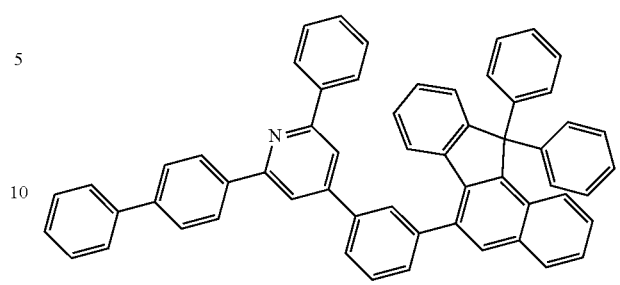
201
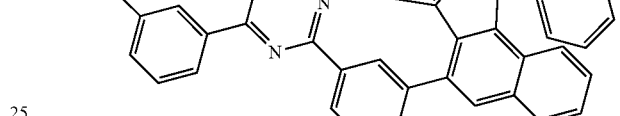
202
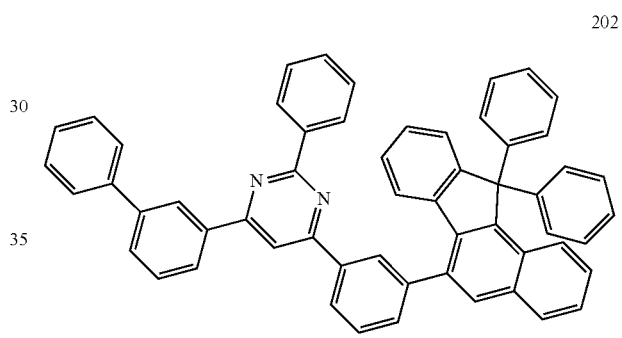
203
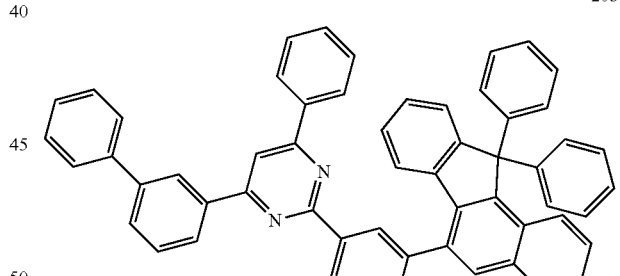
204
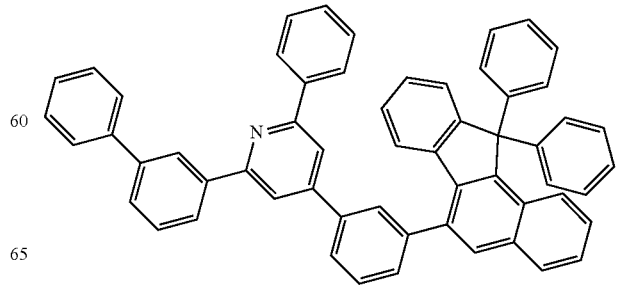

205
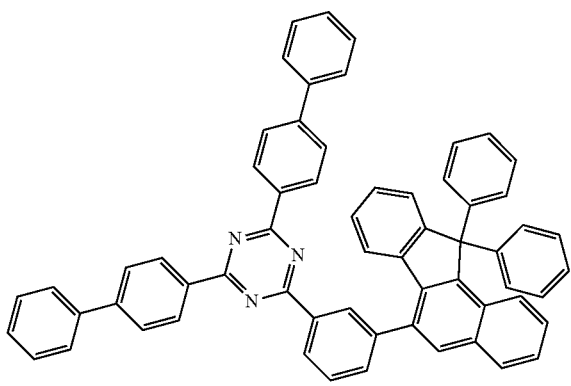
206
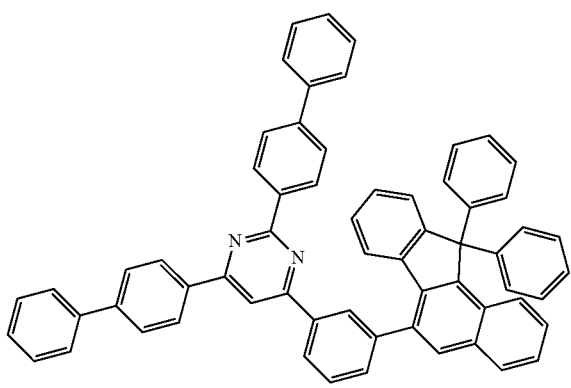
207
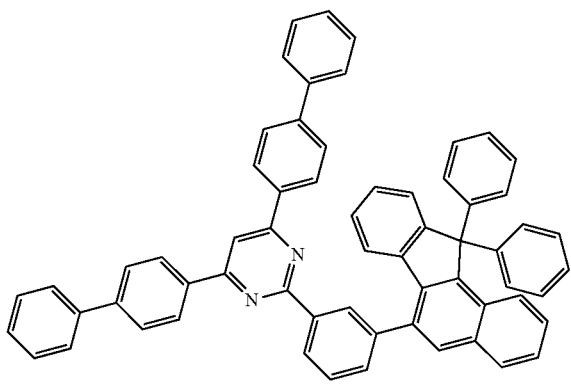
208
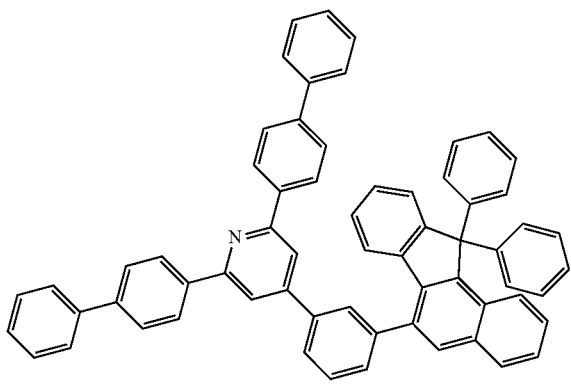
209

210
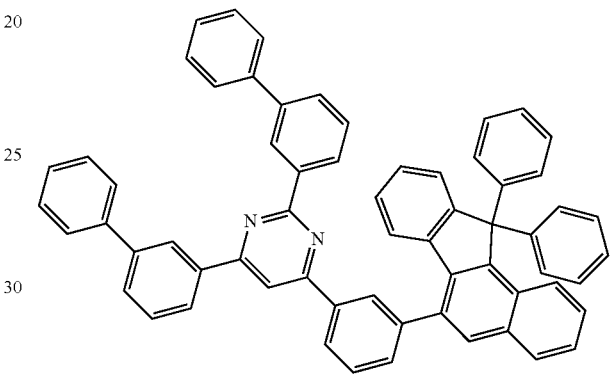
211
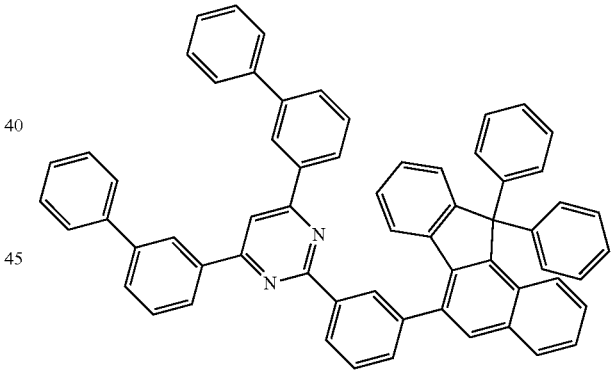
212

-continued
213
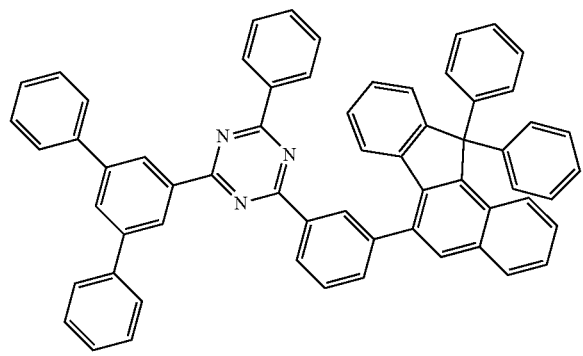
214
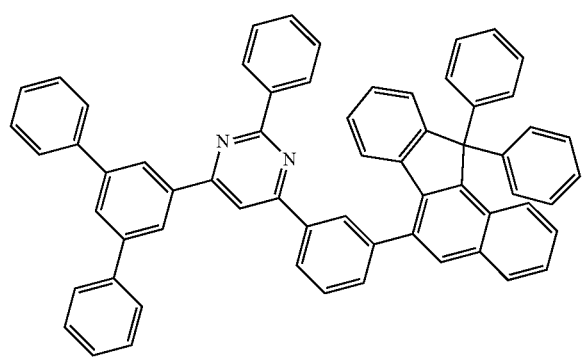
215
216
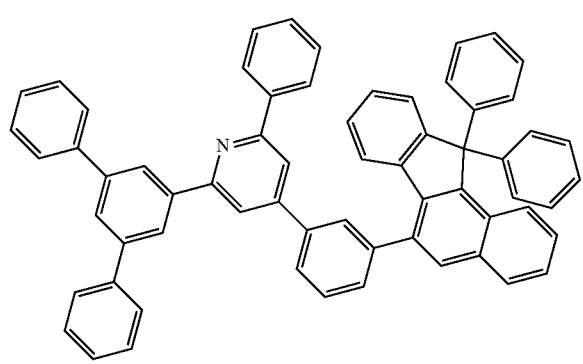
-continued
217
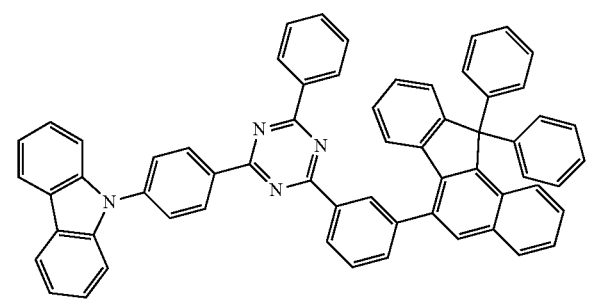
218
219
220
221
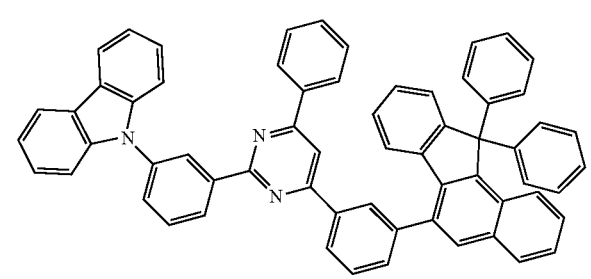

222
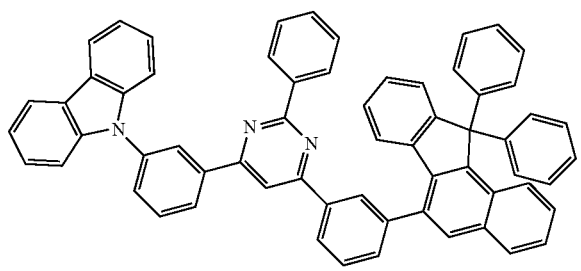
223
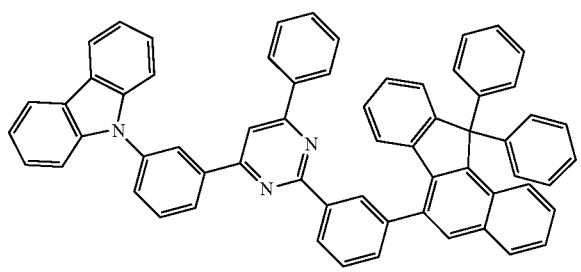
224
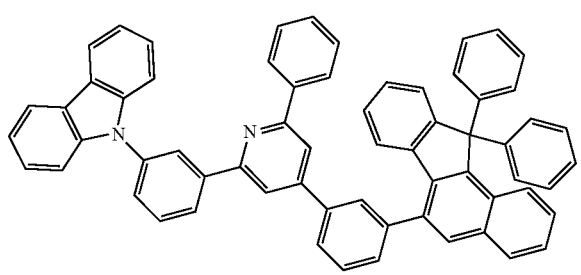
225
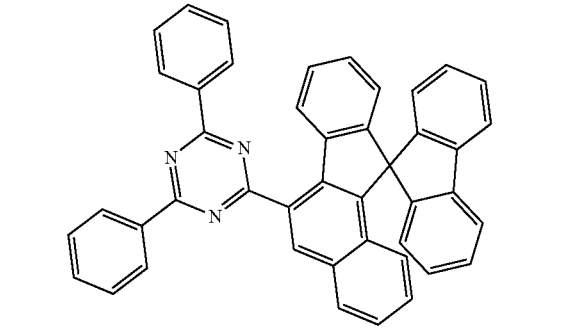
226
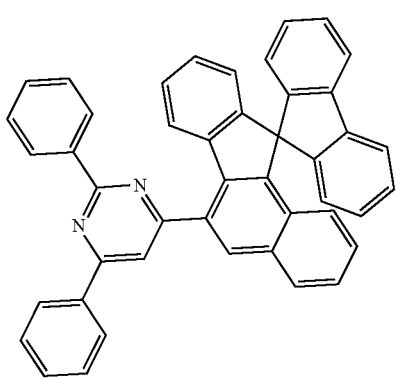
227
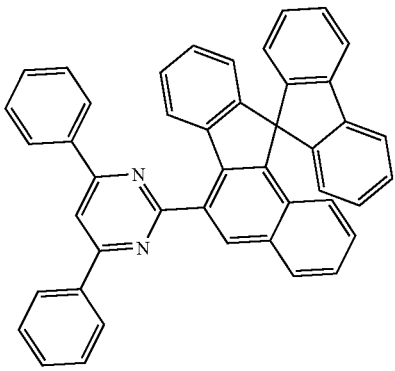
228
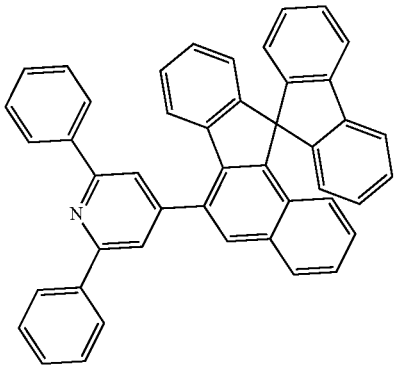
229
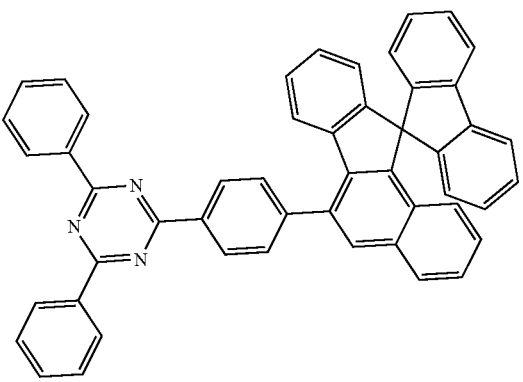
230
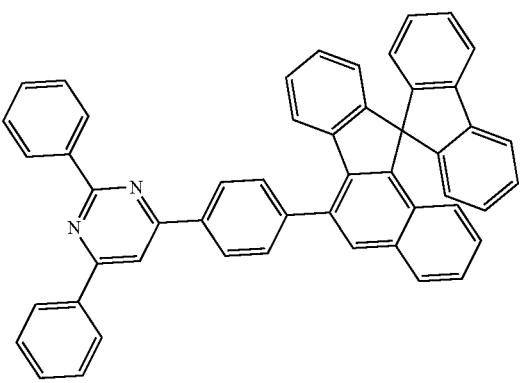

231
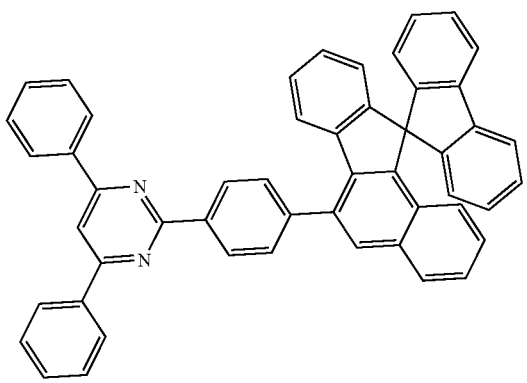
232
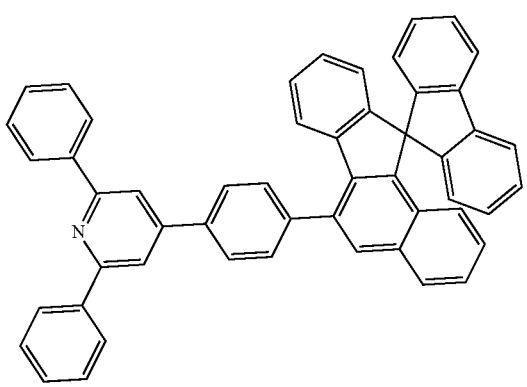
233
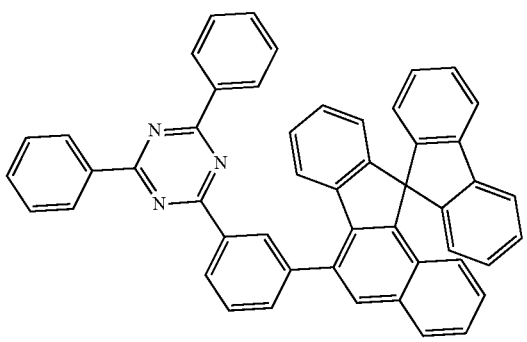
234
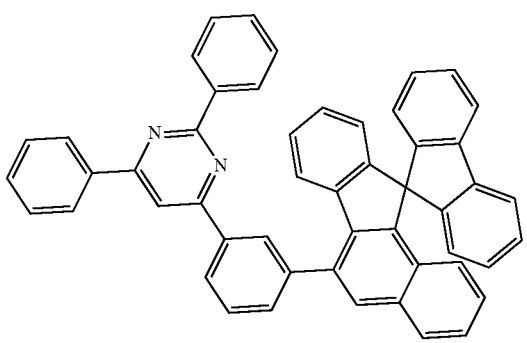
235
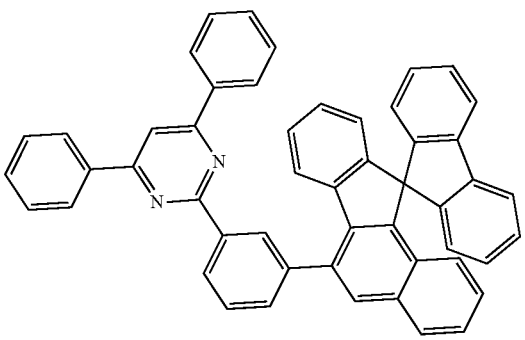
236
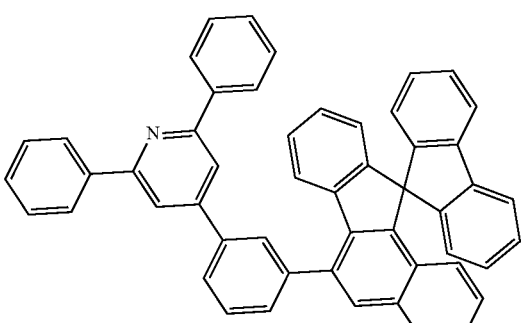
237
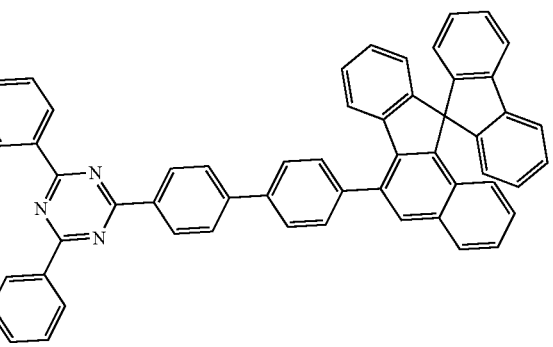
238
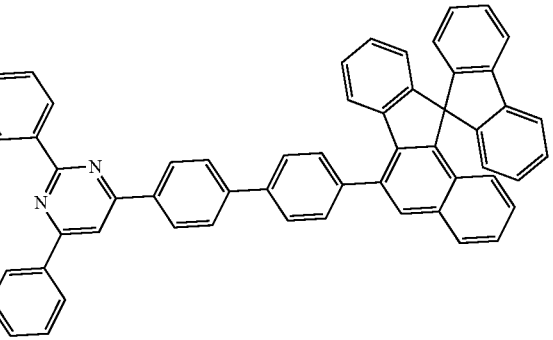

239
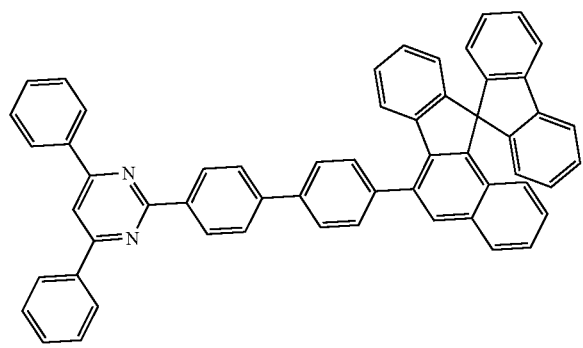
240
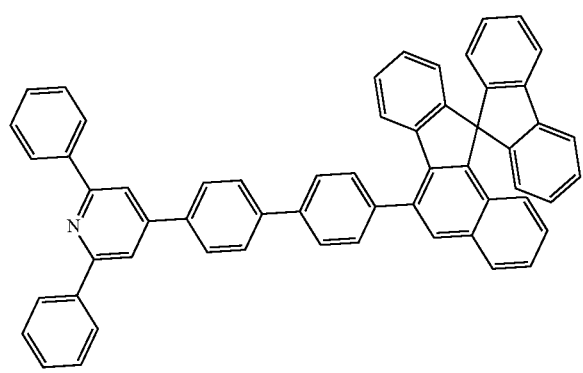
241
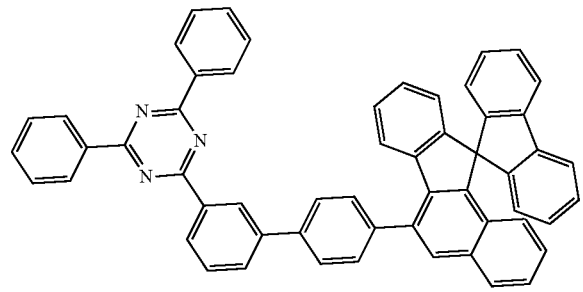
242
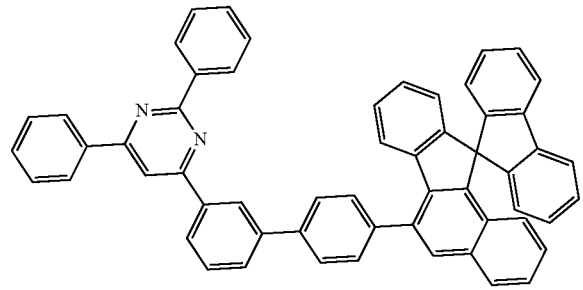
243
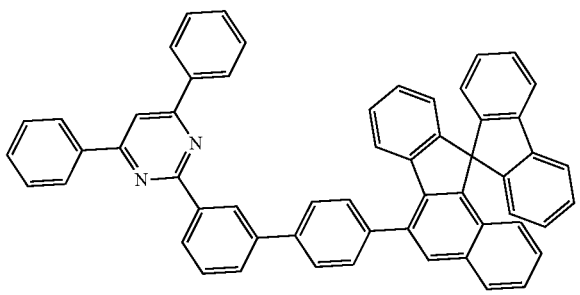
244
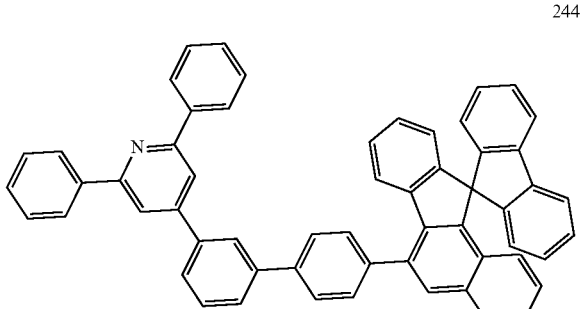
245
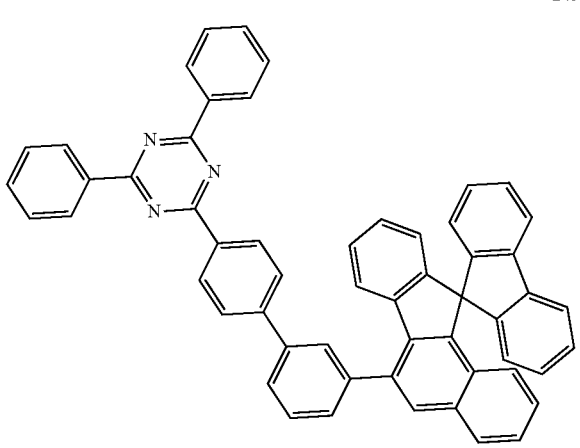
246
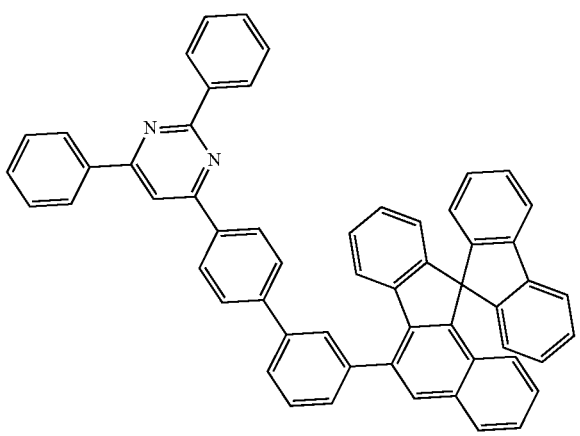

247
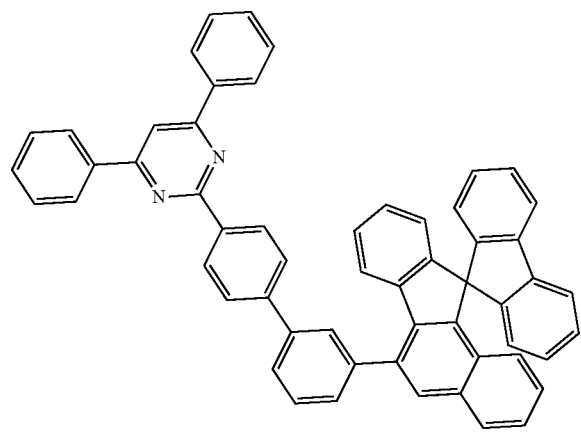
248
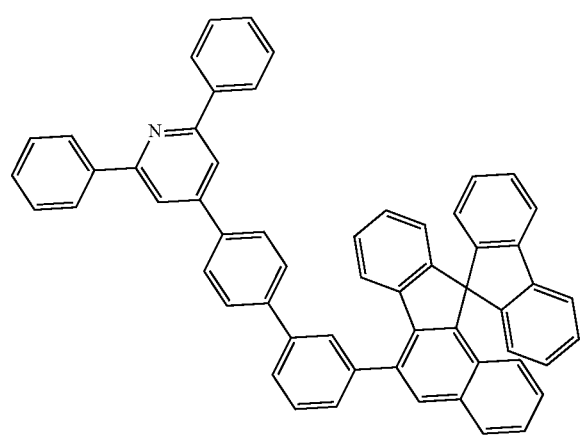
249
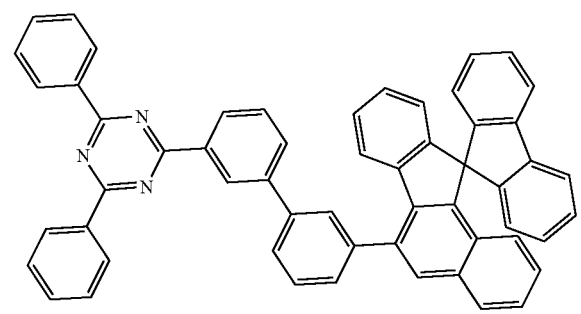
250
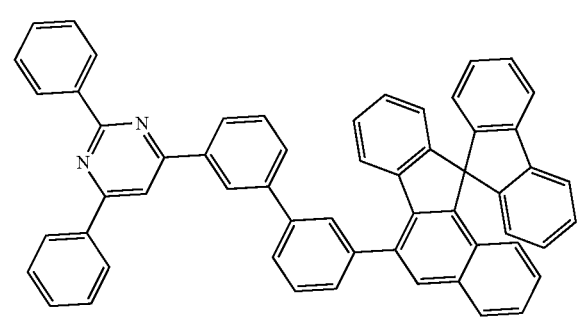
251
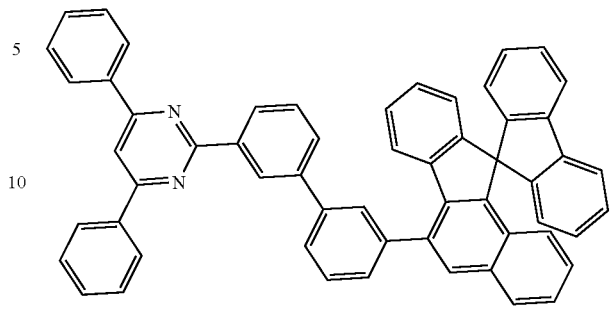
252
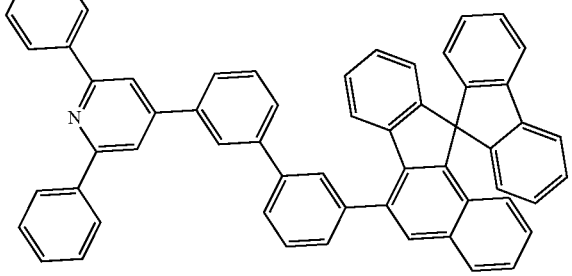
253
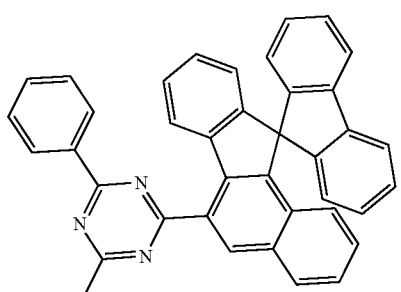
254
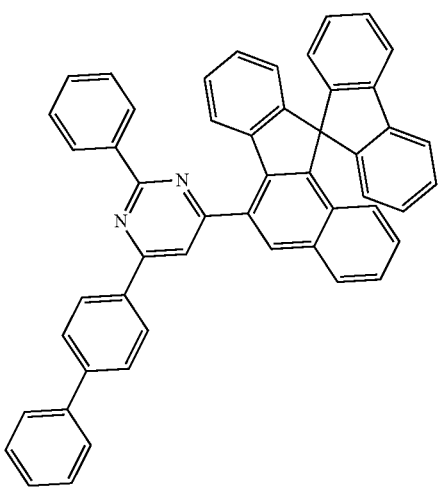

255
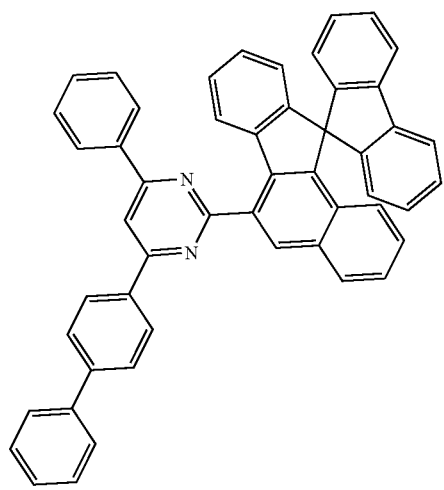
256
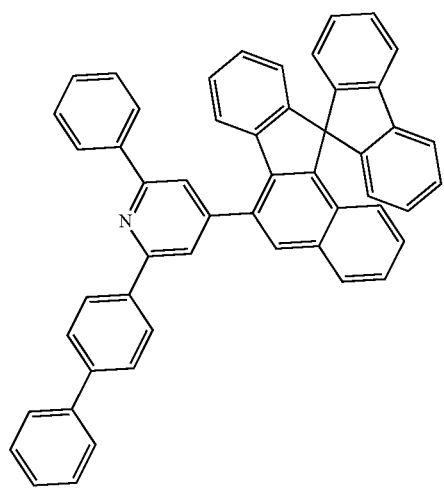
257
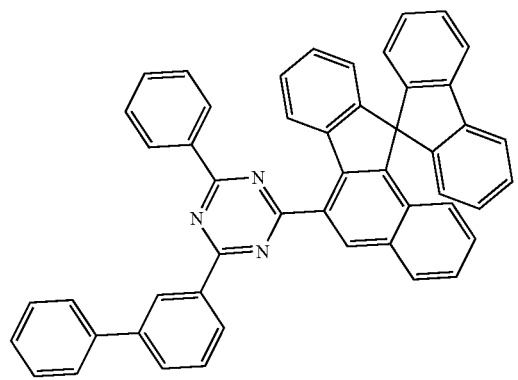
258
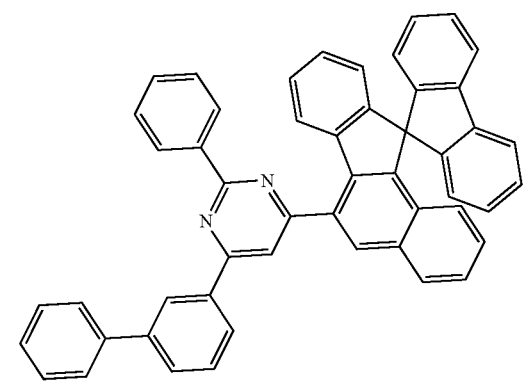
259
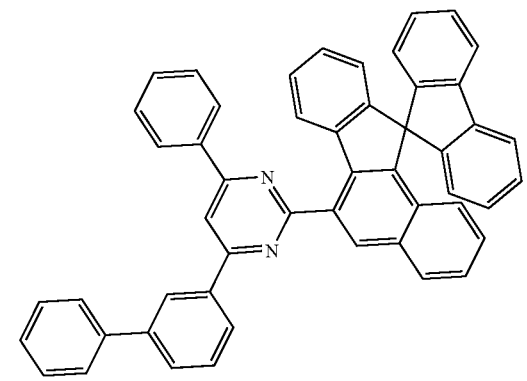
260
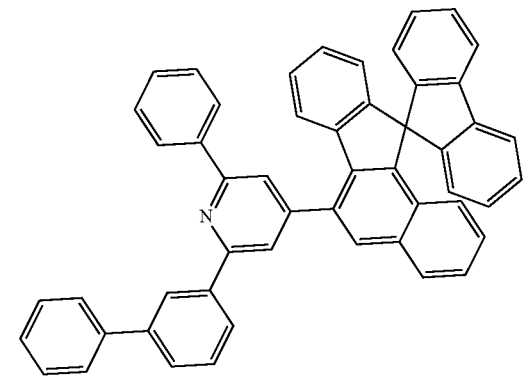

261
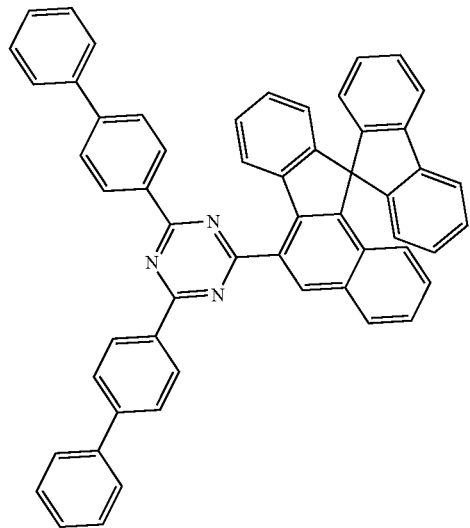
262
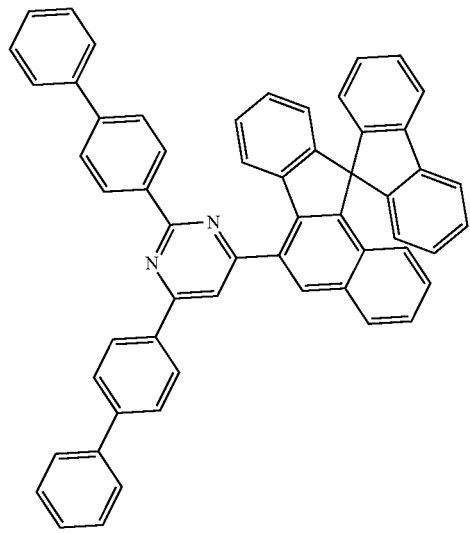
263
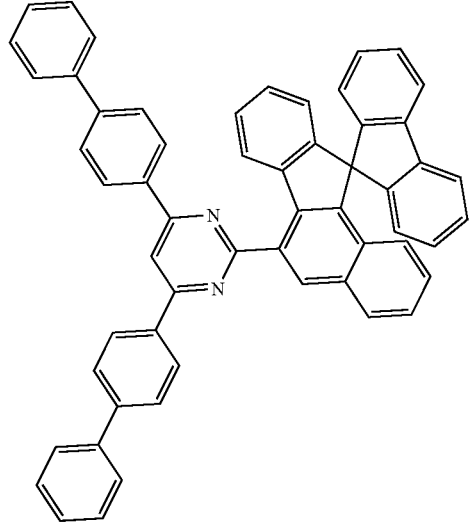
264
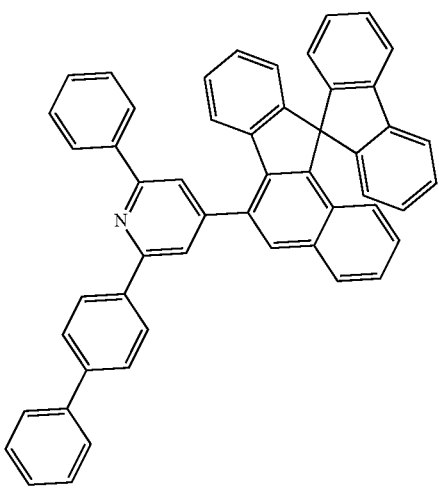
265
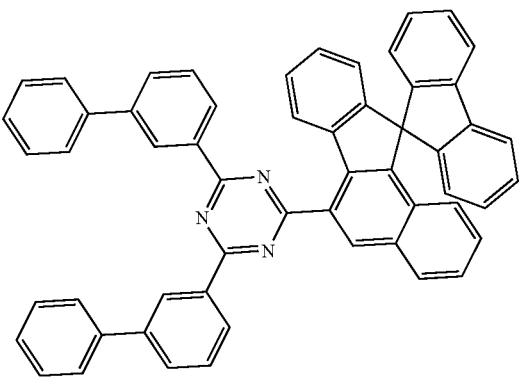
266
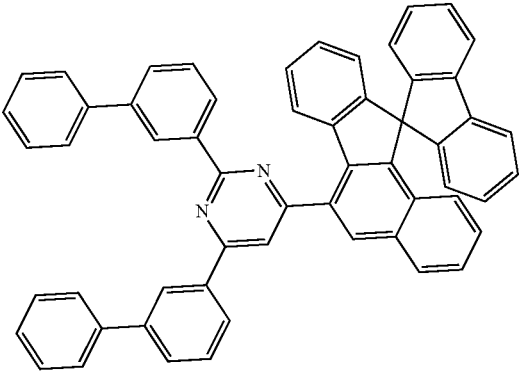

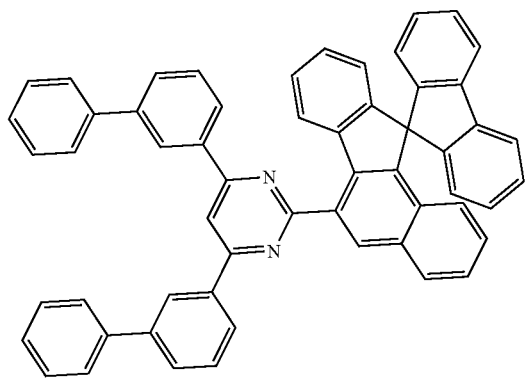
267
268
269
270
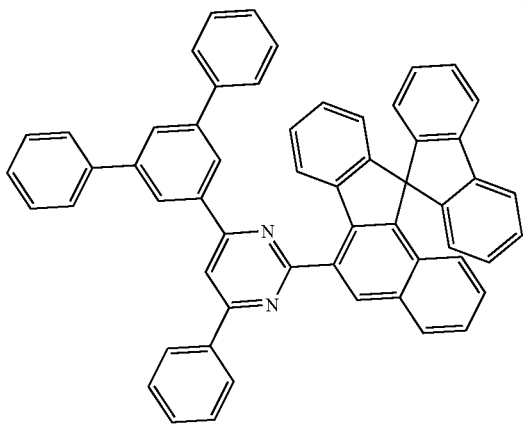
271
272
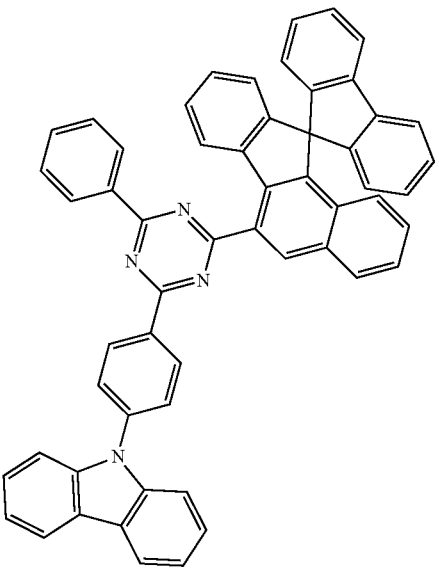
273

274
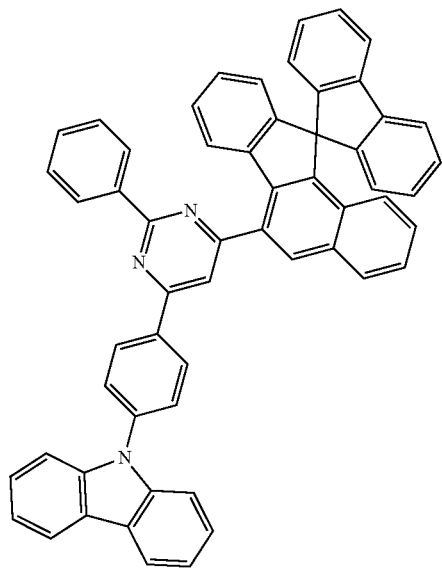
275
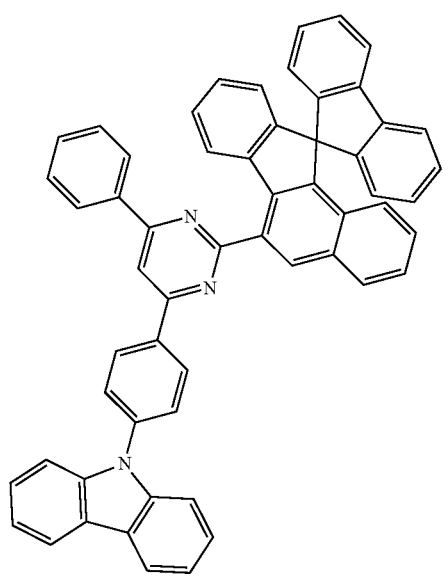
276
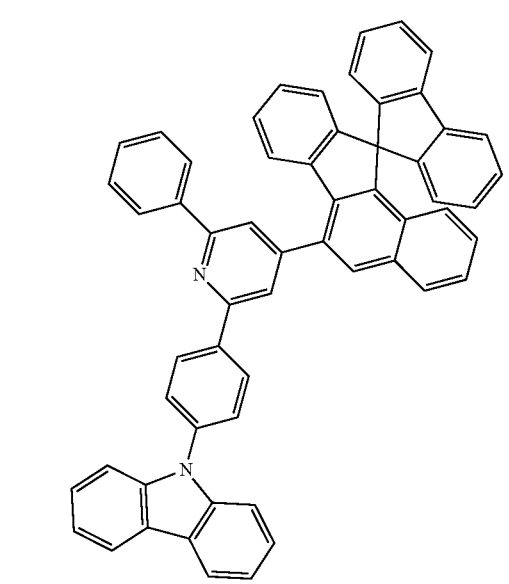
277
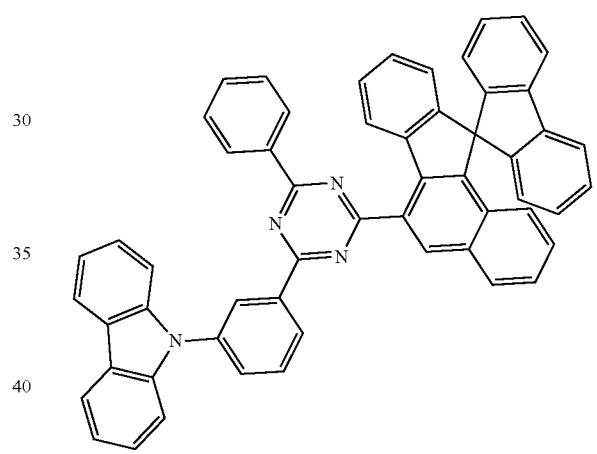
278
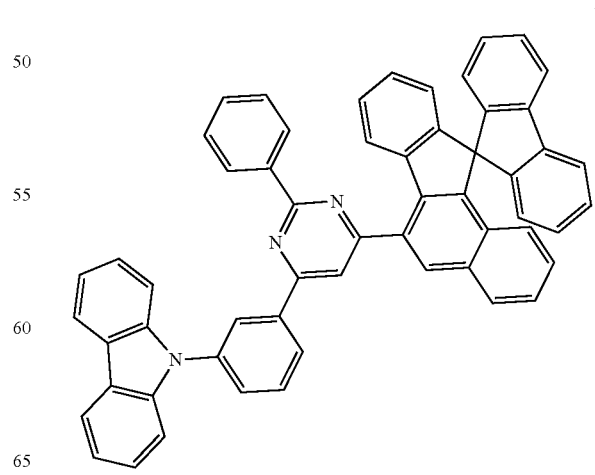

| 279 | 282 |
|---|---|
| 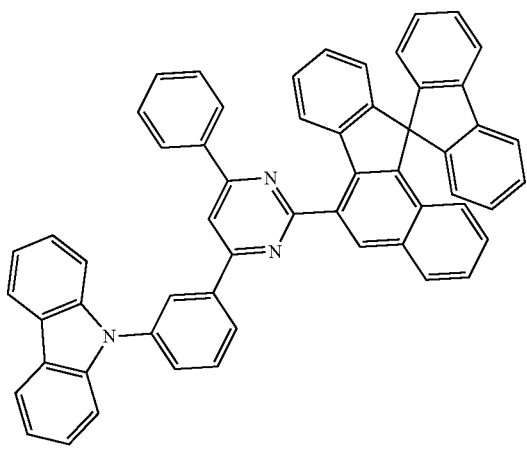 | 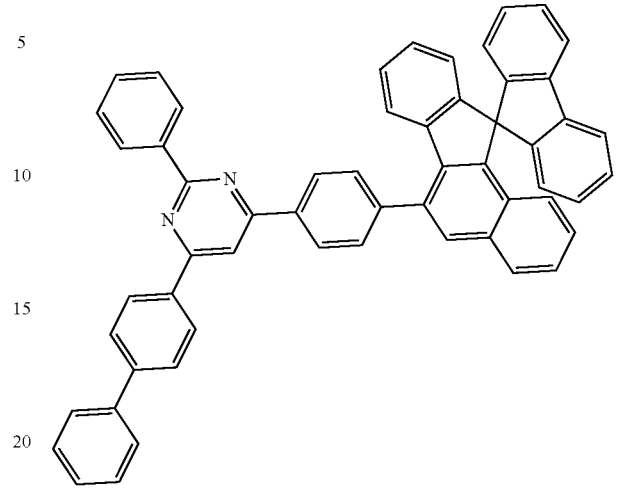 |
| 280 | 283 |
| 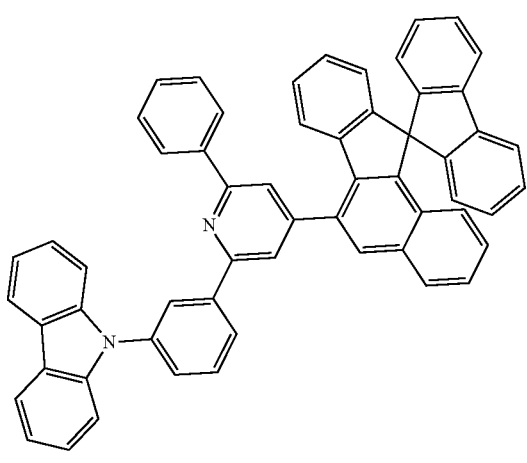 | 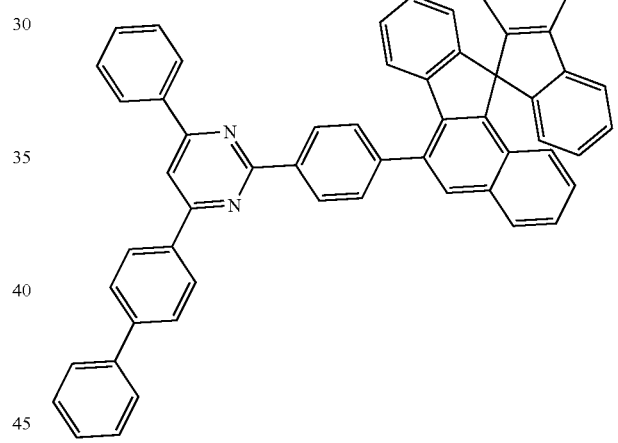 |
| 281 | 284 |
| 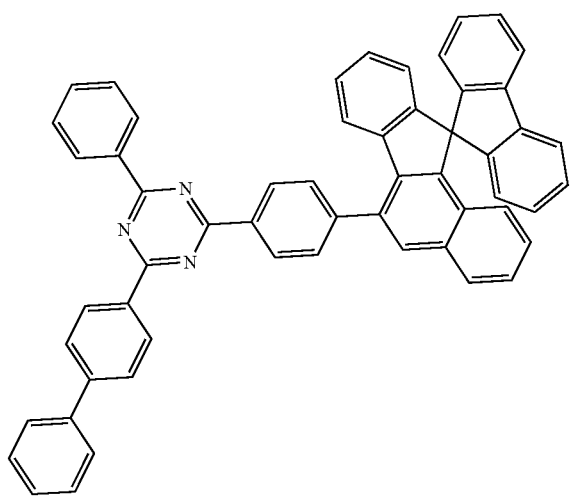 | 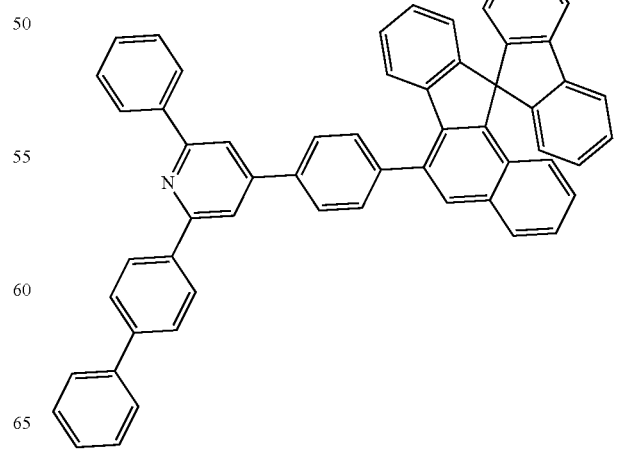 |

285
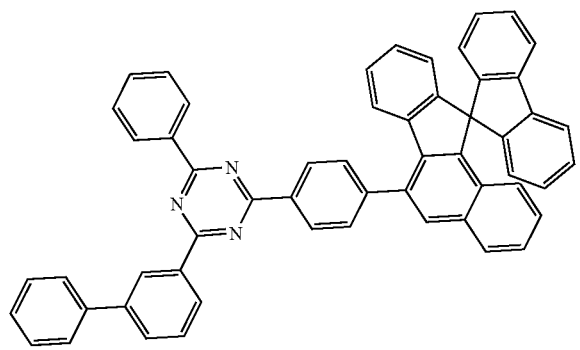
286
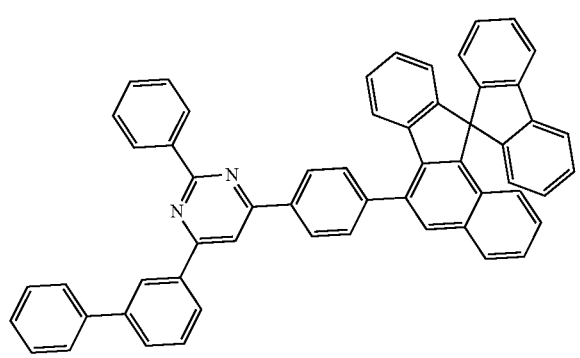
287
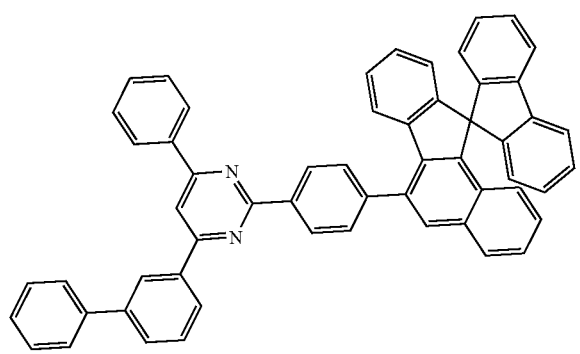
288
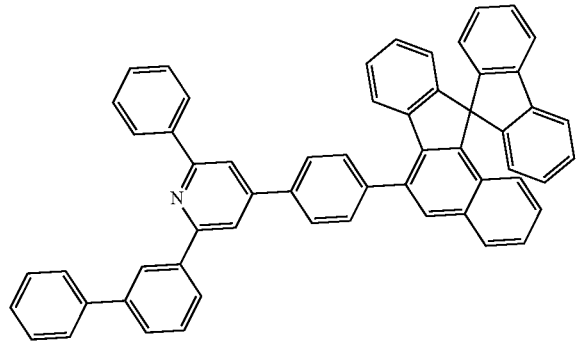
289
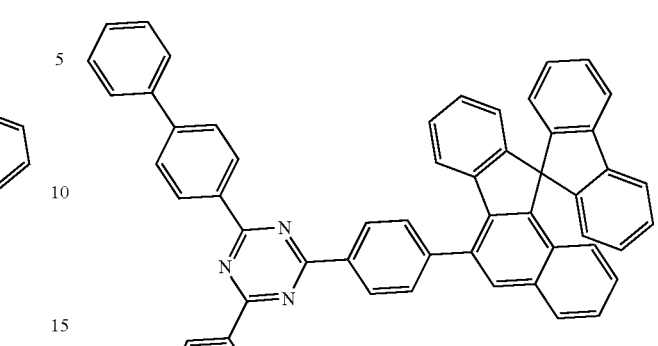
290
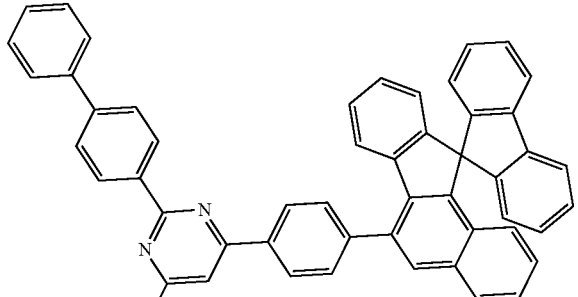
291
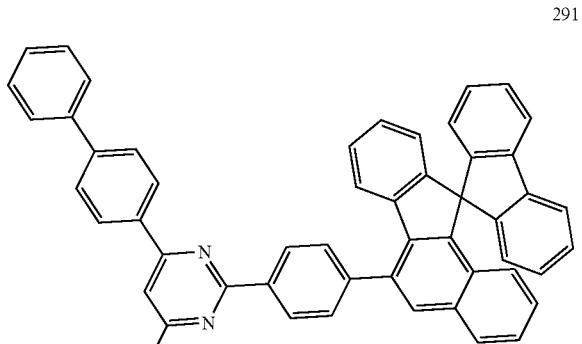

292
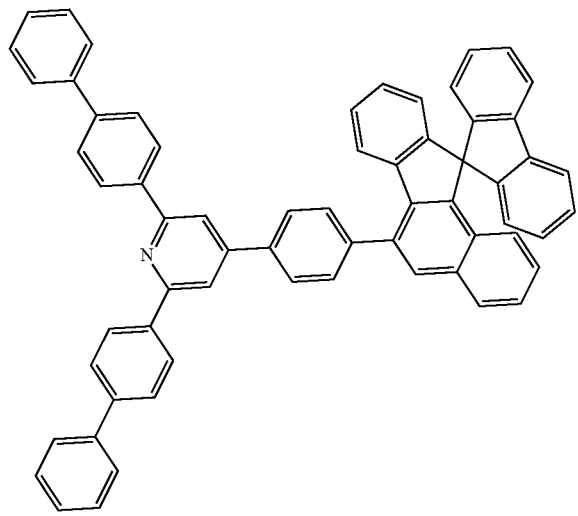
296
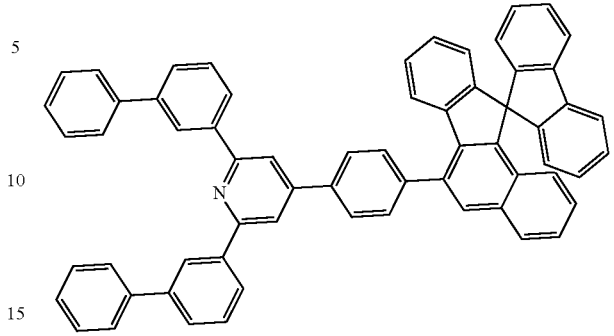
293
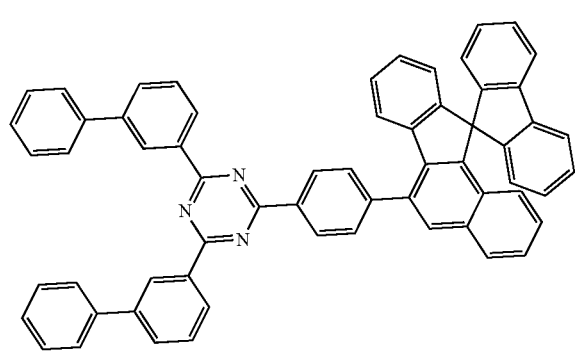
297
294
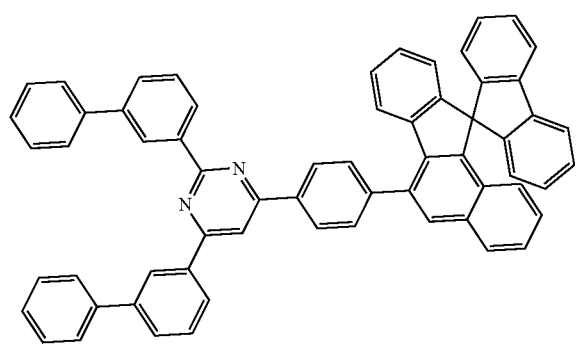
295
298
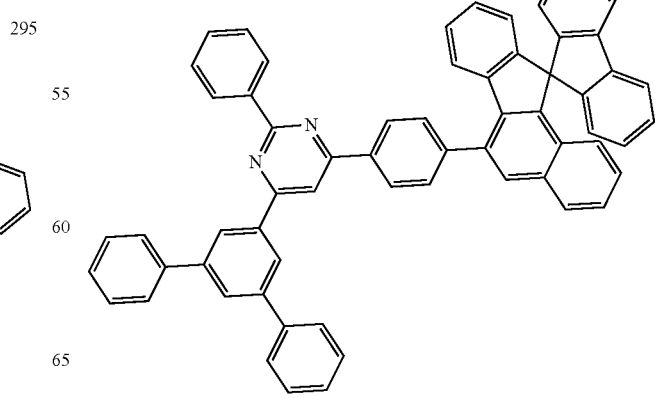

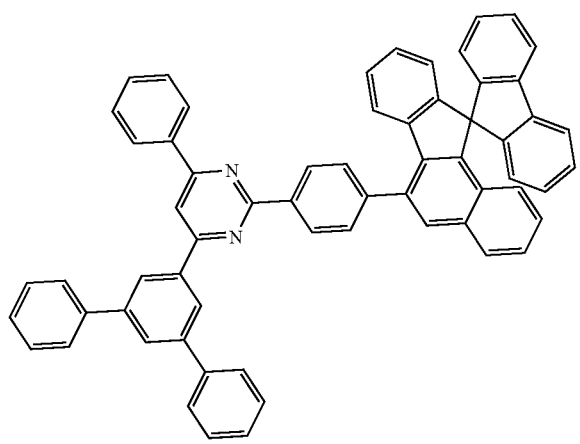
299
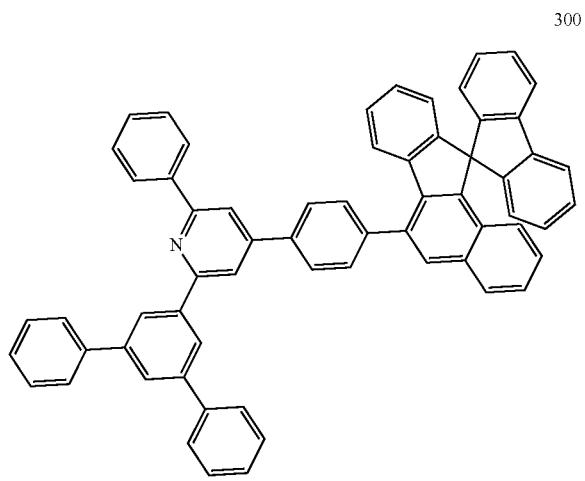
300
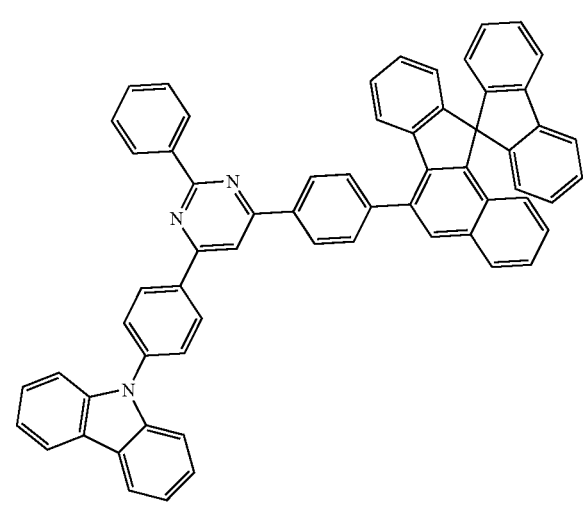
302
303
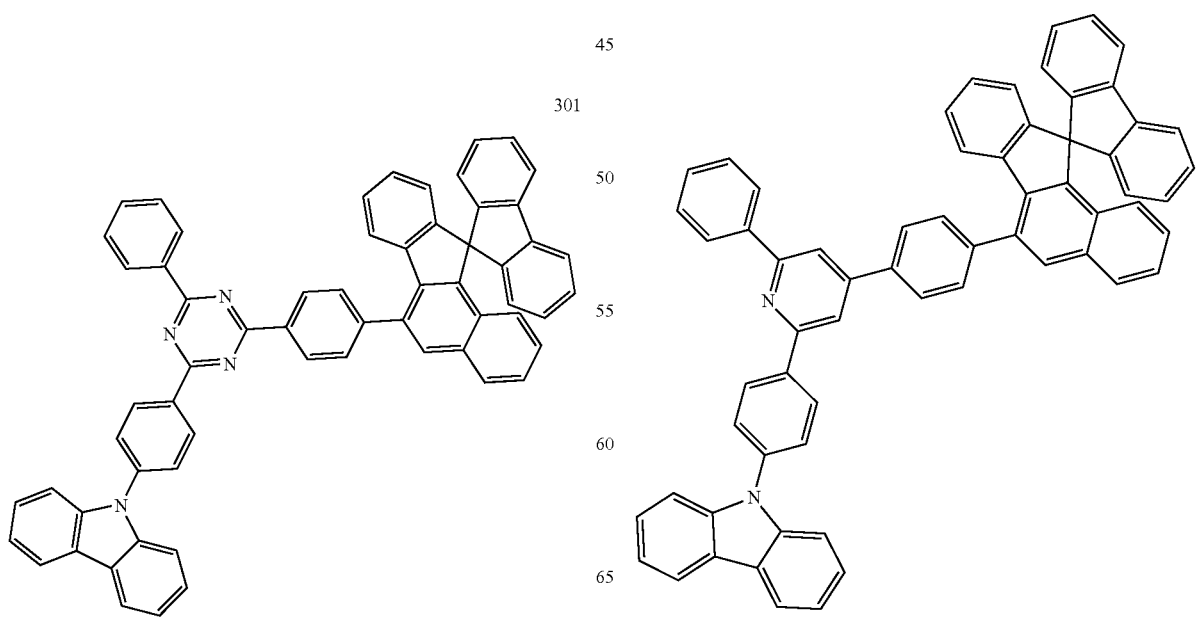
301
304

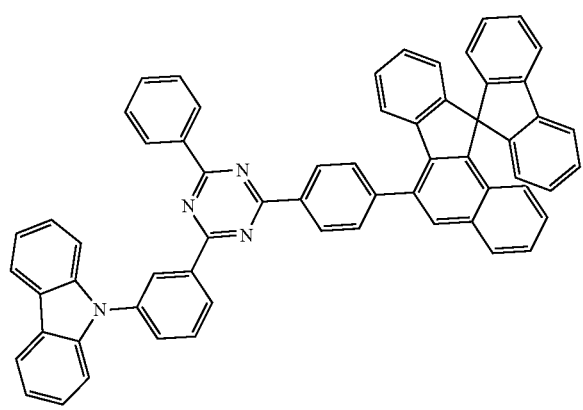
305
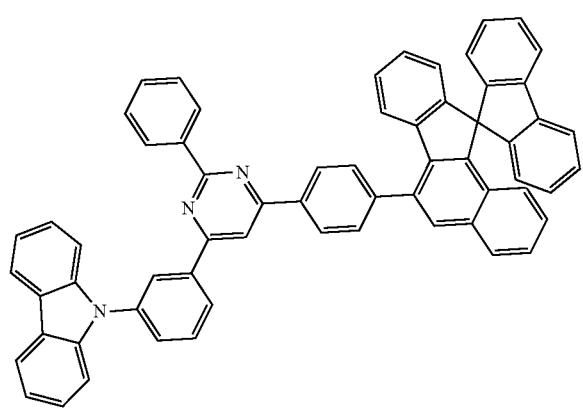
306
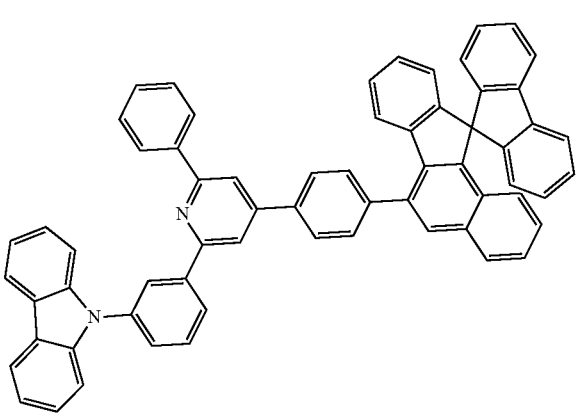
308

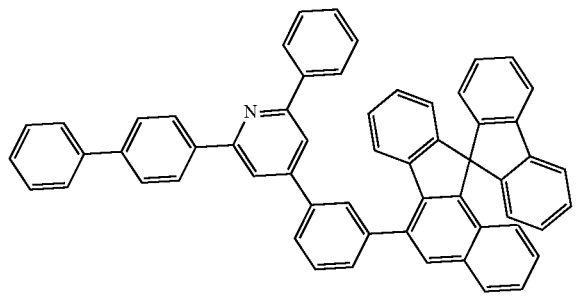
312
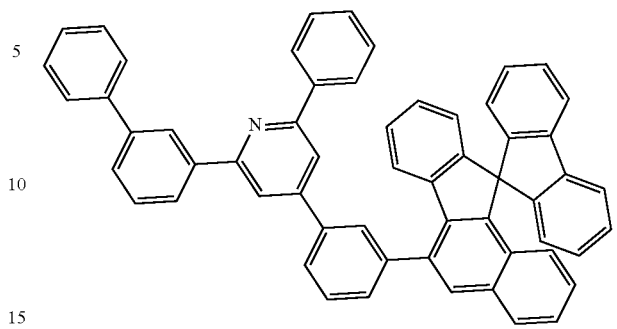
316
317
313
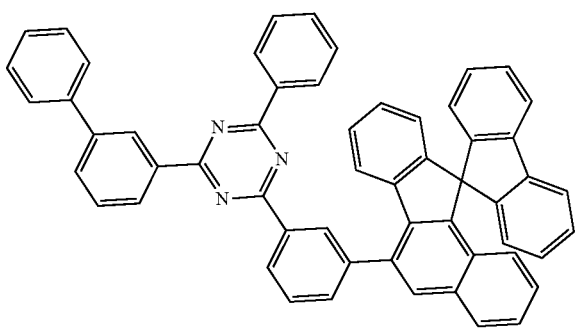
314
318
315
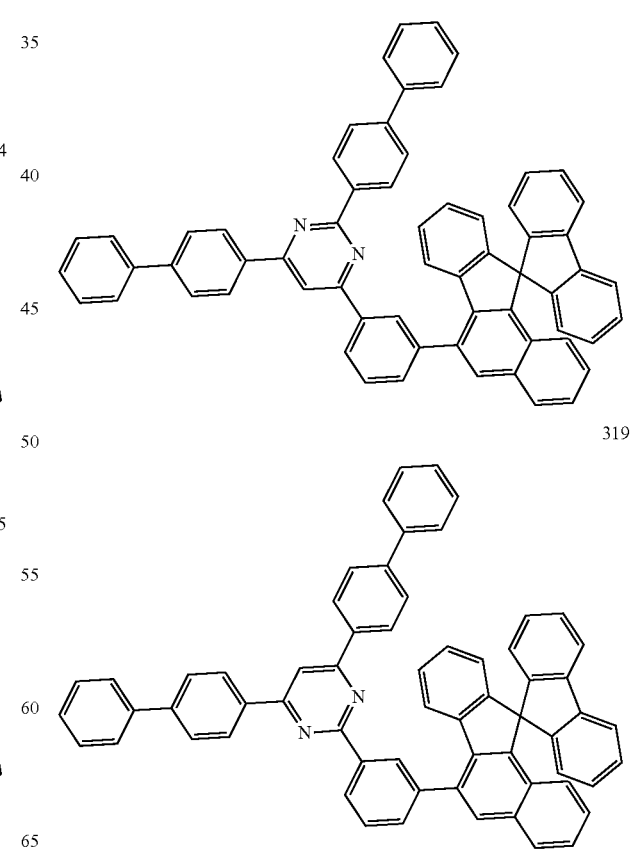
319

320
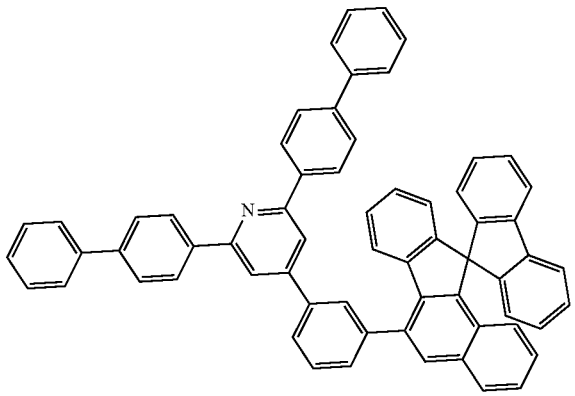
321
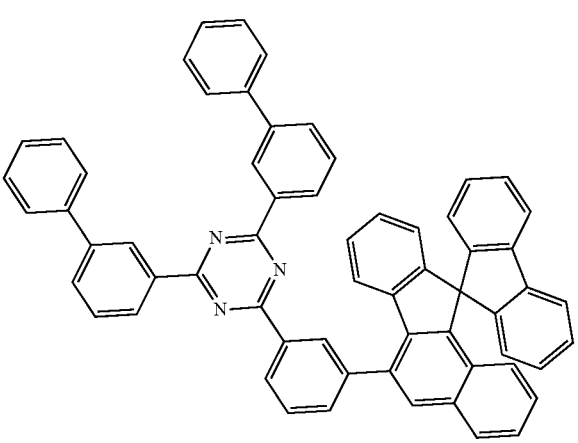
322
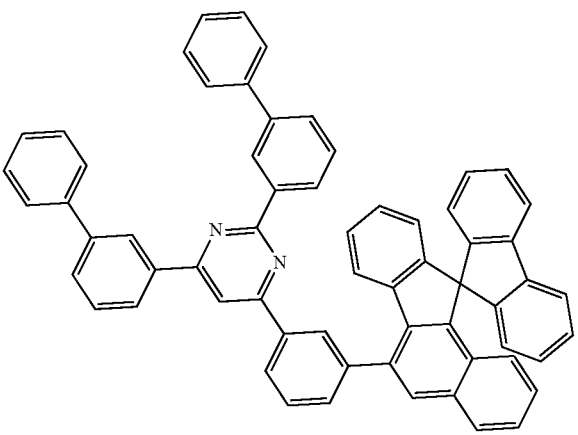
323
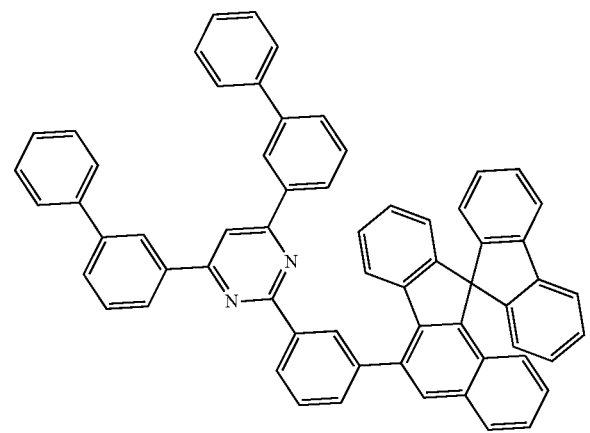
324
325
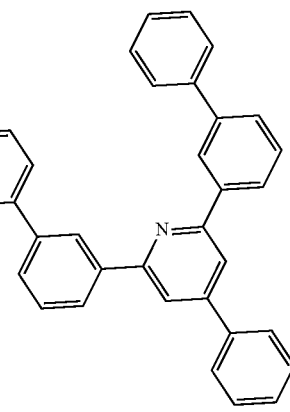
326
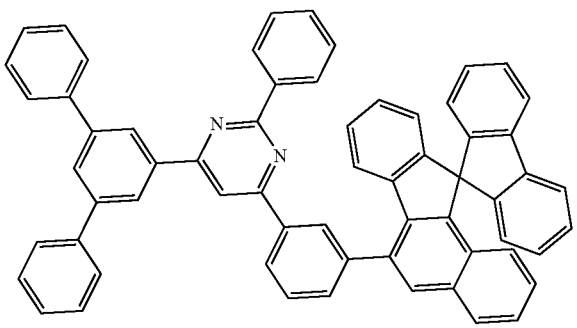

327
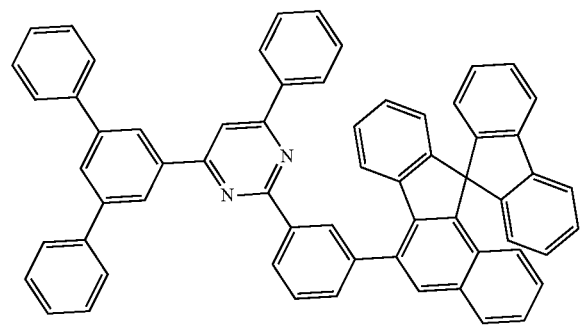
328
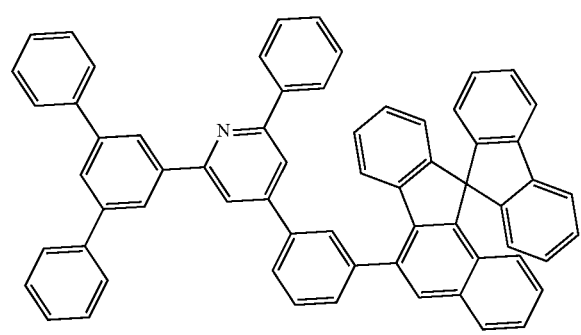
329
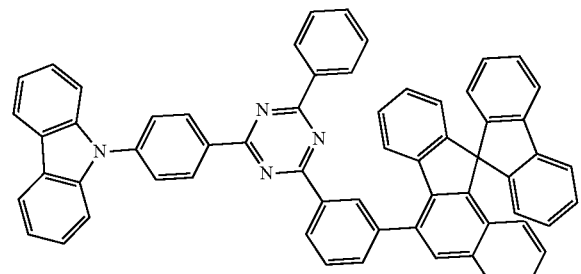
330
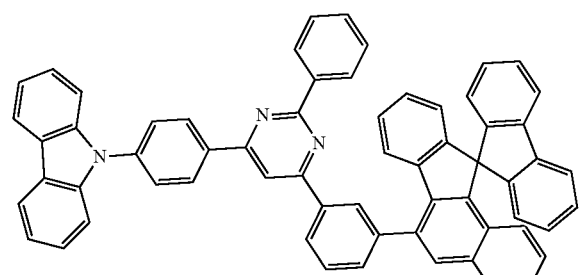
331
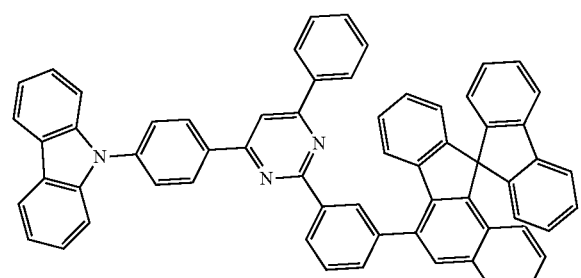
332
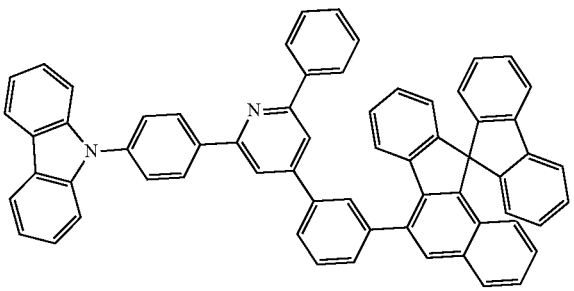
333
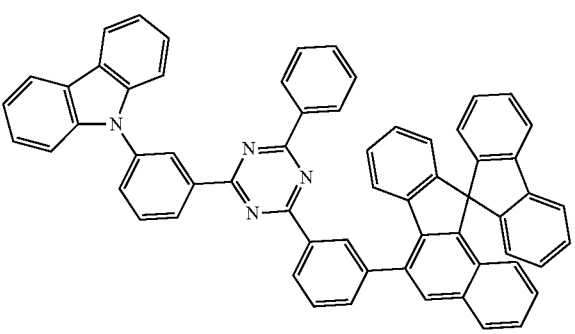
334
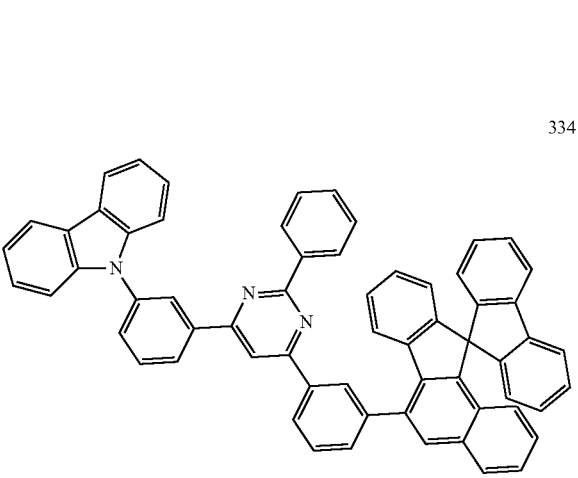
335
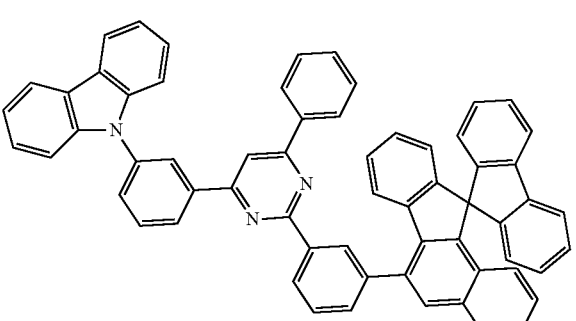

336
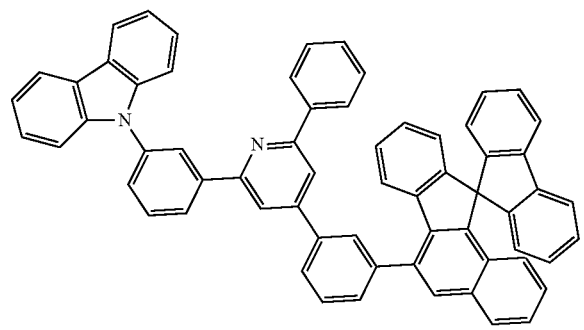
337
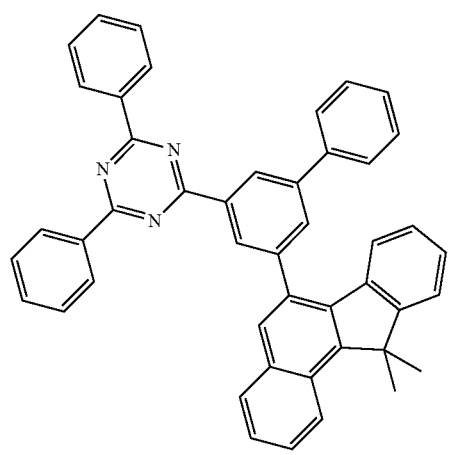
338
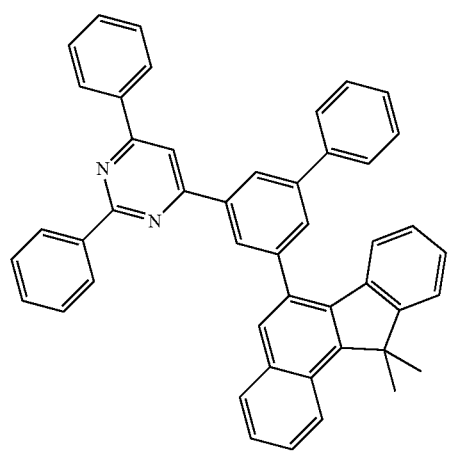
339
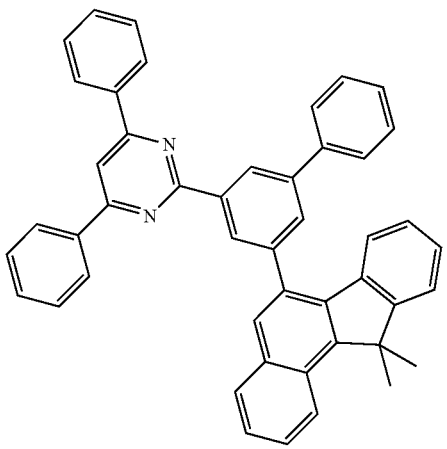
340
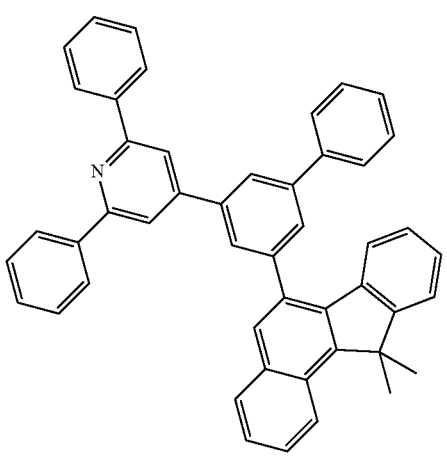
341
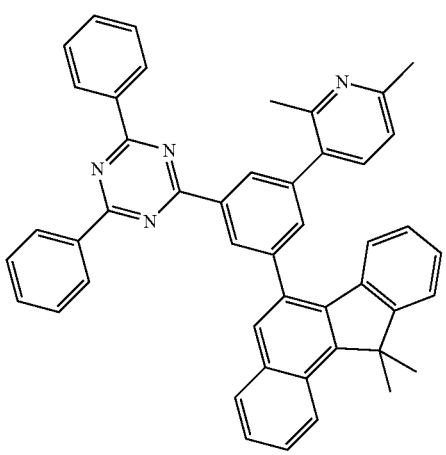

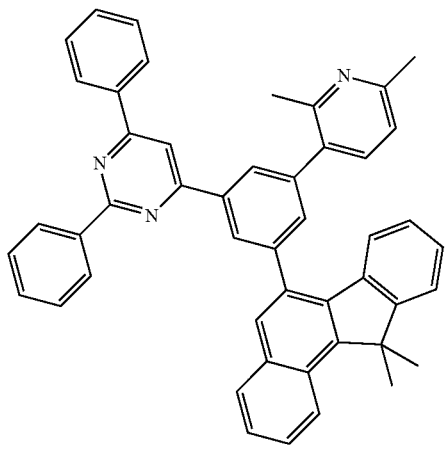# 342
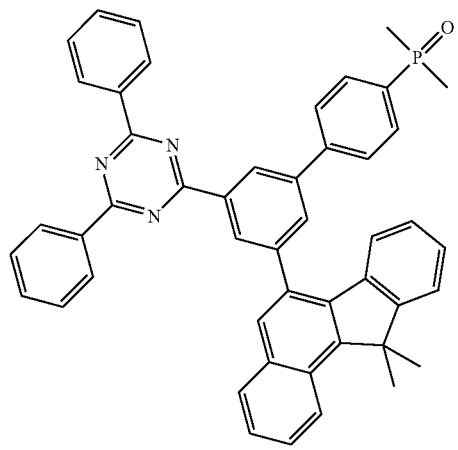# 345
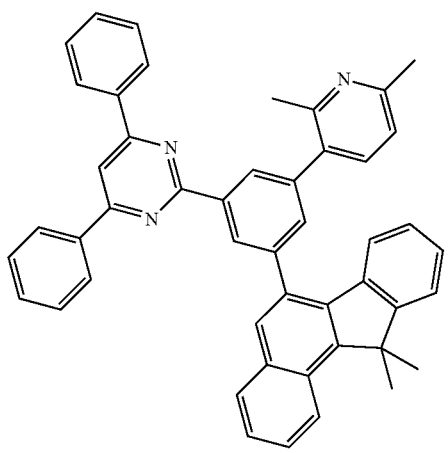# 343
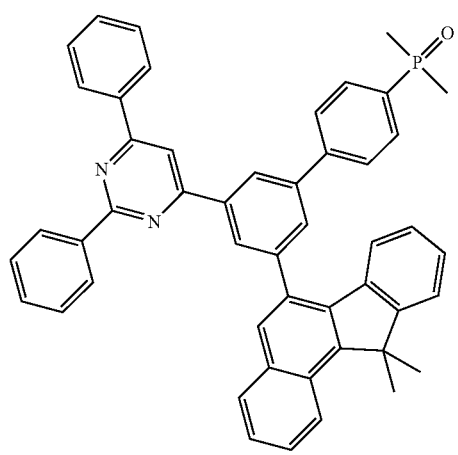# 346
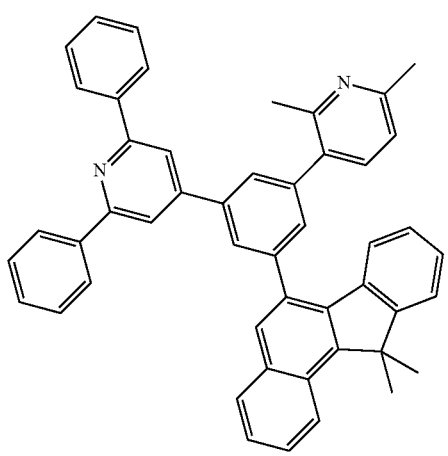# 344
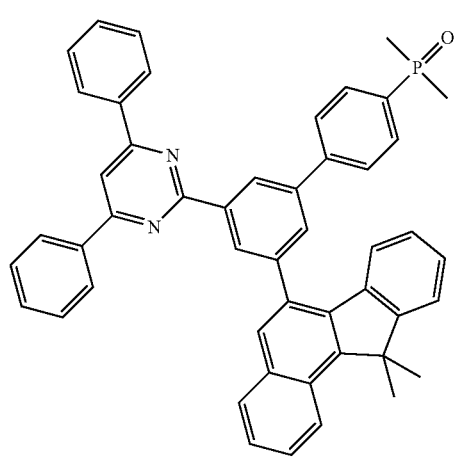# 347

-continued
348
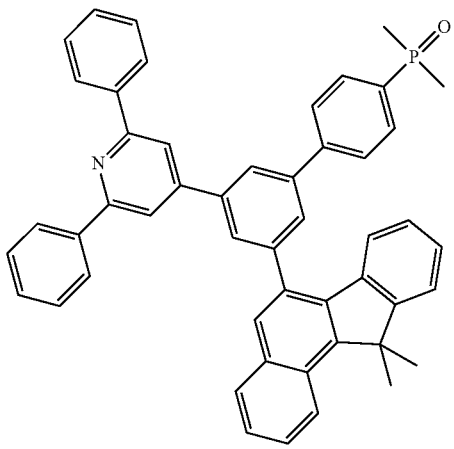
349
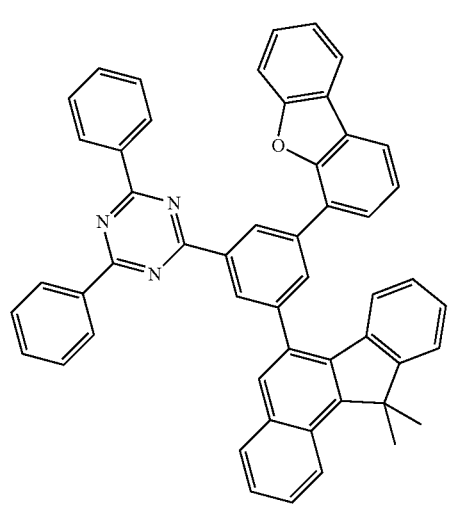
350
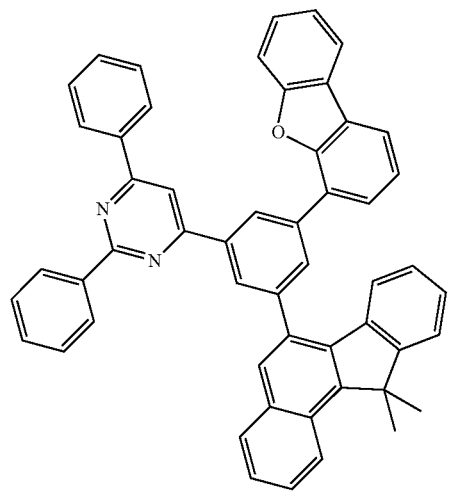
-continued
351
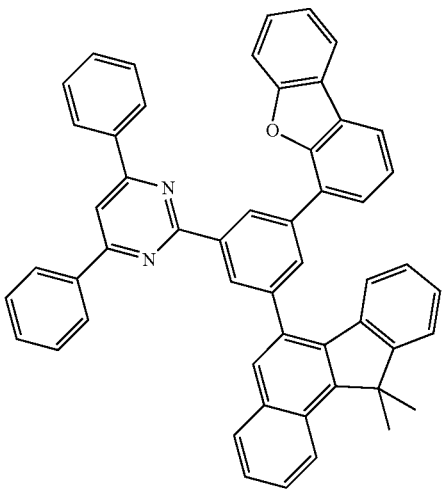
352
353
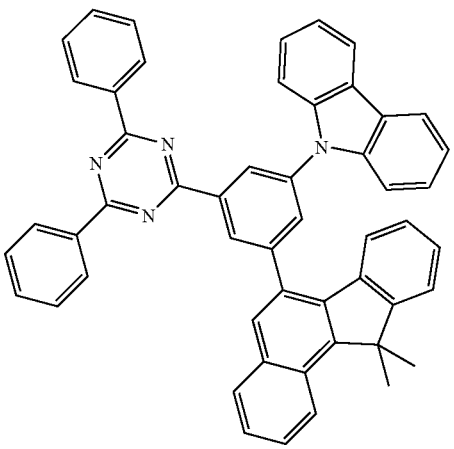

-continued
354
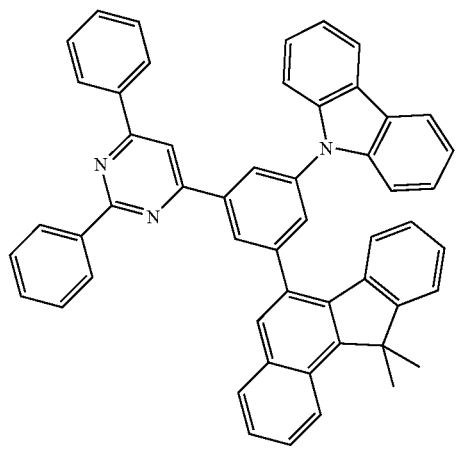
355
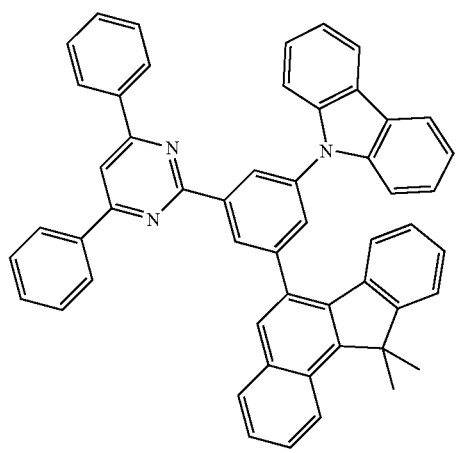
356
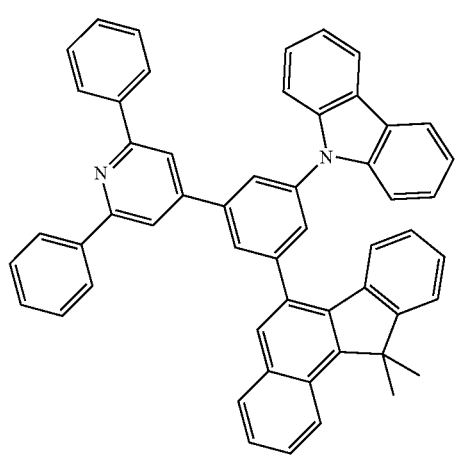
357
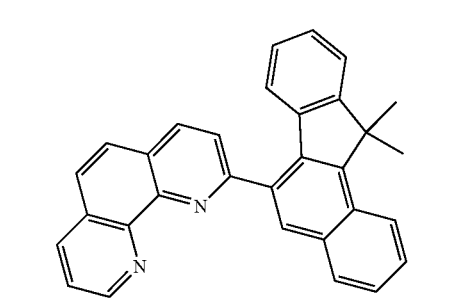
-continued
358
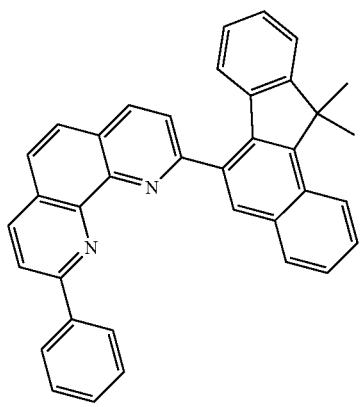
359
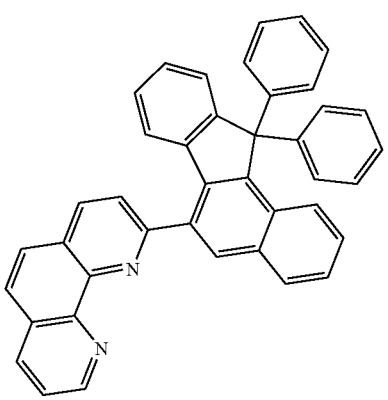
360
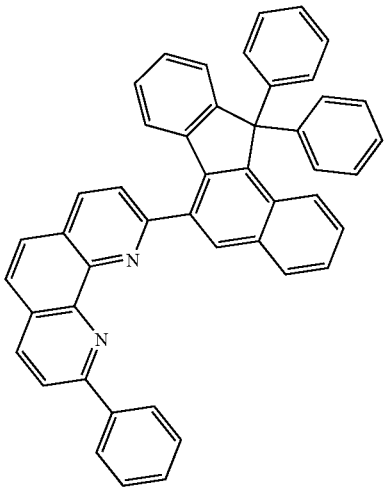

-continued
361
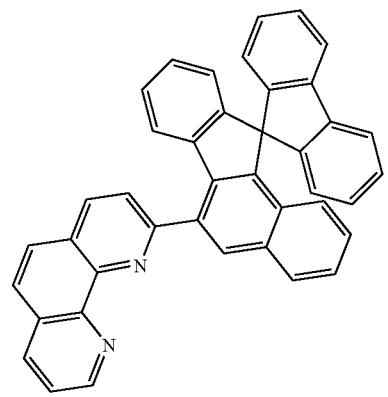
362
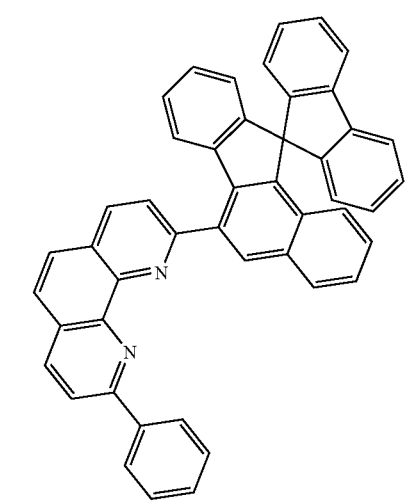
363
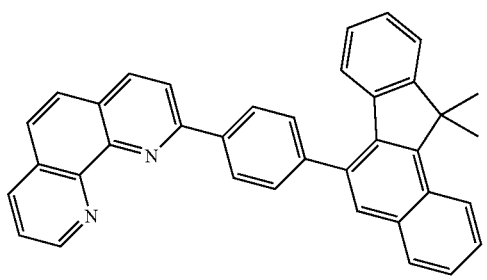
364
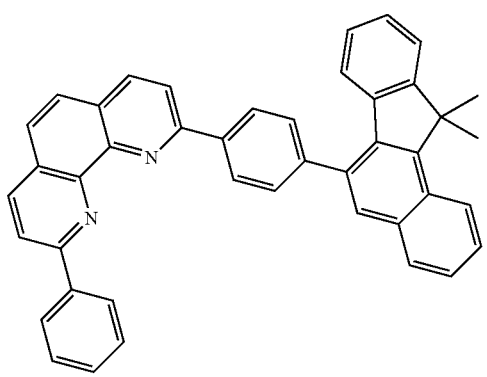
-continued
365
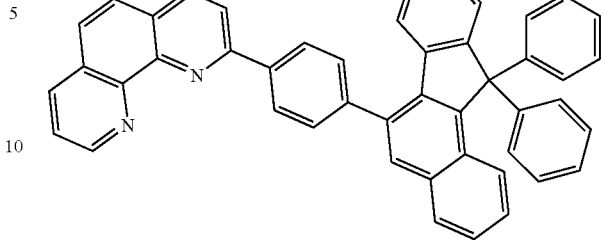
366
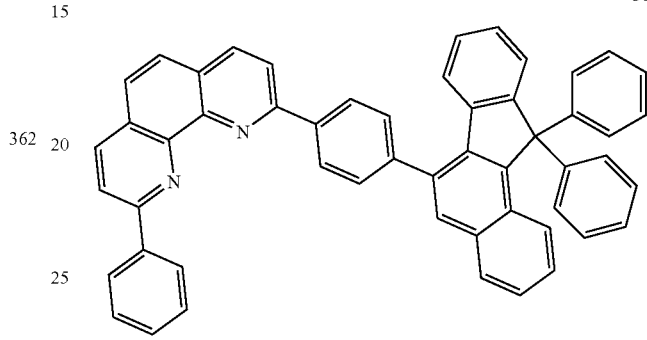
367
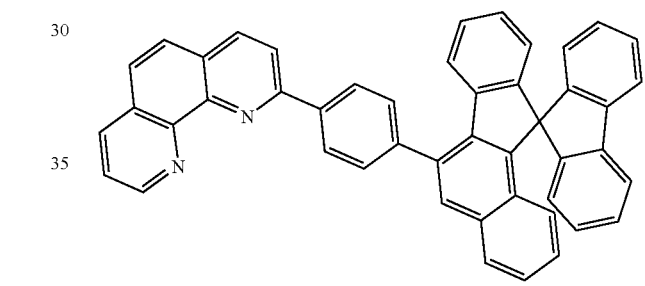
368
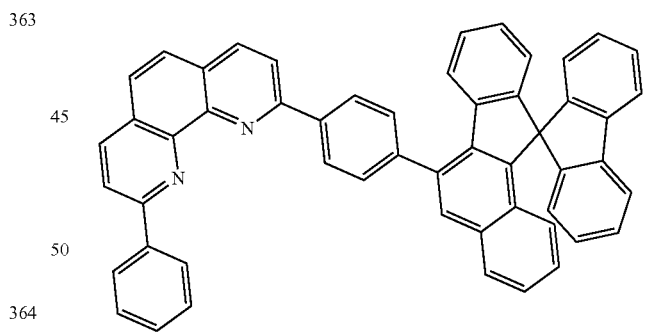
369
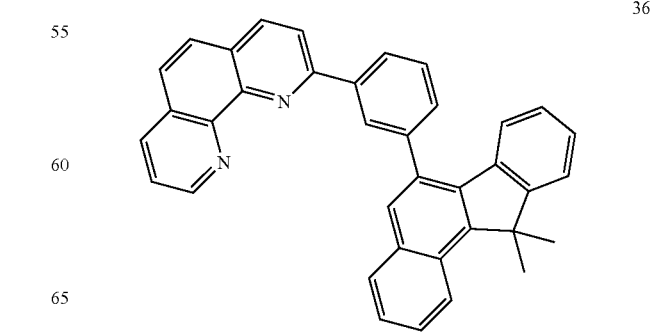

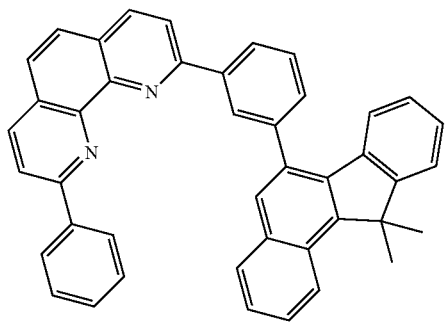
370
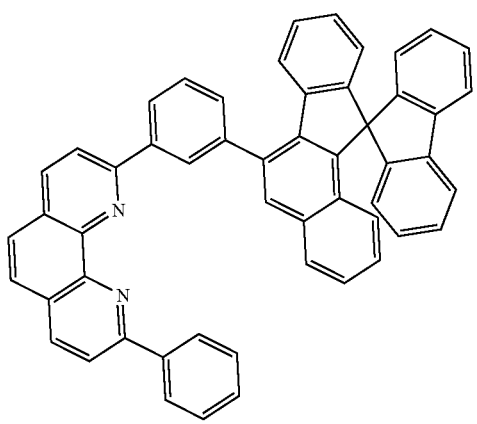
374
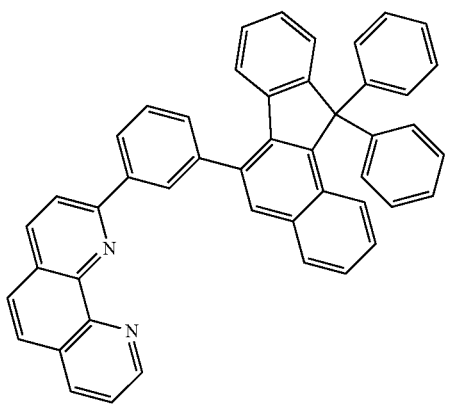
371
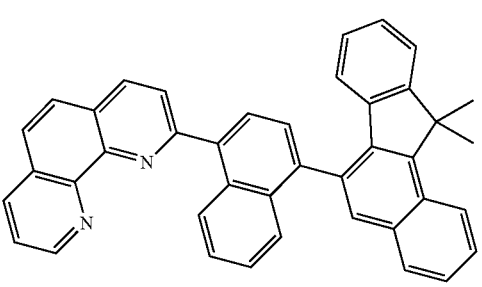
375
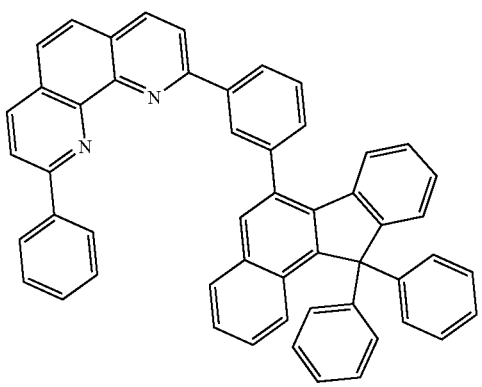
372
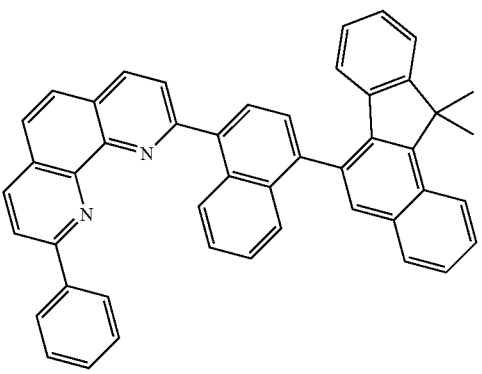
376
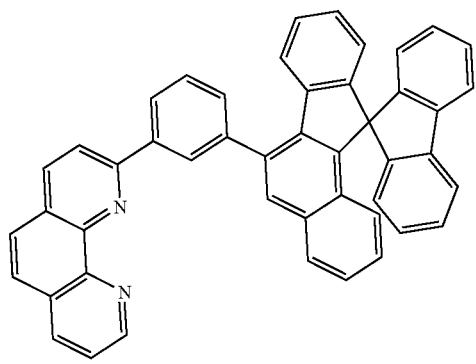
373
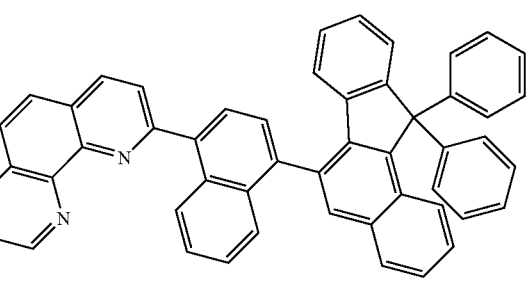
377

-continued
378
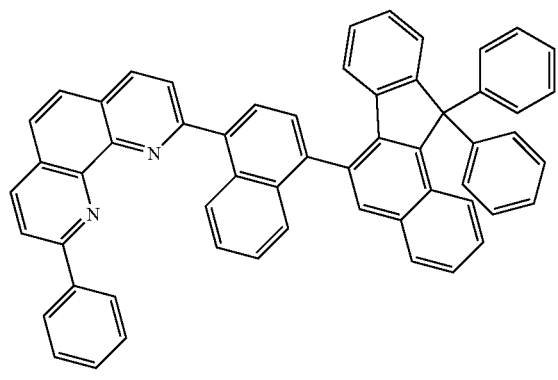
379
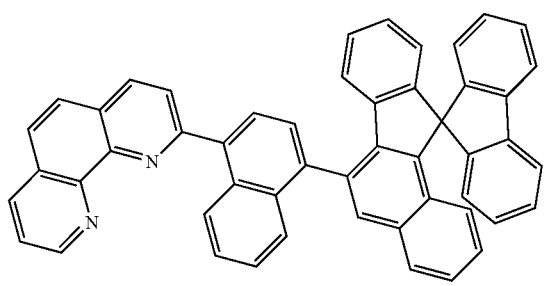
380
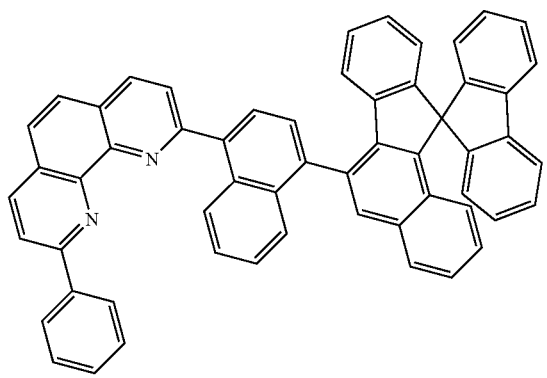
381
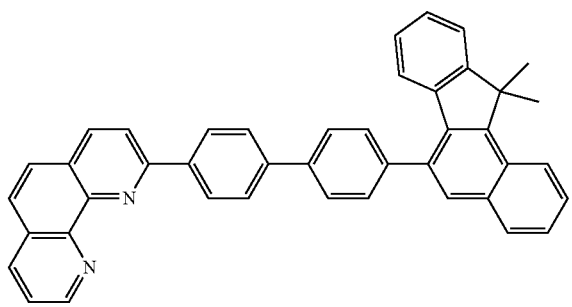
-continued
382
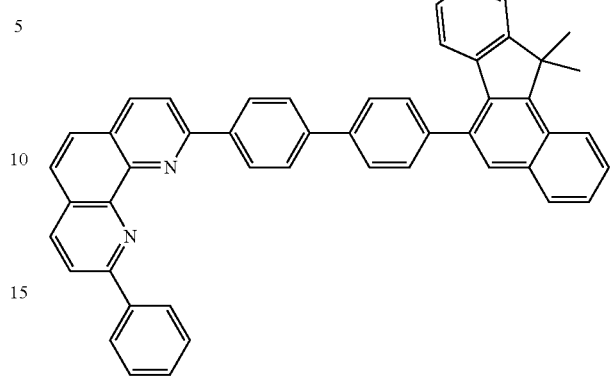
383
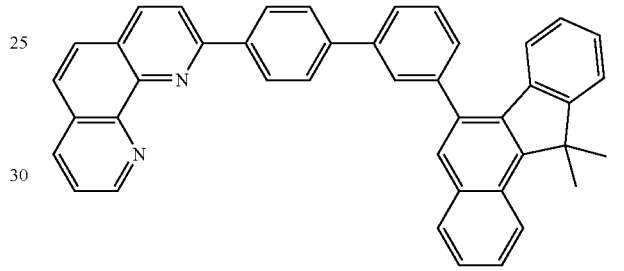
384
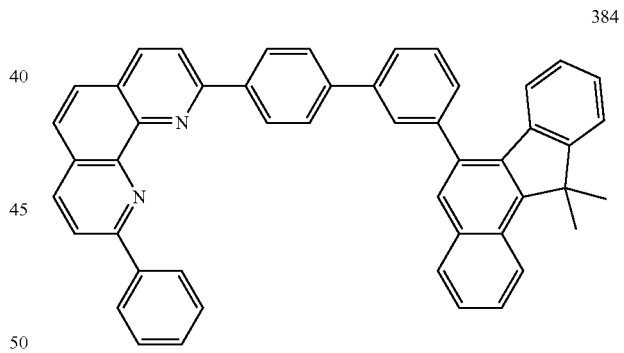
385
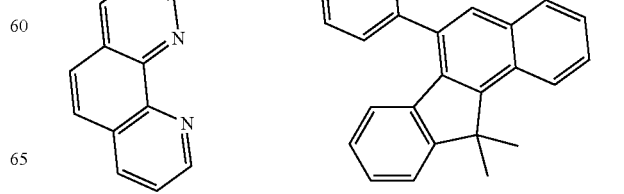

386
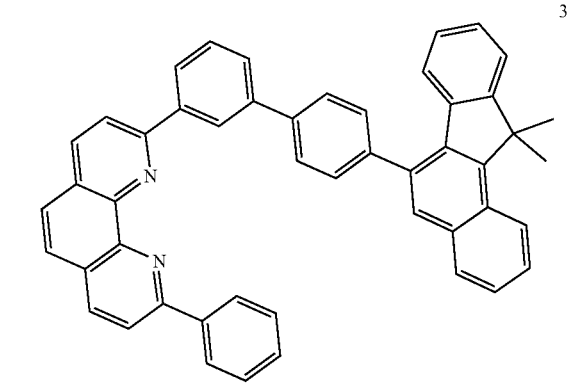
387
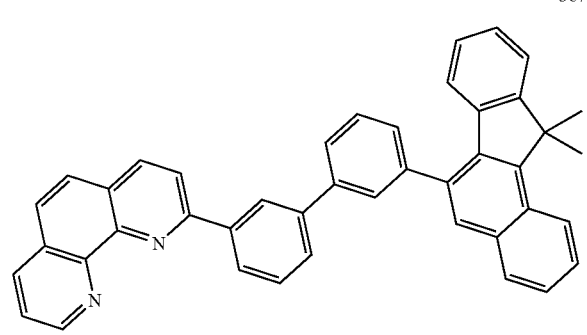
388
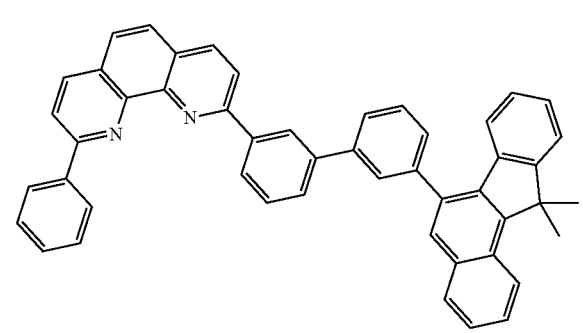
389
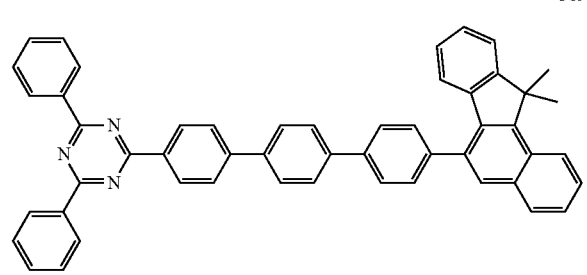
390
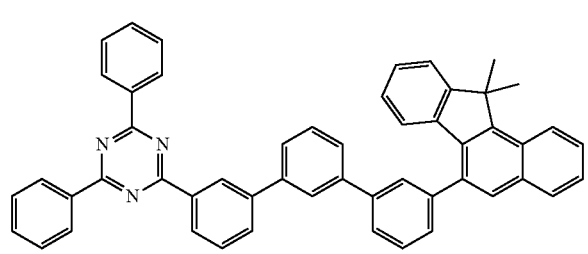
391
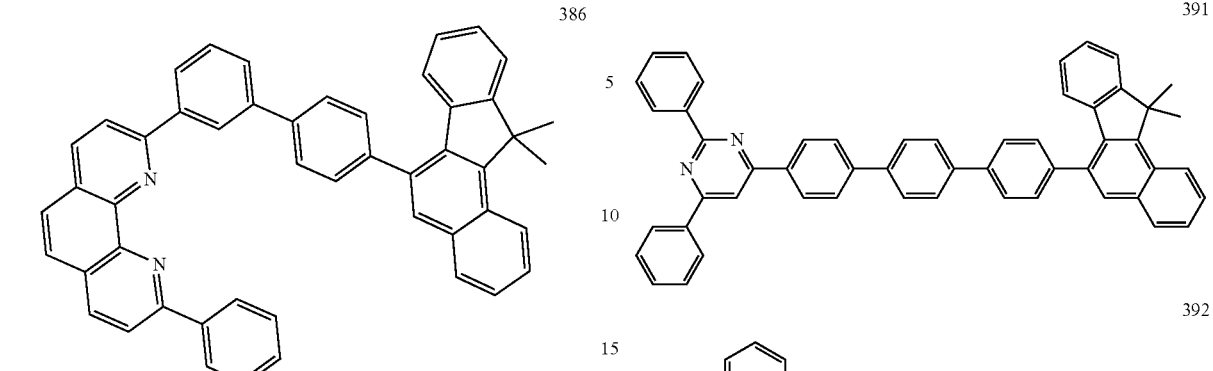
392
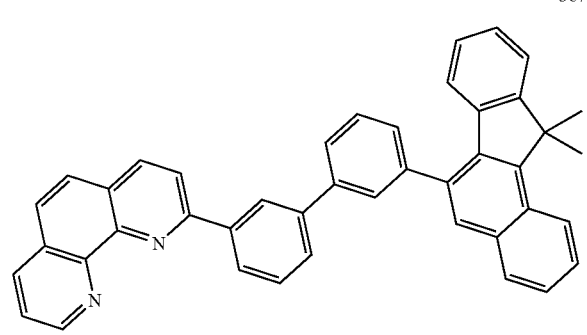
393
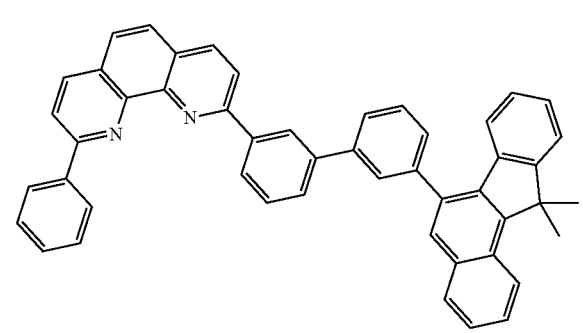
394
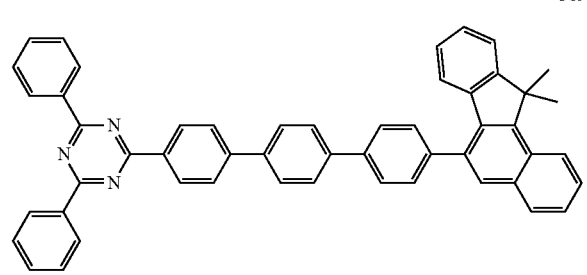
395
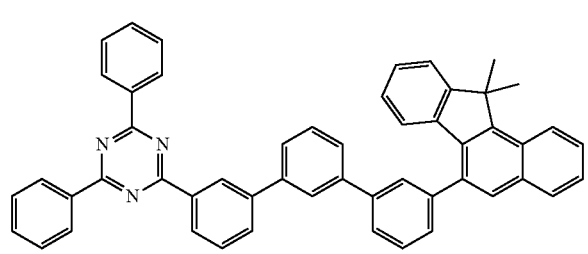

129 -continued
396
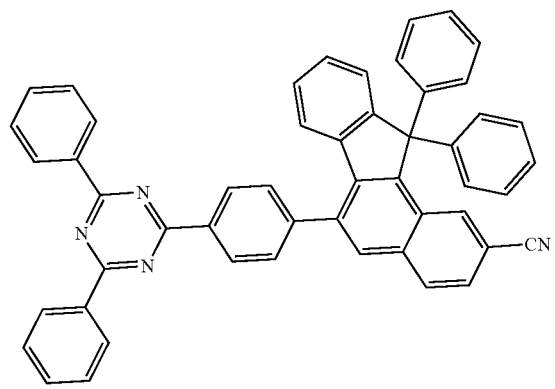
367
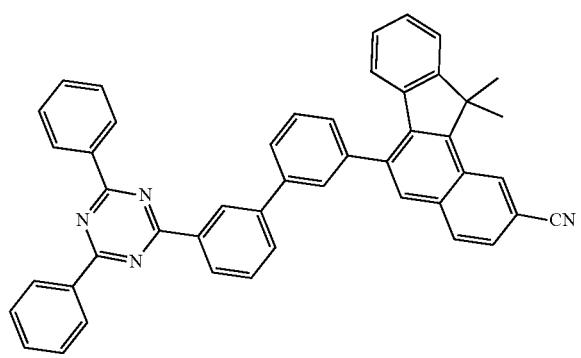
398
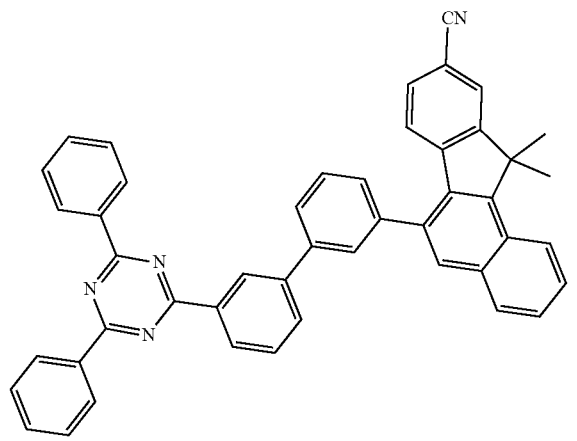
130 -continued
400
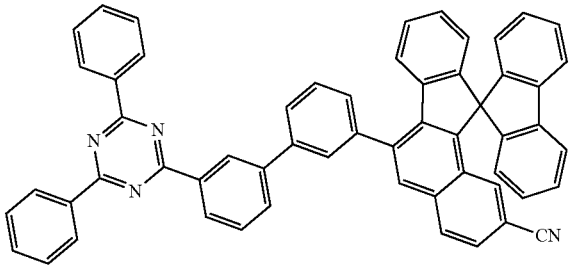
401
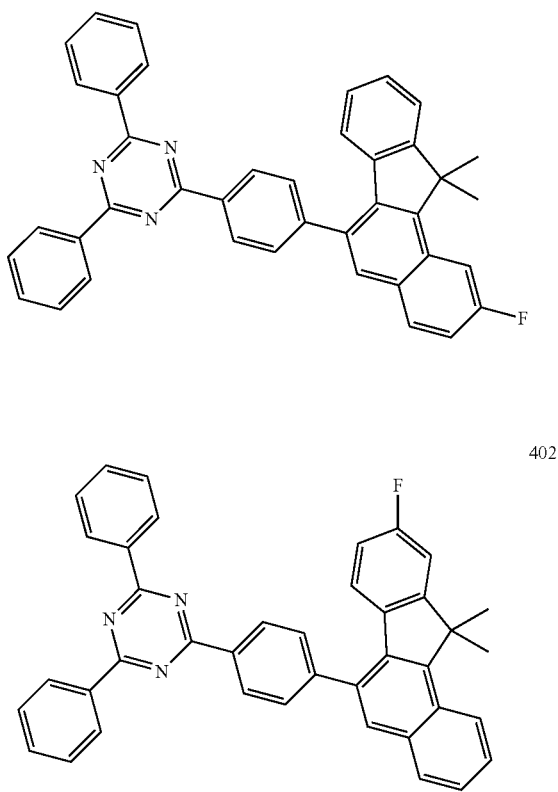
402
403
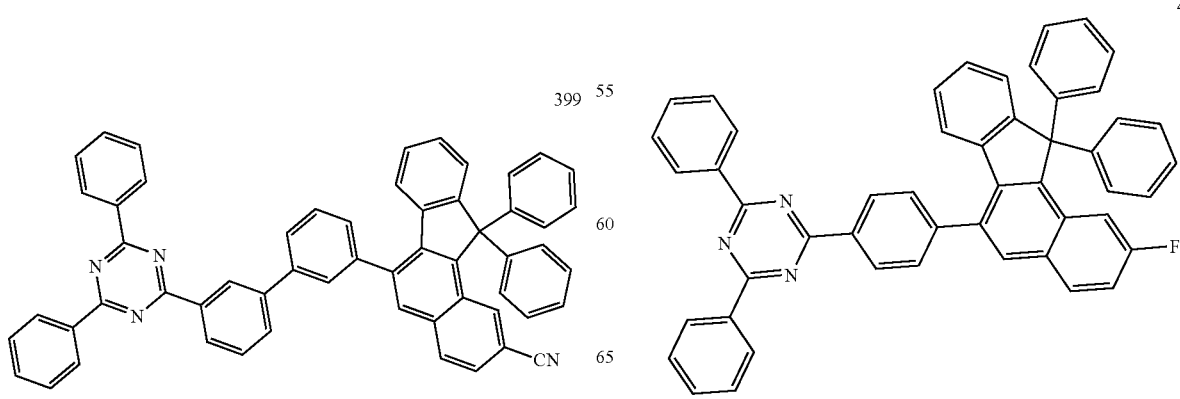
399

-continued
404
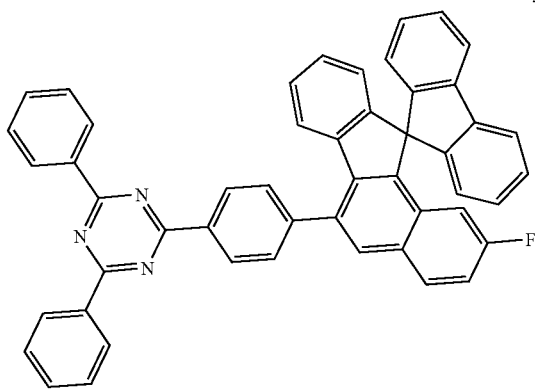
405
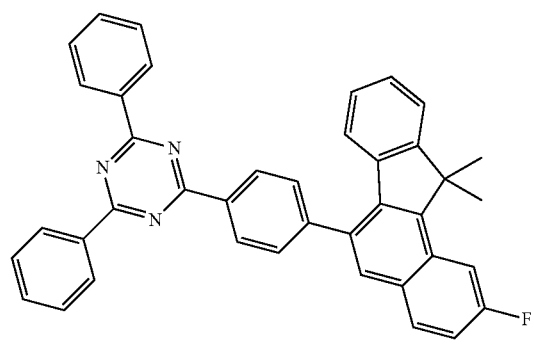
406
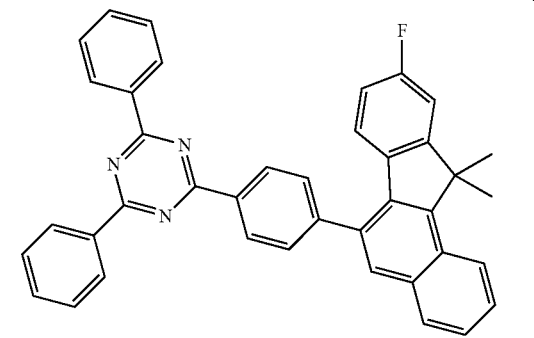
407
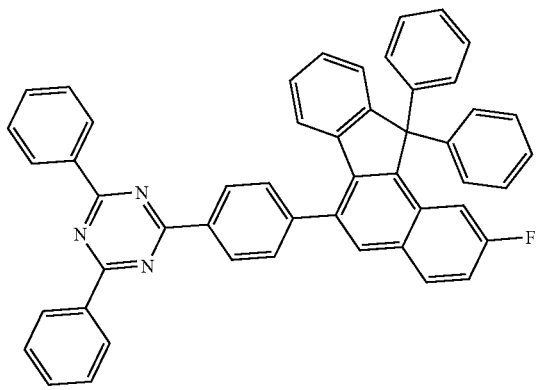
-continued
408
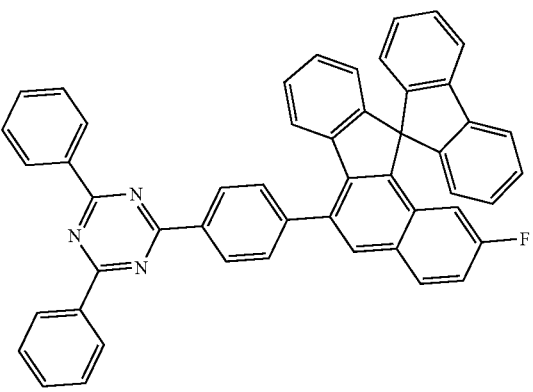
409
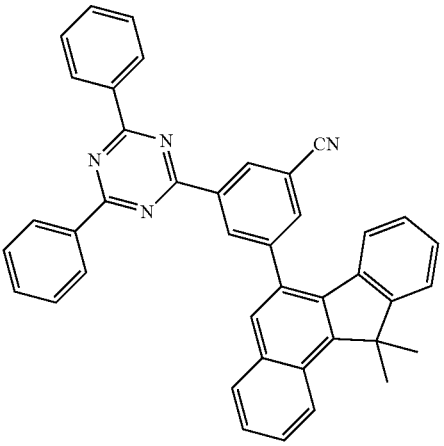
410
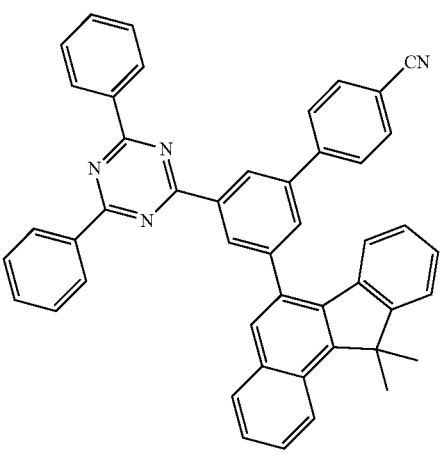

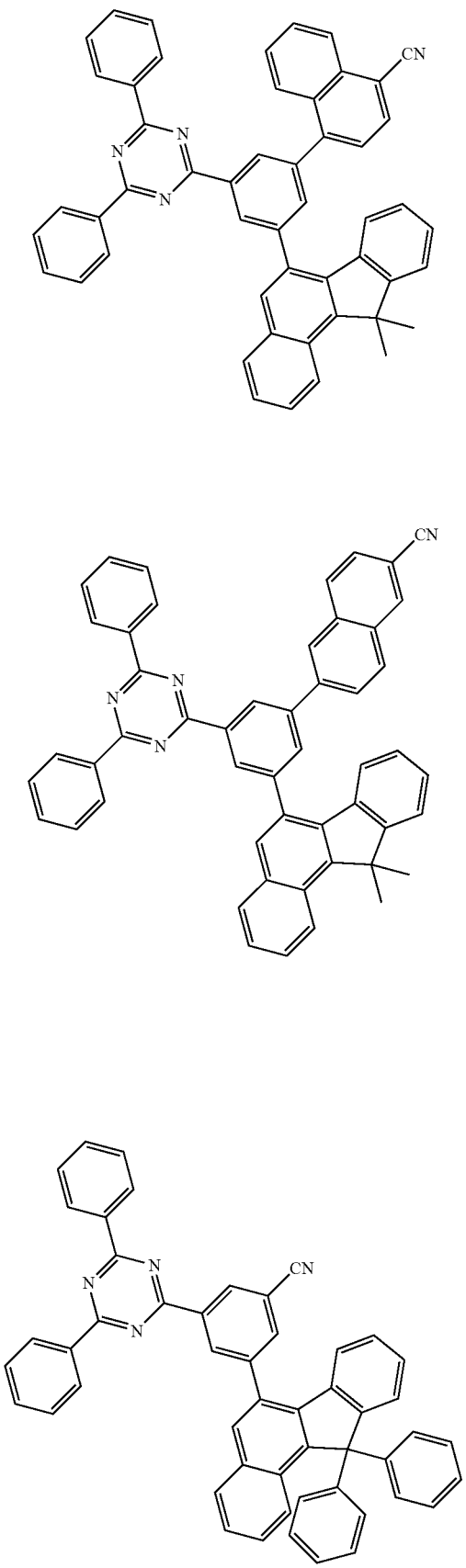
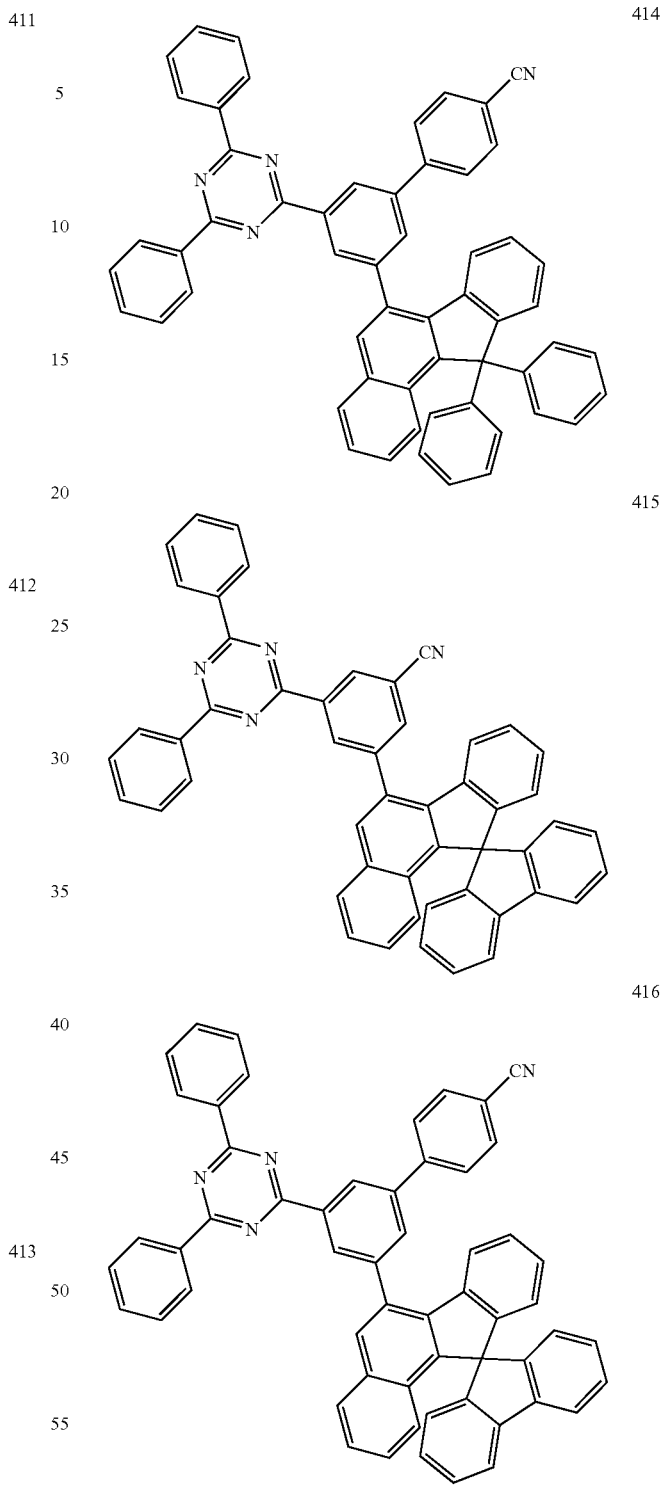

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg) and thereby has superior thermal stability. Such an increase in the thermal stability becomes an important factor in providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific descriptions on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or a hole transfer layer, and the electron injection layer or the hole transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron blocking layer, and the electron blocking layer may comprise the heterocyclic compound.

In one embodiment of the present application, the organic material layer comprises a hole injection layer, and the hole injection layer may comprise the heterocyclic compound.

In one embodiment of the present application, the organic material layer comprises a hole transfer layer, and the hole transfer layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer comprising Chemical Formula 1 may further comprise other materials as necessary.

In addition, the organic light emitting device according to one embodiment of the present application comprises an anode, a cathode, and two or more stacks provided between the anode and the cathode, the two or more stacks each independently comprise a light emitting layer, a charge generation layer is included between the two or more stacks, and the charge generation layer comprises the compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyl-diamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 5

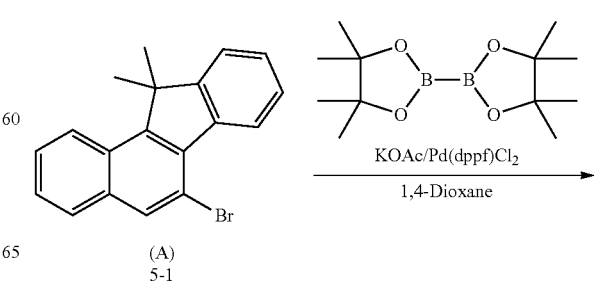

(A)
5-1

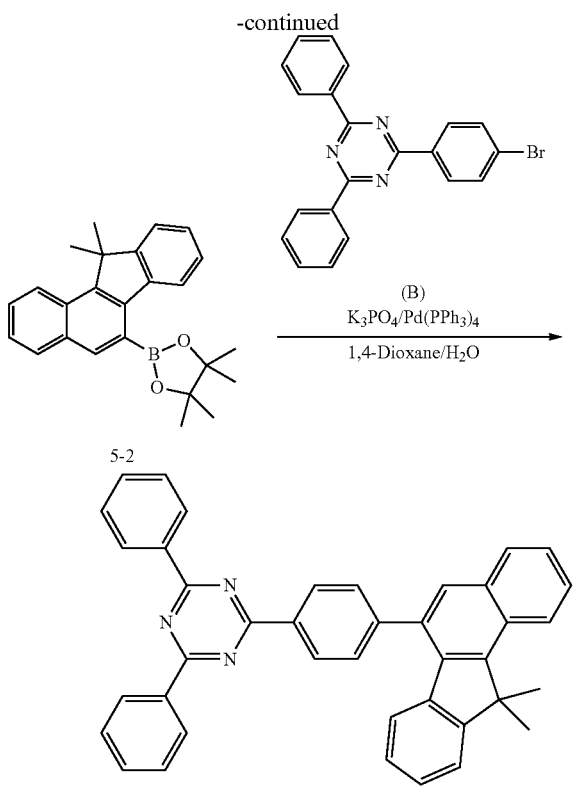

Preparation of Compound 5-2

1,4-Dioxane (100 ml) was introduced to 6-bromo-11,11-dimethyl-11H-benzo[a]fluorene (A) (10 g, 0.03 mol, 1 eq.), bis(pinacolato)diboron (11.8 g, 0.046 mol, 1.5 eq.), KOAc (9.1 g, 0.09 mol, 3 eq.) and Pd(dppf)Cl$_2$ (2.2 g, 0.003 mol, 0.1 eq.), and the result was stirred for 6 hours at 100° C. After terminating the reaction by introducing water thereto, the result was extracted using methylene chloride (MC) and water. Then, moisture was removed therefrom using MgSO$_4$. The result was separated using a silica gel column to obtain Compound 5-2 (9 g) in a 78% yield.

Preparation of Compound 5

1,4-Dioxane (100 ml) was introduced to 2-(4-bromophenyl)-4,6-diphenyl-1,3,5-triazine (B) (10 g, 0.025 mol, 1 eq.), Compound 5-2 (10 g, 0.027 mol, 1.05 eq.), K$_3$PO$_4$ (11 g, 0.05 mol, eq.) and Pd(PPh$_3$)$_4$ (1.5 g, 0.001 mol, 0.05 eq.), and the result was stirred for 6 hours at 100° C. After terminating the reaction by introducing water thereto, the result was extracted using methylene chloride (MC) and water. Then, moisture was removed therefrom using MgSO$_4$. The result was separated using a silica gel column to obtain Compound 5 (7 g) in a 49% yield.

Target compounds were synthesized in the same manner as in Preparation Example 1 except that Intermediate A of the following Table 1 was used instead of 6-bromo-11,11-dimethyl-11H-benzo[a]fluorene (A), and Intermediate B of the following Table 1 was used instead of 2-(4-bromophenyl)-4,6-diphenyl-1,3,5-triazine (B).

TABLE 1

| Compound No. | Intermediate A | Intermediate B | Yield |
|---|---|---|---|
| 5 | | | 63% |
| 9 | | | 67% |

TABLE 1-continued

| Compound No. | Intermediate A | Intermediate B | Yield |
|---|---|---|---|
| 10 | | | 59% |
| 17 | | | 51% |
| 18 | | | 62% |

TABLE 1-continued

| Compound No. | Intermediate A | Intermediate B | Yield |
|---|---|---|---|
| 21 | | | 60% |
| 22 | | | 60% |
| 25 | | | 55% |

TABLE 1-continued
| Compound No. | Intermediate A | Intermediate B | Yield |
|---|---|---|---|
| 27 | 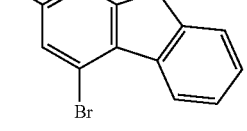 | 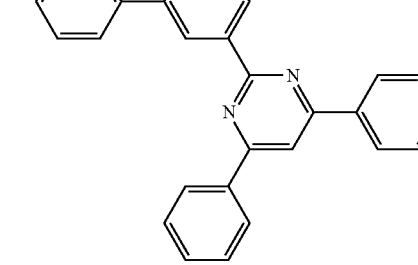 | 61% |
| 29 | 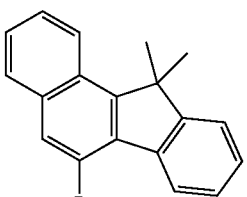 | 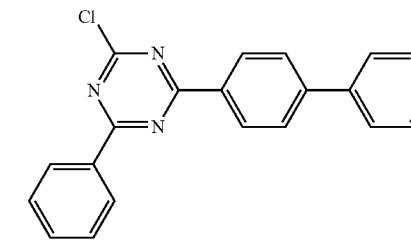 | 58% |
| 30 | 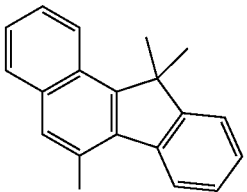 | 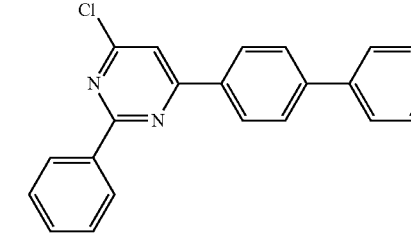 | 53% |
| 54 | 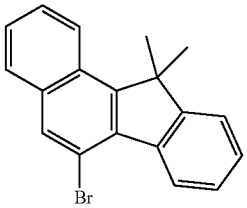 [SMILES: CC1(C)c2ccccc2-c2c(Br)cc3ccccc3c21] | 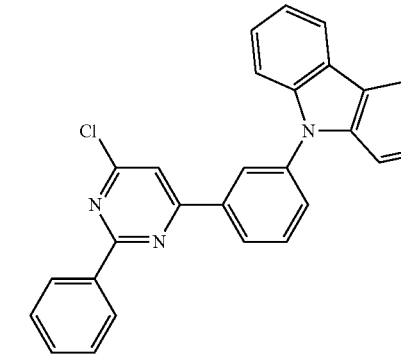 | 66% |
| 117 | 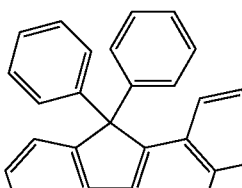 | 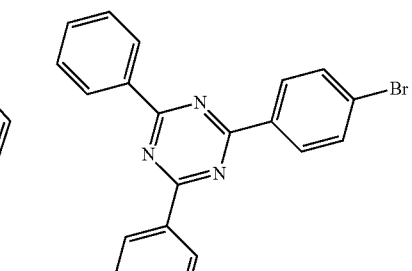 | 60% |

TABLE 1-continued
| Compound No. | Intermediate A | Intermediate B | Yield |
|---|---|---|---|
| 118 | 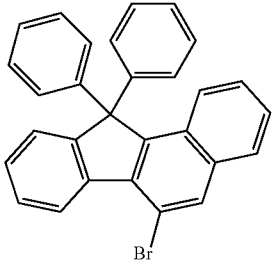 [SMILES: Brc1cc2ccccc2c2c1-c1ccccc1C2(c1ccccc1)c1ccccc1] | 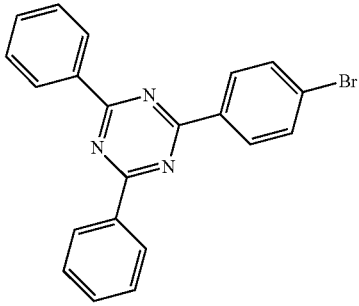 [SMILES: Brc1ccc(-c2nc(-c3ccccc3)nc(-c3ccccc3)n2)cc1] | 52% |
| 145 | 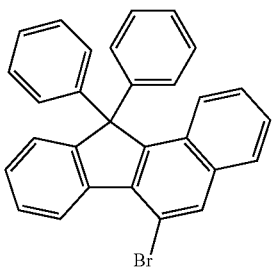 [SMILES: Brc1cc2ccccc2c2c1-c1ccccc1C2(c1ccccc1)c1ccccc1] | 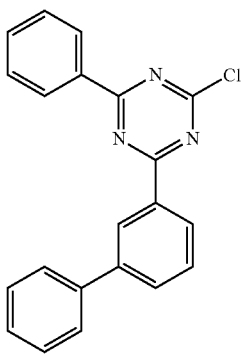 [SMILES: Clc1nc(-c2ccccc2)nc(-c2cccc(-c3ccccc3)c2)n1] | 63% |
| 146 | 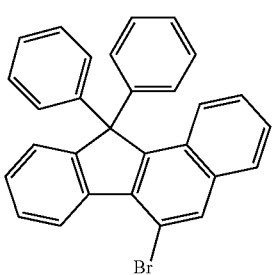 [SMILES: Brc1cc2ccccc2c2c1-c1ccccc1C2(c1ccccc1)c1ccccc1] | 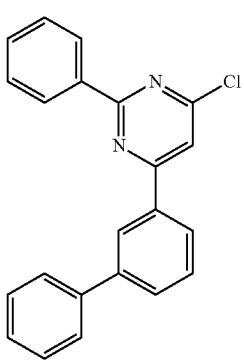 [SMILES: Clc1cc(-c2cccc(-c3ccccc3)c2)nc(-c2ccccc2)n1] | 61% |
| 225 | 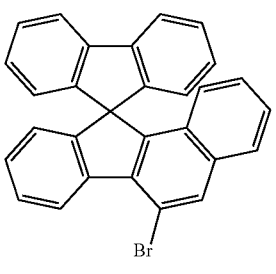 [SMILES: Brc1cc2ccccc2c2c1-c1ccccc1C21c2ccccc2-c2ccccc21] | 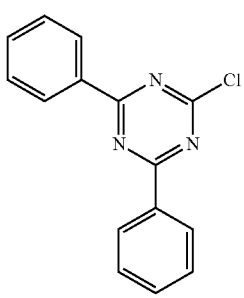 [SMILES: Clc1nc(-c2ccccc2)nc(-c2ccccc2)n1] | 61% |

TABLE 1-continued

| Compound No. | Intermediate A | Intermediate B | Yield |
|---|---|---|---|
| 227 | | | 70% |
| 337 | | | 67% |
| 338 | | | 60% |

Compounds 1 to 416 other than the compounds described in Preparation Example 1 and Table 1 were also prepared in the same manner as above, and the synthesis identification results are shown in Table 2 and Table 3. Table 2 shows measurement values of $^1$H NMR (CDCl$_3$, 200 Mz), and Table 3 shows measurement values of FD-mass spectrometry (FD-MS: field desorption mass spectrometry).

TABLE 2

| Compound | $^1$H NMR (CDCl$_3$, 200 Mz) |
|---|---|
| 5 | δ = 8.28(4 H, m), 8.18(1 H, d), 8.09(2 H, m), 7.85(3 H, m), 7.54~7.41(10 H, m), 7.25(3 H, m), 1.85(6 H, s) |
| 9 | δ = 8.28(6 H, m), 8.05(2 H, m), 7.79(1 H, s), 7.70(1 H, s), 7.57~7.41(10 H, m), 7.24(3 H, m), 1.85(6 H, s) |
| 10 | δ = 8.28(2 H, m), 8.23(1 H, s), 8.18(1 H, d), 8.05(2 H, m), 7.79(5 H, m), 7.57~7.41(12 H, m), 7.24(1 H, t), 1.85(6 H, s) |
| 17 | δ = 8.28(6 H, m), 8.05(2 H, m), 7.79(1 H, s), 7.70(1 H, s), 7.61~7.41(12 H, m), 7.25(5 H, m), 1.85(6 H, s) |
| 18 | δ = 8.28(2 H, m), 8.23(1 H, s), 8.18(1 H, d), 8.05(2 H, m), 7.79(5 H, m), 7.61~7.41(12 H, m), 7.25(5 H, m), 1.85(6 H, s) |

TABLE 2-continued

| Compound | $^1$H NMR (CDCl$_3$, 200 Mz) |
|---|---|
| 21 | δ = 8.28(4 H, m), 8.18(1 H, d), 8.09(2 H, m), 7.85(2 H, m), 7.79(1 H, s), 7.70(1 H, s), 7.61~7.41(13 H, m), 7.25(3 H, m), 1.85(6 H, s) |
| 22 | δ = 8.30(2 H, t), 8.28(2 H, m), 8.23(1 H, s), 8.18(1 H, d), 8.05(2 H, m), 7.79 (5 H, m), 7.70(1 H, s), 7.61~7.41 (13 H, m) , 7.25(1 H, t), 1.85(6 H, s) |
| 25 | δ = 8.28(6 H, m), 8.09 (2 H, m), 7.79 (1 H, s), 7.70(2 H, s), 7.61~7.41(15 H, m), 7.24(1 H, t), 1.85(6 H, s) |
| 27 | δ = 8.23(3 H, m), 8.05(2 H, m), 7.79(5 H, m), 7.70(2 H, s), 7.61~7.41(15 H, m), 7.25(1 H, t), 1.85(6 H, s) |
| 29 | δ = 8.28(2 H, m), 8.18(1 H, d), 8.09(2 H, m), 7.85(2 H, m), 7.79(1 H, s), 7.61~7.41 (12 H, m), 7.25(3 H, m), 1.85(6 H, s) |
| 30 | δ = 8.30(6 H, m), 8.05(2 H, m), 7.85(2 H, m), 7.79(1 H, s), 7.61~7.41(12 H, m), 7.25(1 H, t), 1.85(6 H, s) |
| 54 | δ = 8.55(1 H, d), 8.12(8 H, m), 7.94(1 H, d), 7.79(2 H, m), 7.61~7.25 (15 H, m), 1.85(6 H, s) |
| 117 | δ = 8.28(4 H, m), 8.18(1 H, d), 8.05(2 H, m), 7.85, (2 H, m), 7.92(1 H, s) 7.61~7.2 6 (19 H, m), 7.11(4 H, m) |
| 118 | δ = 8.30(6 H, m), 8.09(2 H, m), 7.79(3 H, m), 7.61~7.25(19 H, m), 7.11(4 H, m) |

TABLE 2-continued

| Compound | $^1$H NMR (CDCl$_3$, 200 Mz) |
|---|---|
| 145 | δ = 8.24(4 H, m), 8.09(2 H, m), 7.79(1 H, s), 7.70(1 H, s), 7.61~7.41(21 H, m), 7.11(4 H, m) |
| 146 | δ = 8.23(4 H, m), 8.09(2 H, m), 8.18(1 H, d), 8.09(2 H, m), 7.61~7.41(21 H, m), 7.11(4 H, m) |
| 225 | δ = 8.28(4 H, m), 8.18(1 H, d), 8.09(2 H, m), 7.75(3 H, m), 7.51~7.41(12 H, m), 7.19(5 H, m) |
| 227 | δ = 8.23(1 H, s), 8.18(1 H, d), 8.09(2 H, m), 7.79(7 H, m), 7.51~7.41(12 H, m), 7.19(5 H, m) |
| 337 | δ = 8.28(4 H, m), 8.18(1 H, d), 8.05(2 H, m), 7.79(1 H, s), 7.76(3 H, m), 7.61(1 H, d), 7.51~7.41(14 H, m), 7.24(1 H, t), 1.85(6 H, s) |
| 338 | δ = 8.28(2 H, m), 8.23(1 H, s), 8.18(1 H, d), 8.05(2 H, m), 7.79(3 H, m), 7.76(3 H, m), 7.61(1 H, d) 7.51~7.41(14 H, m), 7.24(1 H, t), 1.85(6 H, s) |

TABLE 3

| Compound | FD-MS |
|---|---|
| 5 | m/z = 551.68 (C40H29N3 = 551.24) |
| 9 | m/z = 551.68 (C40H29N3 = 551.24) |
| 10 | m/z = 550.69 (C41H30N2 = 550.24) |
| 17 | m/z = 627.77 (C46H33N3 = 627.27) |
| 18 | m/z = 626.79 (C46H33N3 = 626.79) |
| 21 | m/z = 627.77 (C46H33N3 = 627.27) |
| 22 | m/z = 626.79 (C46H33N3 = 626.79) |
| 25 | m/z = 627.77 (C46H33N3 = 627.27) |
| 27 | m/z = 626.79 (C46H33N3 = 626.79) |
| 29 | m/z = 551.68 (C40H29N3 = 551.24) |
| 30 | m/z = 550.69 (C41H30N2 = 550.24) |
| 54 | m/z = 639.79 (C47H33N3 = 639.27) |
| 117 | m/z = 675.82 (C50H33N3 = 675.27) |
| 118 | m/z = 674.83 (C51H34N2 = 674.27) |
| 145 | m/z = 675.82 (C50H33N3 = 675.27) |
| 146 | m/z = 674.83 (C51H34N2 = 674.27) |
| 225 | m/z = 597.71 (C44H27N3O = 597.22) |
| 227 | m/z = 596.72 (C45H28N2 = 596.23) |
| 337 | m/z = 627.77 (C46H33N3 = 627.27) |
| 338 | m/z = 626.79 (C46H33N3 = 626.79) |

EXPERIMENTAL EXAMPLE

Experimental Example 1

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

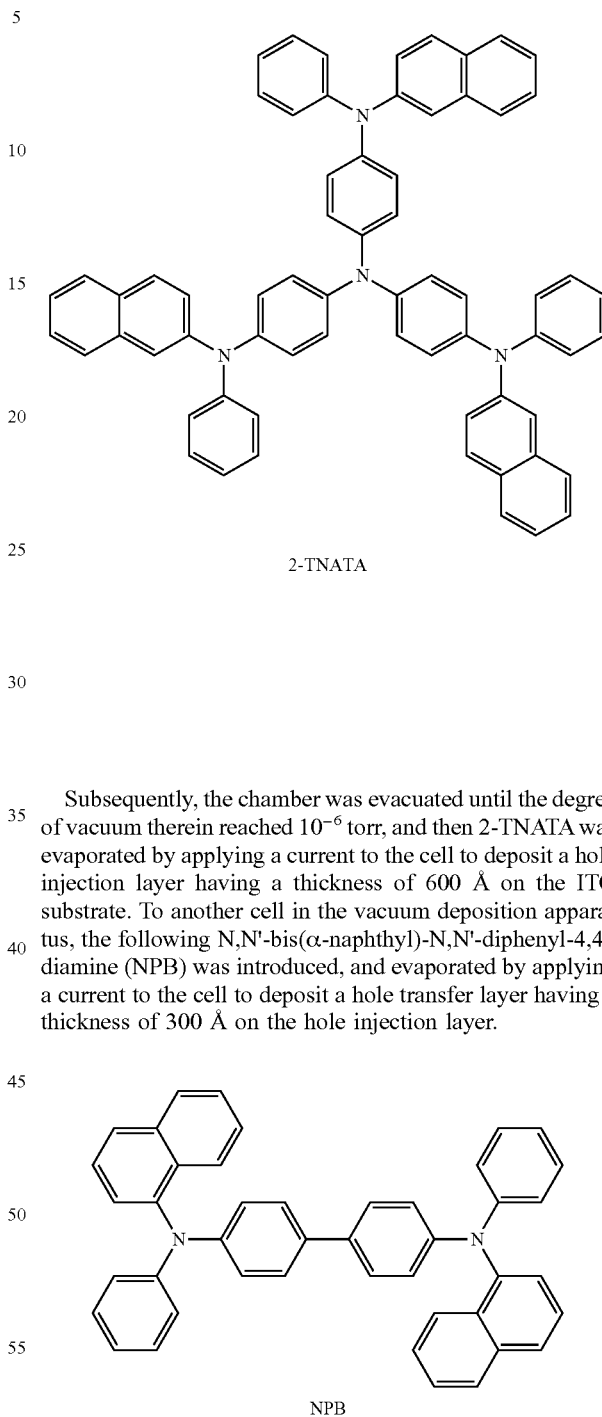

2-TNATA

Subsequently, the chamber was evacuated until the degree of vacuum therein reached 10$^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

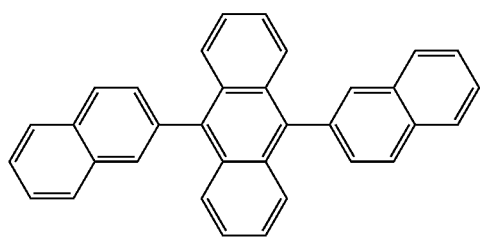

D1

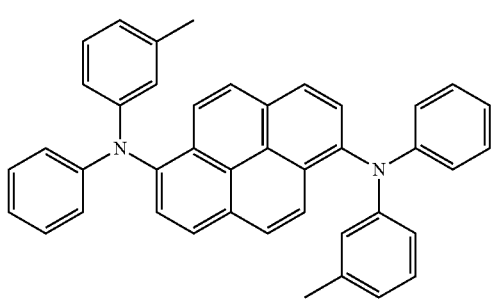

Subsequently, a compound of the following Structural Formula E1 was deposited to a thickness of 300 Å as an electron transfer layer.

E1

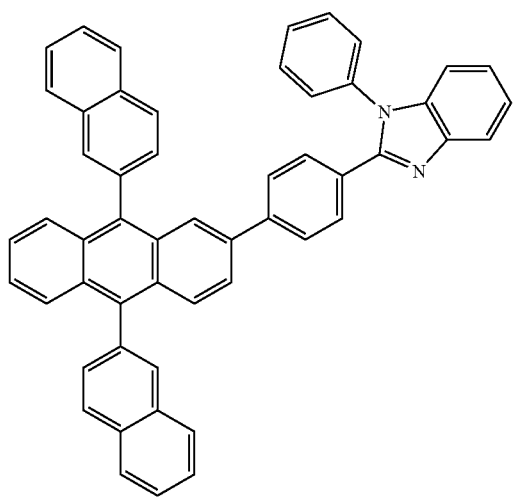

As an electron injection layer, lithium fluoride (LiF) was deposited to a thickness of 10 Å, and an Al cathode was employed to a thickness of 1,000 Å, and as a result, an OLED was manufactured. Meanwhile, all the organic compounds required to manufacture the OLED were vacuum sublimation purified under $10^{-8}$ torr to $10^{-6}$ torr by each material to be used in the OLED manufacture.

Organic electroluminescent devices were manufactured in the same manner as in Experimental Example 1 except that compounds shown in the following Table 4 were used instead of E1 used when foaming the electron transfer layer. Results of measuring driving voltage, light emission efficiency, color coordinate (CIE) and lifetime of the blue organic light emitting devices manufactured according to the present disclosure are as shown in Table 4.

TABLE 4

| | Compound | Driving Voltage (V) | Light Emission Efficiency (cd/A) | CIE (x, y) | Lifetime (T95) |
|---|---|---|---|---|---|
| Example 1 | 5 | 4.90 | 6.67 | (0.134, 0.101) | 43 |
| Example 2 | 9 | 4.98 | 6.71 | (0.134, 0.102) | 40 |
| Example 3 | 10 | 4.80 | 6.72 | (0.134, 0.101) | 41 |
| Example 4 | 17 | 4.94 | 6.78 | (0.134, 0.100) | 41 |
| Example 5 | 18 | 4.81 | 6.77 | (0.134, 0.100) | 48 |
| Example 6 | 21 | 4.86 | 6.70 | (0.134, 0.101) | 48 |
| Example 7 | 22 | 4.90 | 6.83 | (0.134, 0.100) | 47 |
| Example 8 | 25 | 4.92 | 6.74 | (0.134, 0.101) | 40 |
| Example 9 | 27 | 4.88 | 6.72 | (0.134, 0.102) | 46 |
| Example 10 | 29 | 5.02 | 6.80 | (0.134, 0.100) | 43 |
| Example 11 | 30 | 4.99 | 6.72 | (0.134, 0.100) | 49 |
| Example 12 | 54 | 5.00 | 6.84 | (0.134, 0.100) | 42 |
| Example 13 | 117 | 4.98 | 6.73 | (0.134, 0.101) | 50 |
| Example 14 | 118 | 4.89 | 6.83 | (0.134, 0.102) | 45 |
| Example 15 | 145 | 4.92 | 6.80 | (0.134, 0.101) | 43 |
| Example 16 | 146 | 4.90 | 6.70 | (0.134, 0.100) | 51 |
| Example 17 | 225 | 4.96 | 6.83 | (0.134, 0.100) | 46 |
| Example 18 | 227 | 4.98 | 6.85 | (0.134, 0.100) | 48 |
| Example 19 | 337 | 5.09 | 6.80 | (0.134, 0.101) | 52 |
| Example 20 | 338 | 4.98 | 6.88 | (0.134, 0.101) | 50 |
| Comparative Example 1 | E1 | 5.60 | 6.10 | (0.134, 0.101) | 30 |
| Comparative Example 2 | E2 | 5.50 | 6.13 | (0.134, 0.101) | 32 |
| Comparative Example 3 | E3 | 5.53 | 6.22 | (0.134, 0.100) | 31 |
| Comparative Example 4 | E4 | 5.57 | 6.27 | (0.134, 0.100) | 32 |
| Comparative Example 5 | E5 | 5.61 | 6.19 | (0.134, 0.101) | 30 |
| Comparative Example 6 | E6 | 5.52 | 6.20 | (0.134, 0.101) | 33 |
| Comparative Example 7 | E7 | 5.50 | 6.16 | (0.134, 0.100) | 33 |
| Comparative Example 8 | E8 | 5.98 | 5.92 | (0.134, 0.101) | 35 |

E1

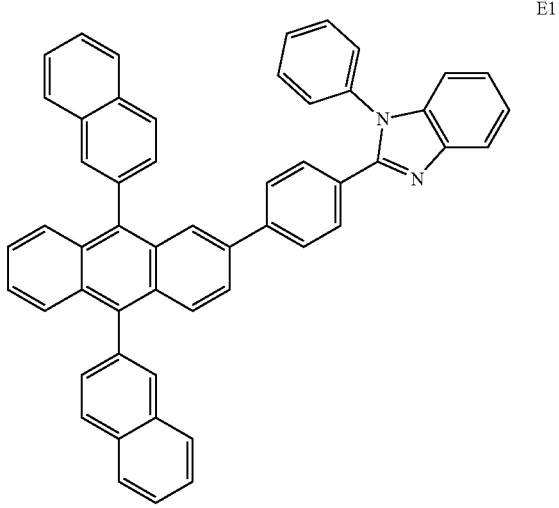

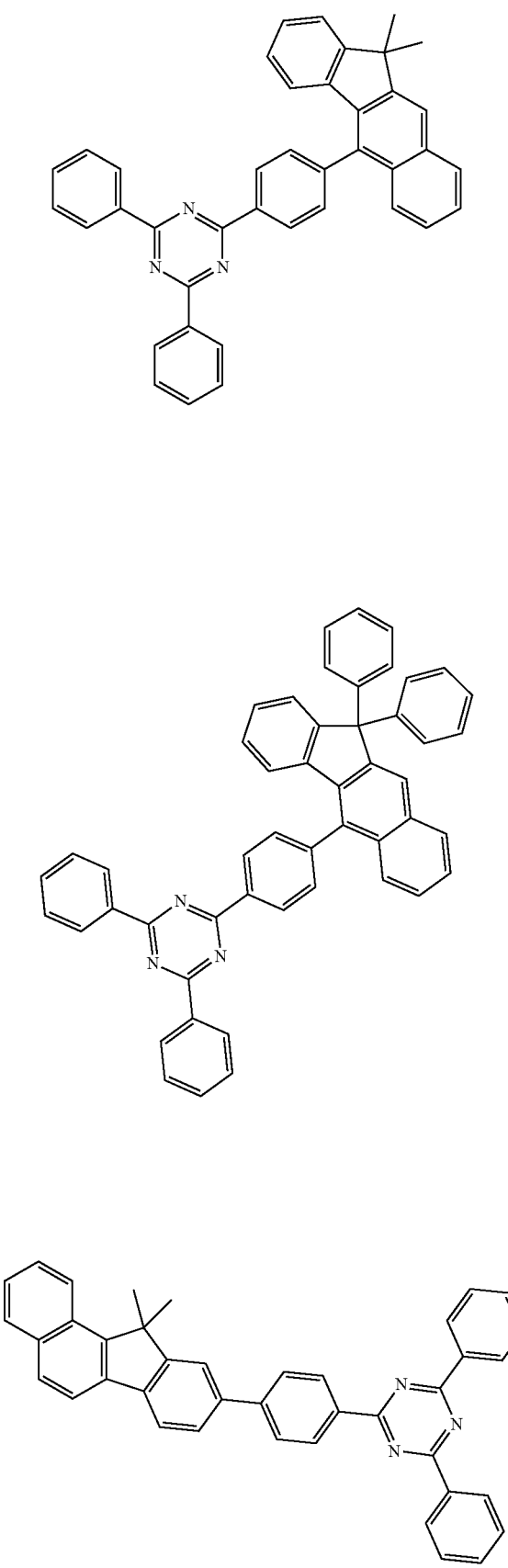
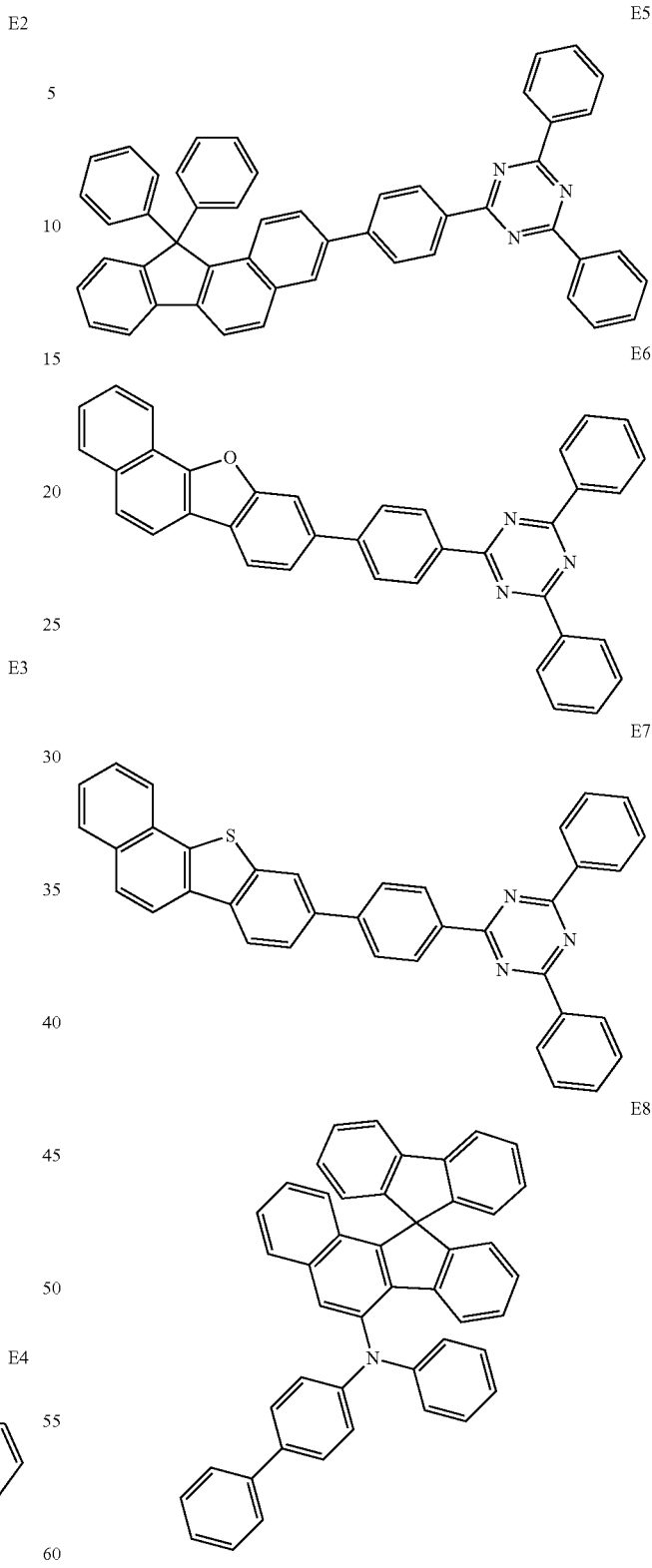
As seen from the results of Table 4, the organic light emitting device using the electron transfer layer material of the blue organic light emitting device of the present disclosure had lower driving voltage and significantly improved light emission efficiency and lifetime compared to Comparative Examples 1 to 8. Such a result is considered to be due to the fact that, when using the compound having proper length and strength, and flatness as an electron transfer layer, a compound in an excited state is made by receiving electrons under a specific condition, and particularly when an excited state is formed in the hetero-skeleton site of the compound, excited energy will move to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

The compounds of Examples 1 to 20 have an azine-based substituent having excellent electron transfer properties at a specific position on the skeleton having a fluorene group, and it was identified that, through adjusting band gap and T1 value by strengthening electron withdrawing properties, superior efficiency and driving were obtained when comprising the compounds in the organic light emitting device.

Particularly, when using the azine derivative as the electron transfer layer, it was identified that superior electron withdrawing properties of the azine functional group improved the flow of electrons enhancing electron transfer capability of the electron transfer layer, and by combining the azine moiety with a substituent with enhanced hole properties, planarity of the azine derivative and the glass transition temperature increased, which increased thermal stability of the compound. It was also identified that electron transfer capability and hole blocking capability were enhanced through adjusting band gap and T1 value, and molecular stability increased as well, and as a result, the device had lowered driving voltage, enhanced light efficiency, and lifetime properties of the device were enhanced due to thermal stability of the compound.

Experimental Example 2

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

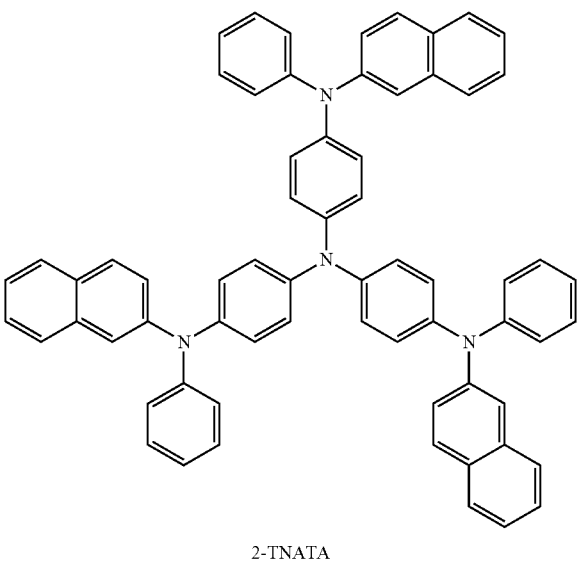 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

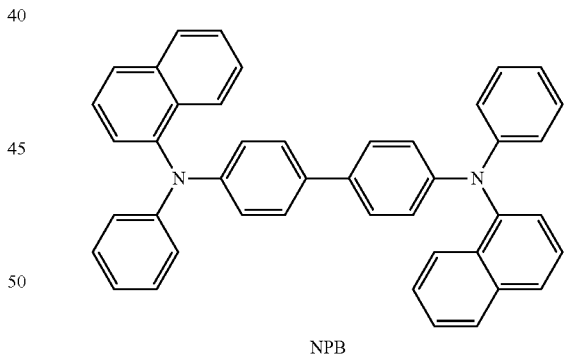

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

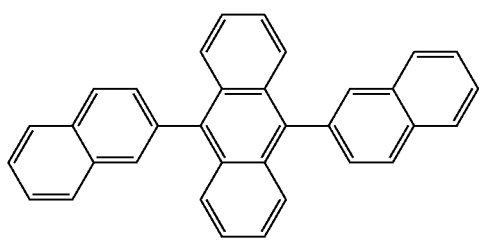

H1

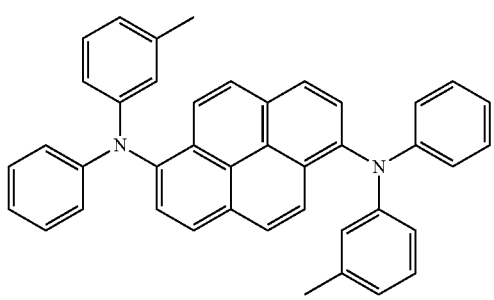

D1

Subsequently, a compound of the following Structural Formula E1 was deposited to a thickness of 300 Å as an electron transfer layer.

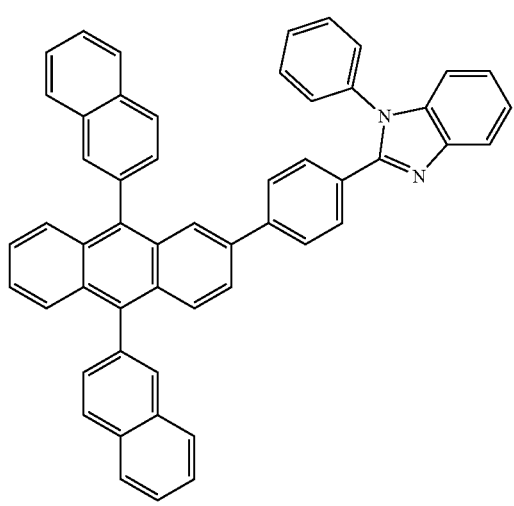

E1

As an electron injection layer, lithium fluoride (LiF) was deposited to a thickness of 10 Å, and an Al cathode was employed to a thickness of 1,000 Å, and as a result, an OLED was manufactured. Meanwhile, all the organic compounds required to manufacture the OLED were vacuum sublimation purified under $10^{-6}$ torr to $10^{-8}$ torr by each material to be used in the OLED manufacture. Organic electroluminescent devices were manufactured in the same manner as in Experimental Example 2 except that, after forming the electron transfer layer E1 to a thickness of 250 Å, a hole blocking layer was formed to a thickness of 50 Å on the electron transfer layer using compounds shown in the following Table 5. Results of measuring driving voltage, light emission efficiency, color coordinate (CIE) and lifetime of the blue organic light emitting devices manufactured according to the present disclosure are as shown in the following Table 5.

TABLE 5

| | Compound | Driving Voltage (V) | Light Emission Efficiency (cd/A) | CIE (x, y) | Lifetime (T95) |
|---|---|---|---|---|---|
| Example 21 | 5 | 5.00 | 6.51 | (0.134, 0.101) | 58 |
| Example 22 | 9 | 5.00 | 6.67 | (0.134, 0.100) | 54 |
| Example 23 | 10 | 4.96 | 6.38 | (0.134, 0.100) | 57 |
| Example 24 | 17 | 4.99 | 6.55 | (0.134, 0.100) | 53 |
| Example 25 | 18 | 4.80 | 6.61 | (0.134, 0.101) | 59 |
| Example 26 | 21 | 4.89 | 6.68 | (0.134, 0.100) | 60 |
| Example 27 | 22 | 4.89 | 6.51 | (0.134, 0.100) | 57 |
| Example 28 | 25 | 4.81 | 6.59 | (0.134, 0.101) | 60 |
| Example 29 | 27 | 4.87 | 6.49 | (0.134, 0.101) | 60 |
| Example 30 | 29 | 4.88 | 6.44 | (0.134, 0.102) | 59 |
| Example 31 | 30 | 4.87 | 6.60 | (0.134, 0.101) | 54 |
| Example 32 | 54 | 4.90 | 6.61 | (0.134, 0.100) | 53 |
| Example 33 | 117 | 5.02 | 6.54 | (0.134, 0.101) | 52 |
| Example 34 | 118 | 4.93 | 6.39 | (0.134, 0.101) | 50 |
| Example 35 | 145 | 4.93 | 6.39 | (0.134, 0.101) | 53 |
| Example 36 | 146 | 4.89 | 6.51 | (0.134, 0.101) | 57 |
| Example 37 | 225 | 5.04 | 6.46 | (0.134, 0.100) | 56 |
| Example 38 | 227 | 4.94 | 6.50 | (0.134, 0.101) | 52 |
| Example 39 | 337 | 5.07 | 6.59 | (0.134, 0.100) | 51 |
| Example 40 | 338 | 5.03 | 6.62 | (0.134, 0.101) | 50 |
| Comparative Example 9 | E1 | 5.78 | 6.07 | (0.134, 0.102) | 44 |
| Comparative Example 10 | E2 | 5.70 | 6.09 | (0.134, 0.101) | 44 |
| Comparative Example 11 | E3 | 5.78 | 6.00 | (0.134, 0.101) | 43 |
| Comparative Example 12 | E4 | 5.66 | 6.12 | (0.134, 0.100) | 40 |
| Comparative Example 13 | E5 | 5.71 | 6.15 | (0.134, 0.100) | 45 |
| Comparative Example 14 | E6 | 5.68 | 6.07 | (0.134, 0.102) | 45 |
| Comparative Example 15 | E7 | 5.60 | 6.09 | (0.134, 0.102) | 42 |
| Comparative Example 16 | E8 | 5.88 | 5.90 | (0.134, 0.101) | 48 |

As seen from the results of Table 5, the organic light emitting device using the hole blocking layer material of the blue organic light emitting device of the present disclosure had lower driving voltage and significantly improved light emission efficiency and lifetime compared to Comparative Examples 9 to 16. Such results are due to the fact that, when holes pass through an electron transfer layer and reach a cathode without binding in a light emitting layer, efficiency and lifetime decrease in an OLED.

When using a compound having a deep HOMO level as a hole blocking layer in order to prevent such a phenomenon, the holes trying to pass through the light emitting layer and reach the cathode are blocked by an energy barrier of the hole blocking layer. As a result, it is considered that probability of the holes and electrons forming excitons increases, and possibility of being emitted as light increases, and the compound of the present disclosure brings excellence in all aspects of driving, efficiency and lifetime.

The invention claimed is:

1. A heterocyclic compound represented by the following Chemical Formula 1:

[Chemical Formula 1]

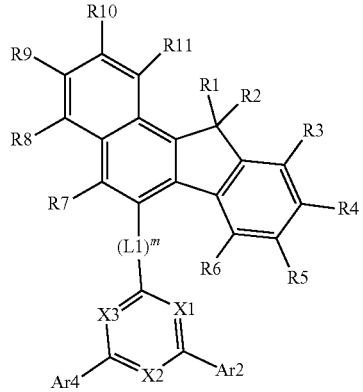

wherein, in Chemical Formula 1,

R1 and R2 are the same as or different from each other, and each independently a substituted or unsubstituted C1 to C60 alkyl group; or a substituted or unsubstituted C6 to C60 aryl group; or groups adjacent to each other bond to each other to form a substituted or unsubstituted C6 to C60 aromatic hydrocarbon ring or a substituted or unsubstituted C2 to C60 heteroring;

L1 is a direct bond; a substituted or unsubstituted C6 to C60 arylene group; or a substituted or unsubstituted C2 to C60 heteroarylene group;

X1 to X3 are the same as or different from each other, and each independently N; or CRa, and at least one thereof is N;

Ra, Ar2 and Ar4 are the same as or different from each other, and each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring;

R3 to R11 are the same as or different from each other, and each independently selected from the group consisting of hydrogen; deuterium; a halogen group; and —CN;

R, R' and R" are the same as or different from each other, and each independently hydrogen; a substituted or unsubstituted C1 to C40 alkyl group; or a substituted or unsubstituted C6 to C40 aryl group; and m is an integer of 1 to 6, and when m is 2 or greater, substituents in the parentheses are the same as or different from each other.

2. The heterocyclic compound of claim 1, wherein L1 is any one of the following structural formulae:

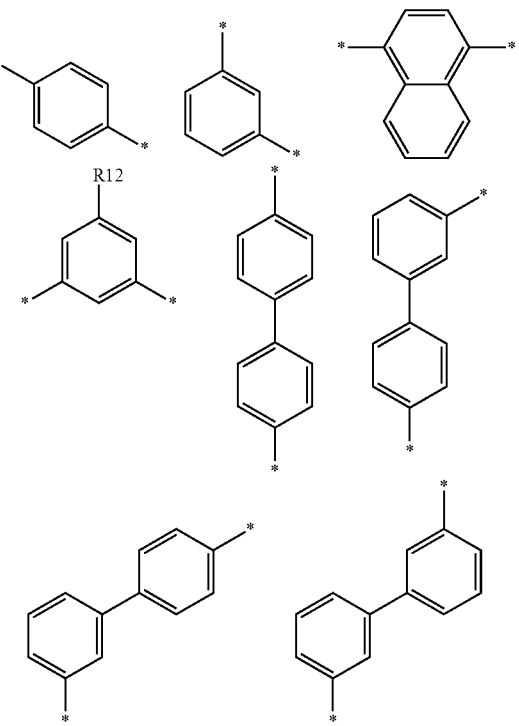

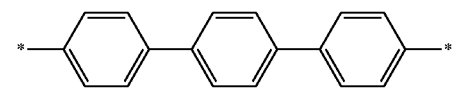

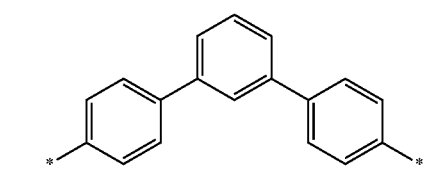

in the structural formulae,

means a position linked to the substituents of Chemical Formula 1;

R12 is a substituted or unsubstituted C1 to C60 alkyl group; a substituted or unsubstituted C6 to C60 aryl group; a substituted or unsubstituted C2 to C60 heteroaryl group; —CN; or —P(=O)RR'; and R and R' have the same definitions as in Chemical Formula 1.

3. The heterocyclic compound of claim 1, wherein Chemical Formula 1 is represented by any one of the following Chemical Formula 2 to Chemical Formula 4:

[Chemical Formula 2]

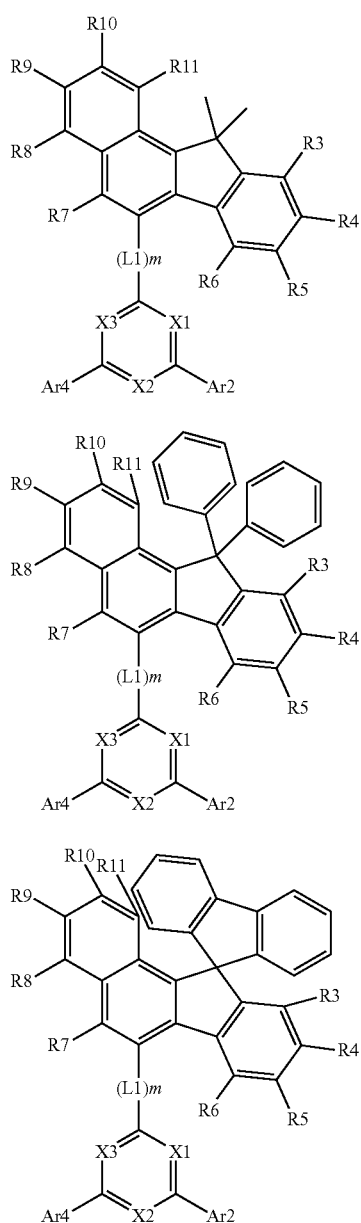

[Chemical Formula 3]

[Chemical Formula 4]

in Chemical Formulae 2 to 4,

X1 to X3, R3 to R11, L1, Ar2, Ar4 and m have the same definitions as in Chemical Formula 1.

4. The heterocyclic compound of claim 1, wherein

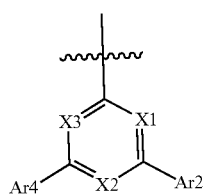

of Chemical Formula 1 is represented by any one of the following Chemical Formulae 1-1 to 1-5:

[Chemical Formula 1-1]

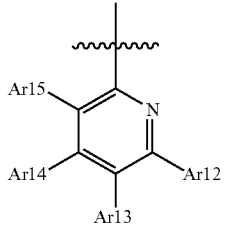

[Chemical Formula 1-2]

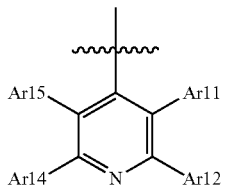

[Chemical Formula 1-3]

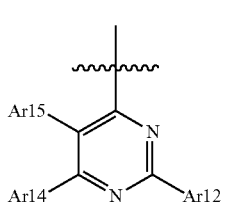

[Chemical Formula 1-4]

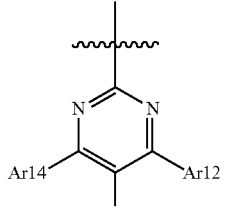

[Chemical Formula 1-5]

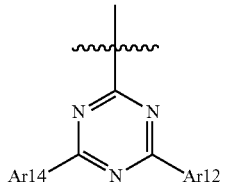

in Chemical Formulae 1-1 to 1-5,

means a position linked to L1 of Chemical Formula 1;

Ar11 to Ar15 are the same as or different from each other, and each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R''; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group; and R, R' and R" have the same definitions as in Chemical Formula 1.

5. The heterocyclic compound of claim 1, wherein

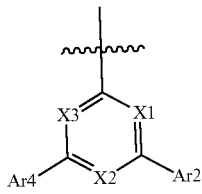

of Chemical Formula 1 is represented by the following Chemical Formula 1-6 or 1-7:

[Chemical Formula 1-6]

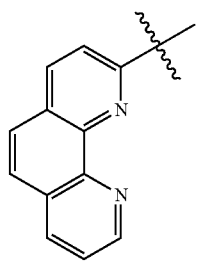

[Chemical Formula 1-7]

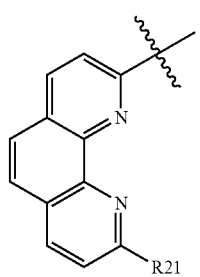

in Chemical Formulae 1-6 and 1-7,

means a position linked to L1 of Chemical Formula 1; and

R21 is hydrogen; a substituted or unsubstituted C6 to C60 aryl group; or a substituted or unsubstituted C2 to C60 heteroaryl group.

6. The heterocyclic compound of claim 4, wherein Ar12 is represented by

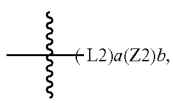

and Ar14 is a substituted or unsubstituted C6 to C60 aryl group;

L2 is a direct bond; a substituted or unsubstituted C6 to C60 arylene group; or a substituted or unsubstituted C2 to C60 heteroarylene group;

Z2 is a substituted or unsubstituted C6 to C60 aryl group; or a substituted or unsubstituted C2 to C60 heteroaryl group; and a and b are the same as or different from each other and each an integer of 1 to 6, and when a and b are 2 or greater, substituents in the parentheses are the same as or different from each other.

7. The heterocyclic compound of claim 1, wherein Chemical Formula 1 is represented by any one of the following compounds:

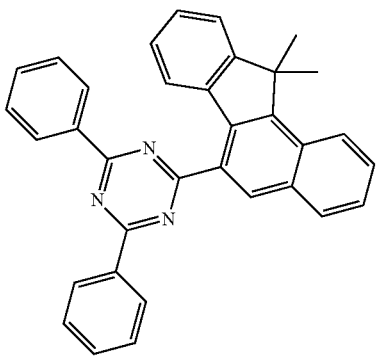

1

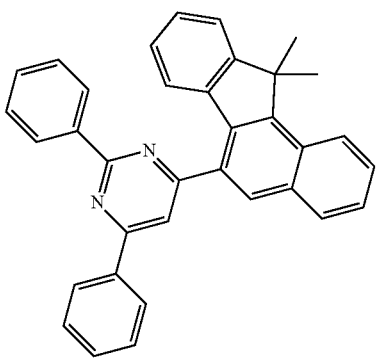

2

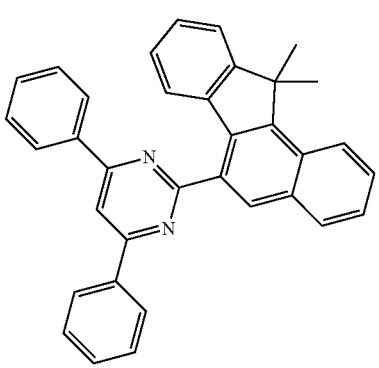

3

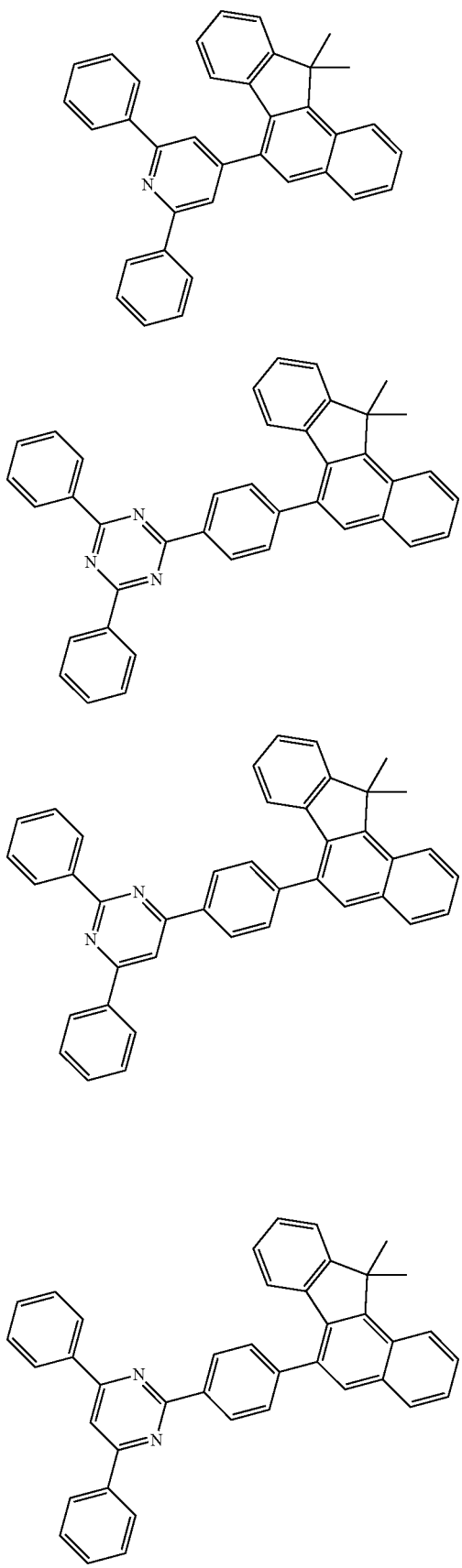
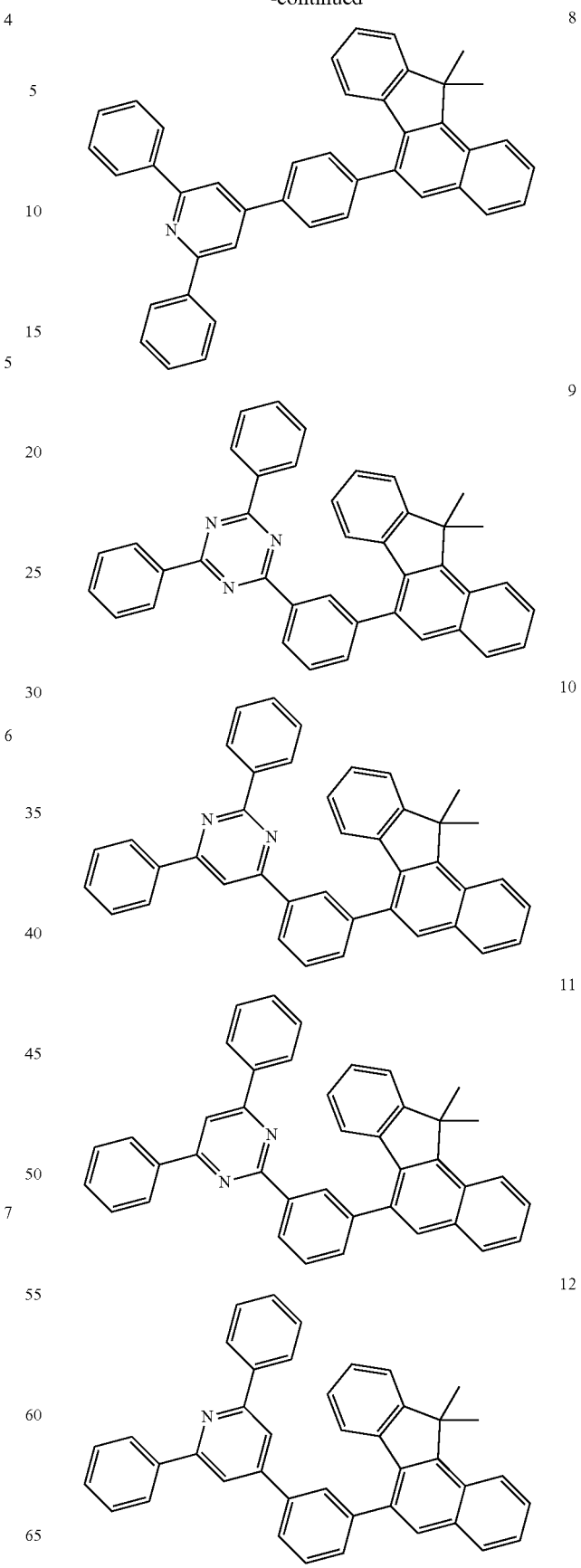

-continued
13
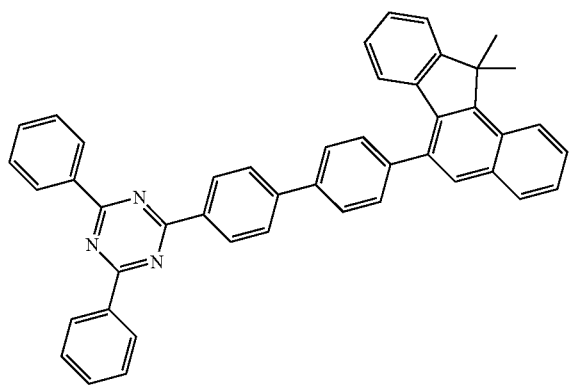
14
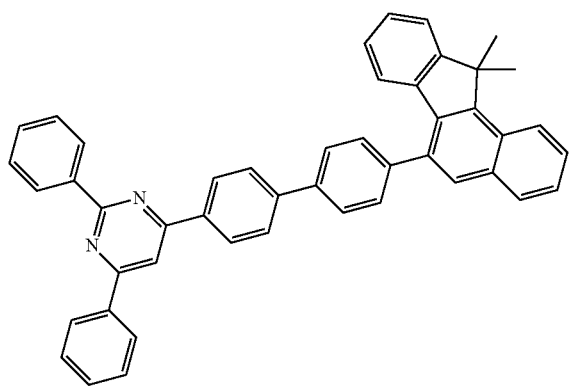
15
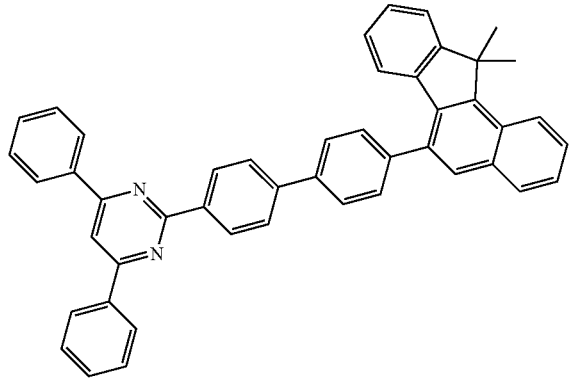
16
-continued
17
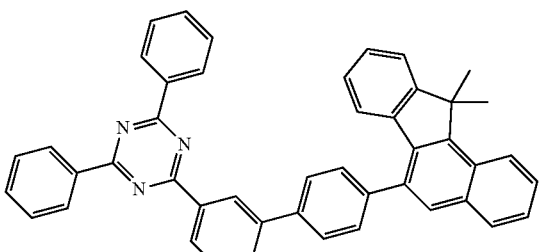
18
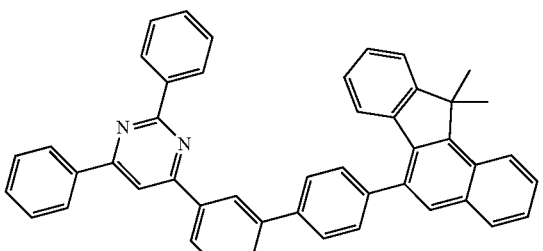
19
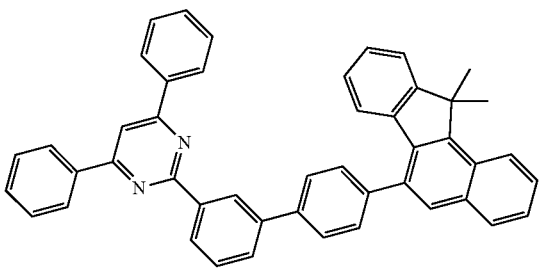
20
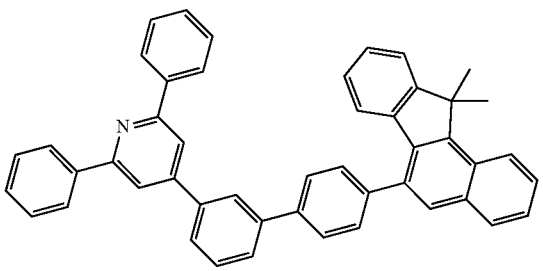
21
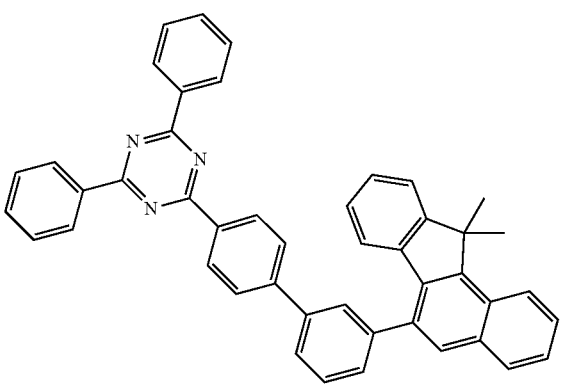

-continued
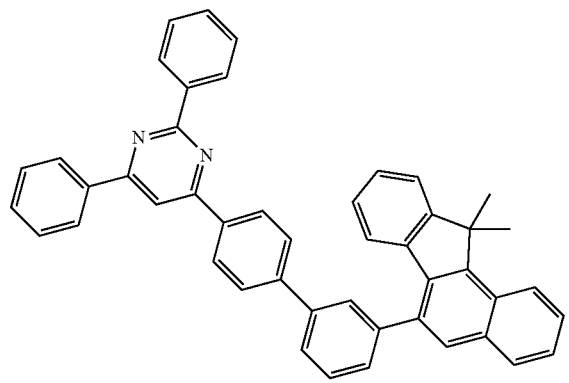
22
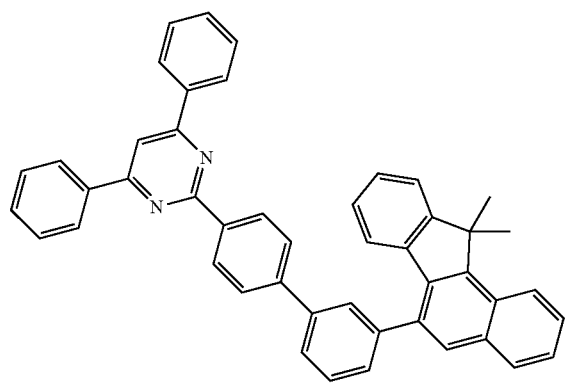
23
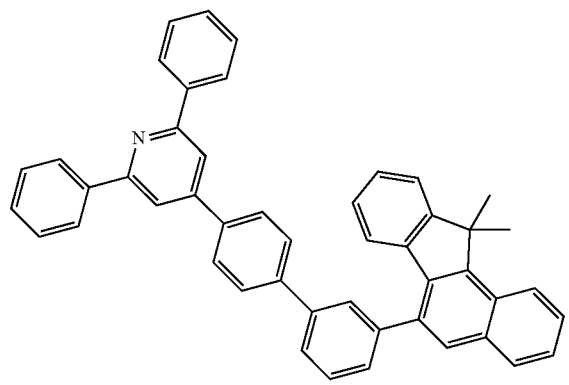
24
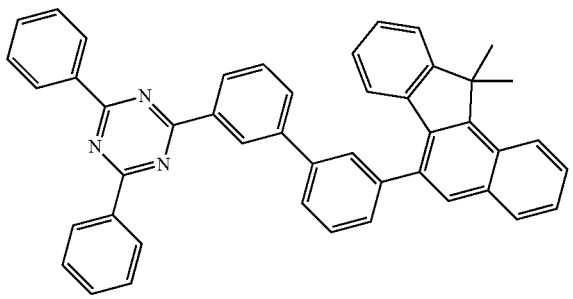
25
-continued
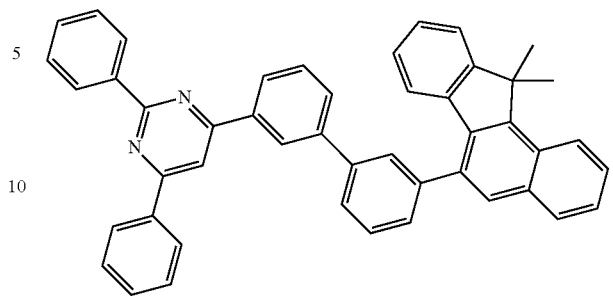
26
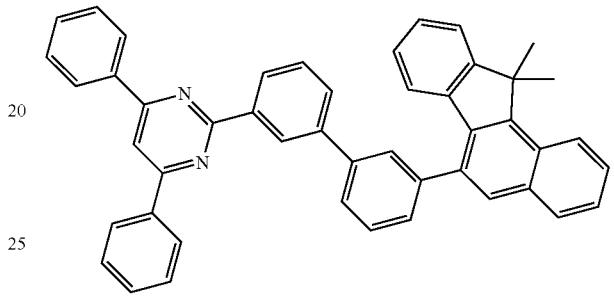
27
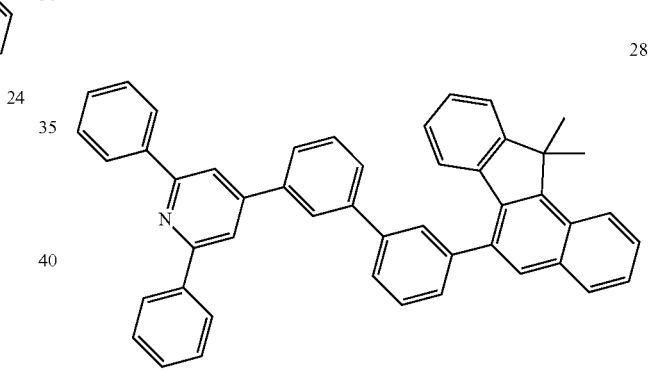
28
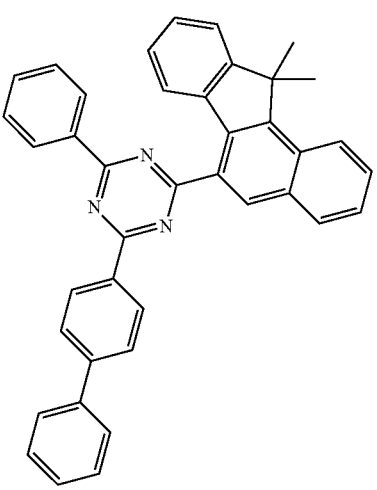
29

30
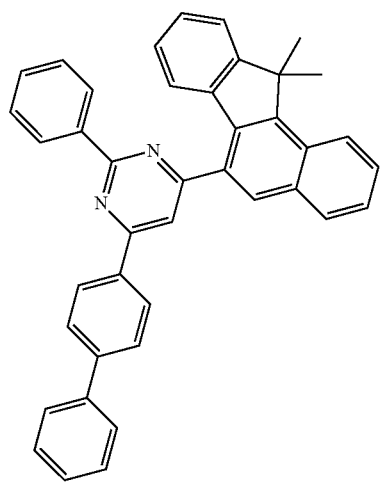
31
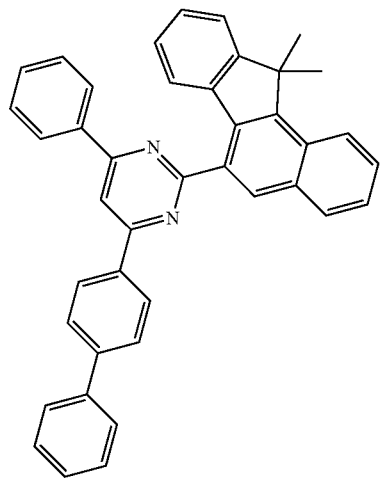
32
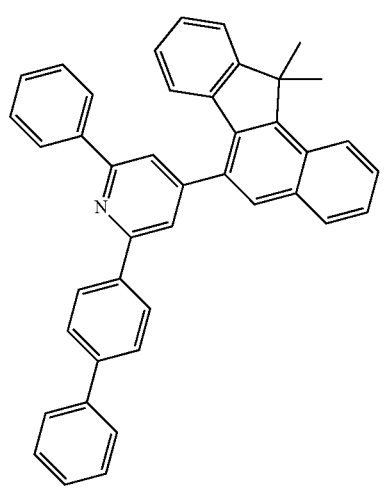
33
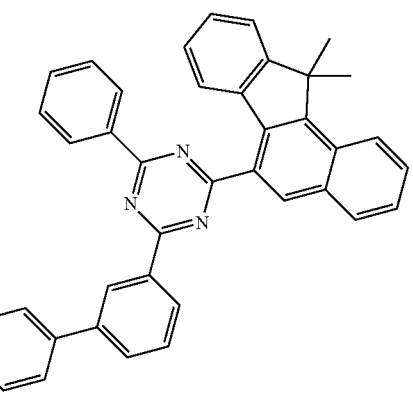
34
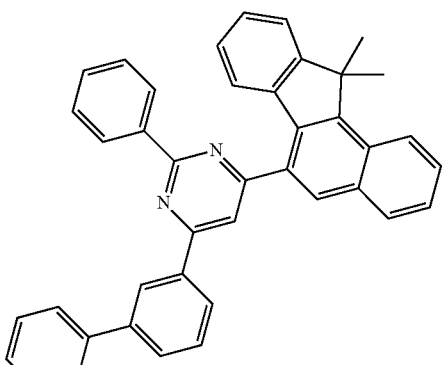
35
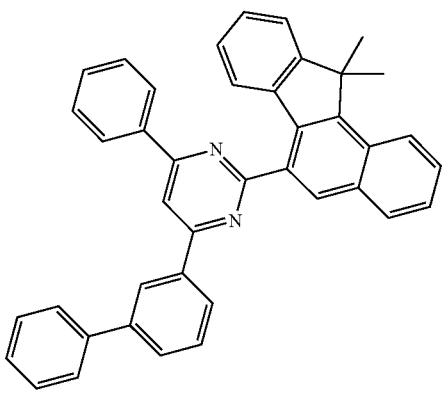
36
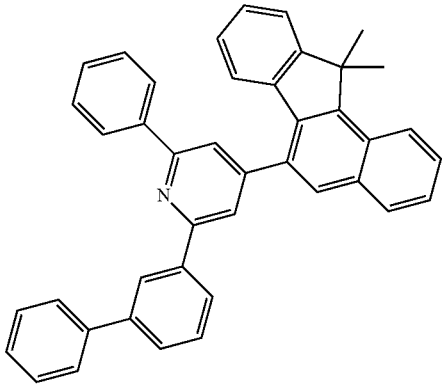

37
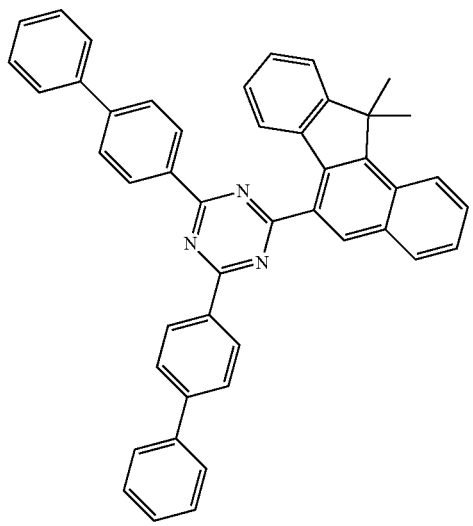
38
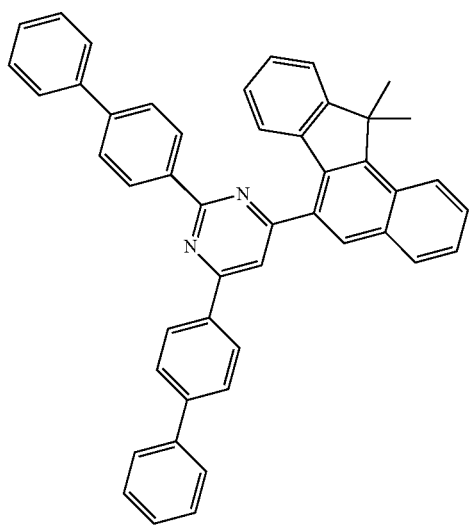
39
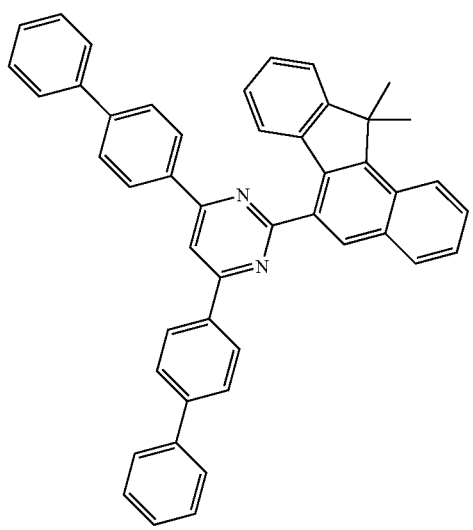
40
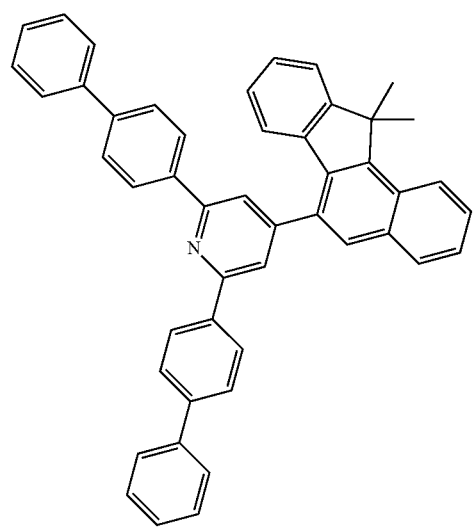
41
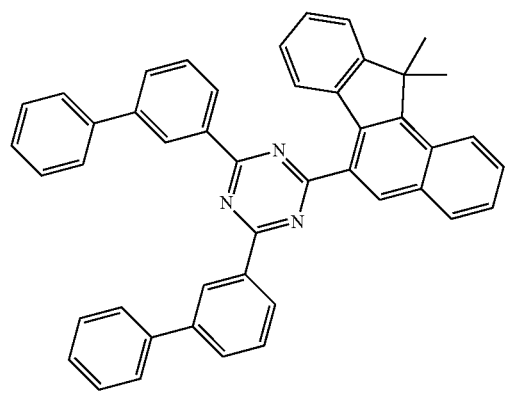
42
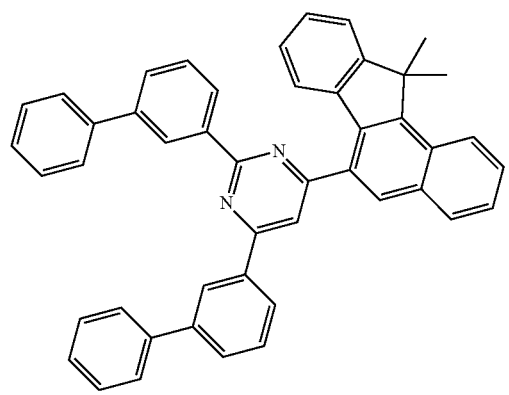

43
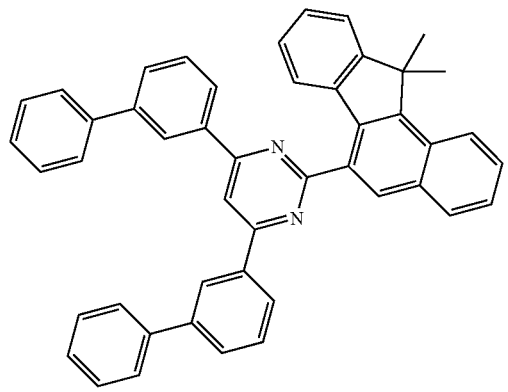
44
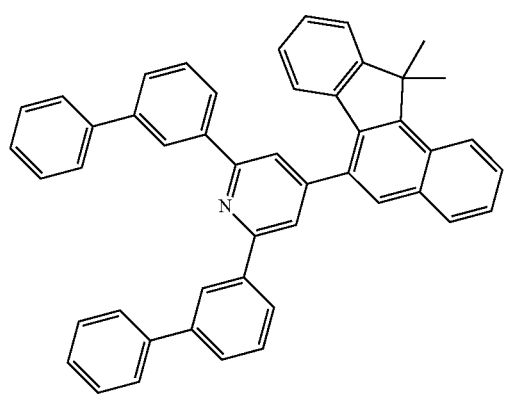
45
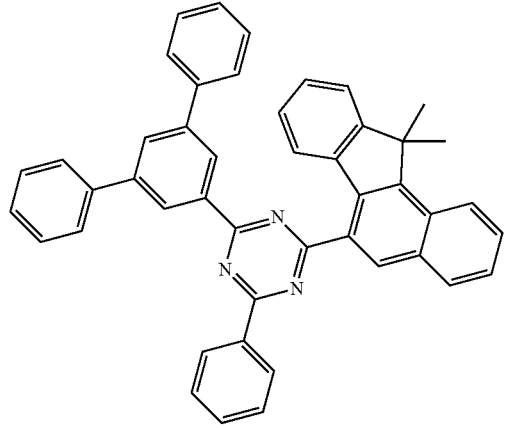
46
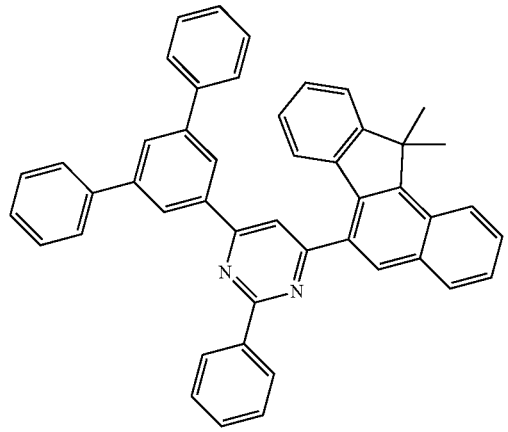
47
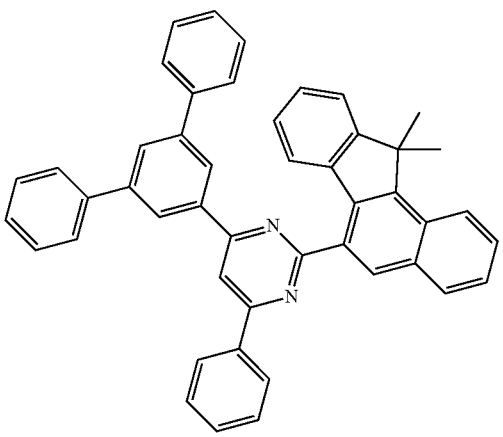
48
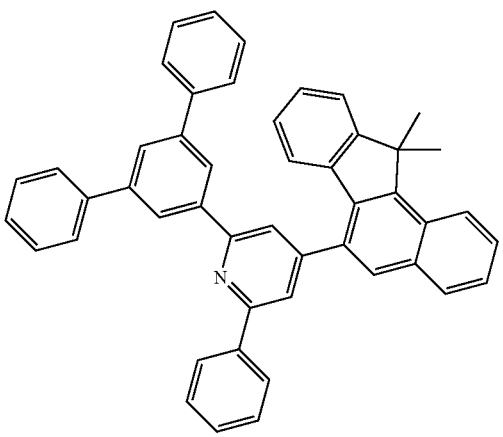
49
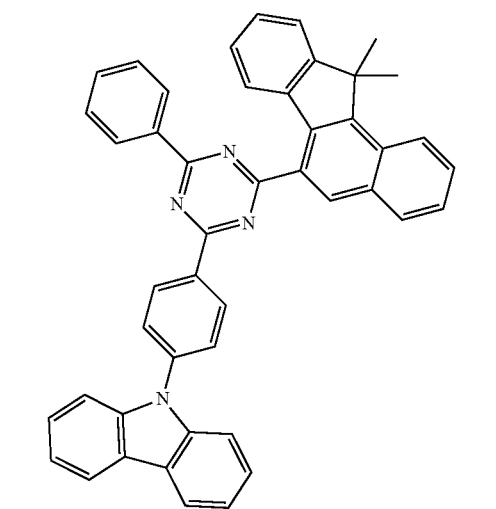

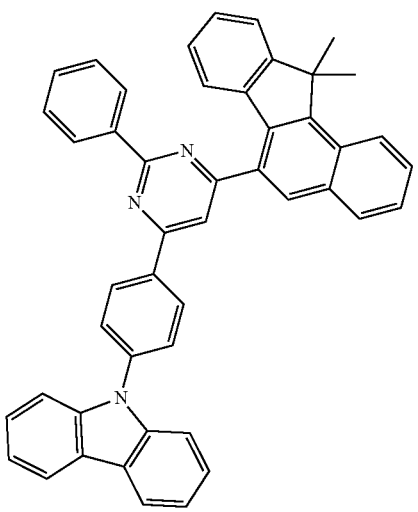
50
51
52
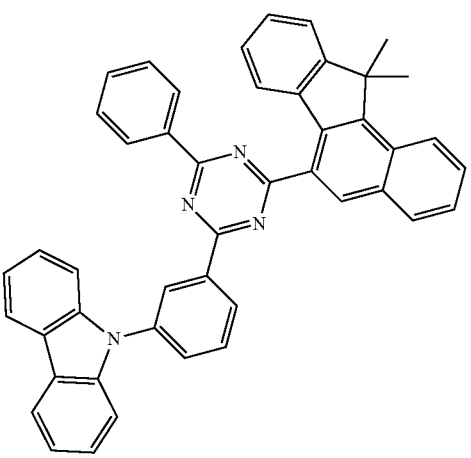
53
54
55

56
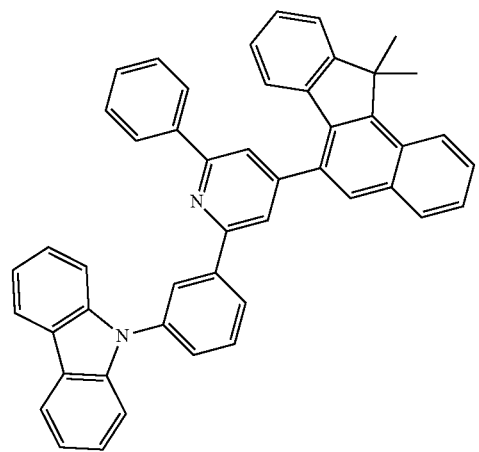
57
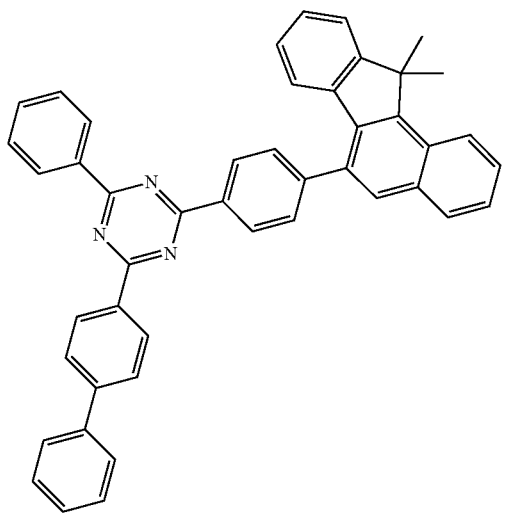
58
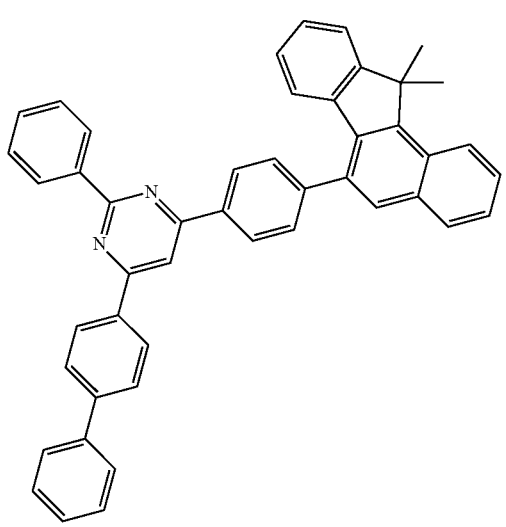
59
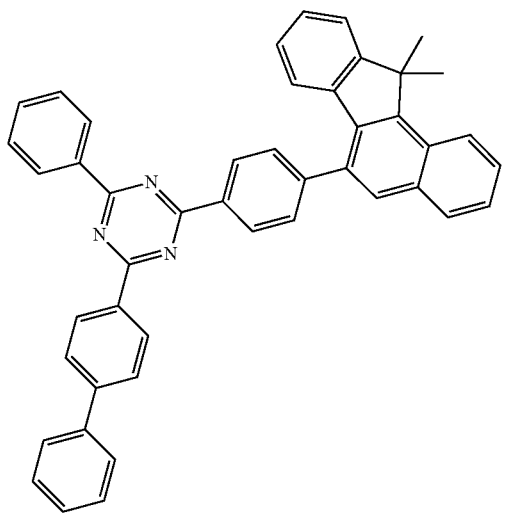
60
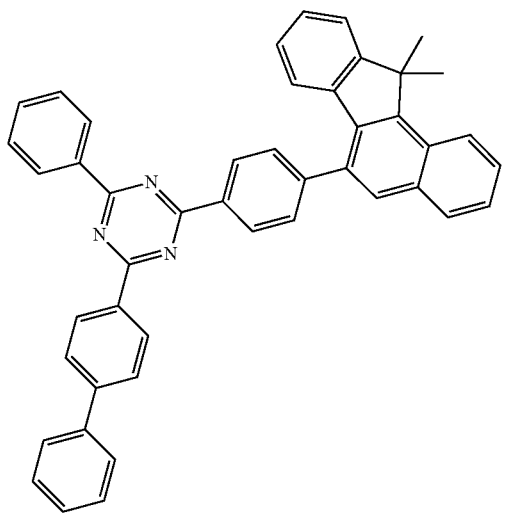
61
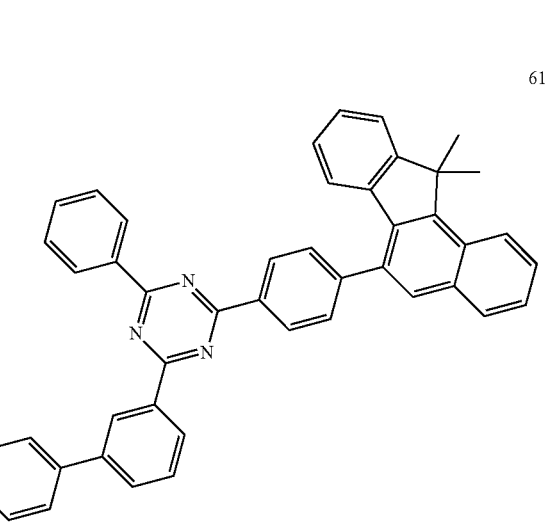

62
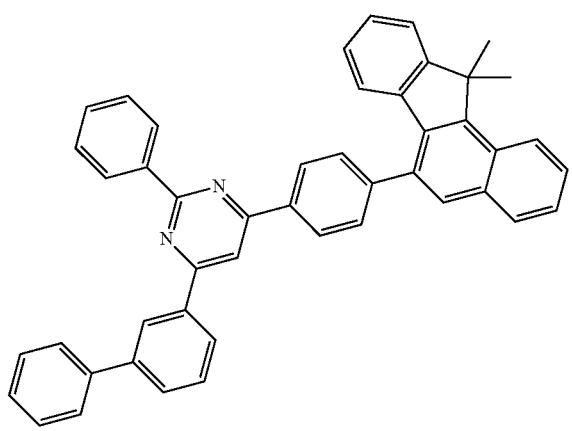
63
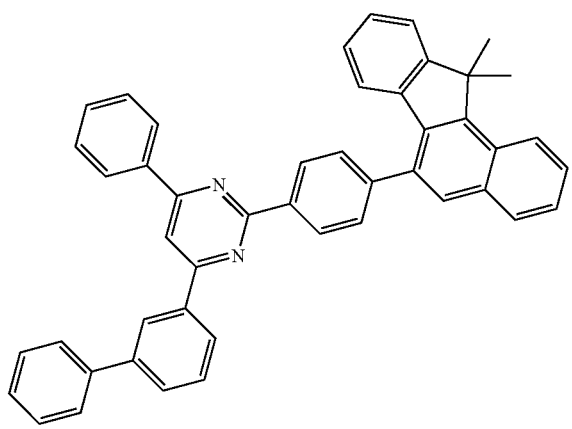
64
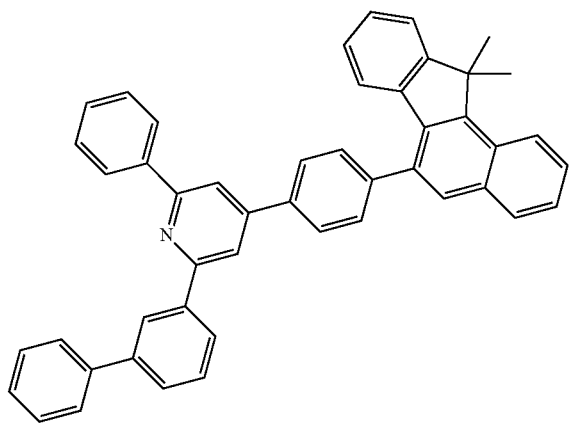
65
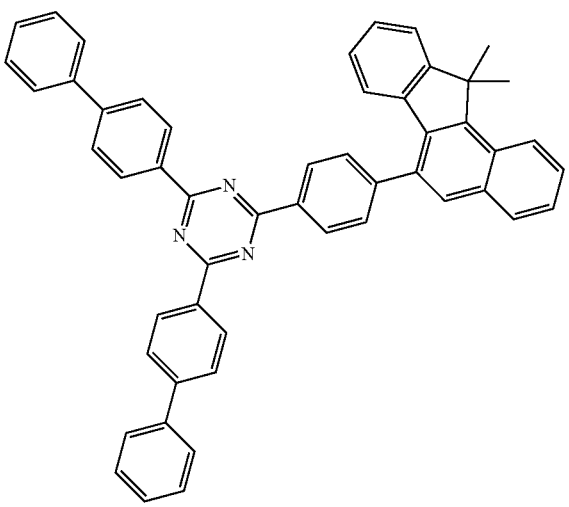
66
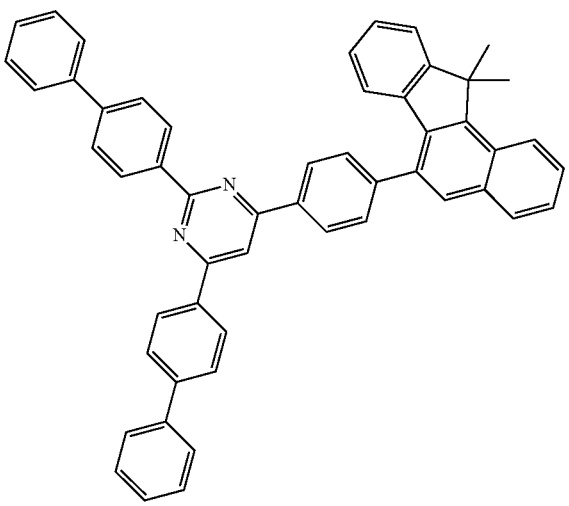
67
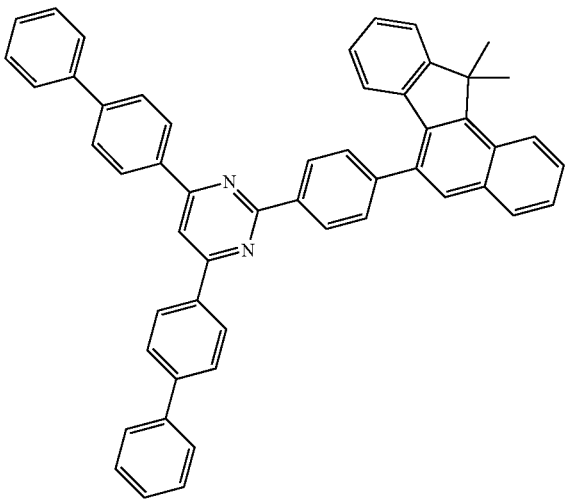

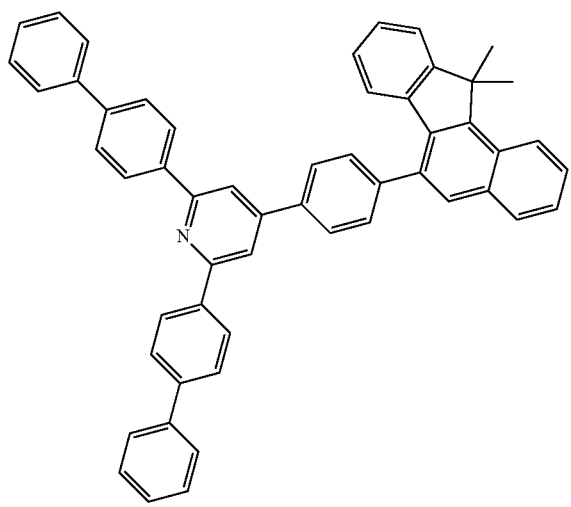
68
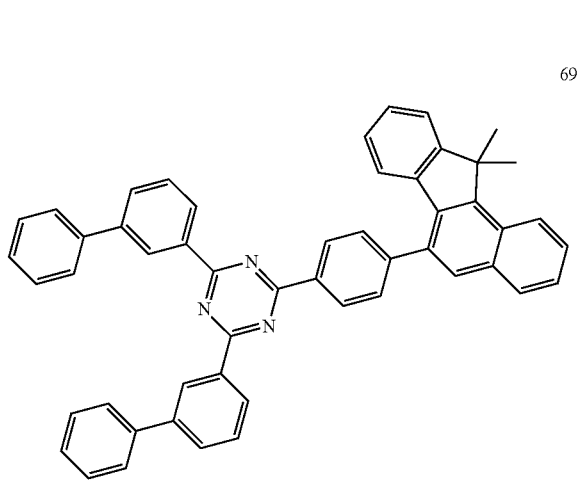
69
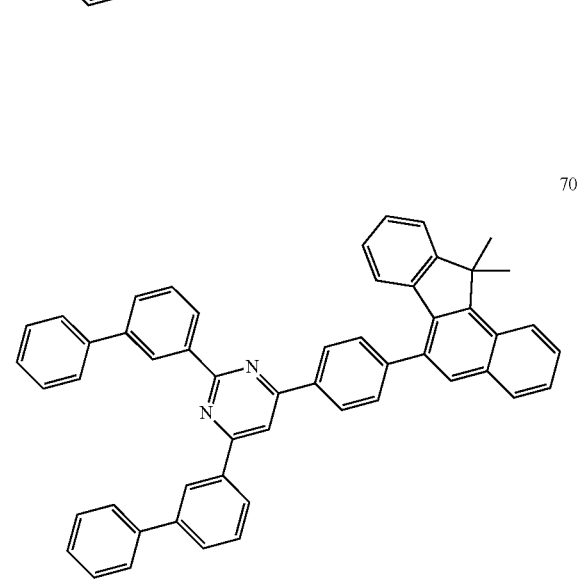
70
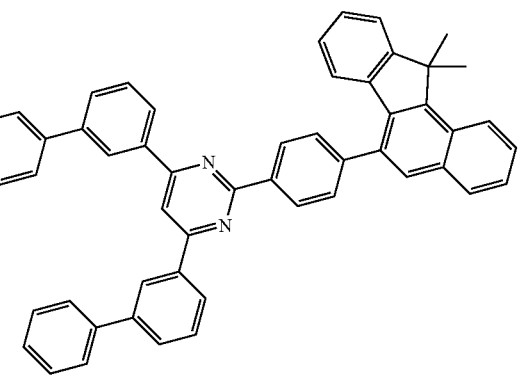
71
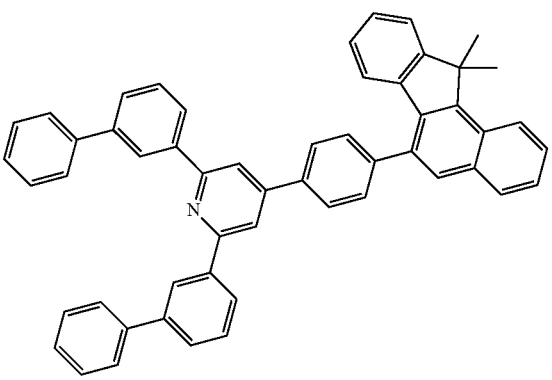
72
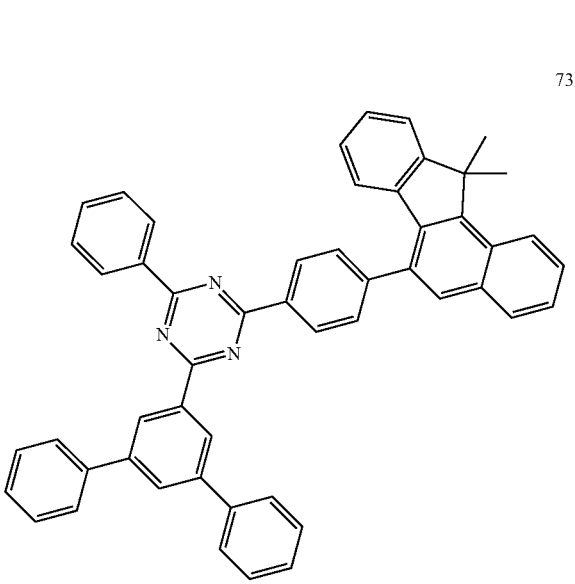
73

74
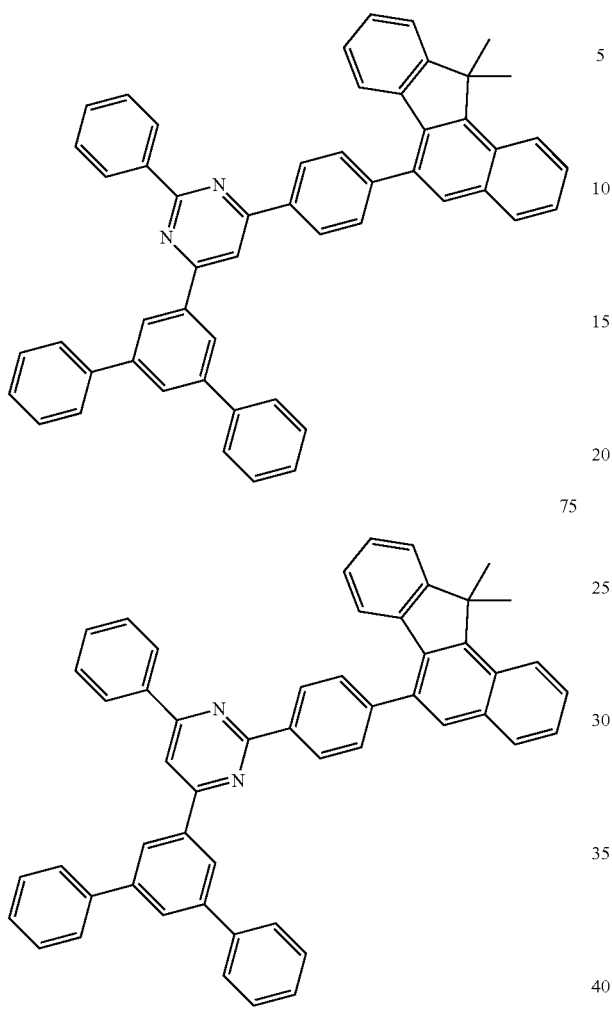
75
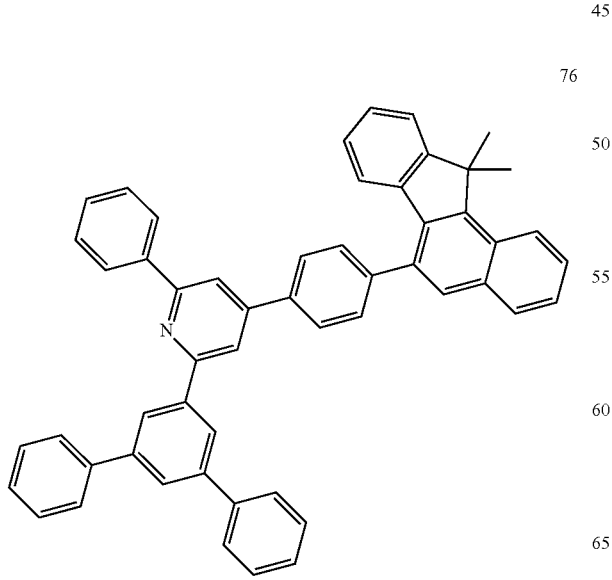
77
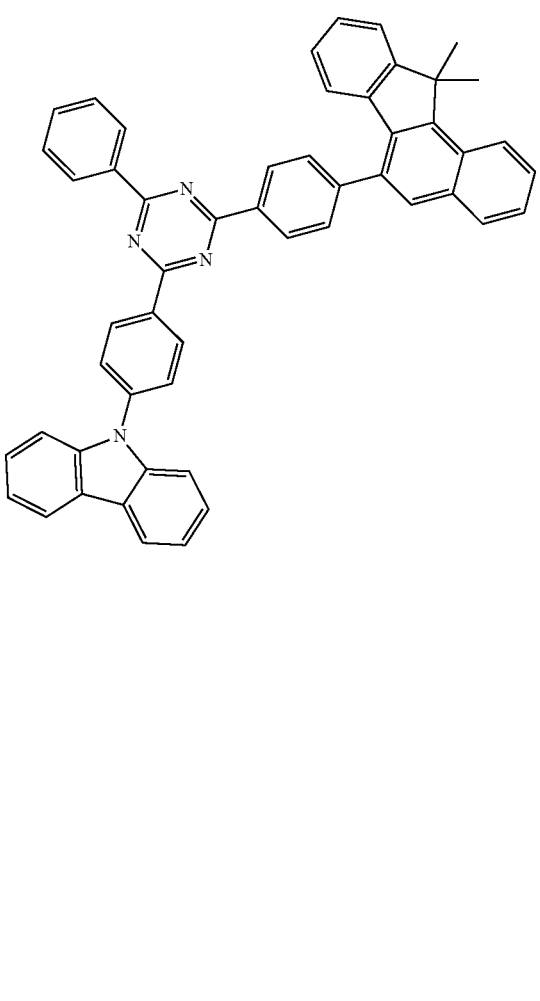
78
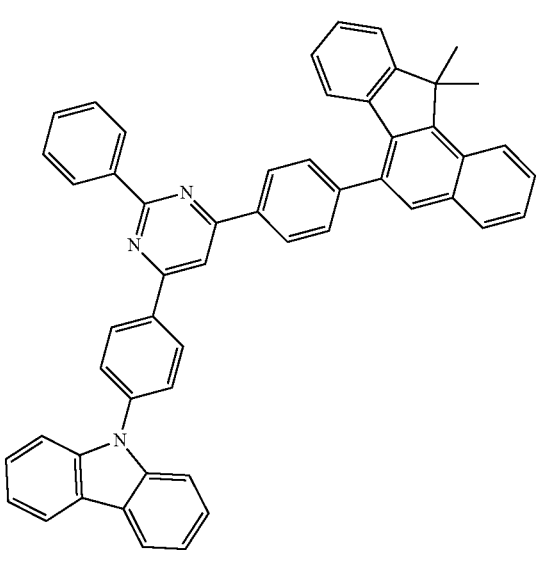

-continued
79
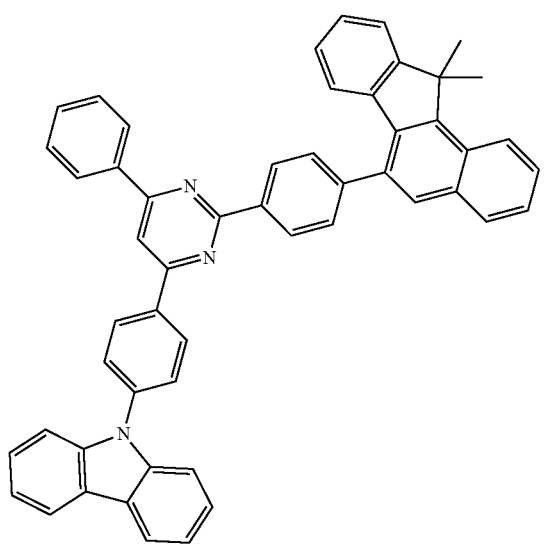
80
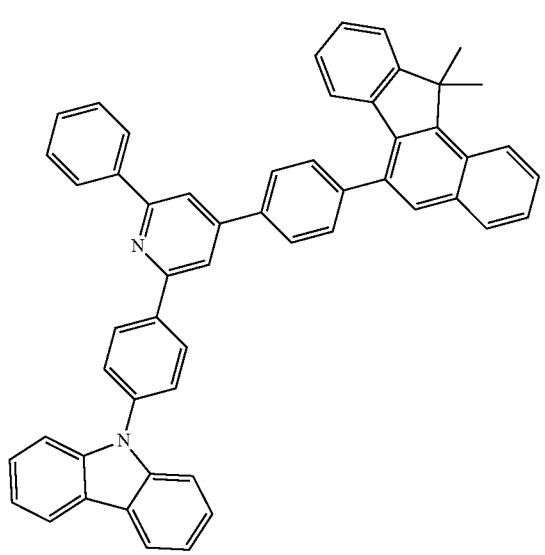
81
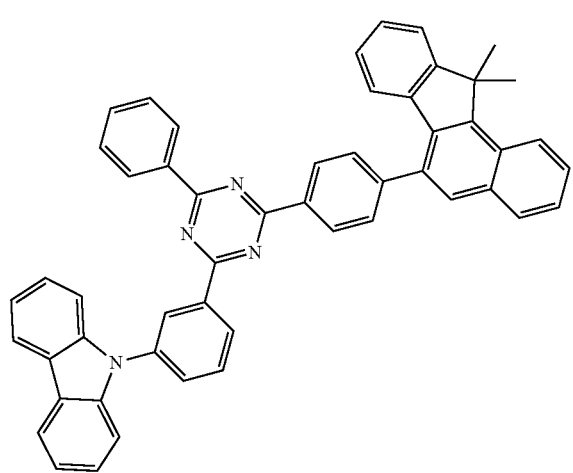
-continued
82
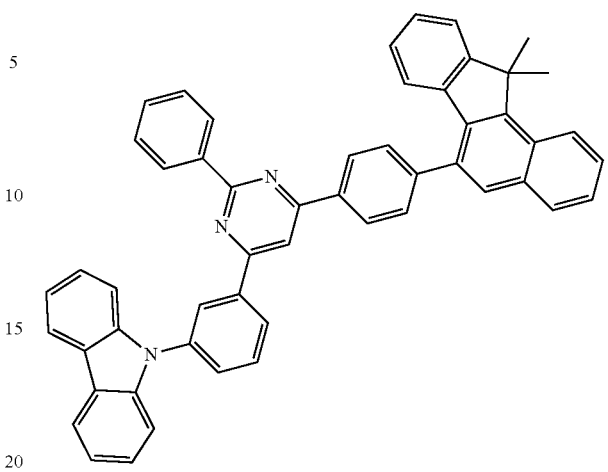
83
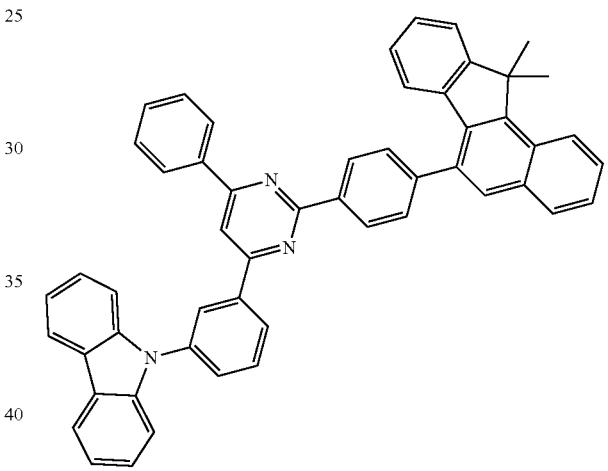
84
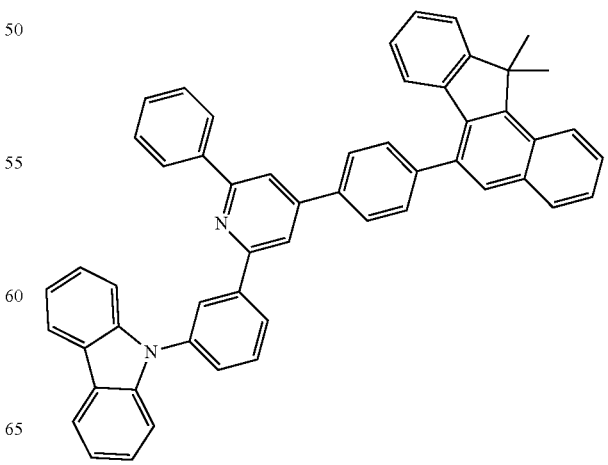

191
-continued
85
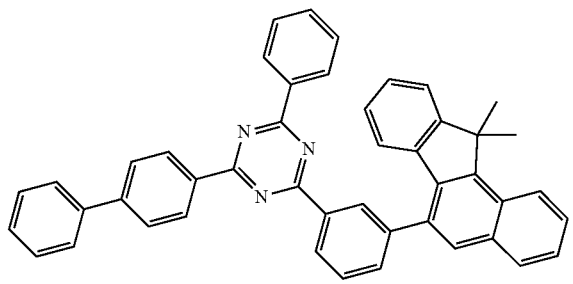
86
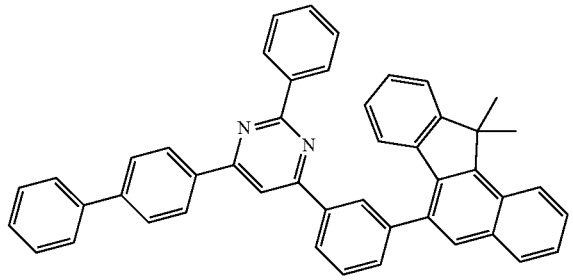
87
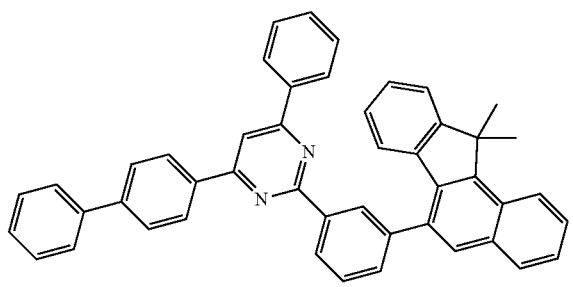
88
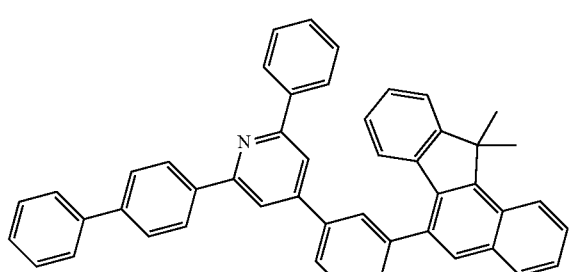
89
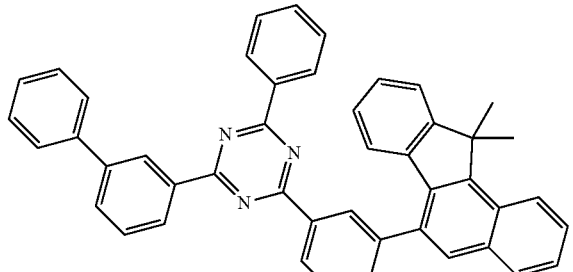
192
-continued
90
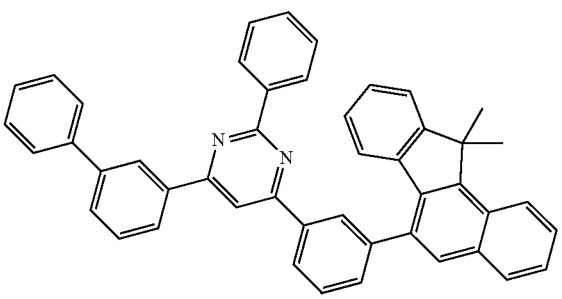
91
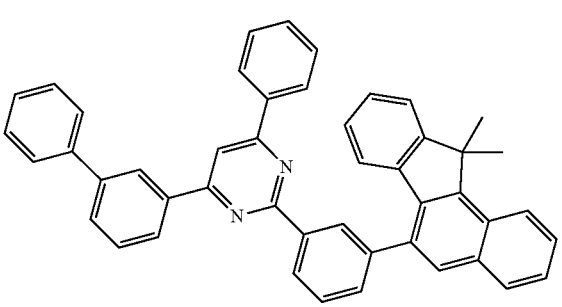
92
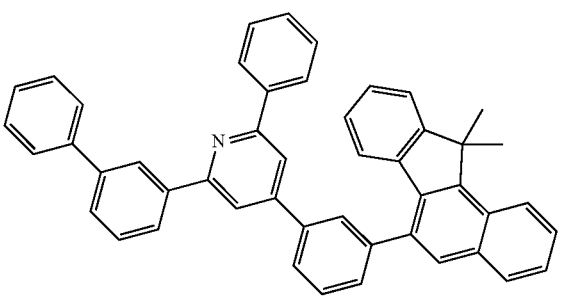
93
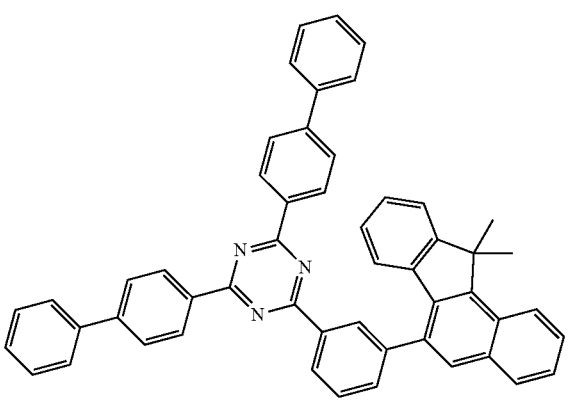

94
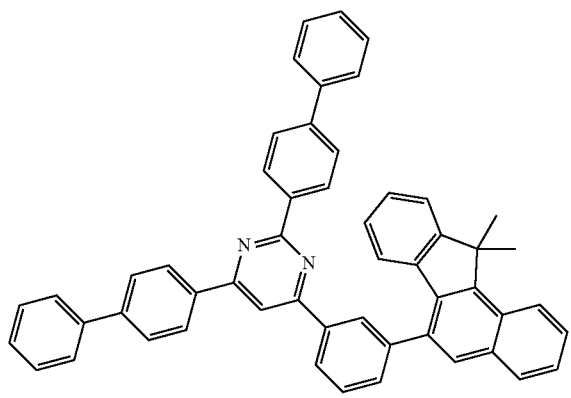
95
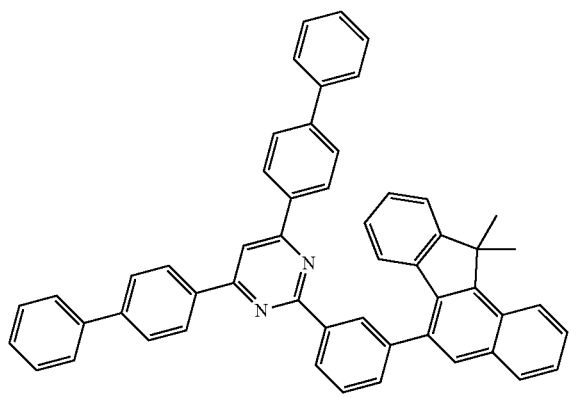
96
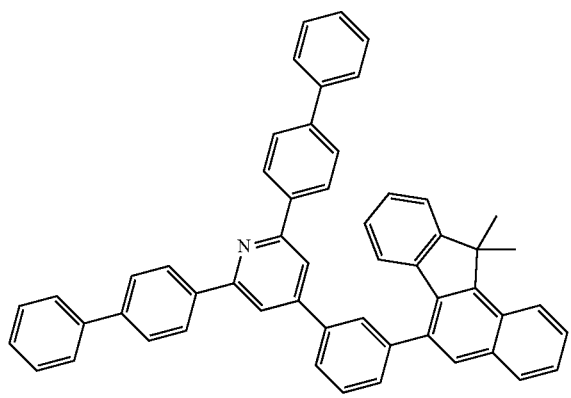
97
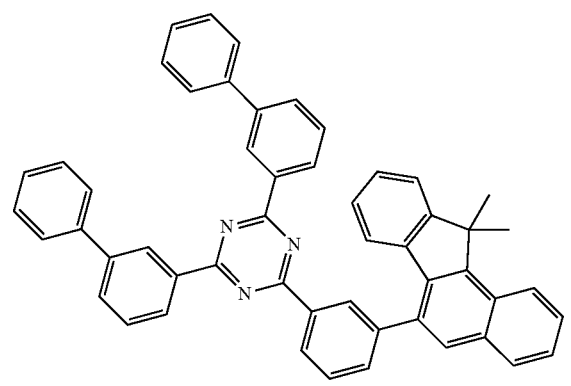
98
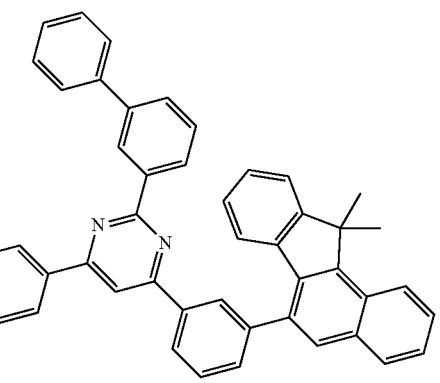
99
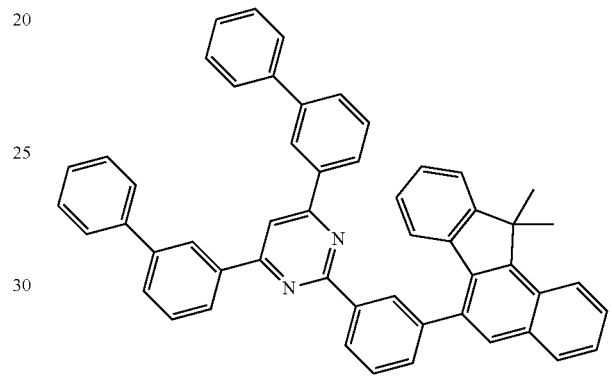
100
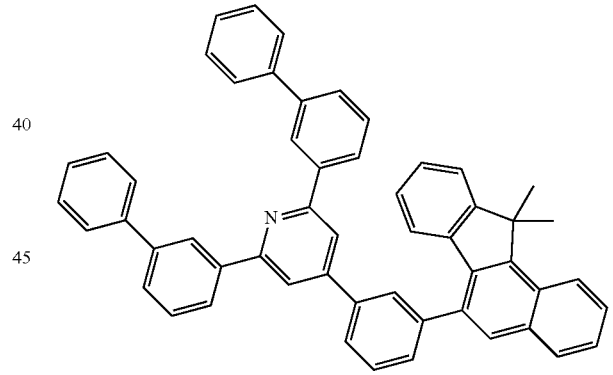
101
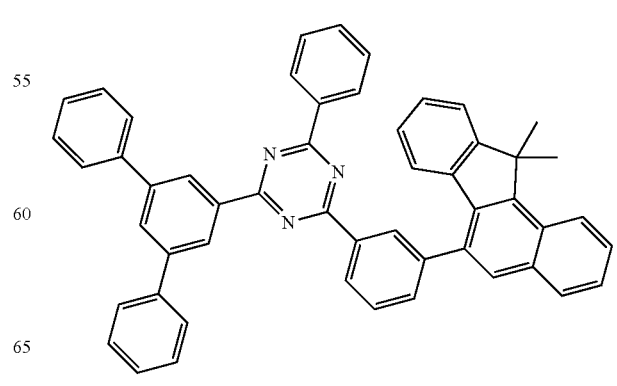

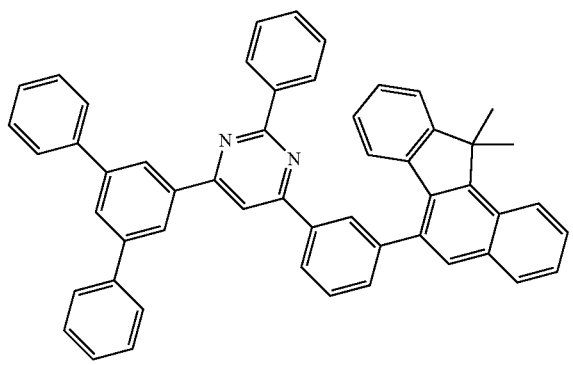
102
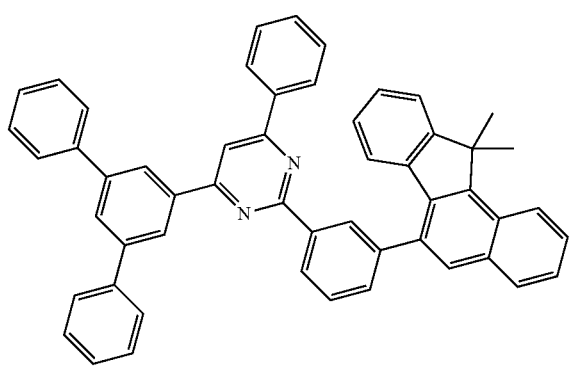
103
104
105
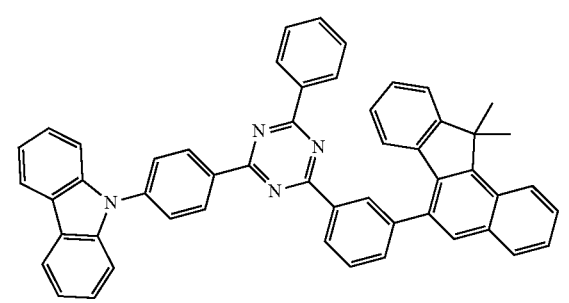
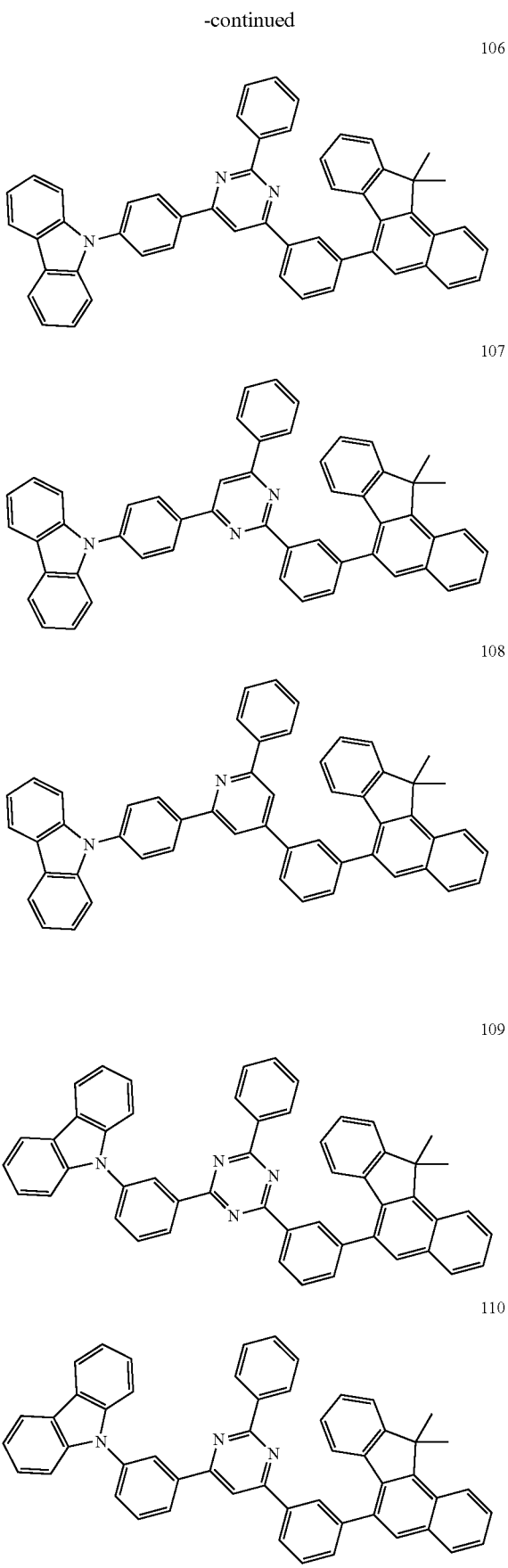

111
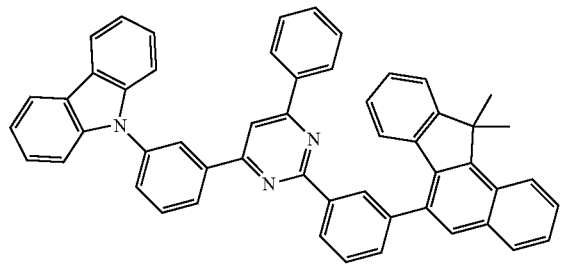
112
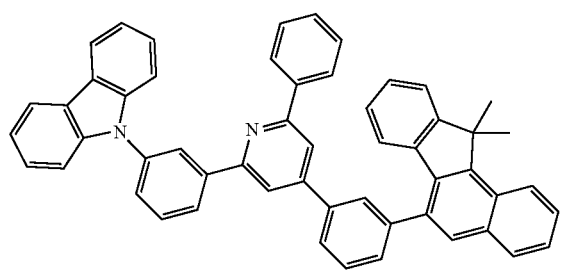
113
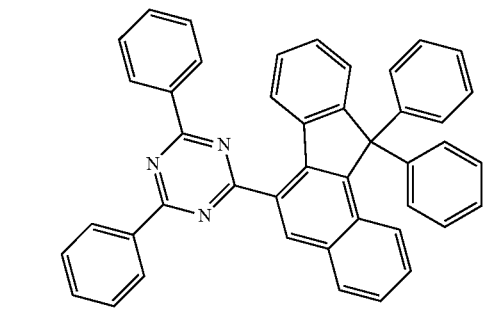
114
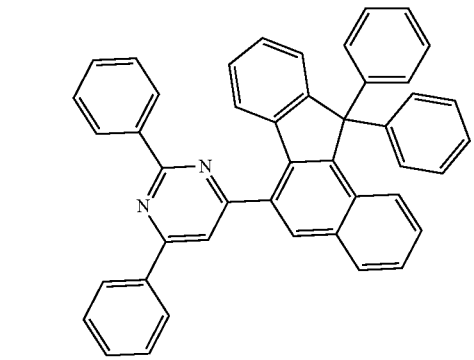
115
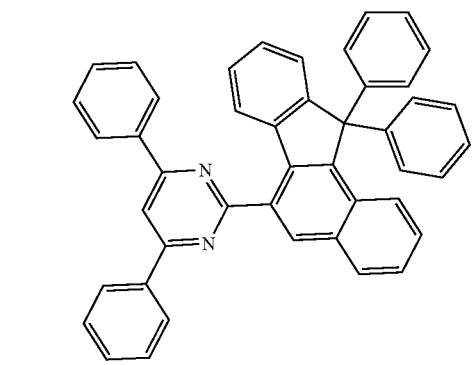
116
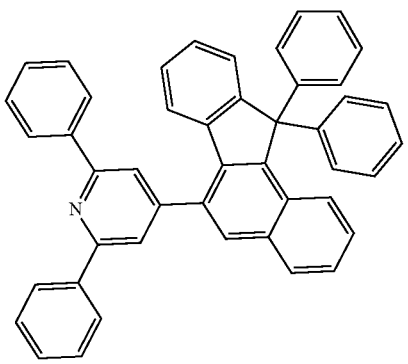
117
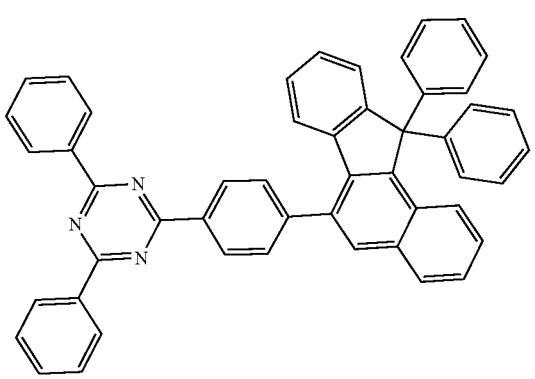
118
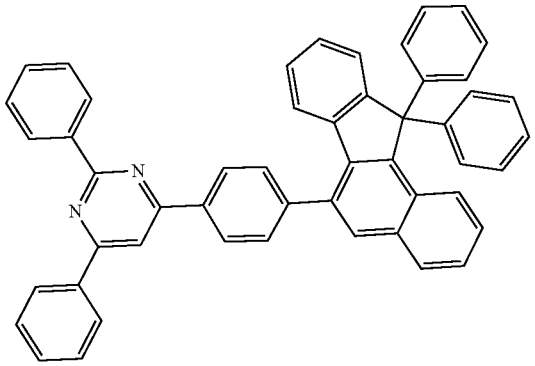
119
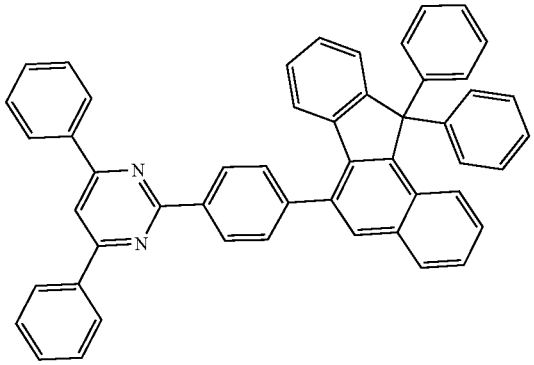

120
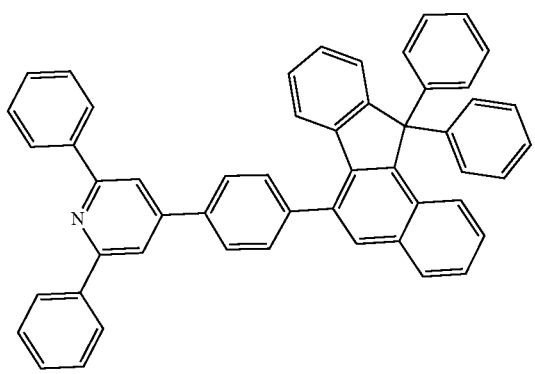
121
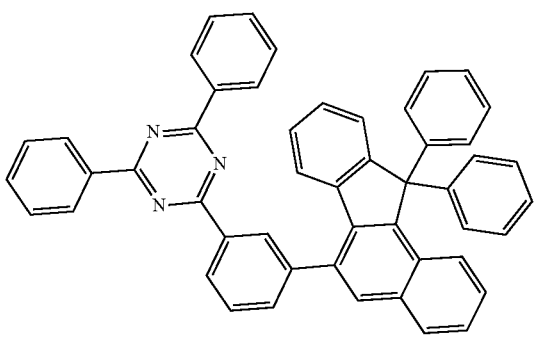
122
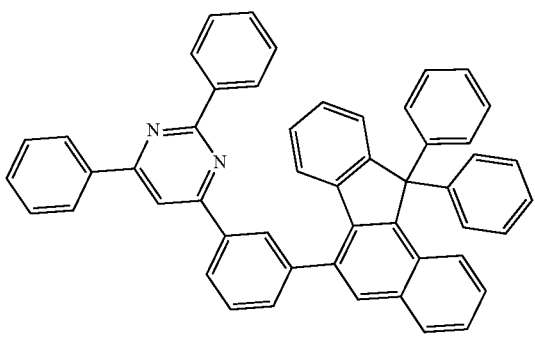
123
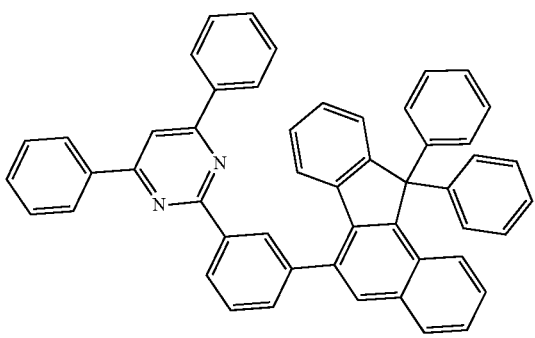
124
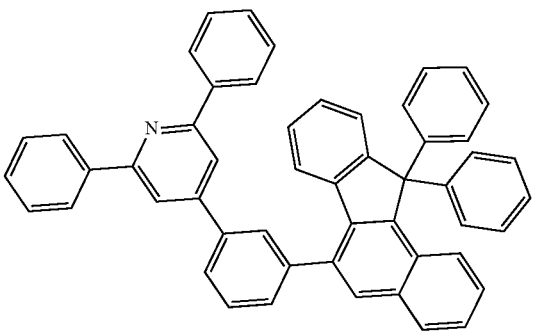
125
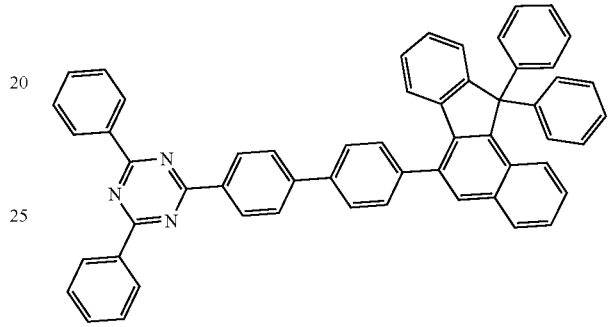
126
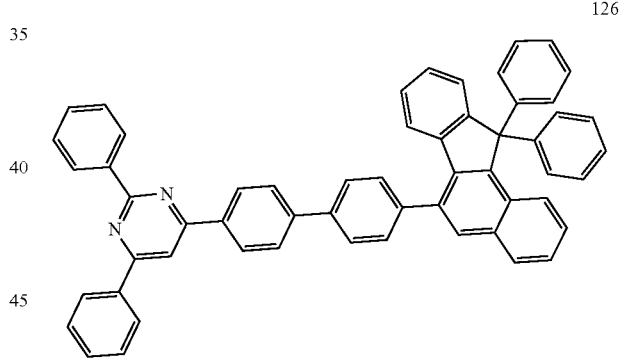
127
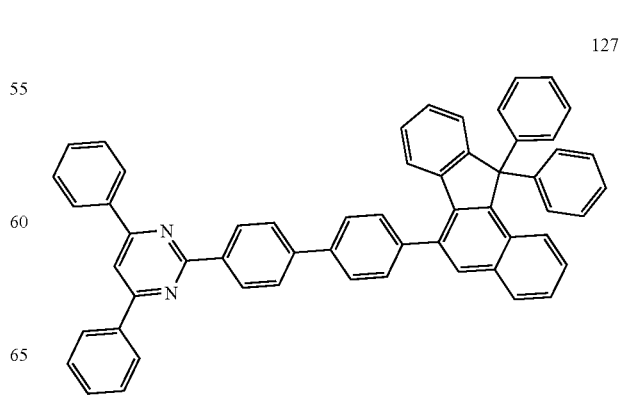

128
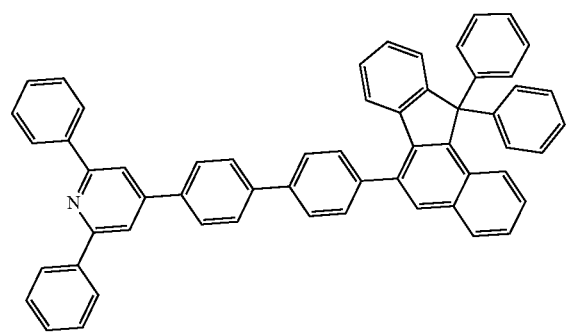
129
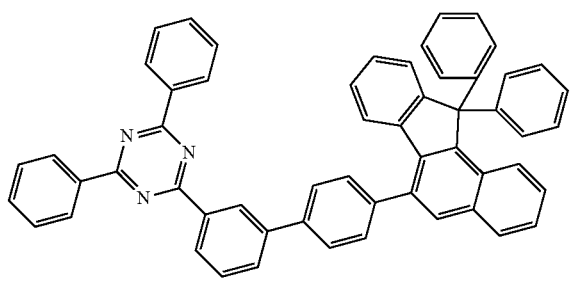
130
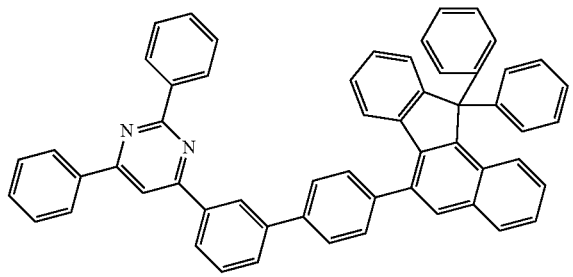
131
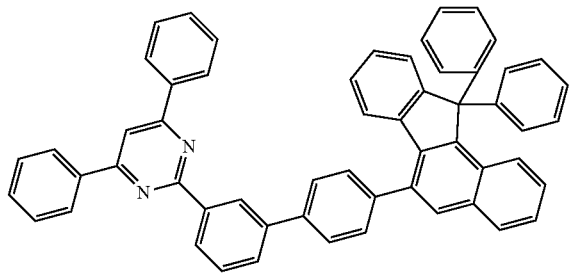
132
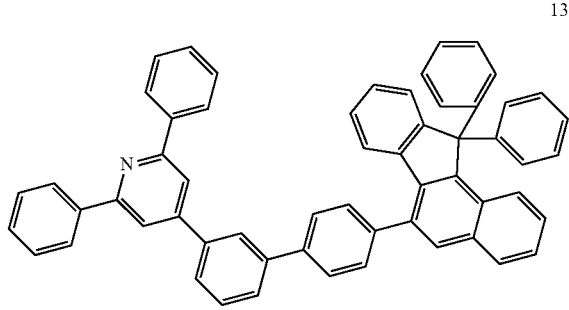
133
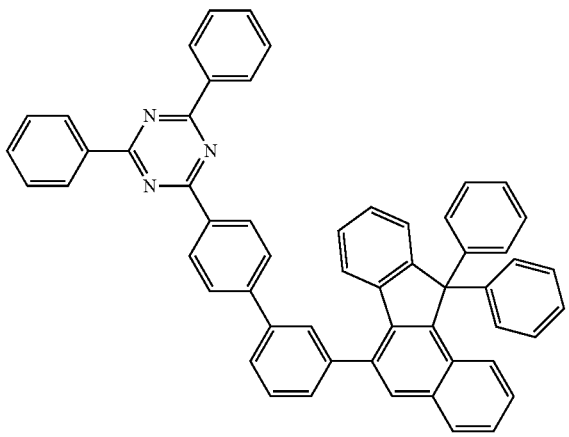
134
135

136
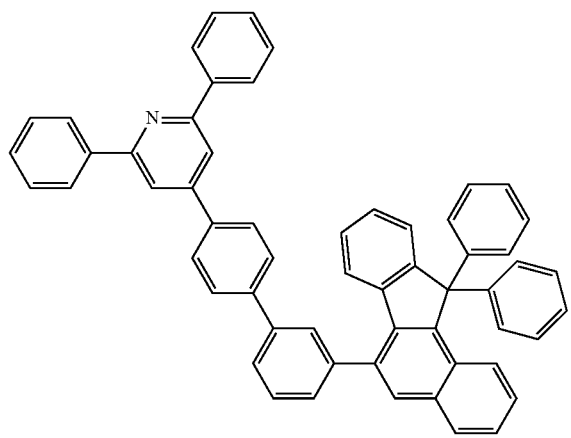
137
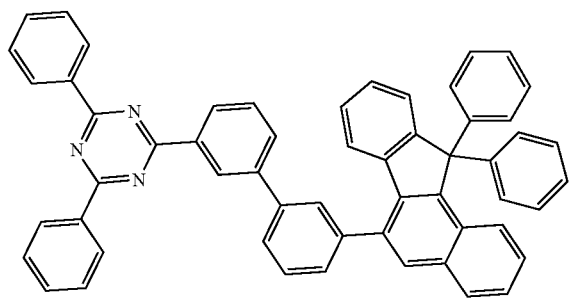
138
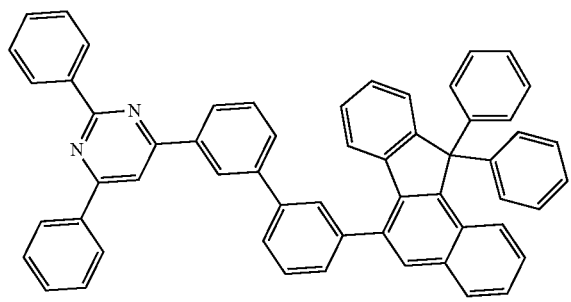
139
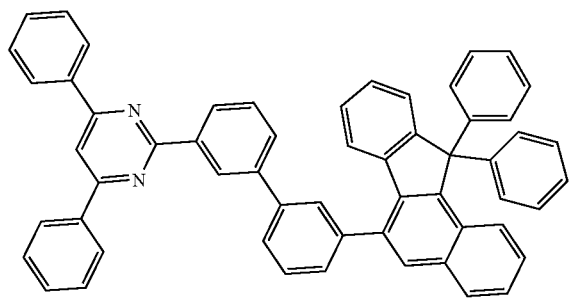
140
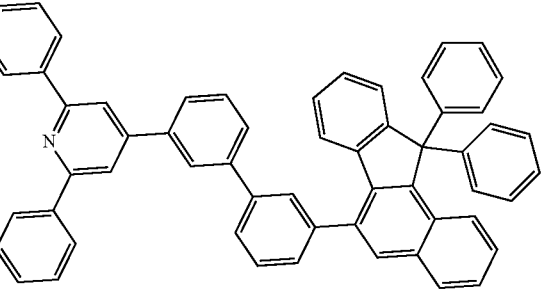
141
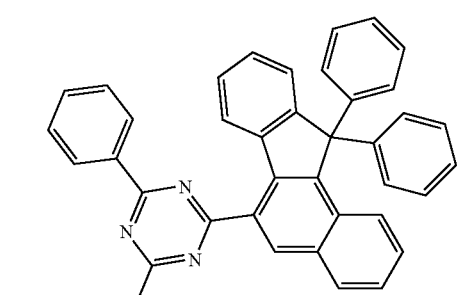
142
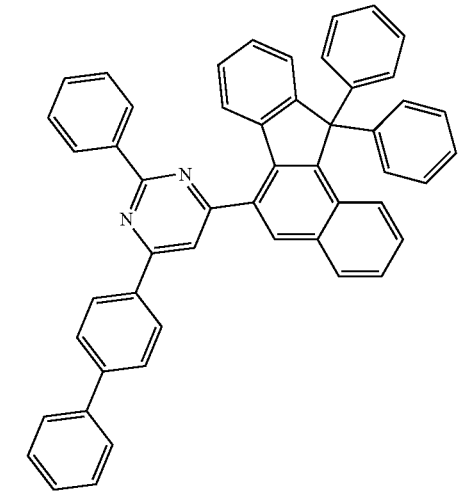

143 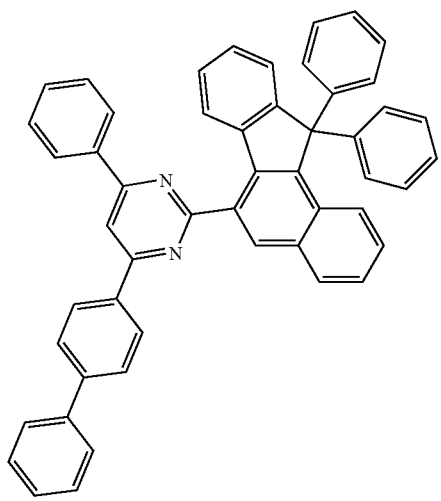
144 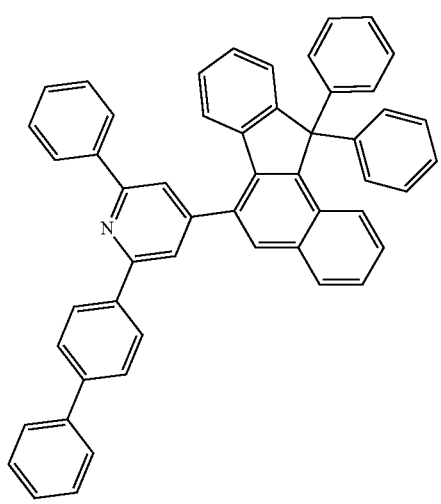
145 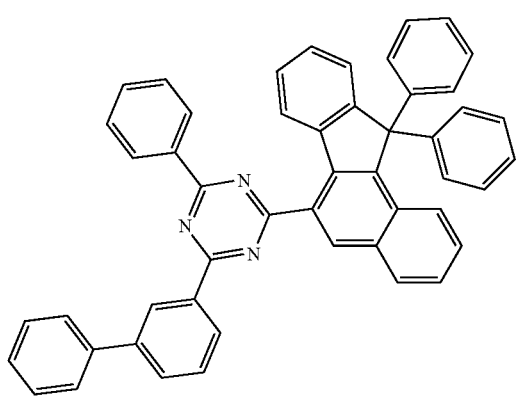
146 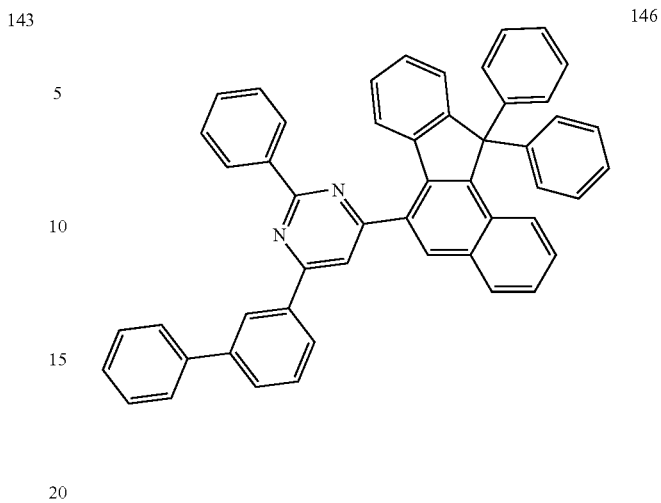
147 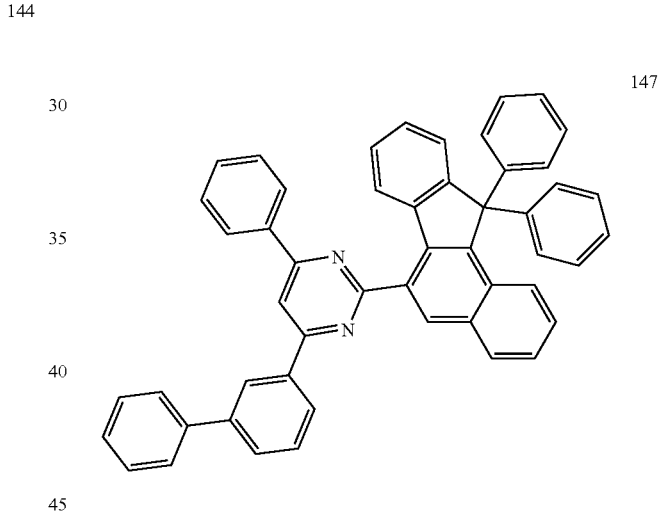
148 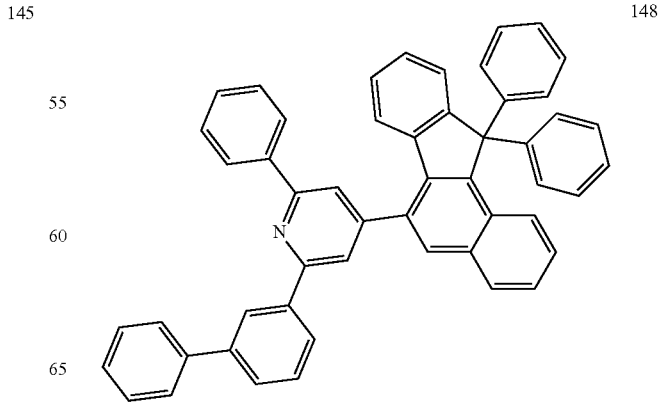

207
-continued
149
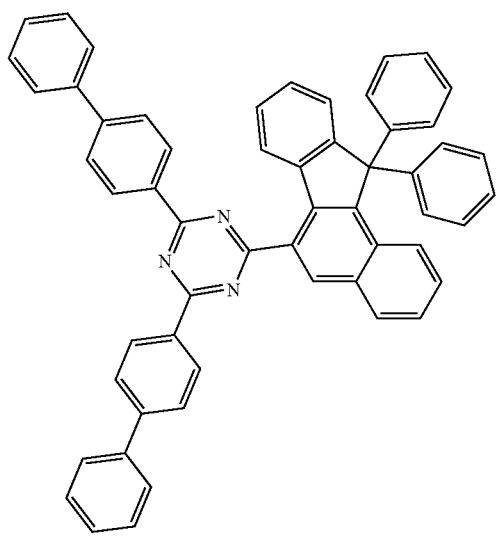
150
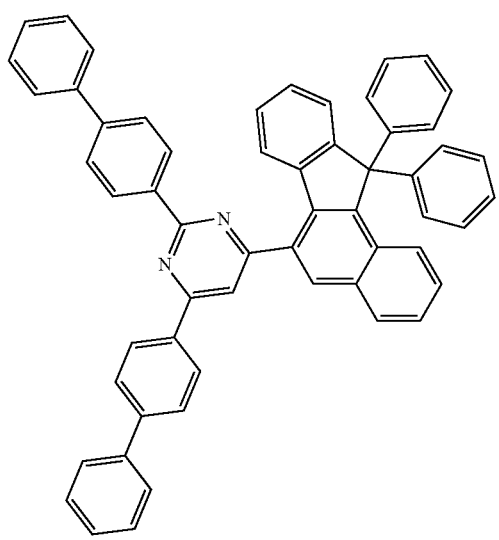
151
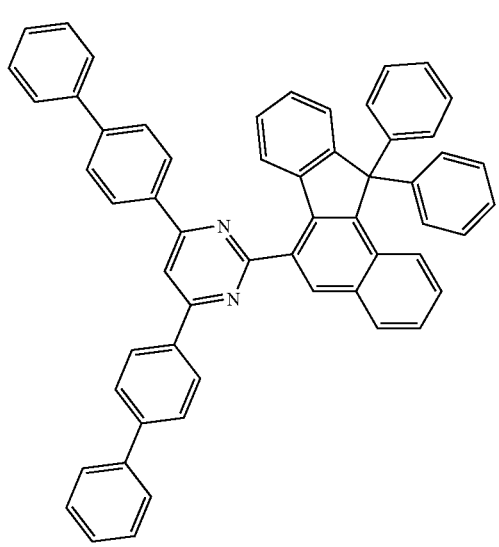
208
-continued
152
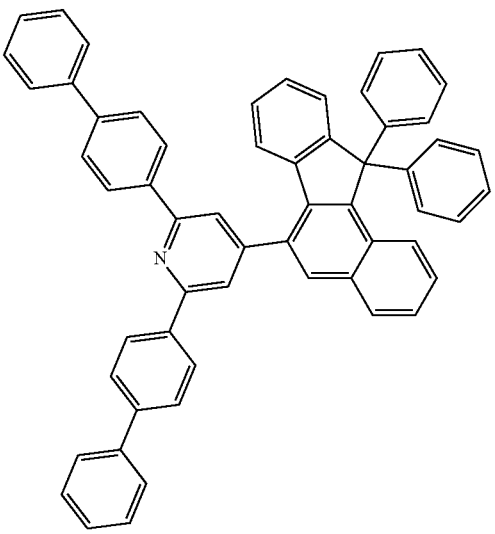
153
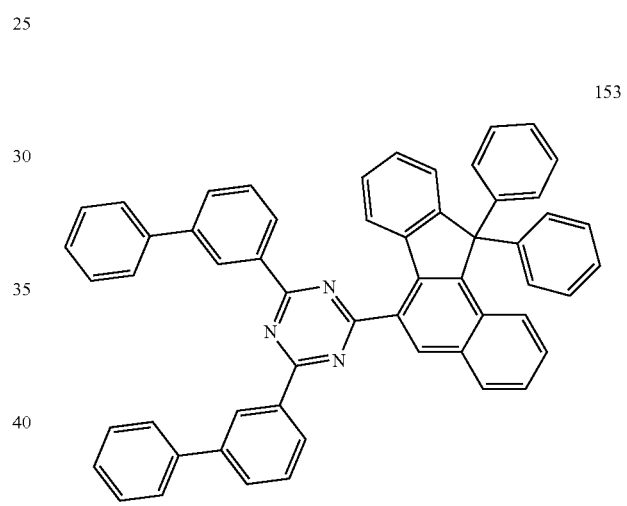
154
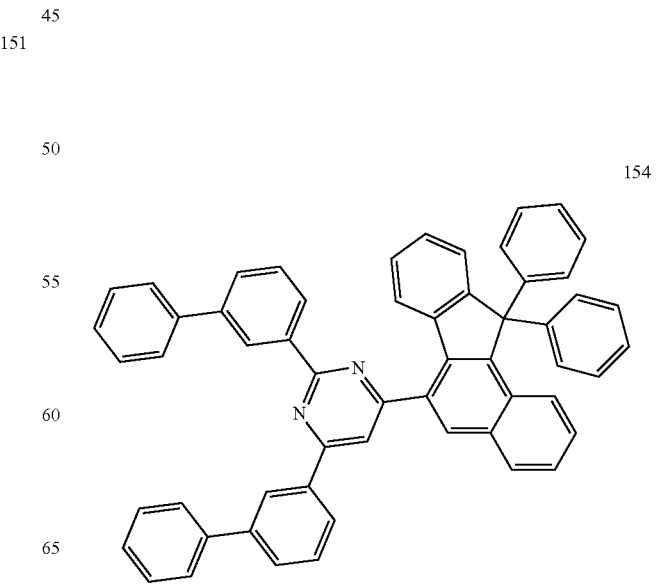

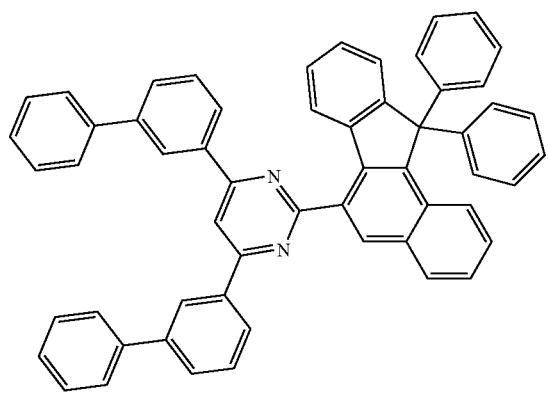
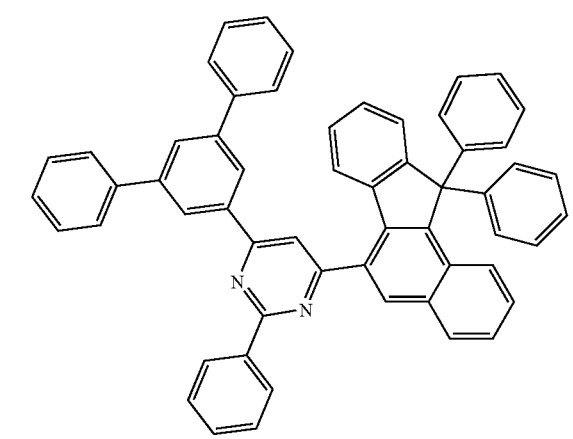

-continued
161
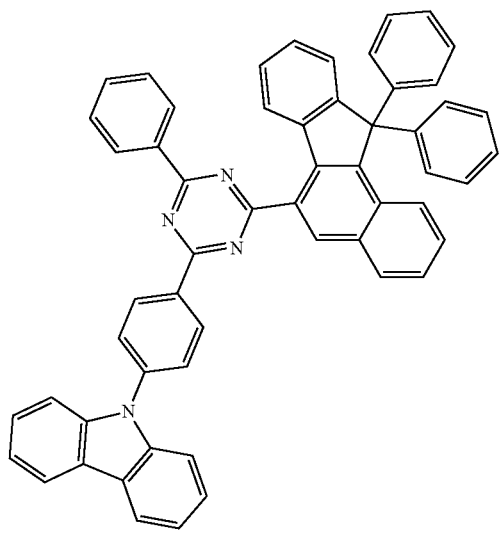
162
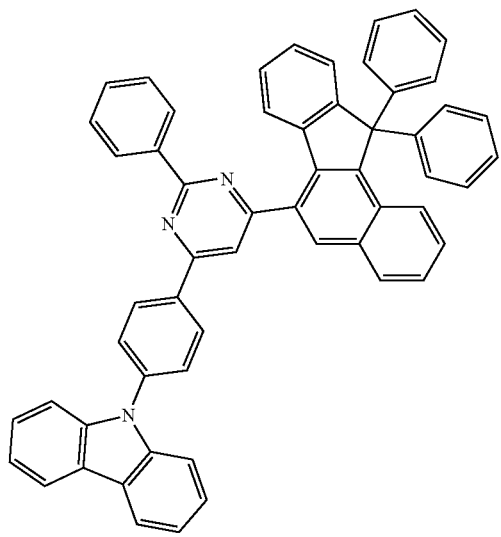
163
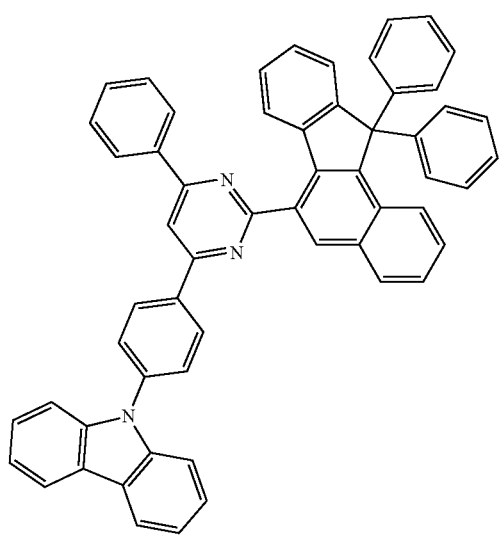
-continued
164
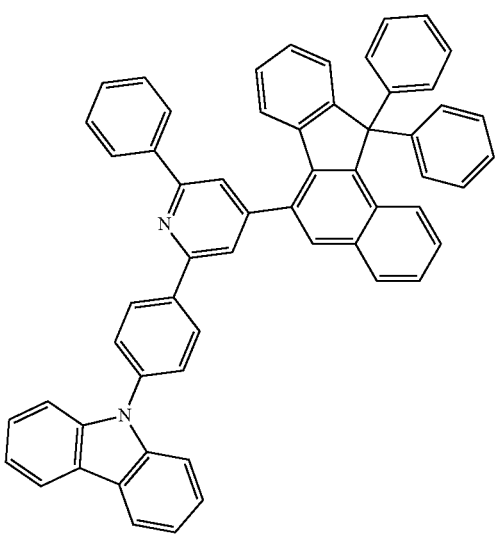
165
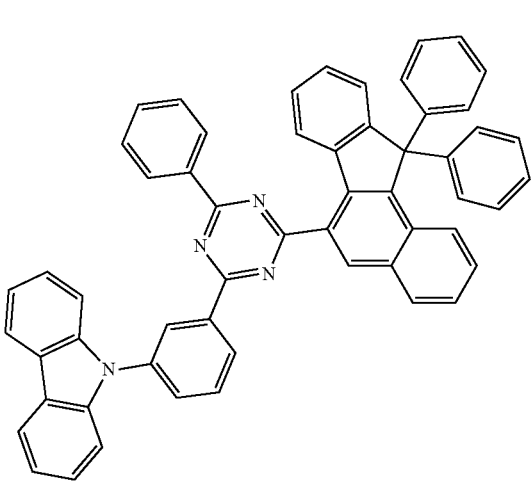
166
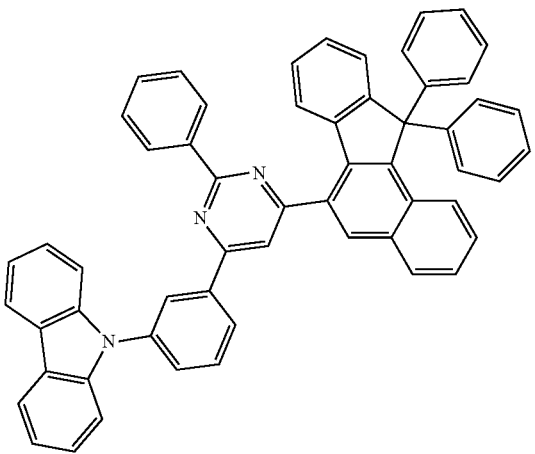

-continued
167
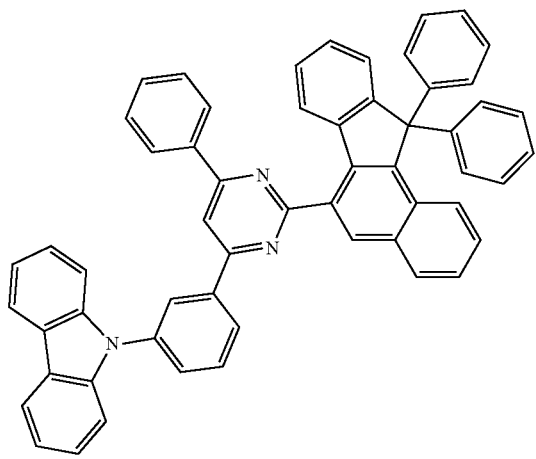
168
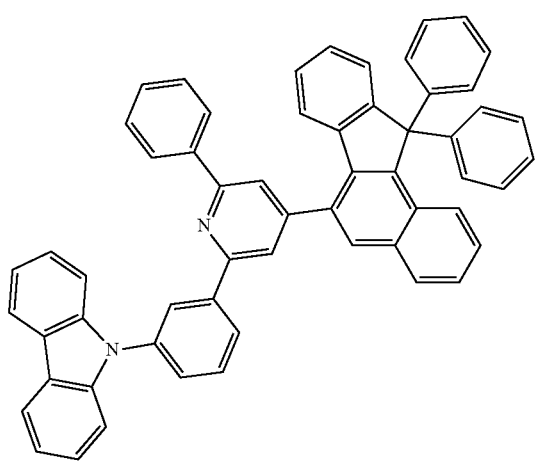
169
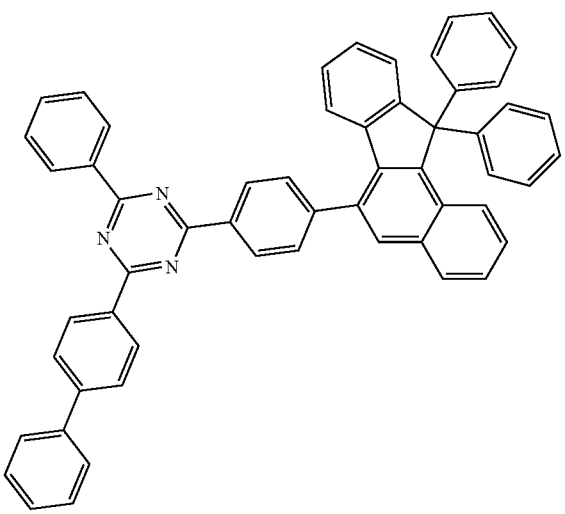
-continued
170
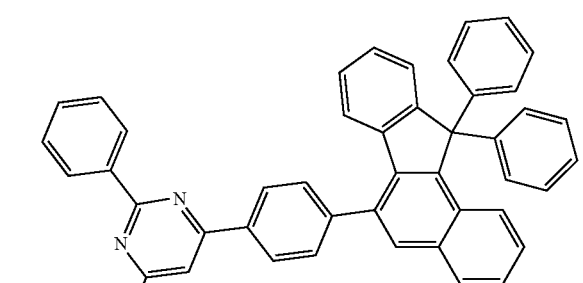
171
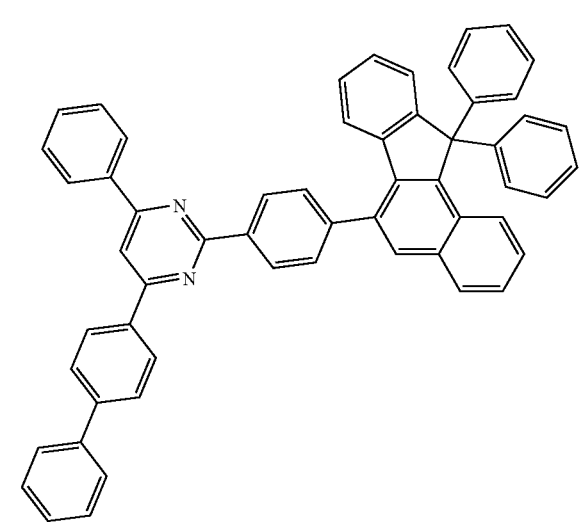
172
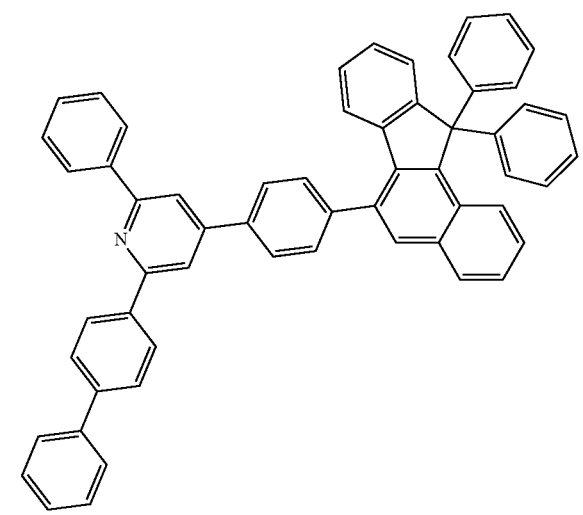

173
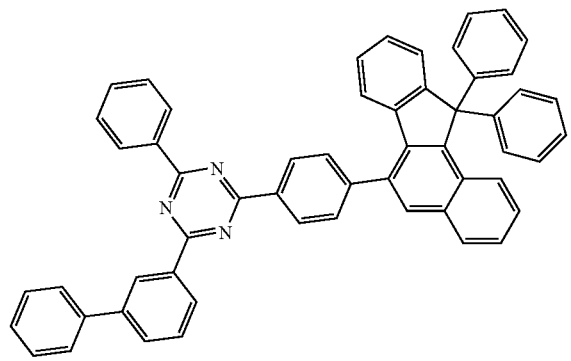
174
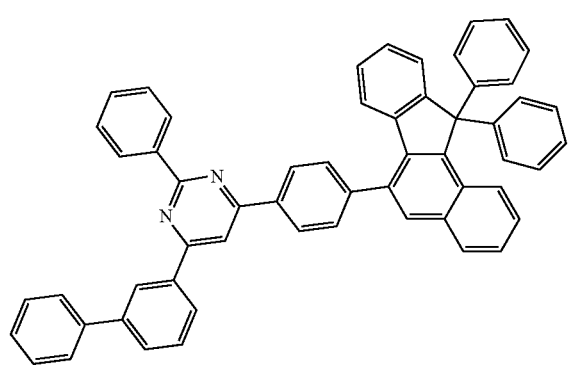
175
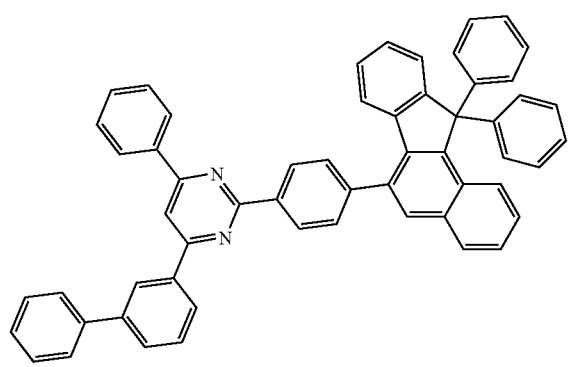
176
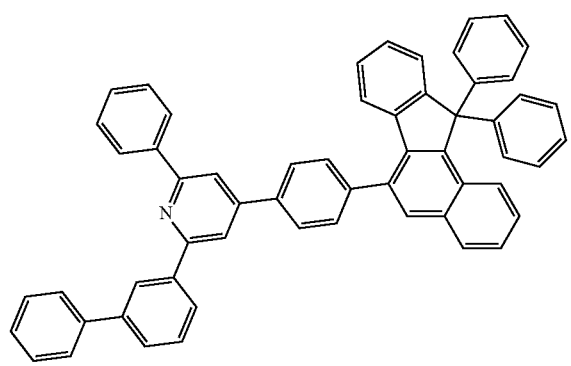
177
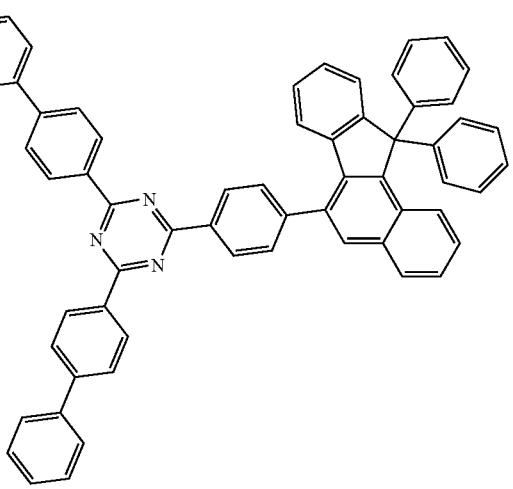
178
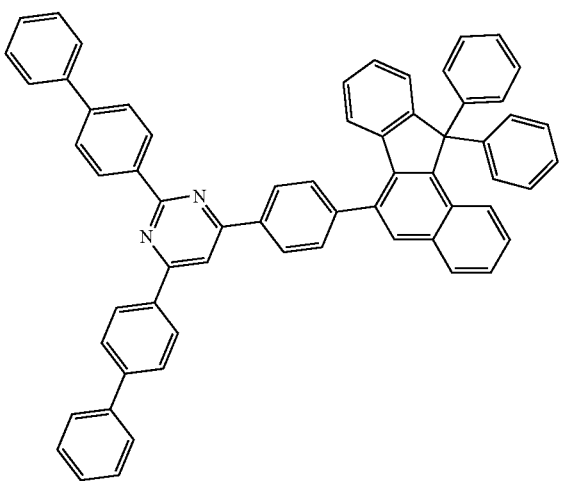
179
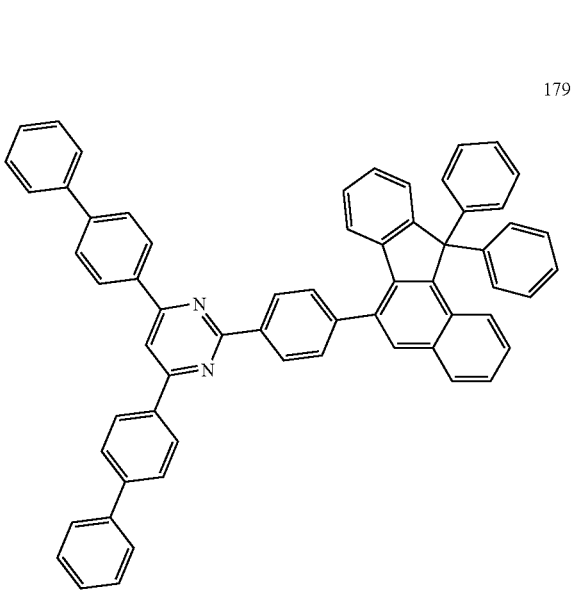

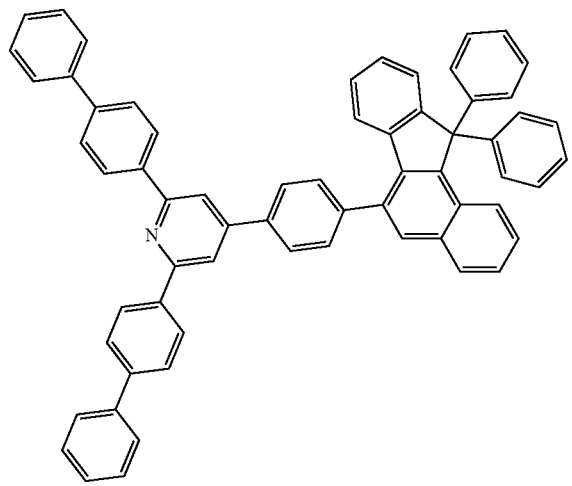
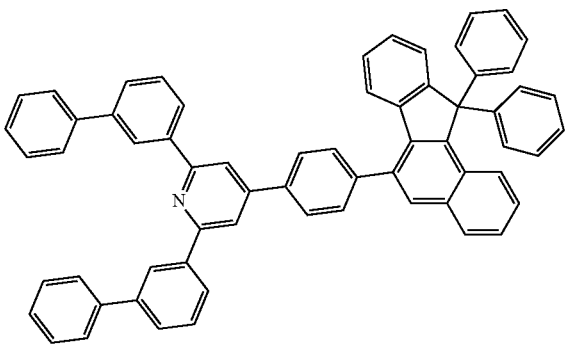
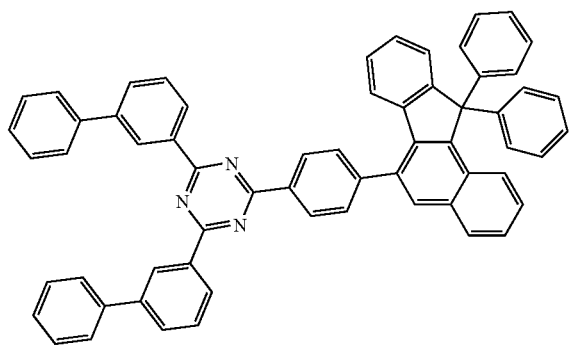

187
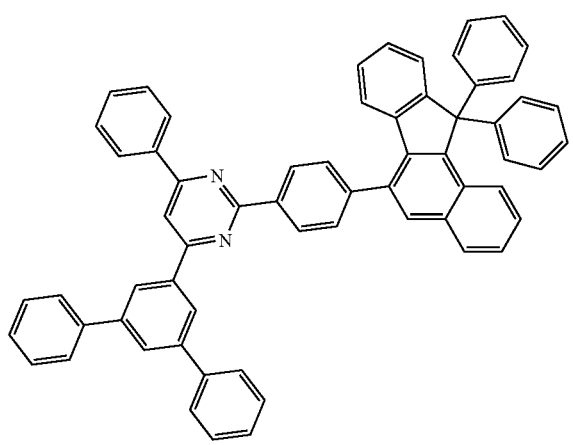
188
190
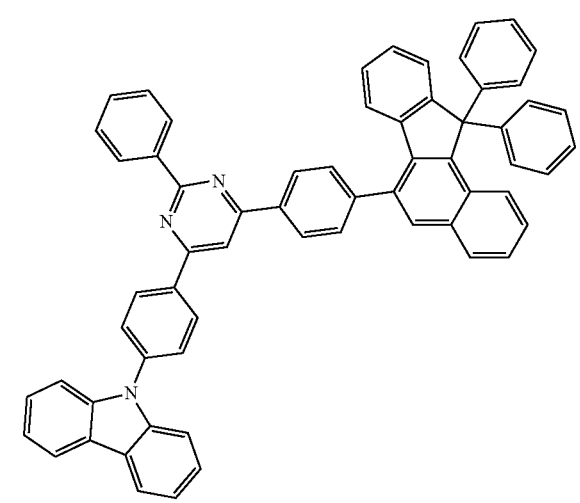
191
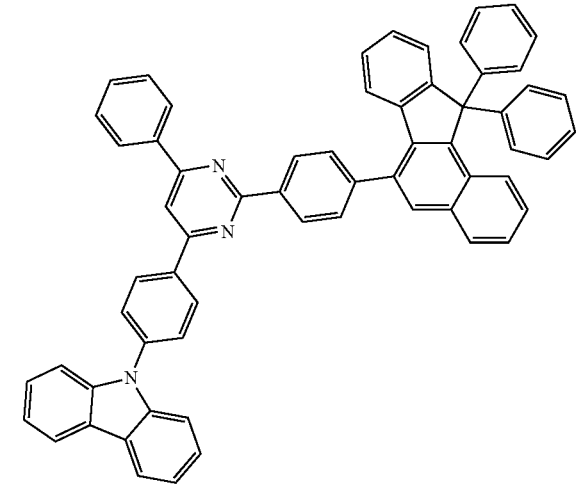
189
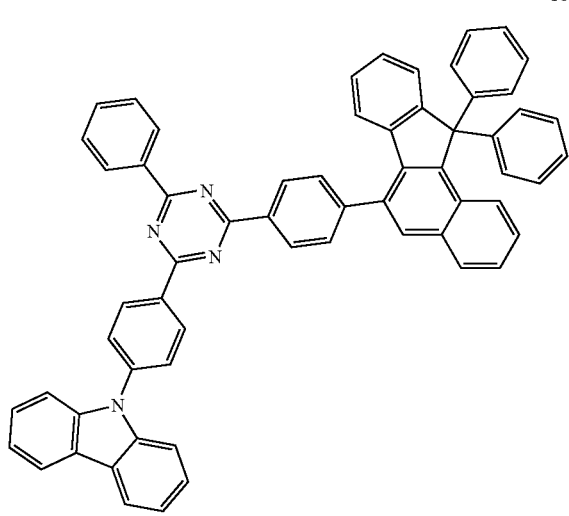
192
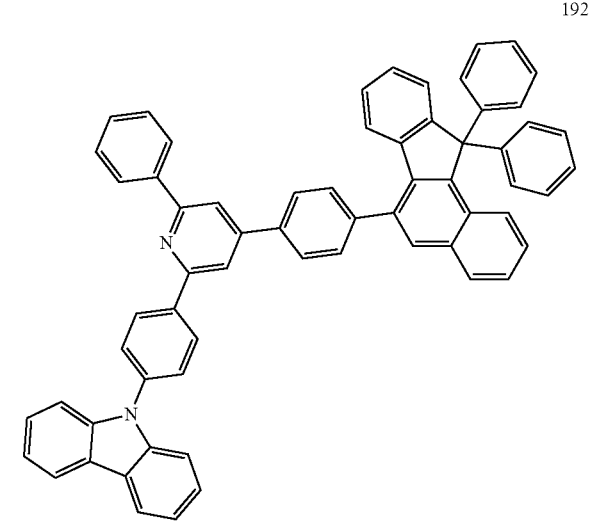

193
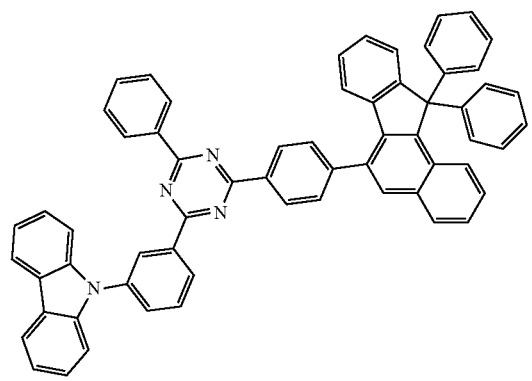
194
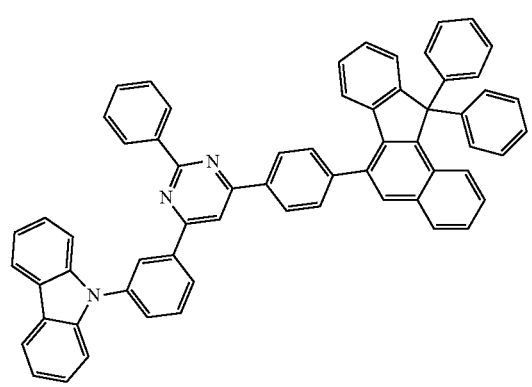
195
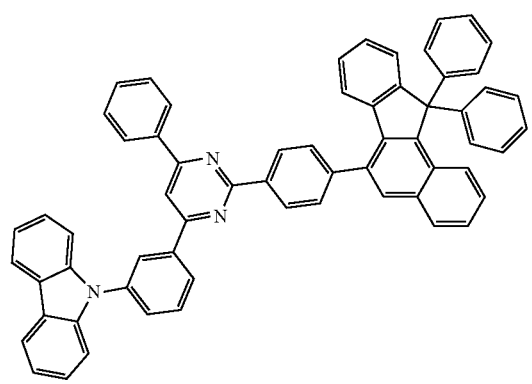
196
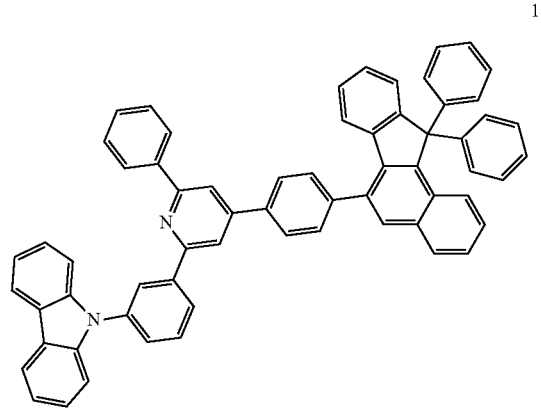
197
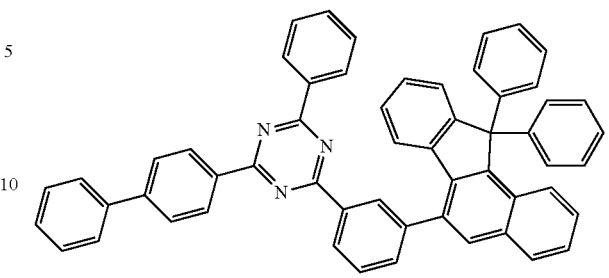
198
199
200
201
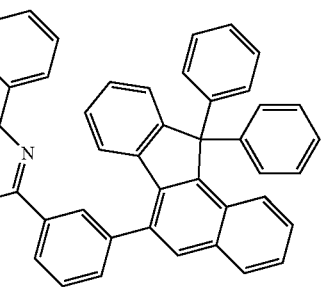

202
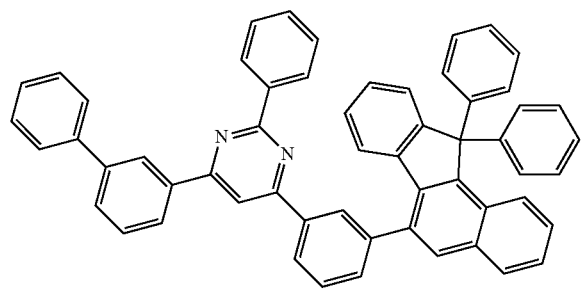
203
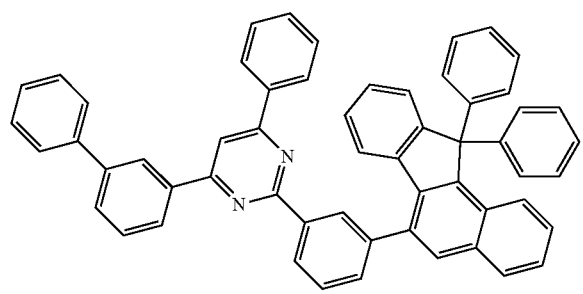
204
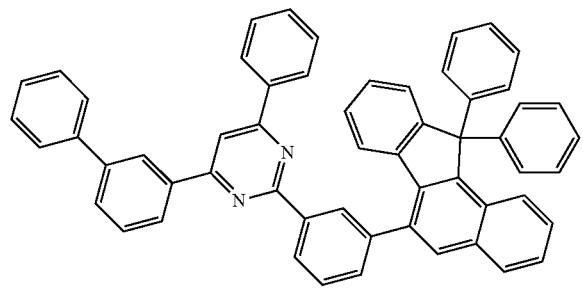
205
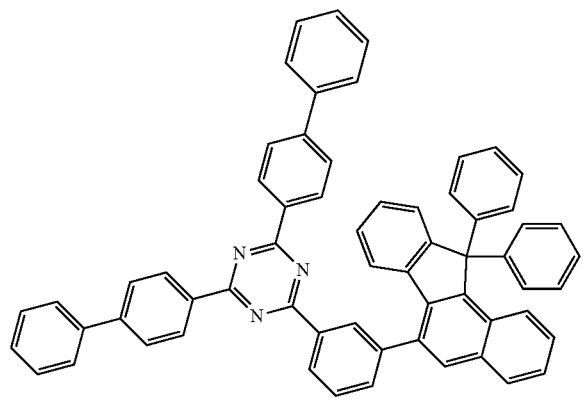
206
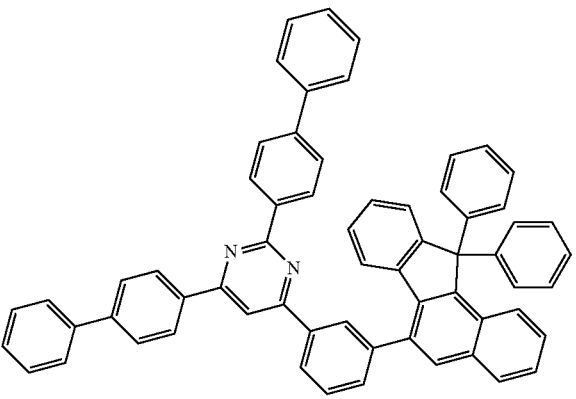
207
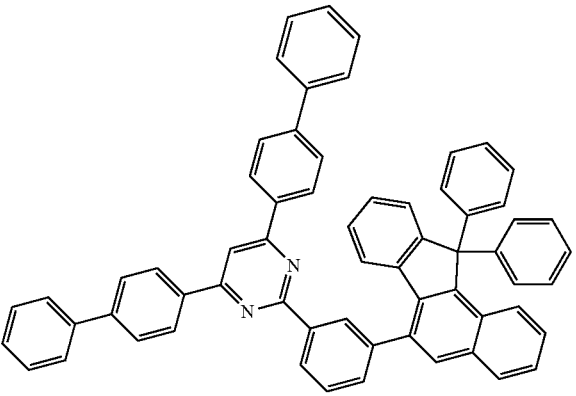
208
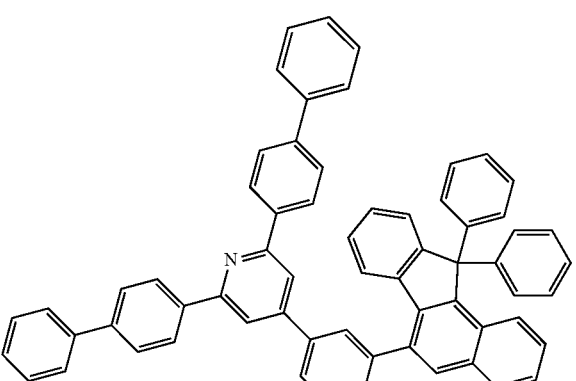
209
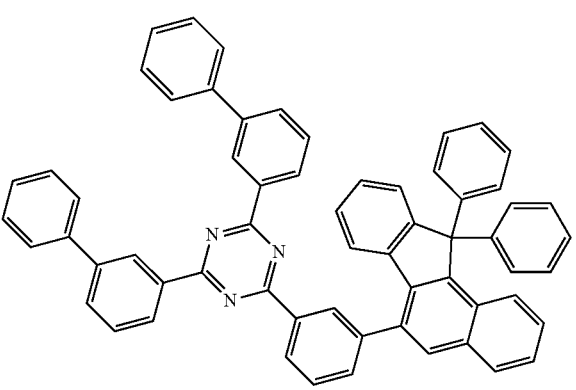

-continued
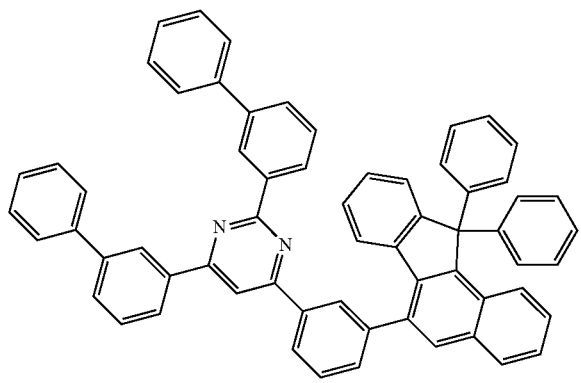
210
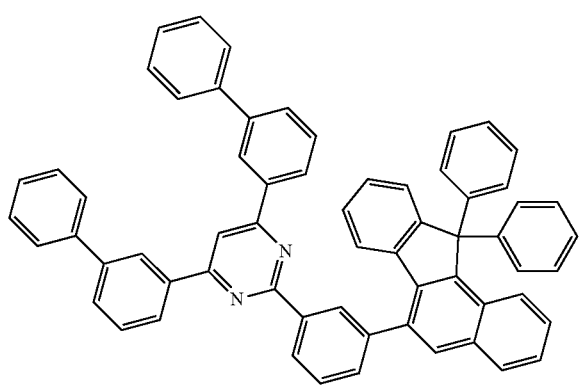
211
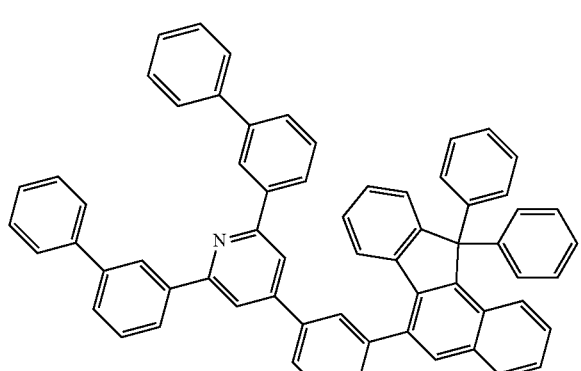
212
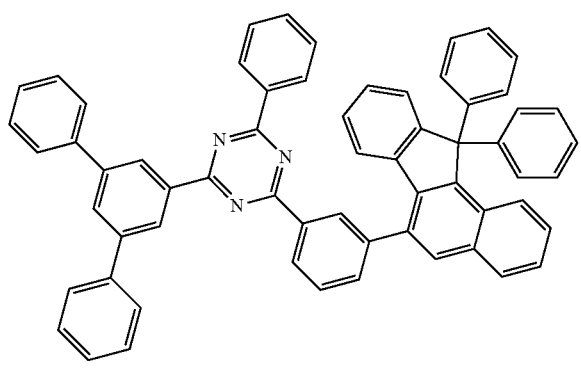
213
-continued
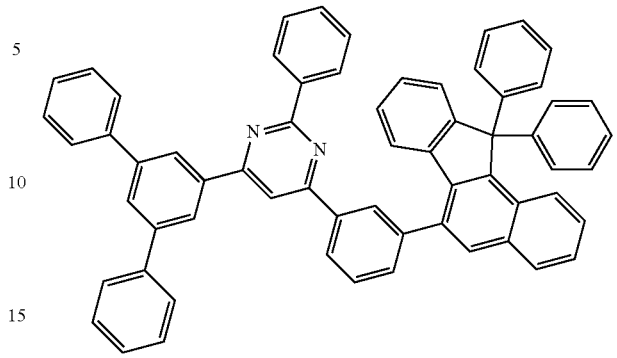
214
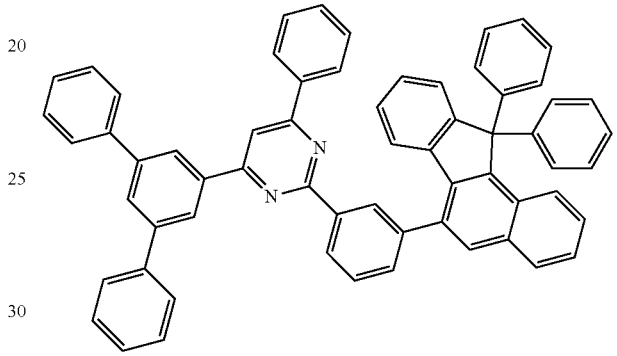
215
216
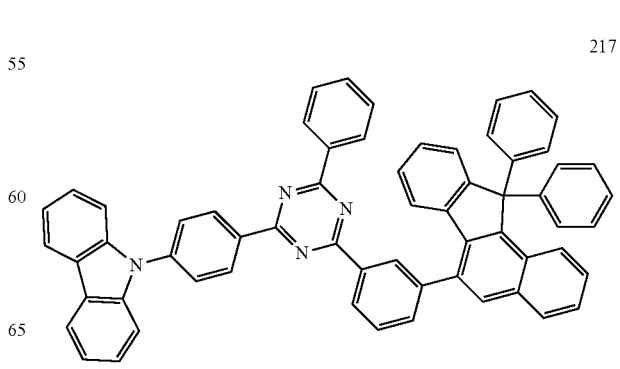
217

227
-continued
218
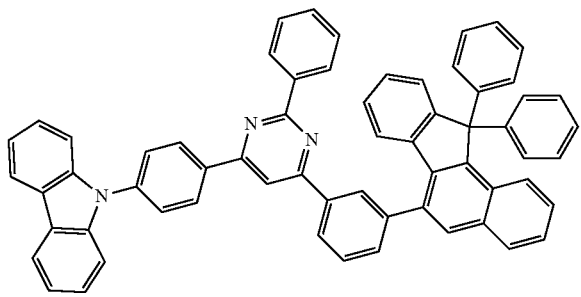
219
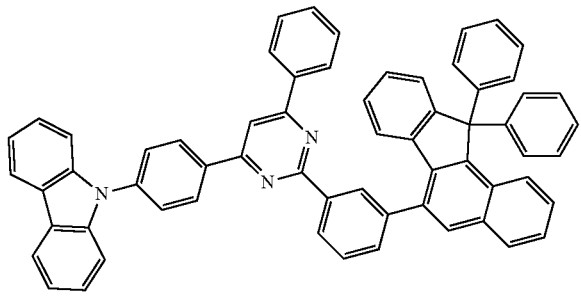
220
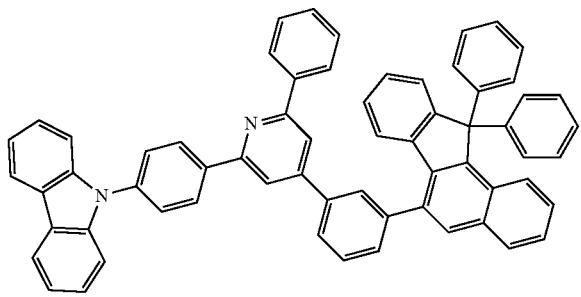
221
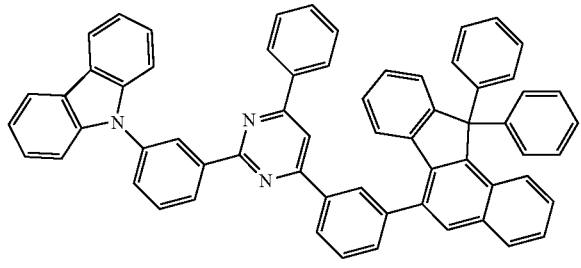
222
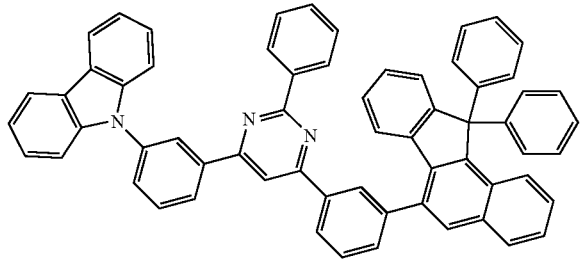
228
-continued
223
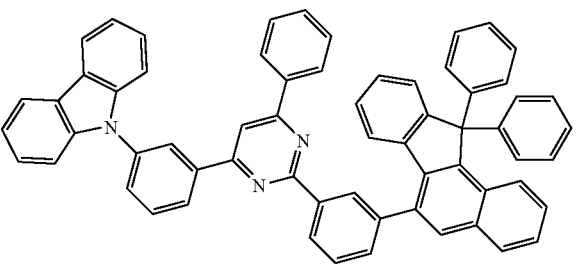
224
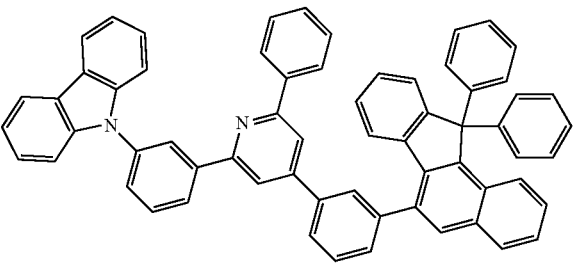
225
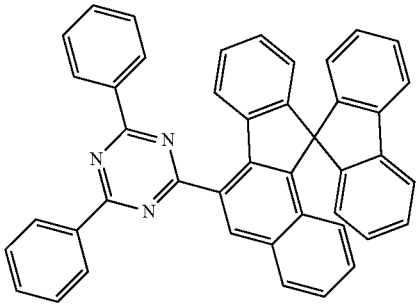
226
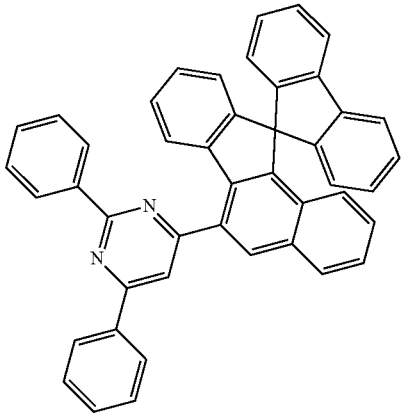

-continued
227
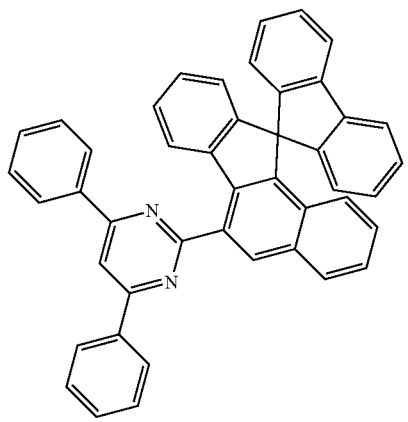
228
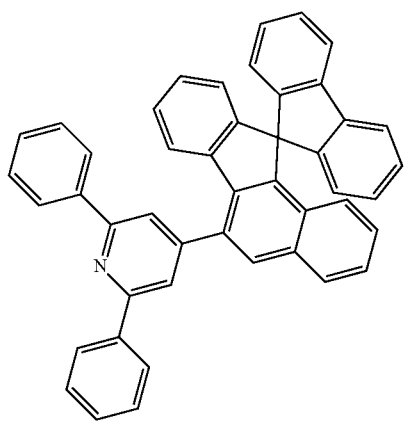
229
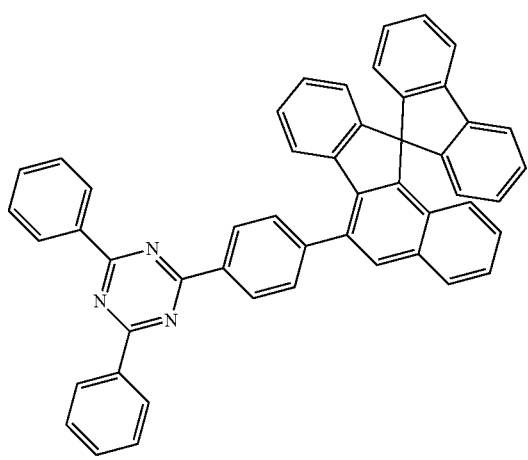
-continued
230
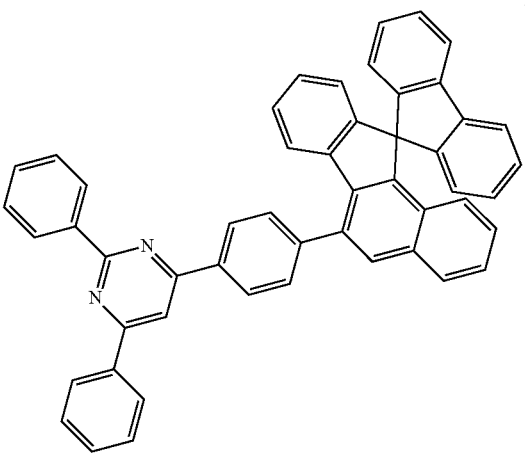
231
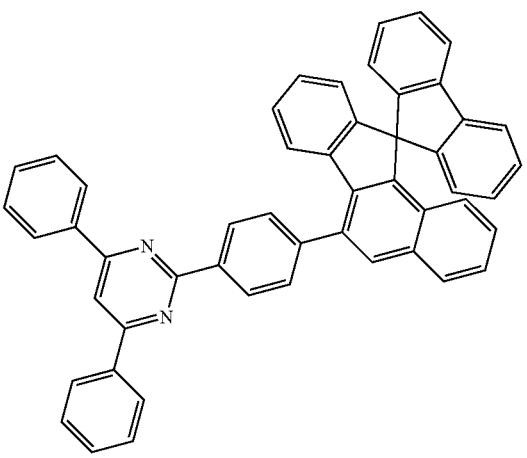
232
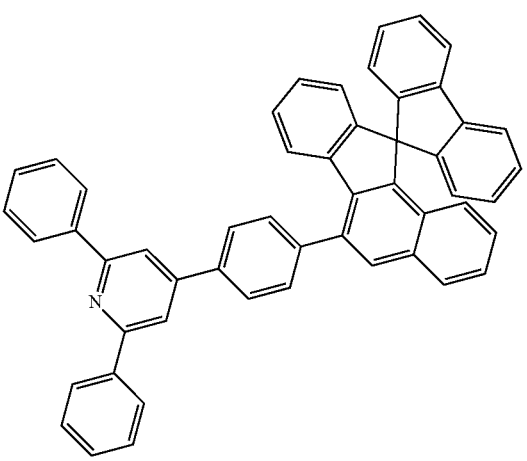

233
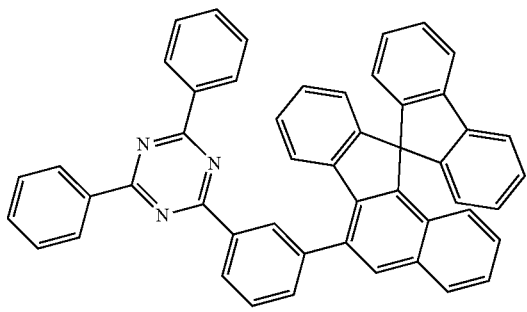
234
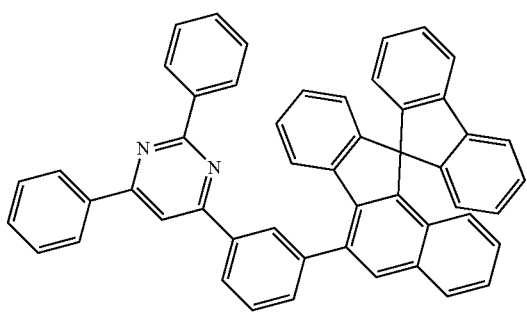
235
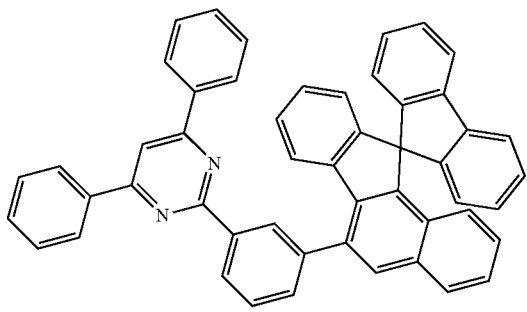
236
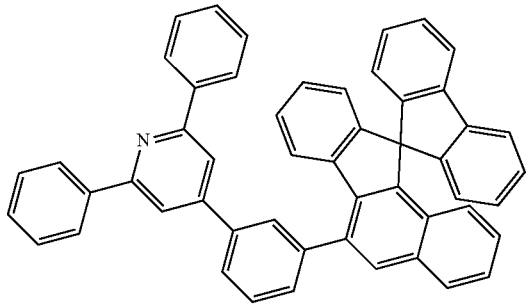
237
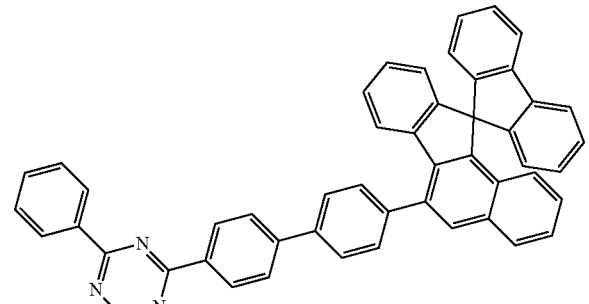
238
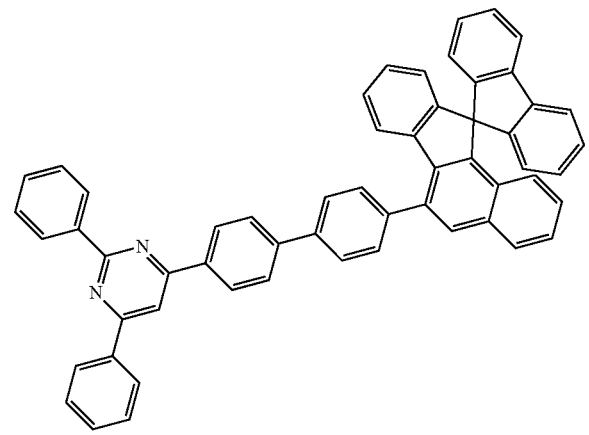
239
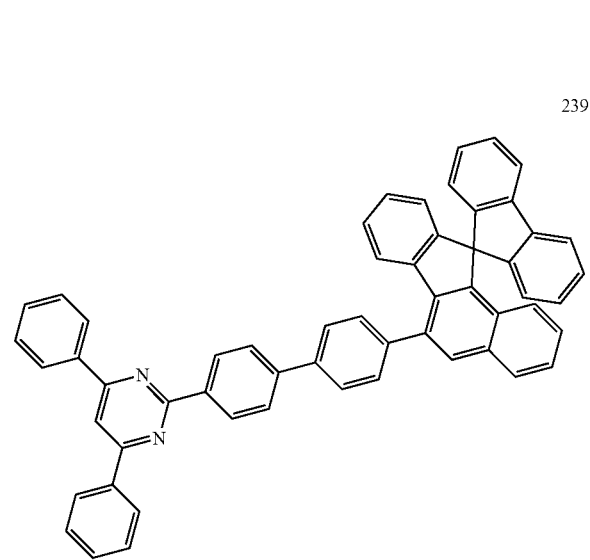

-continued
240
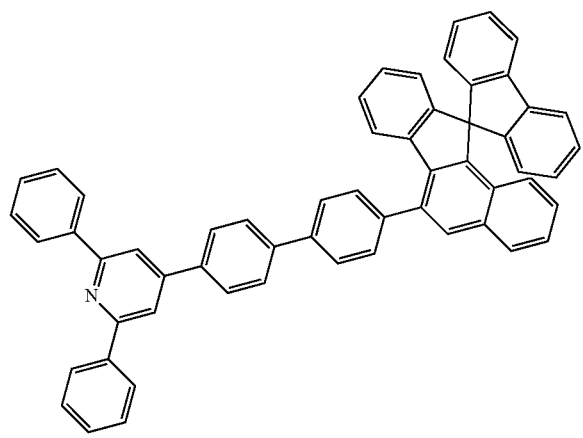
241
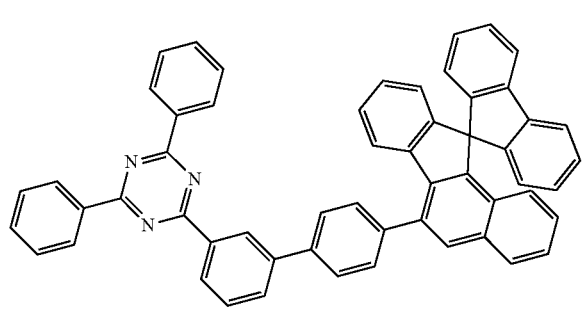
242
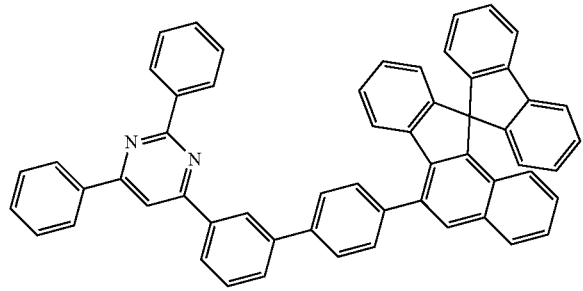
243
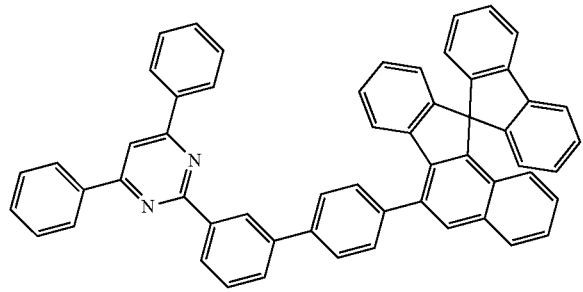
-continued
244
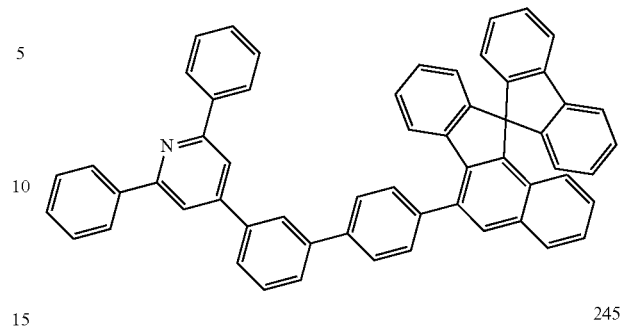
245
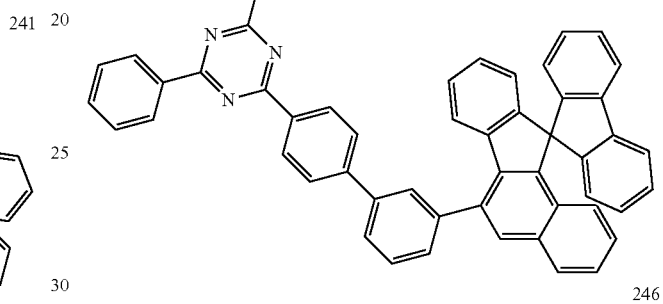
246
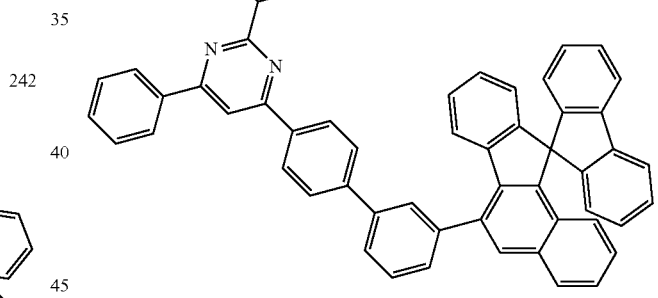
247
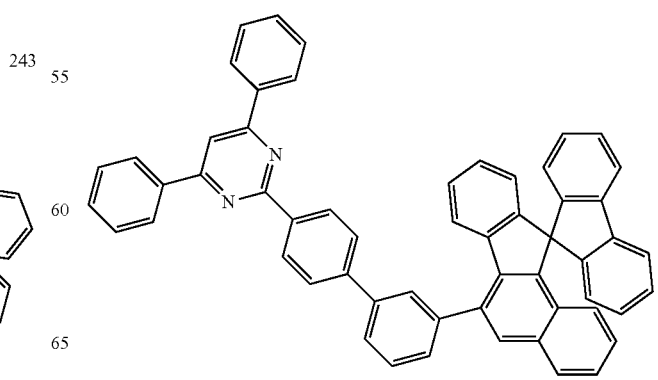

248
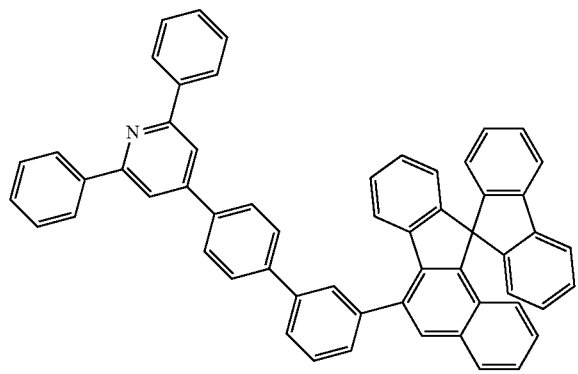
249
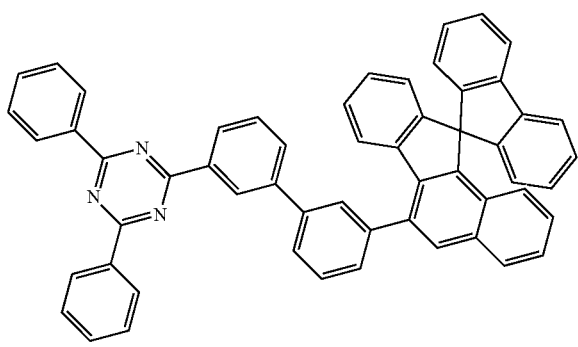
250
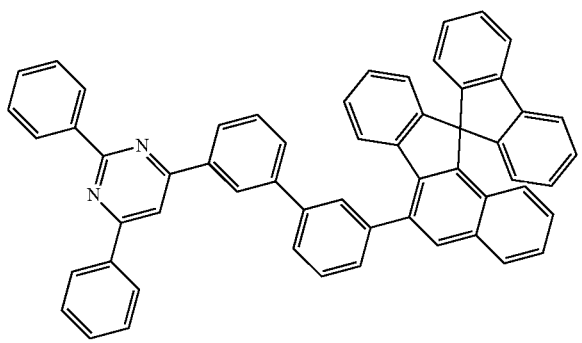
251
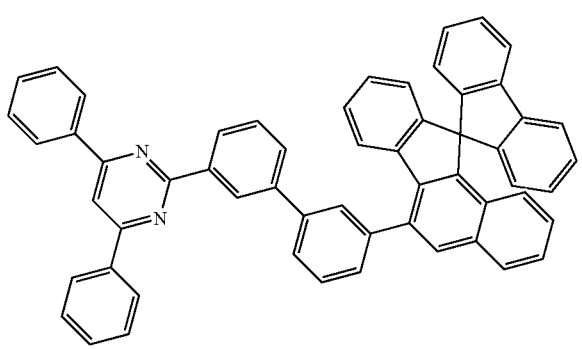
252
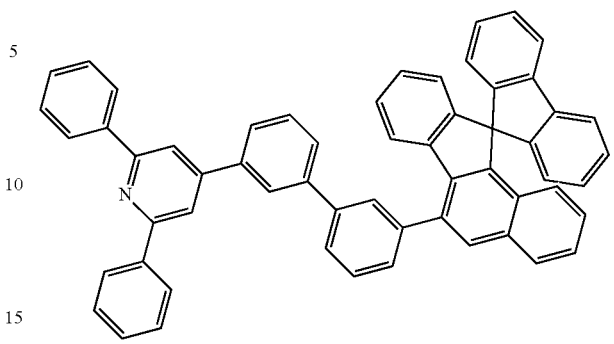
253
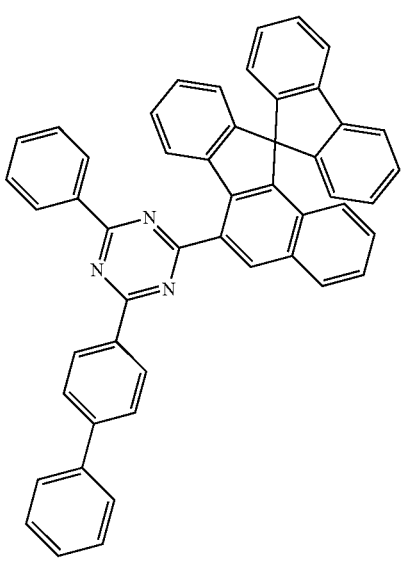
254
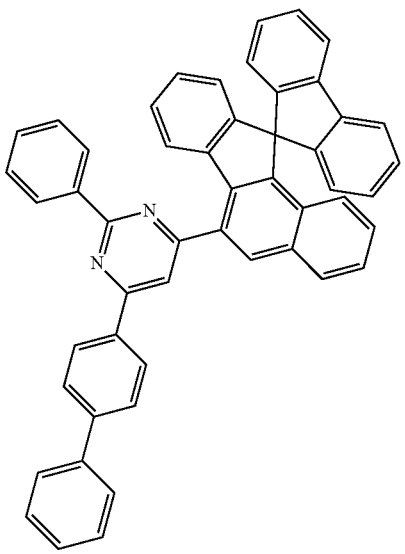

255 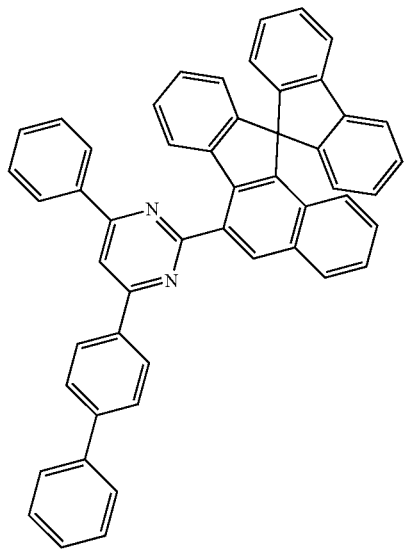
256 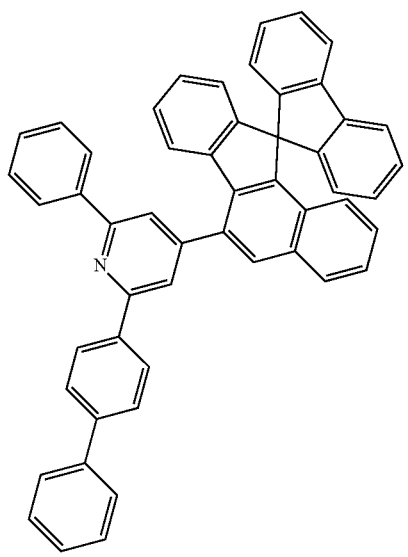
257 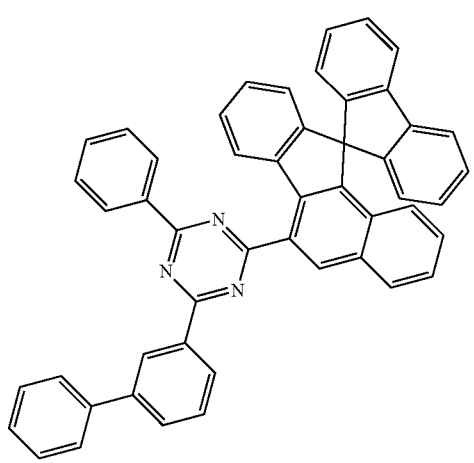
258 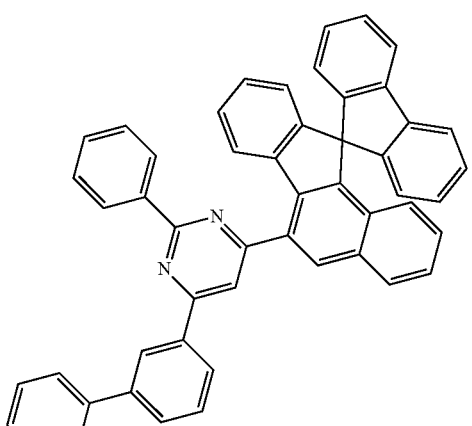
259 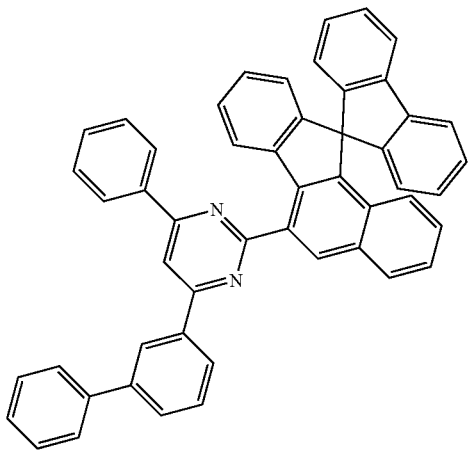
260 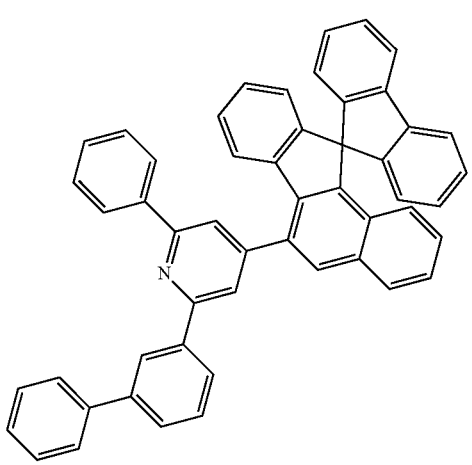

261
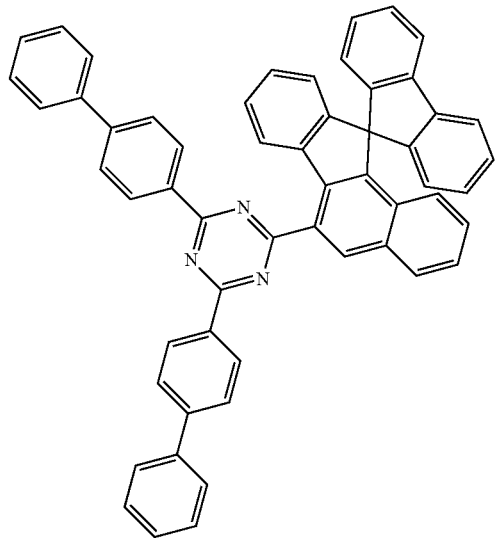
262
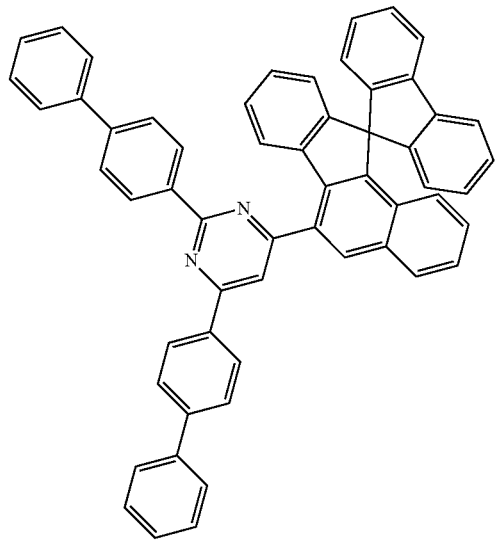
263
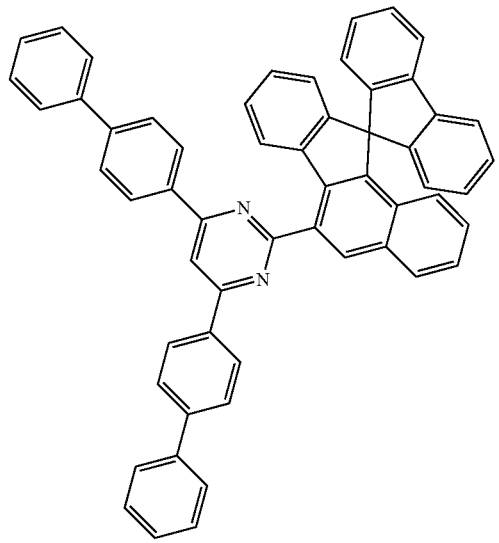
264
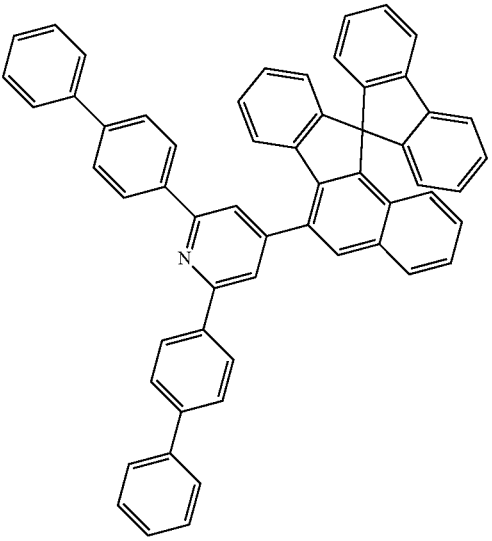
265
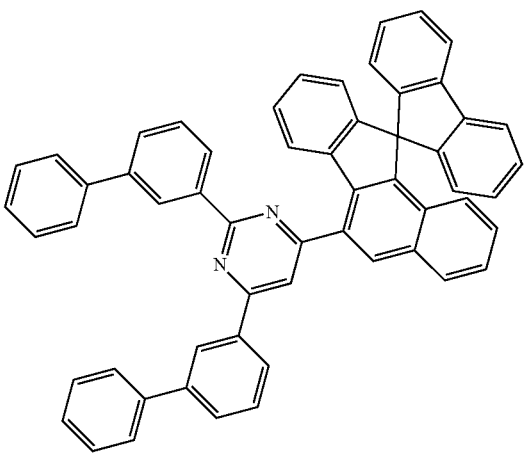
266

-continued
267
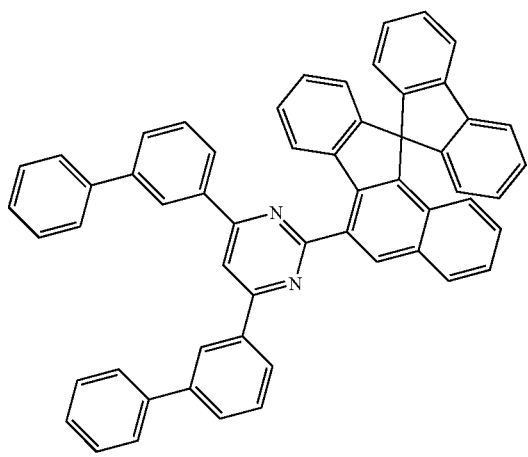
268
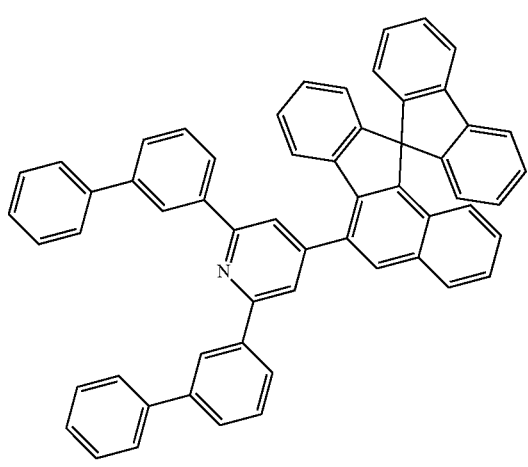
269
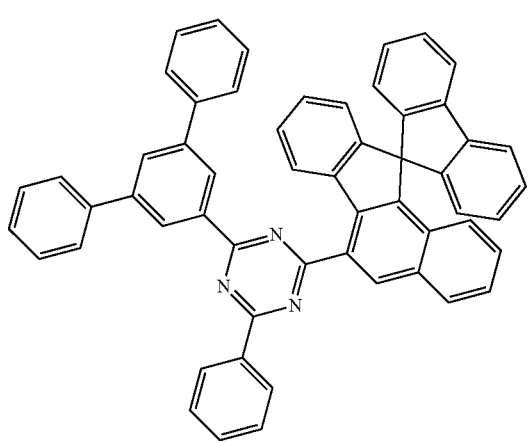
-continued
270
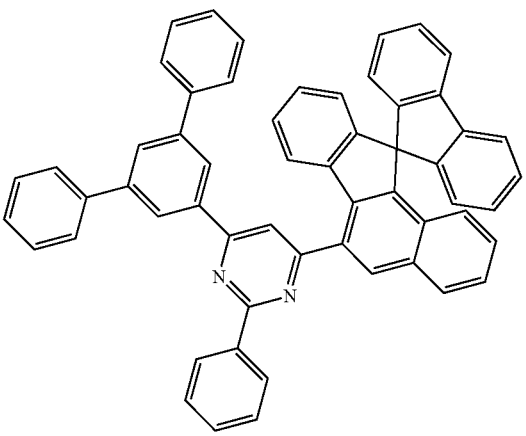
271
272
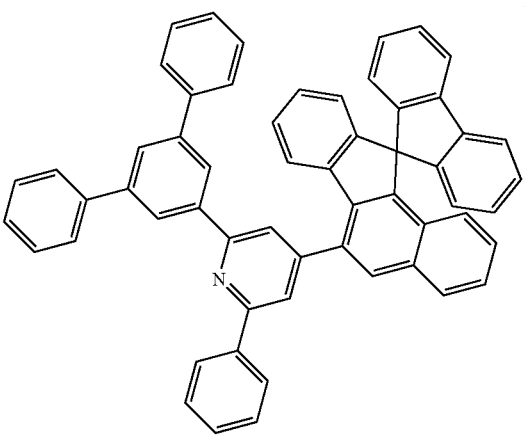

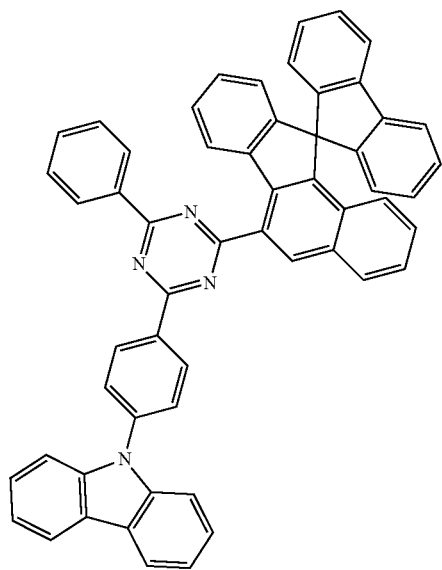
273
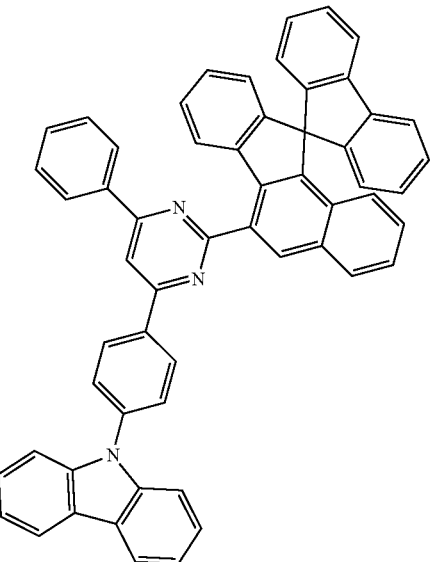
275
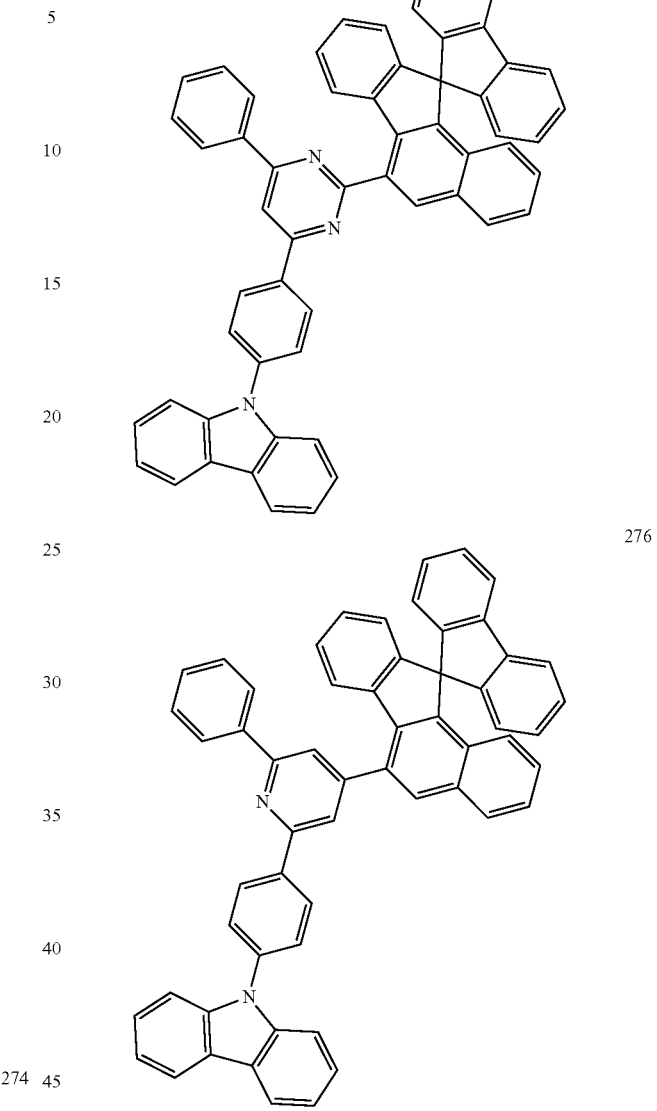
276
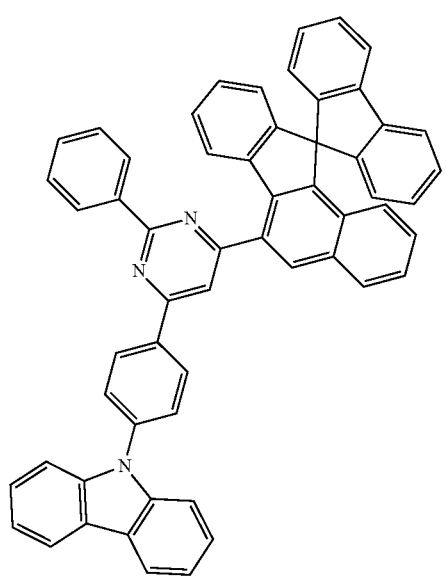
274
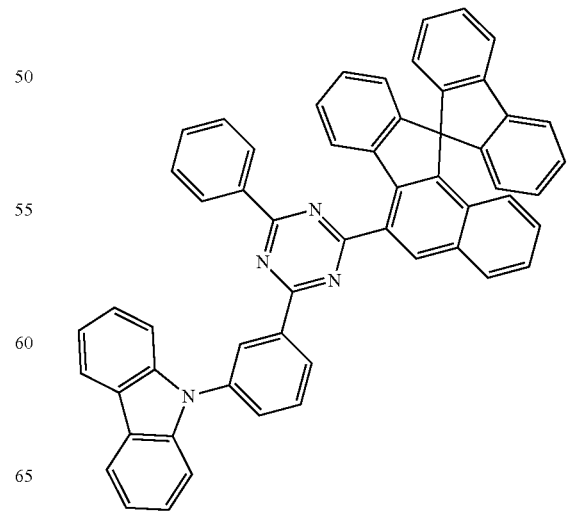
277

278
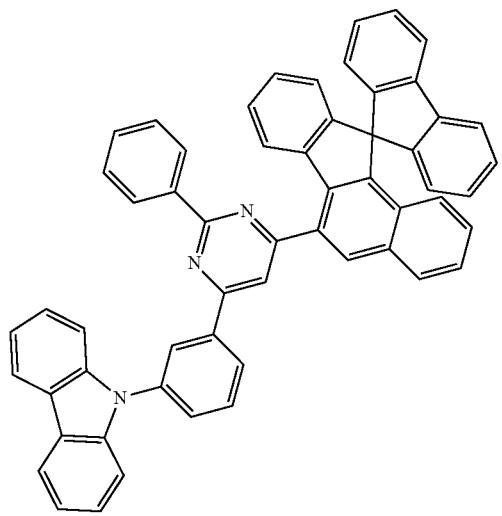
279
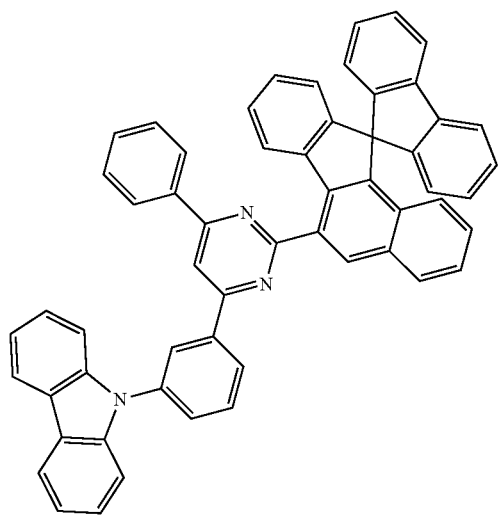
280
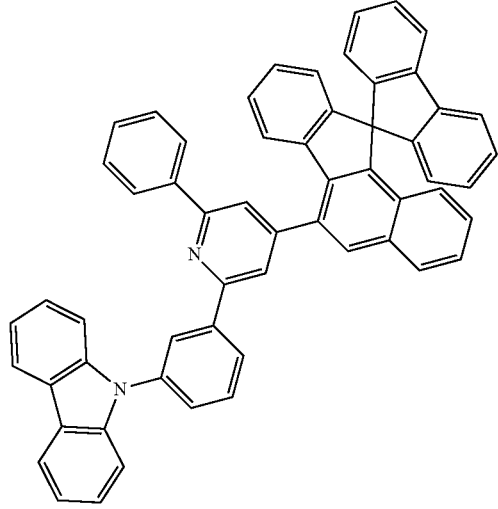
281
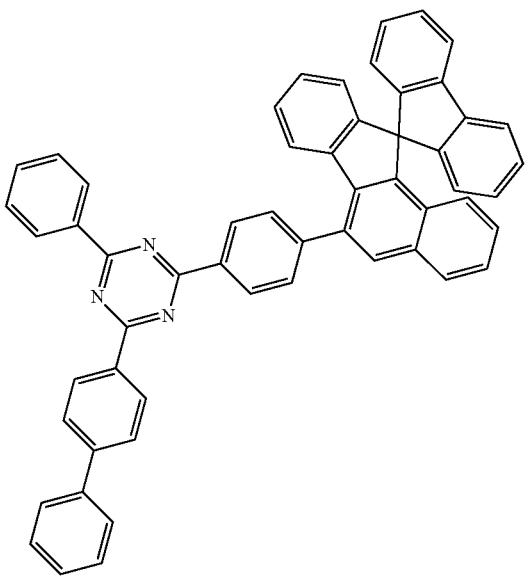
282
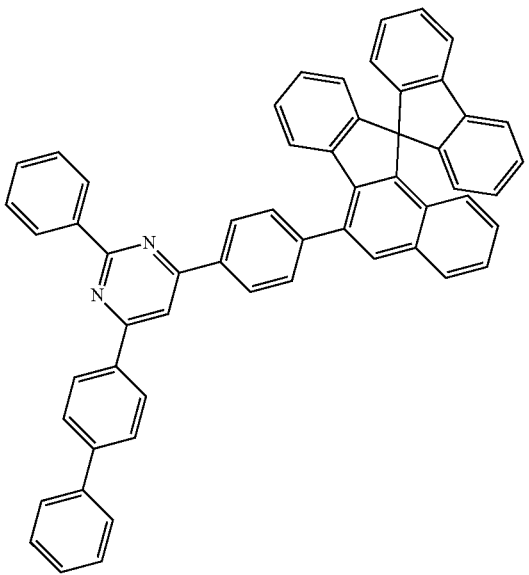

283
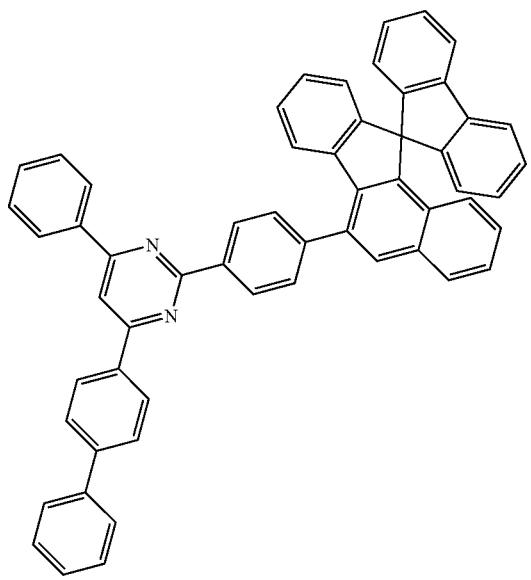
284
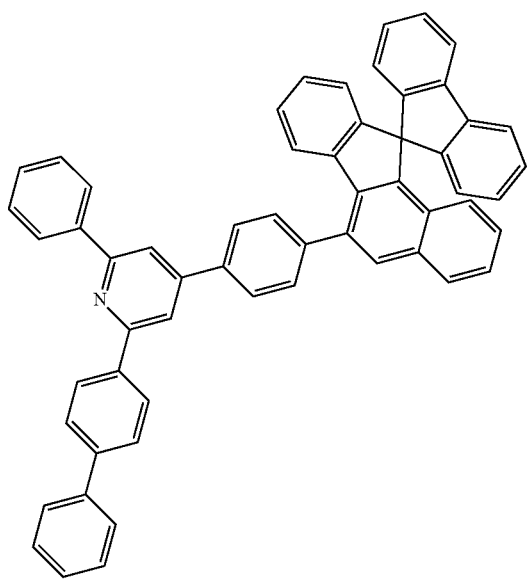
285
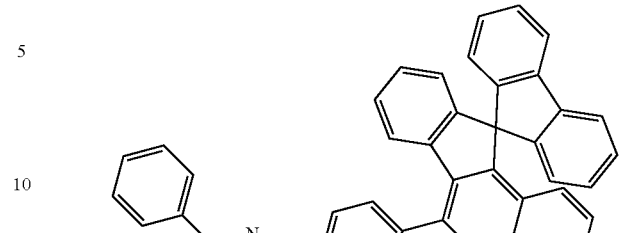
286
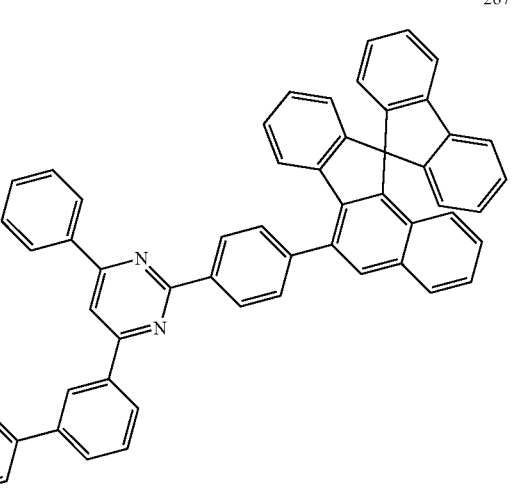
287

288
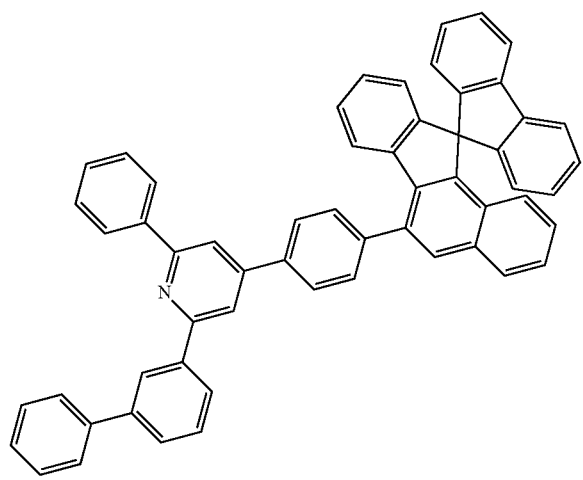
289
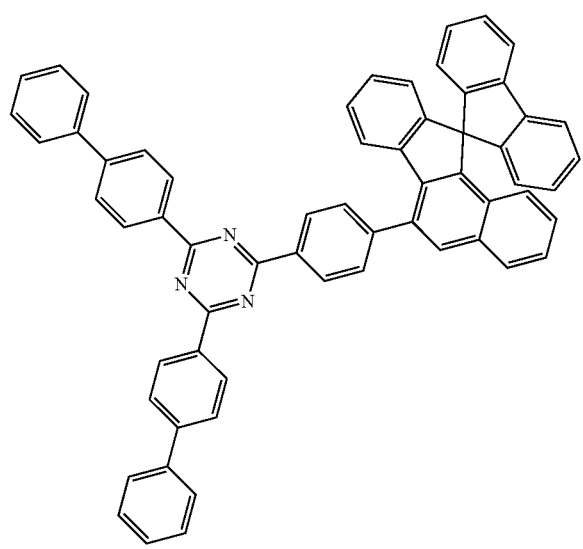
290
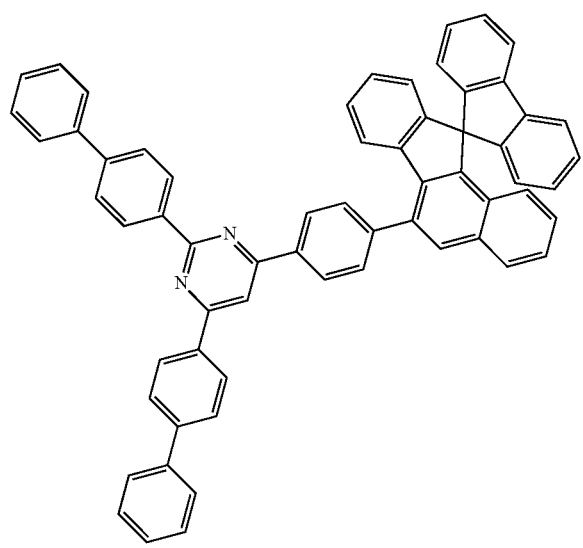
291
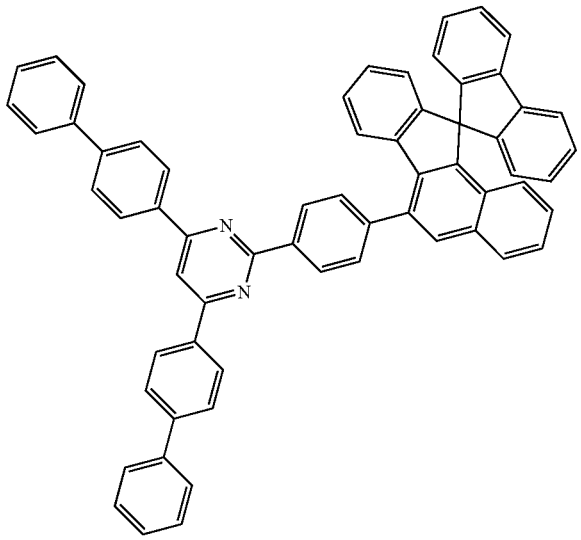
292
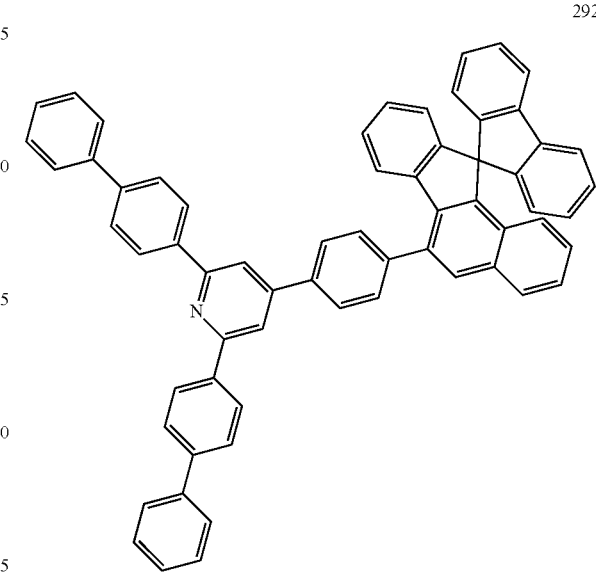
293
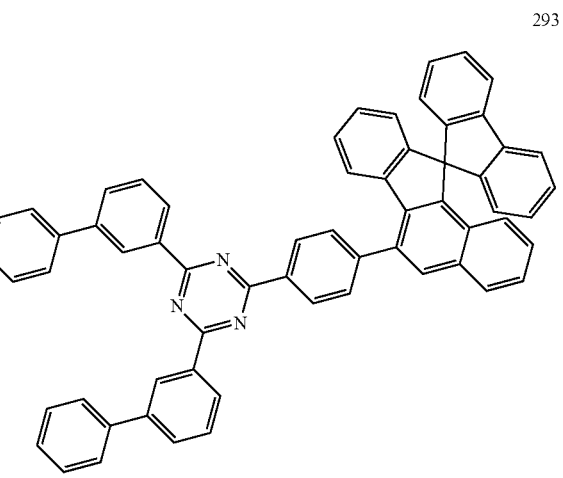

251
-continued
294
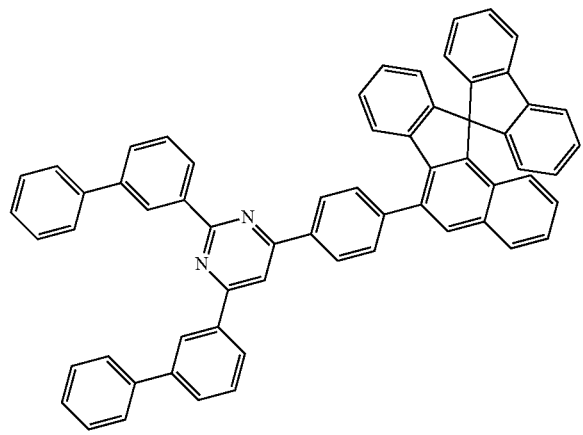
295
296
252
-continued
297
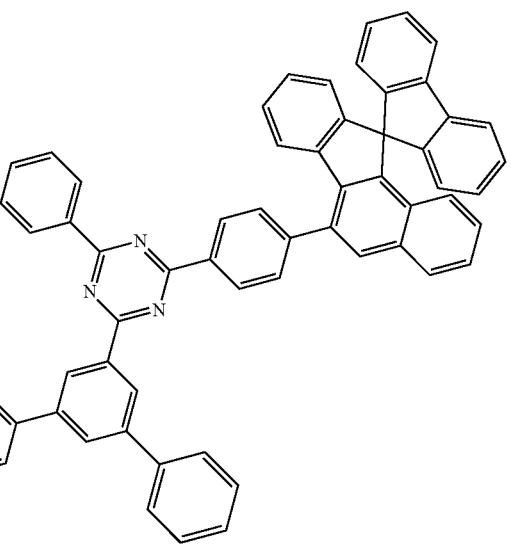
298

253
-continued
299
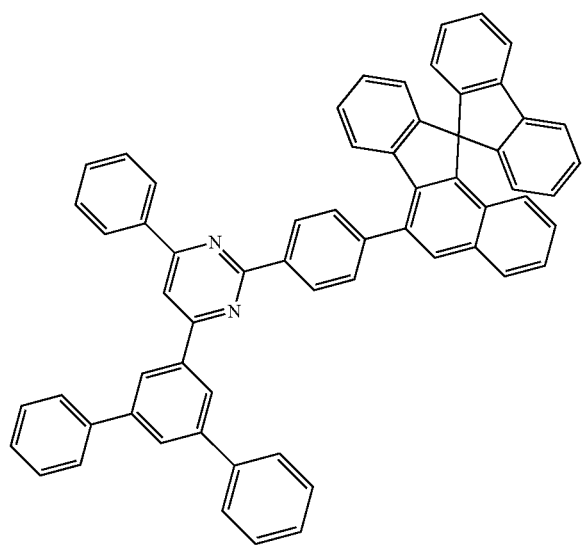
300
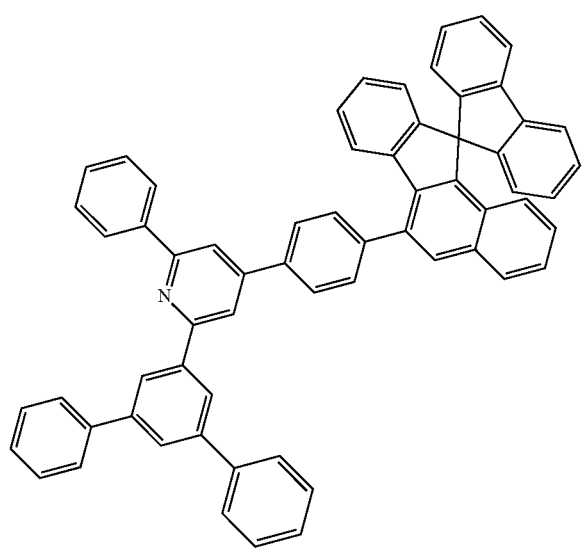
254
-continued
301
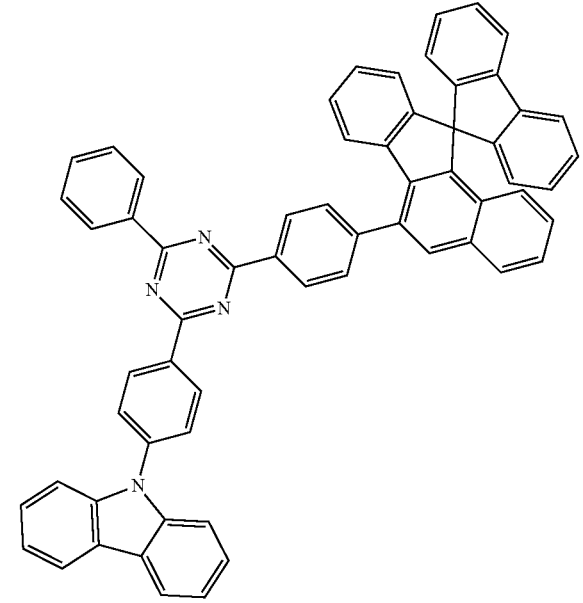
302
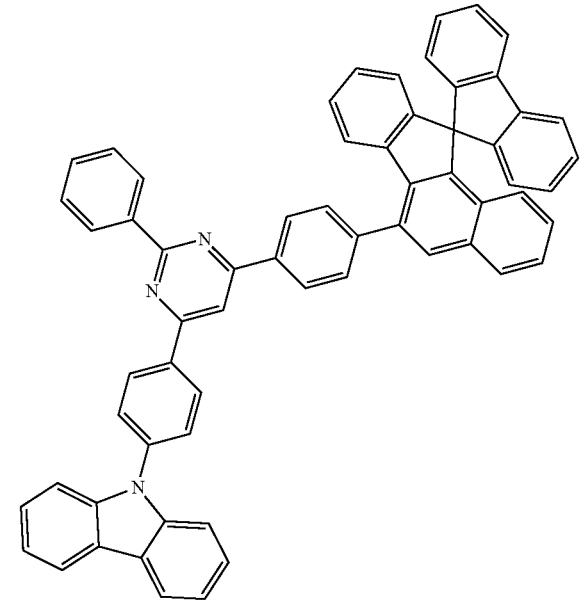

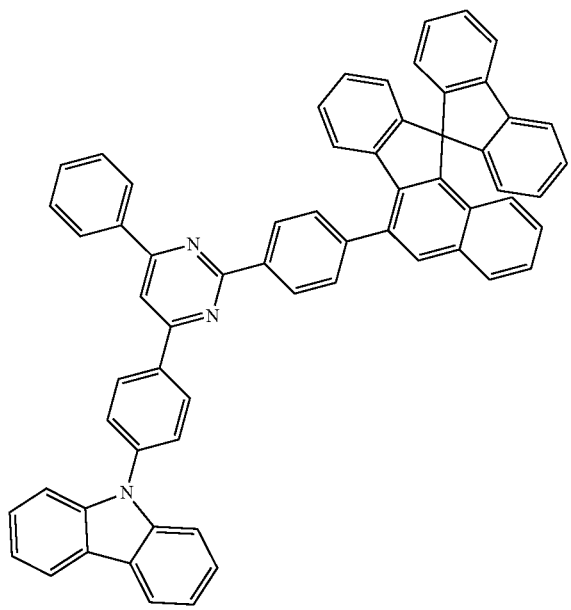
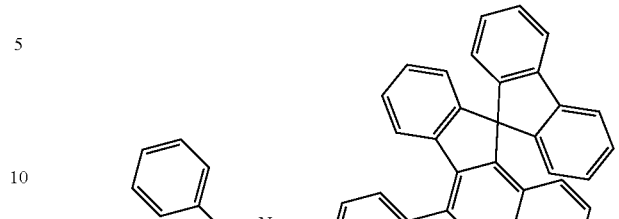
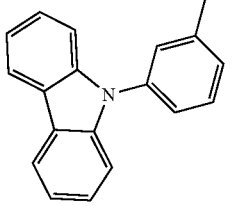
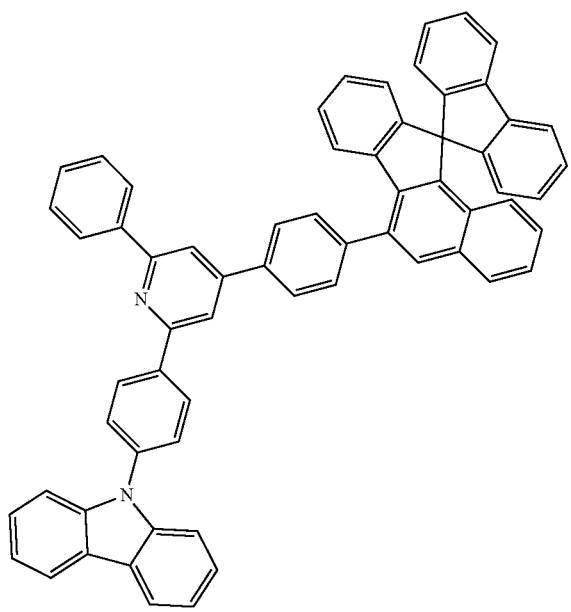
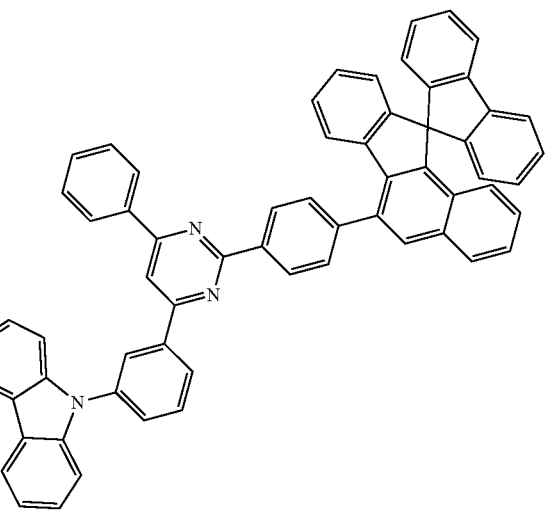

308
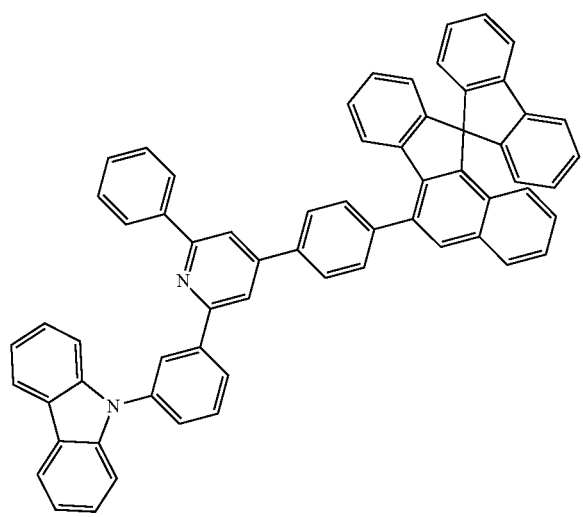
309
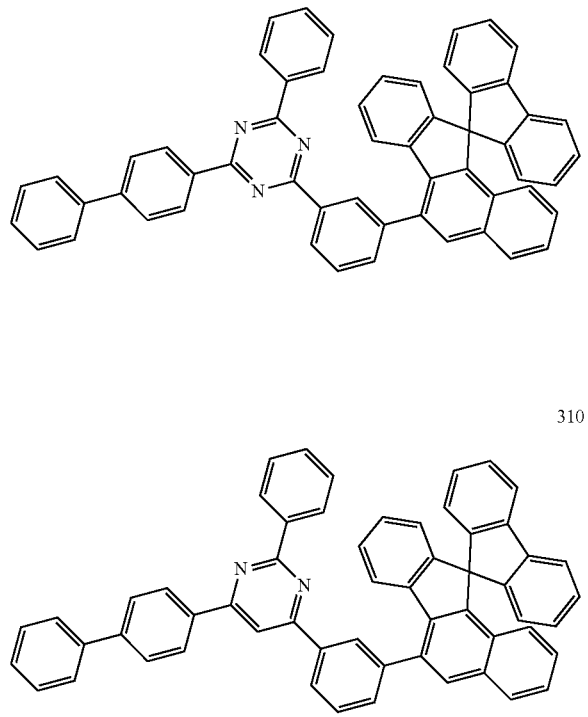
310
311
312
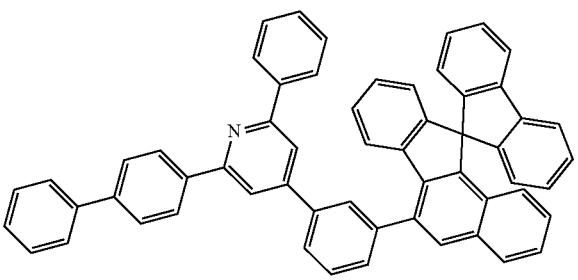
313
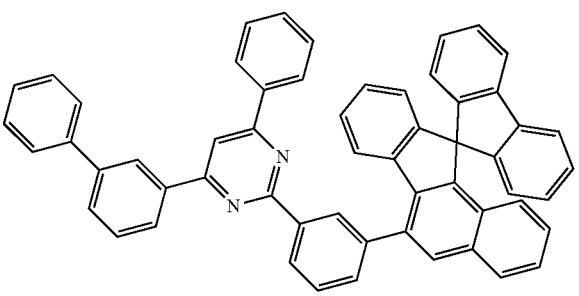
314
315
316
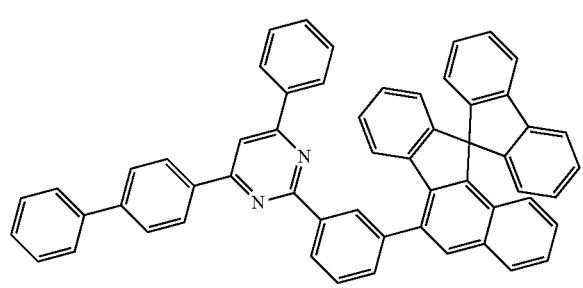
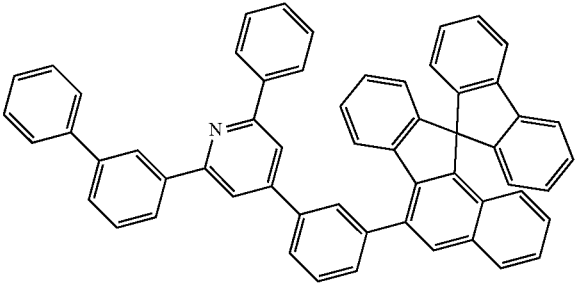

317
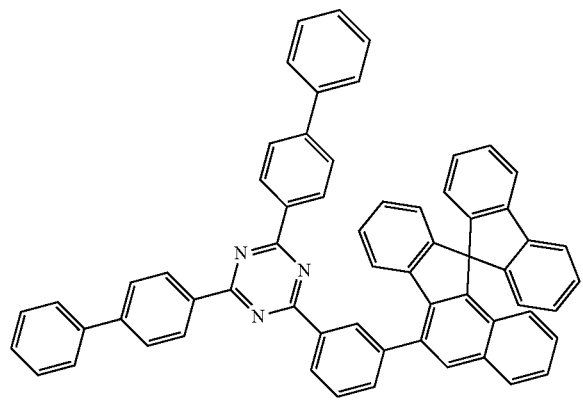
318
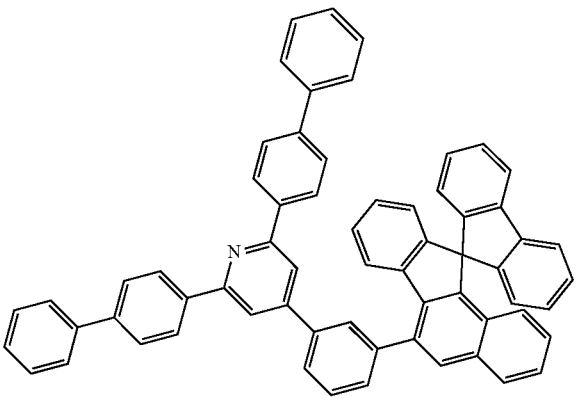
319
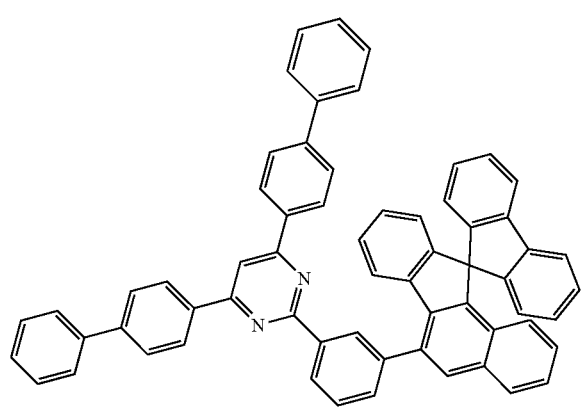
320
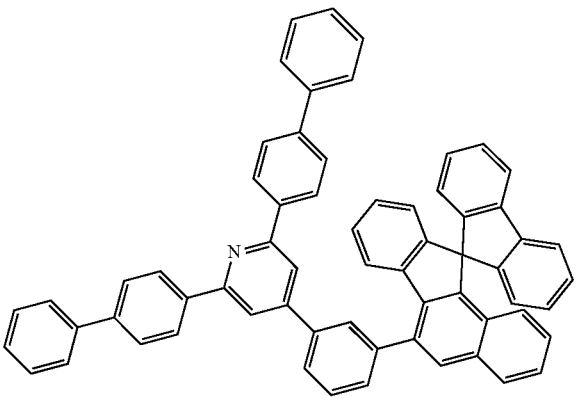
321
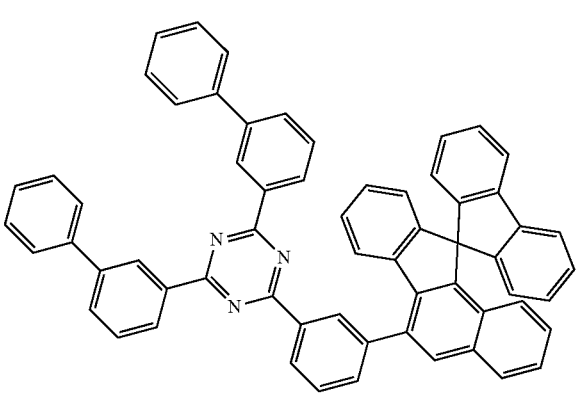
322
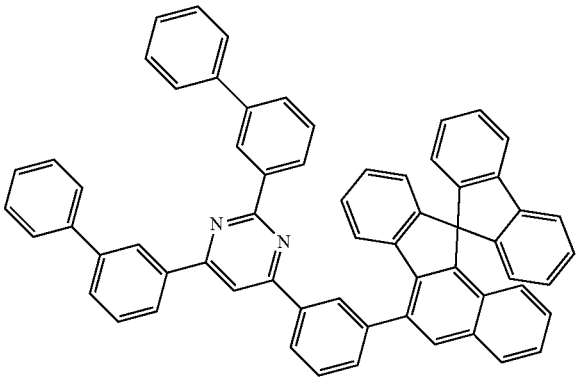
323
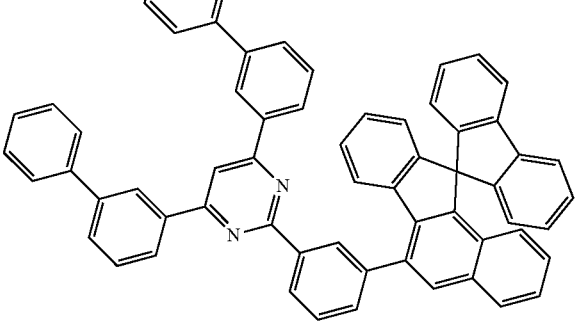

324
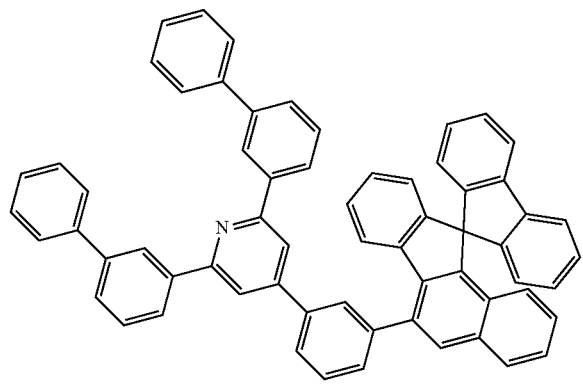
325
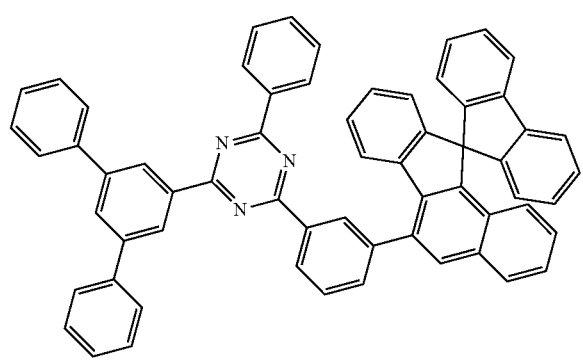
326
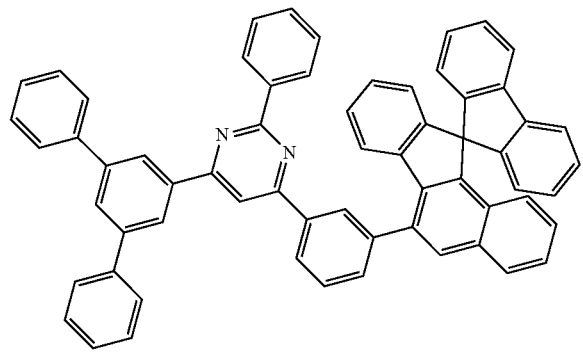
327
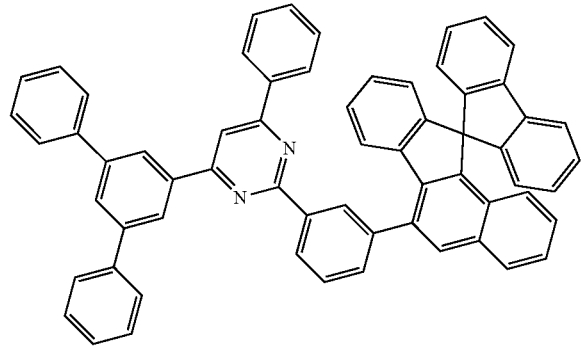
328
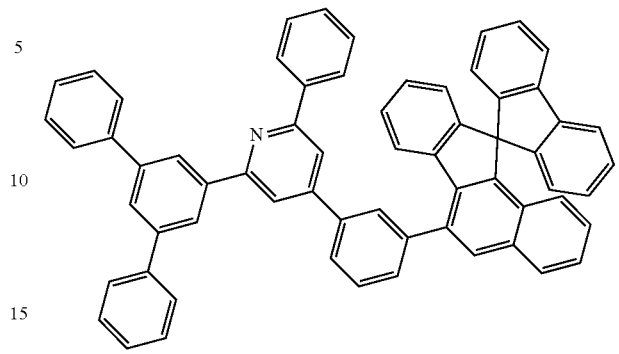
329
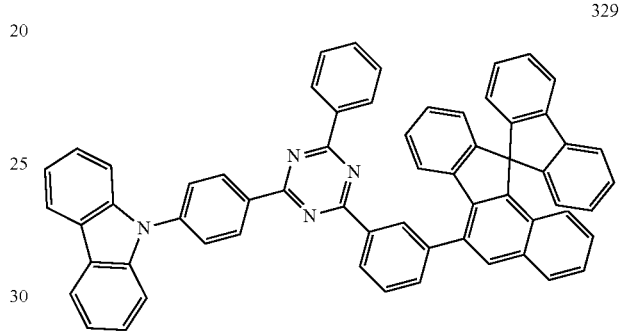
330
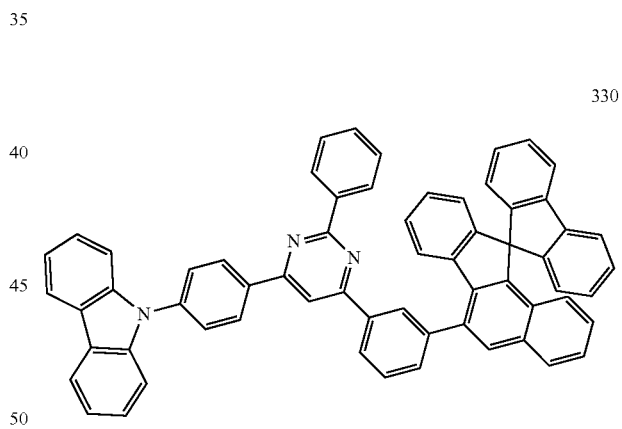
331
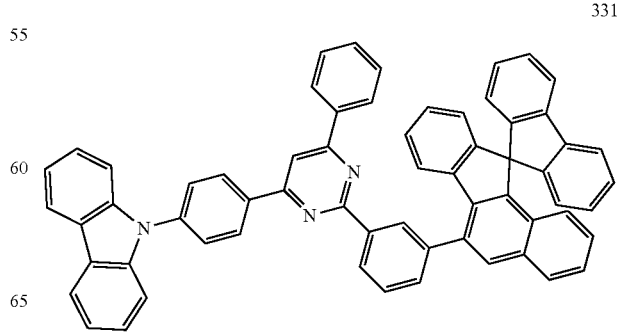

263
-continued
332
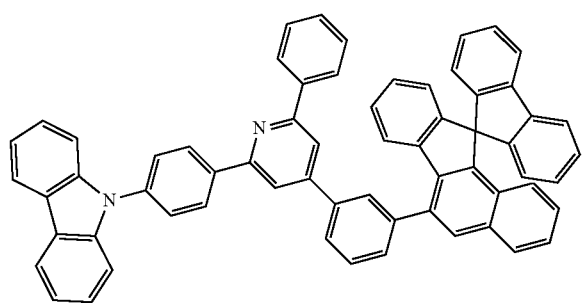
333
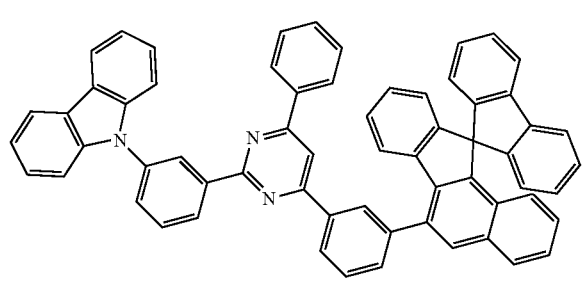
334
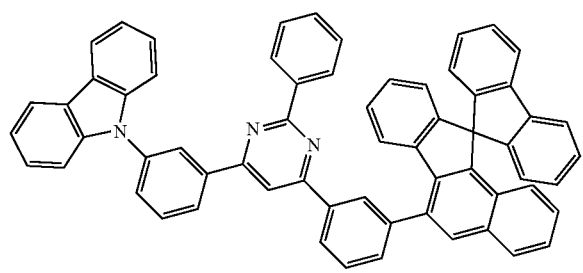
335
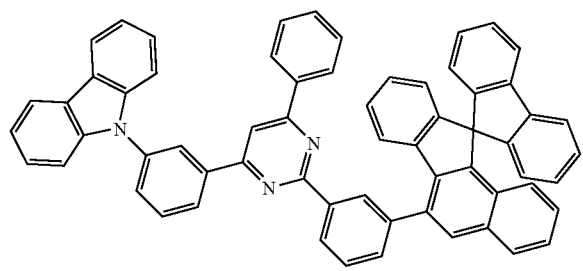
336
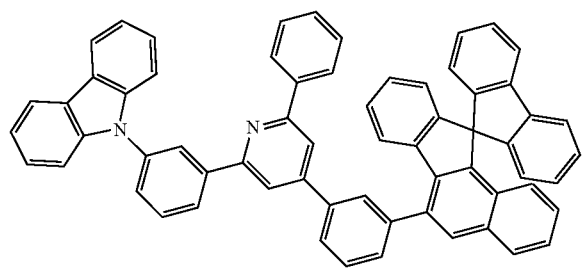
264
-continued
337
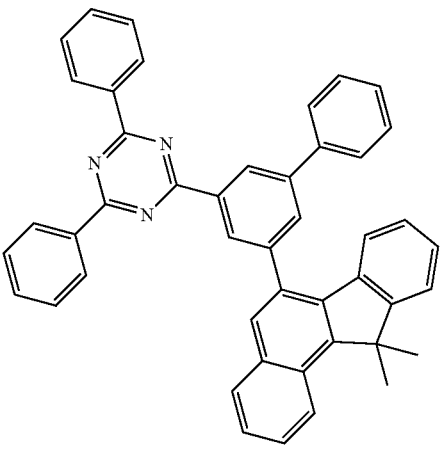
338
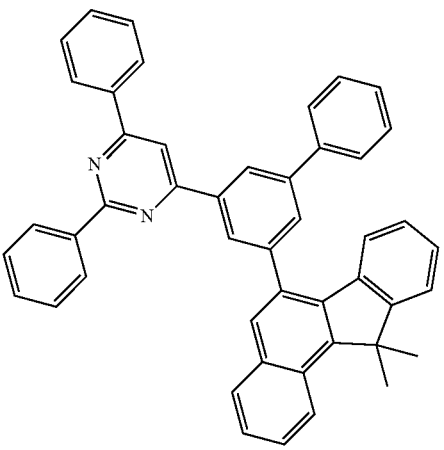
339
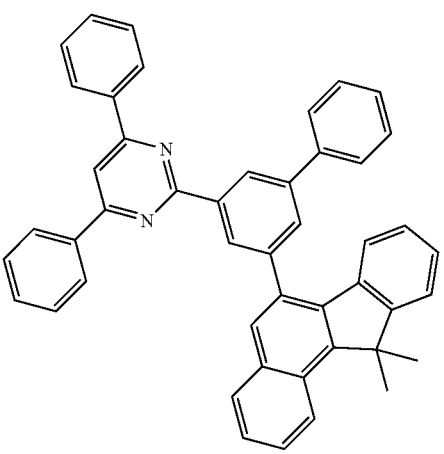

340
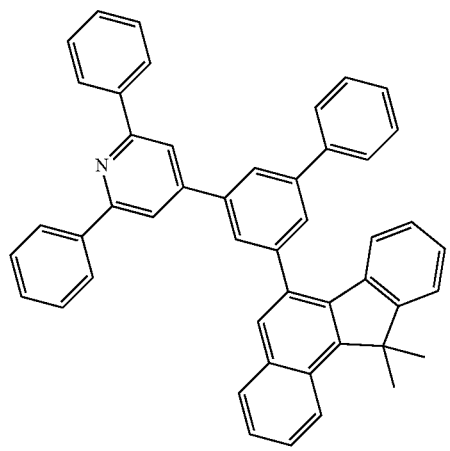
341
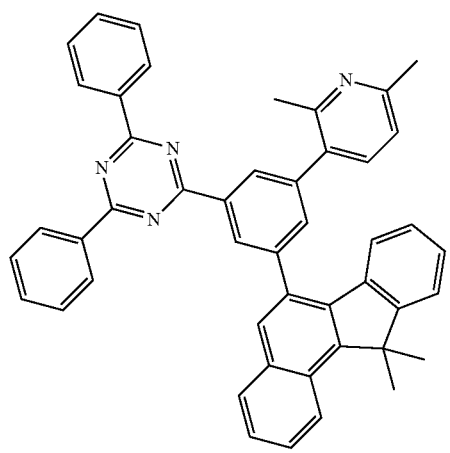
342
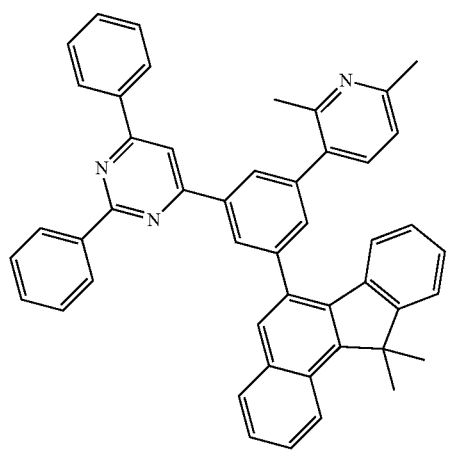
343
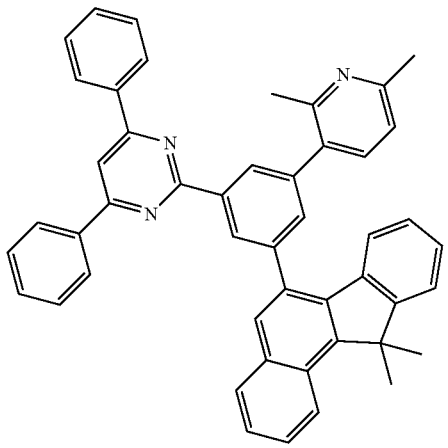
344
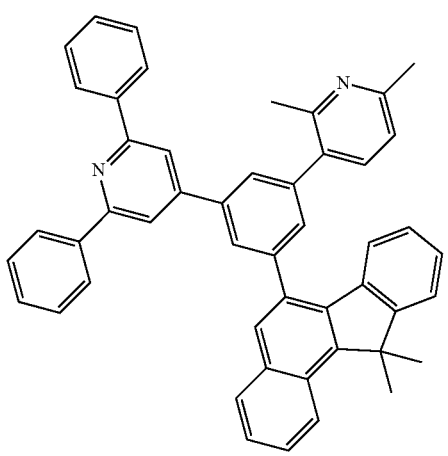
345
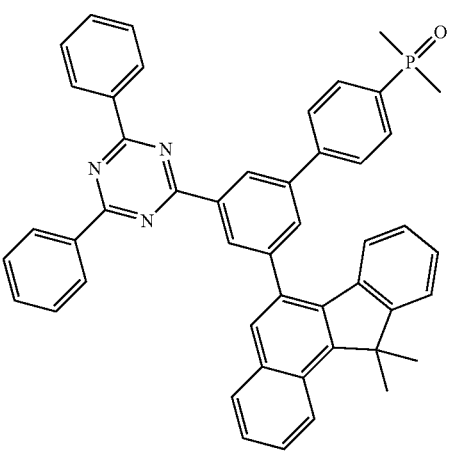

267
-continued
346
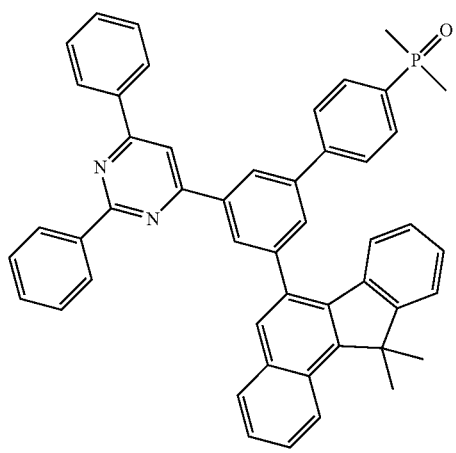
347
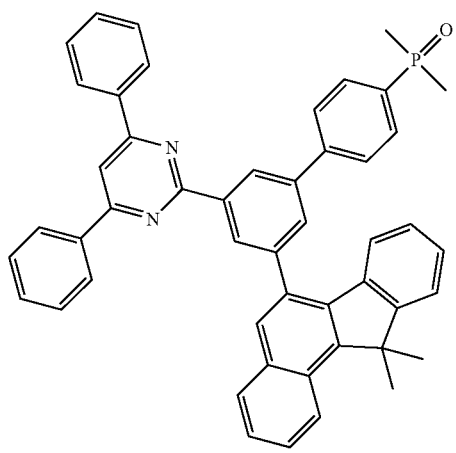
348
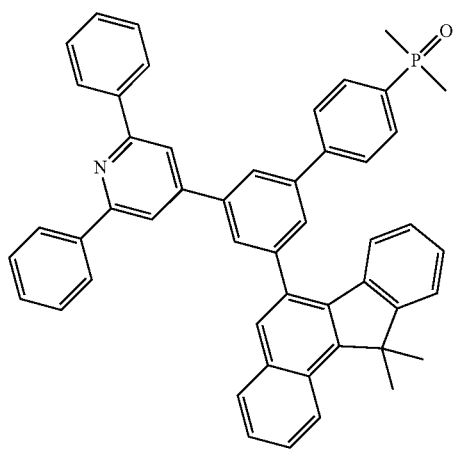
268
-continued
349
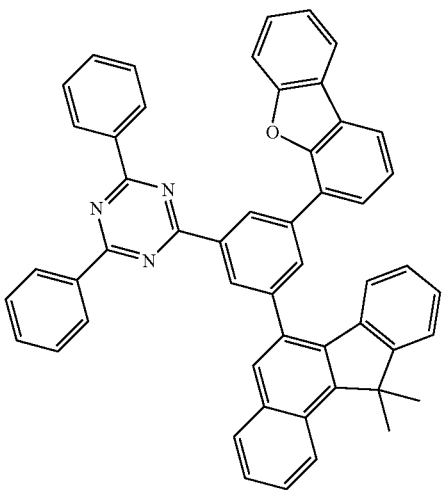
350
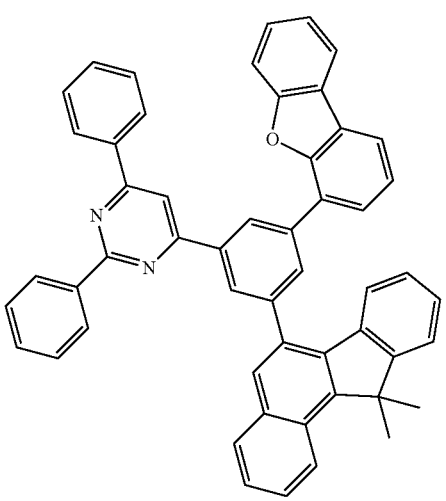
351
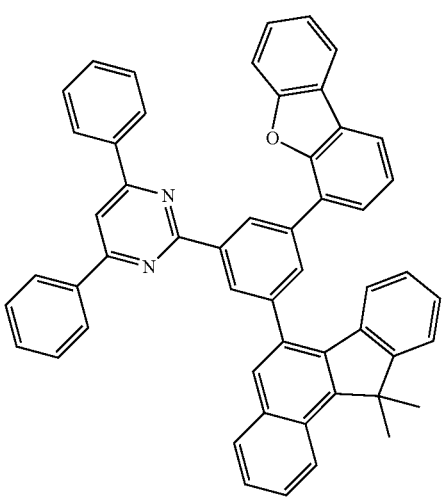

352
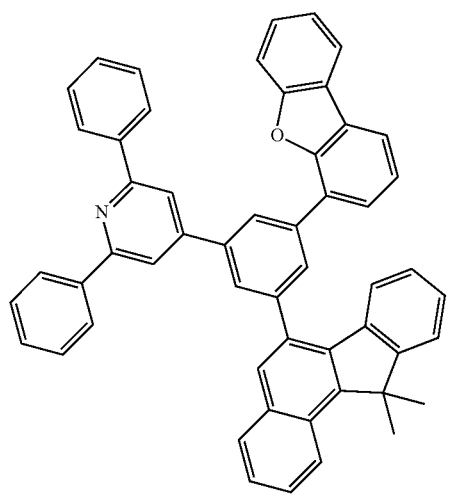
353
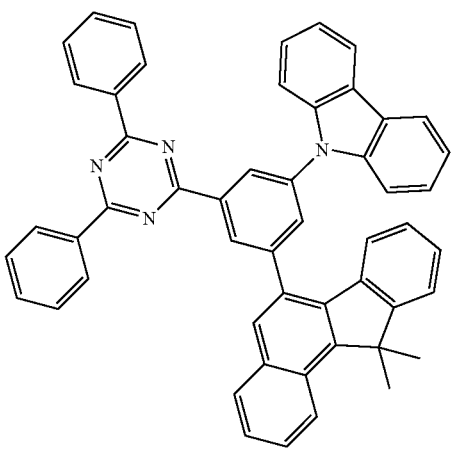
354
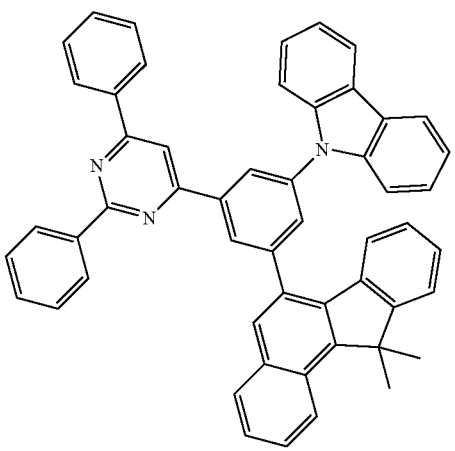
355
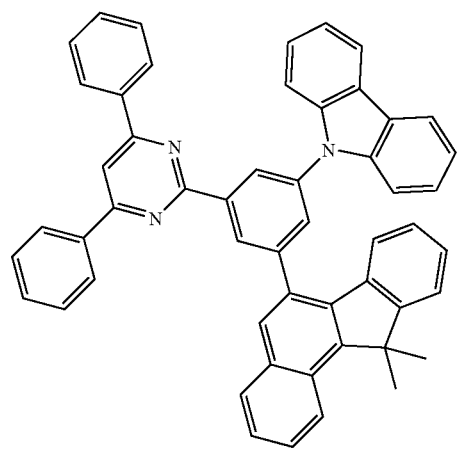
356
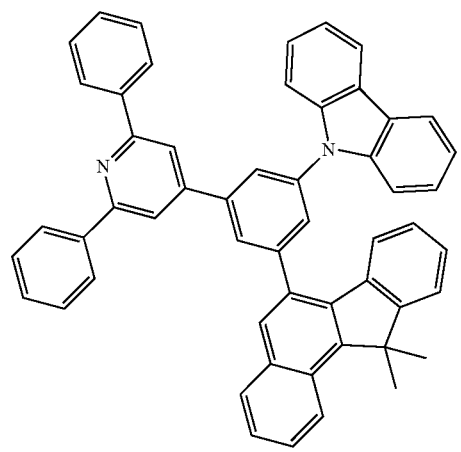
357
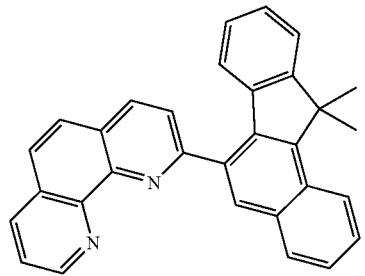
358
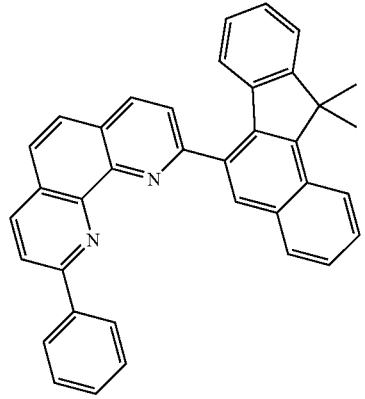

-continued
359
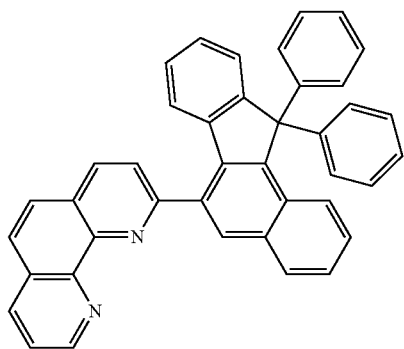
360
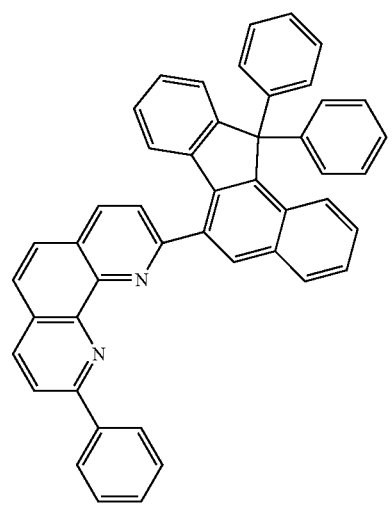
361
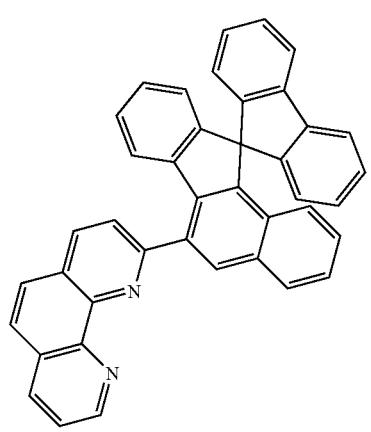
-continued
362
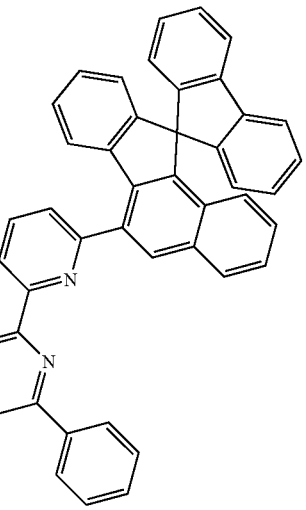
363
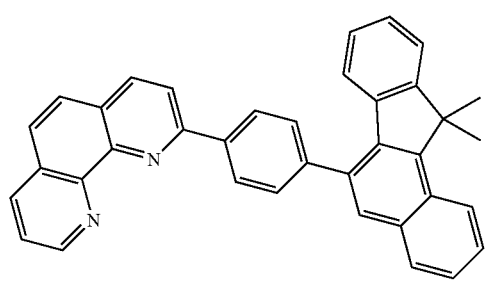
364
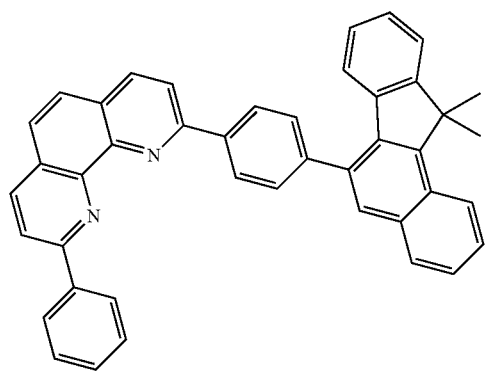
365
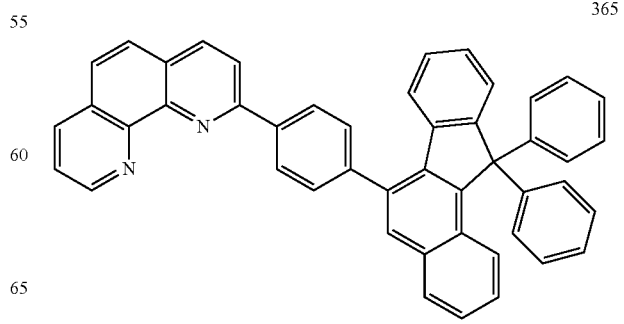

366
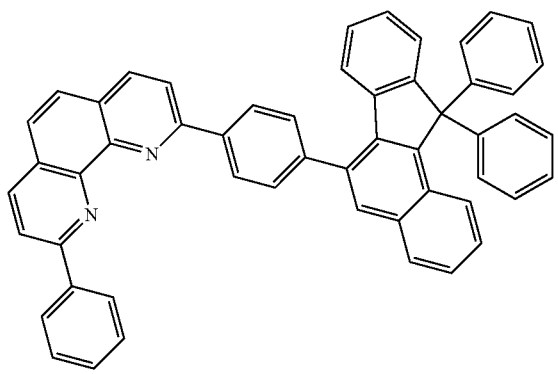
367
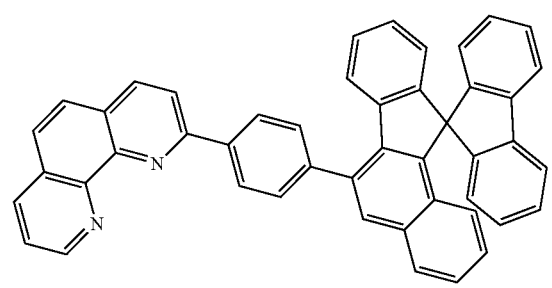
368
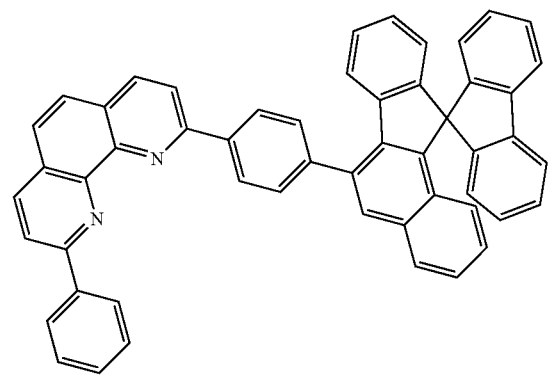
369
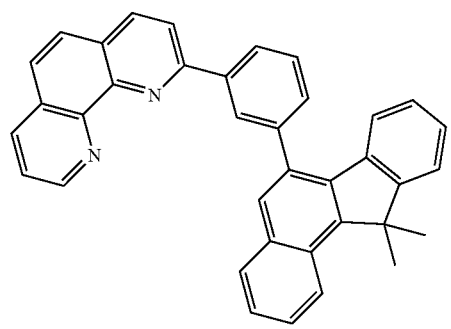
370
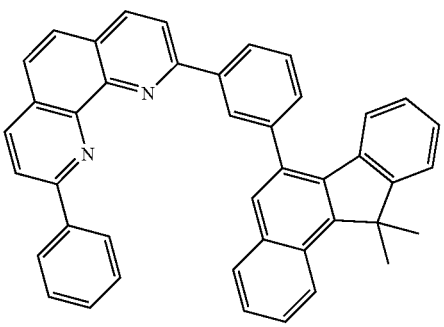
371
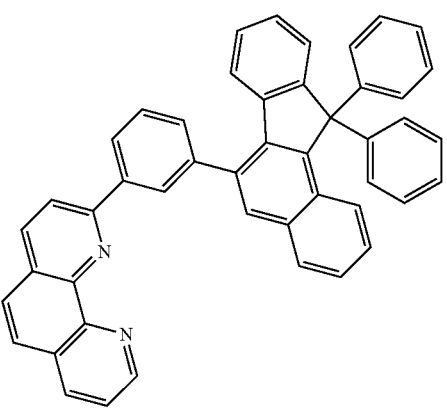
372
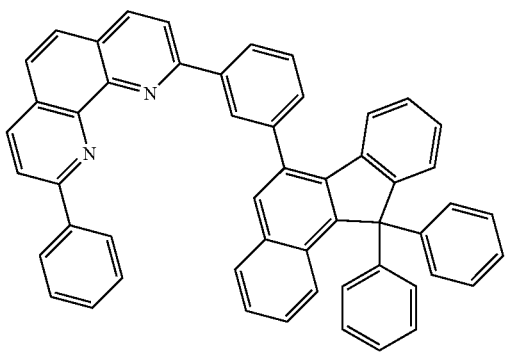
373
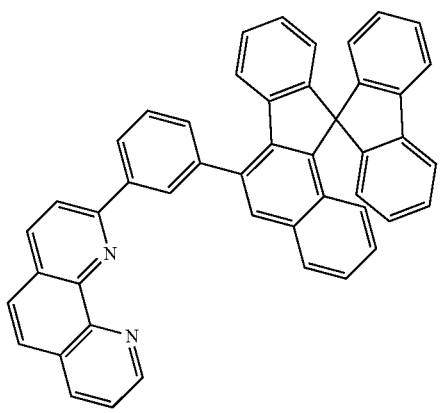

-continued
374
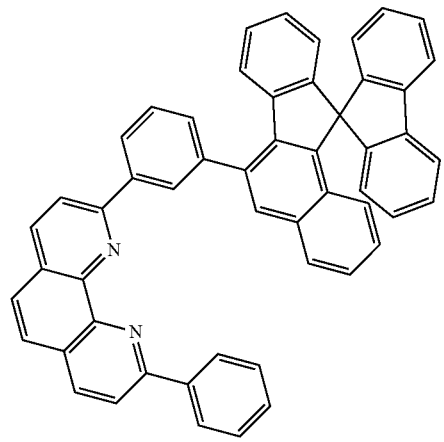
375
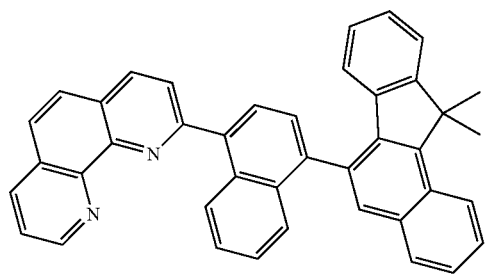
376
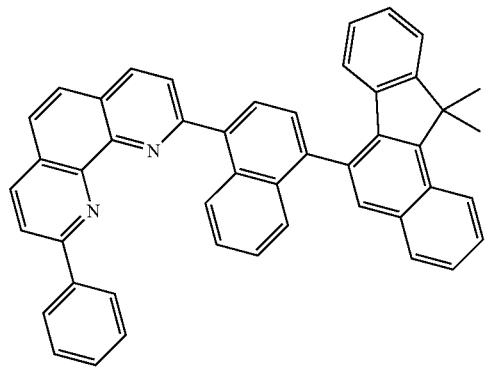
377
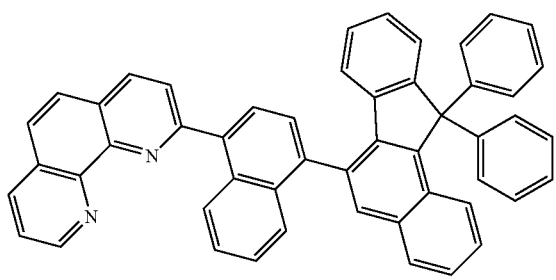
-continued
378
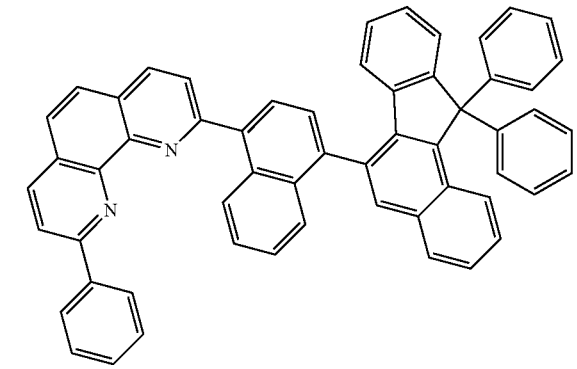
379
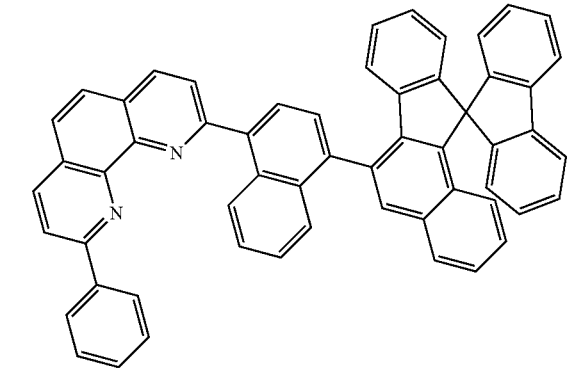
380
381
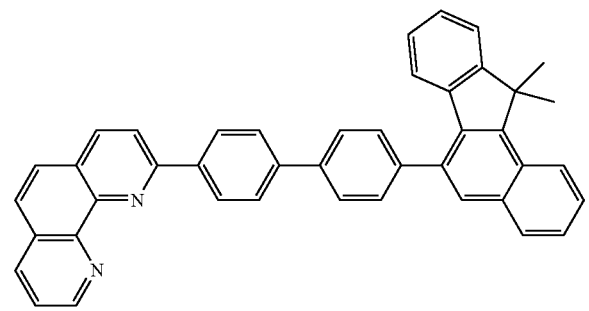

382
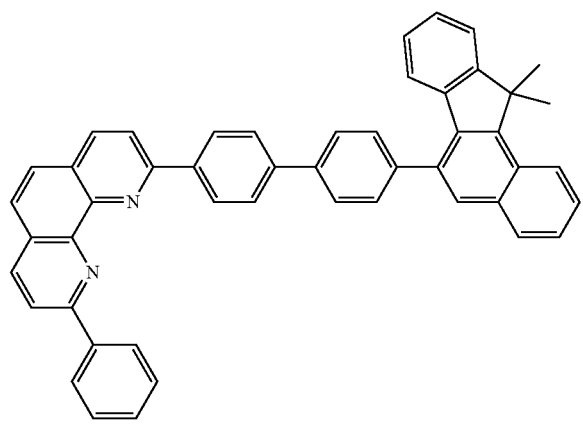
383
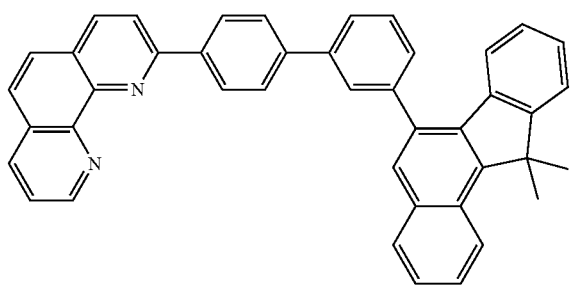
384
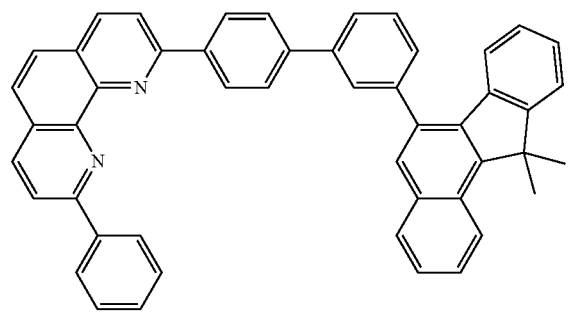
385
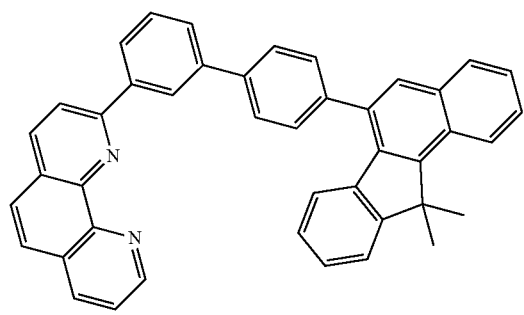
386
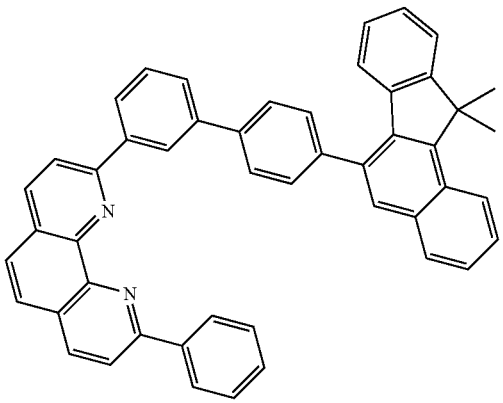
387
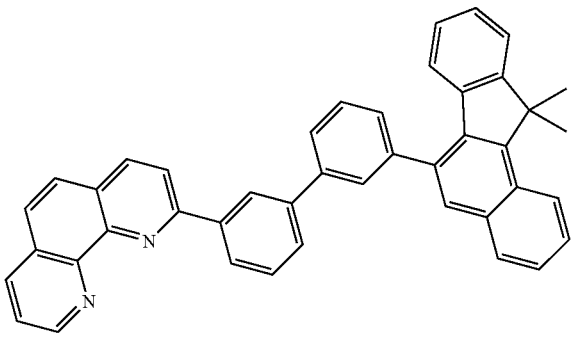
388
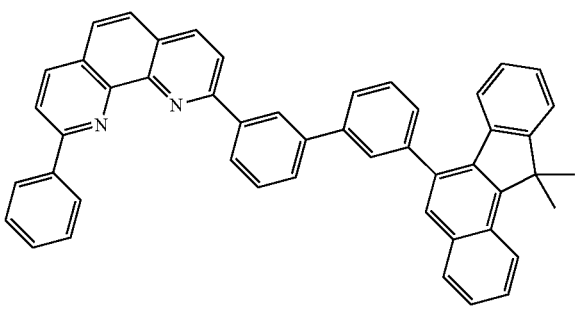
389
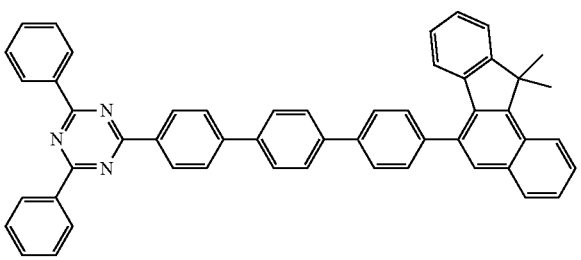

390
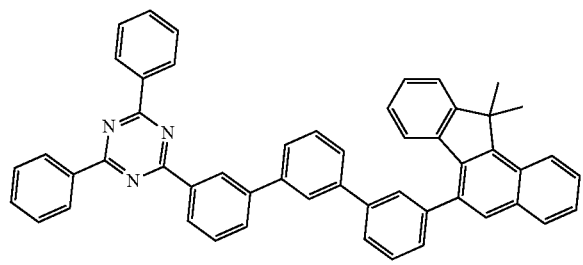
391
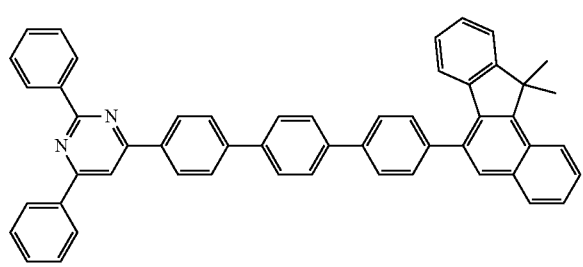
392
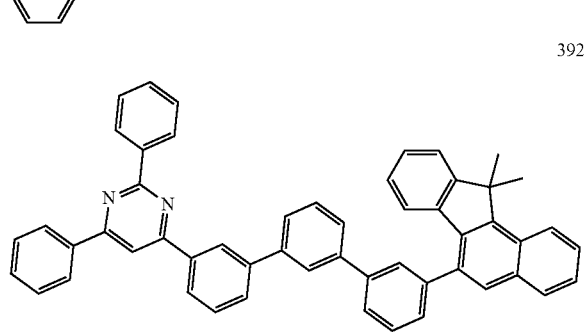
393
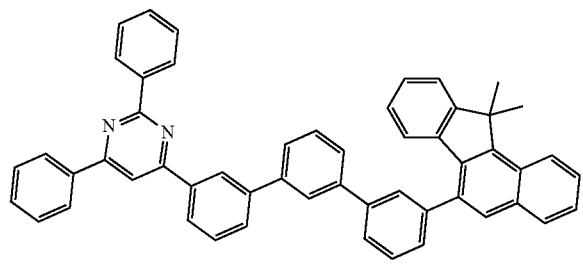
394
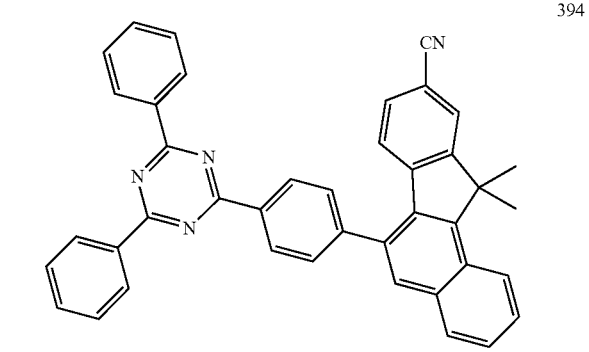
395
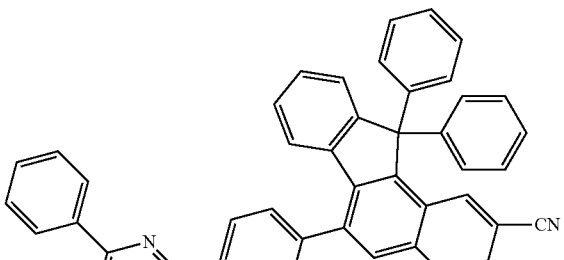
396
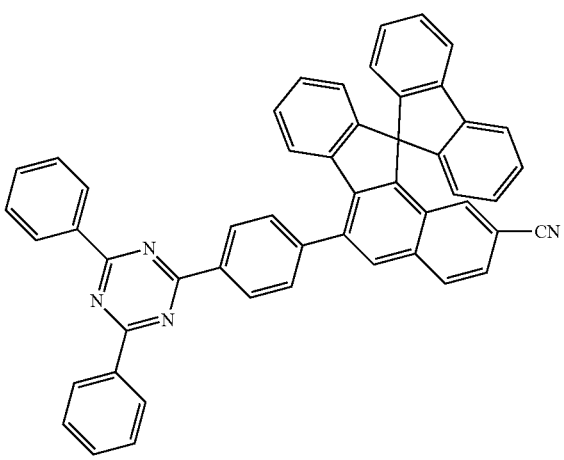
397
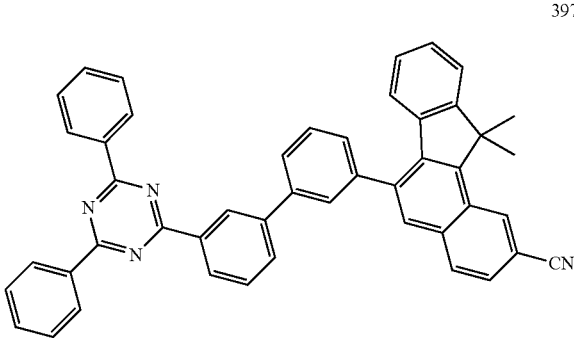
398
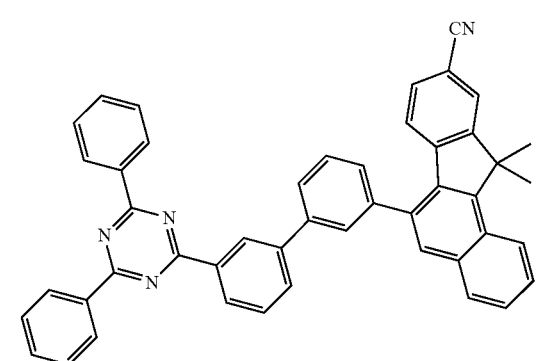

281
-continued
399
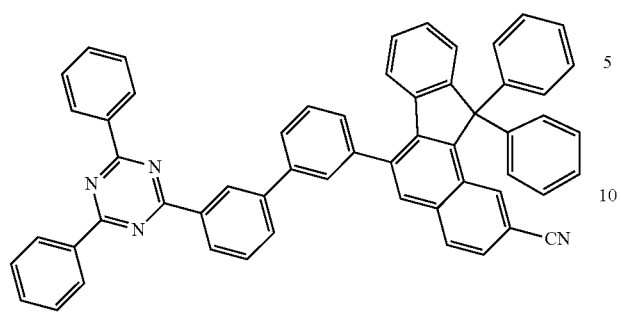
400
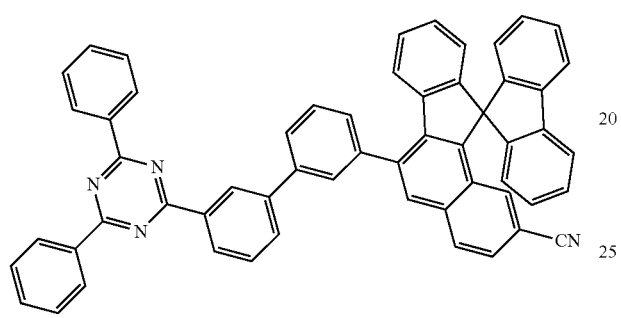
401
402
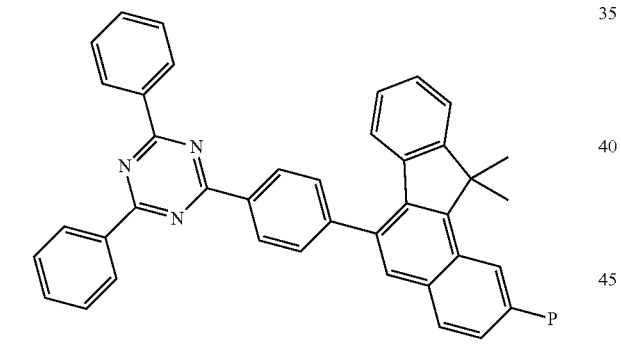
282
-continued
403
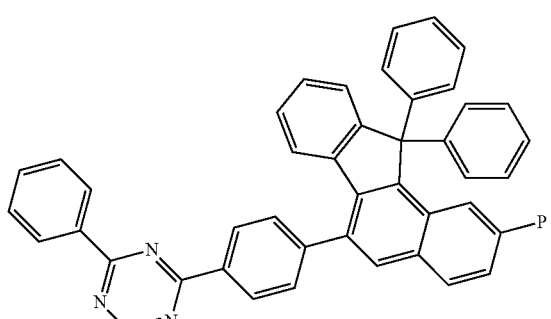
404
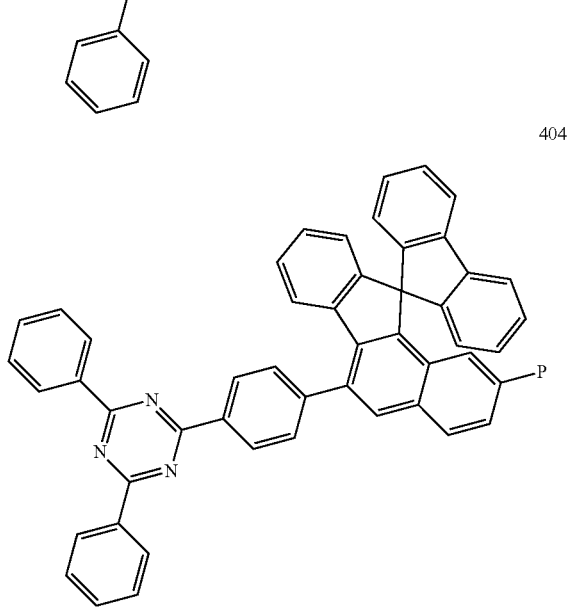
405
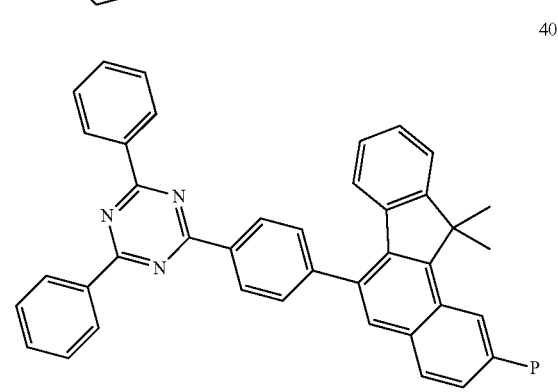
406
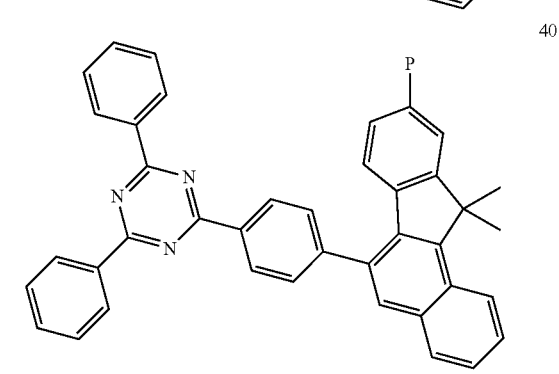

407
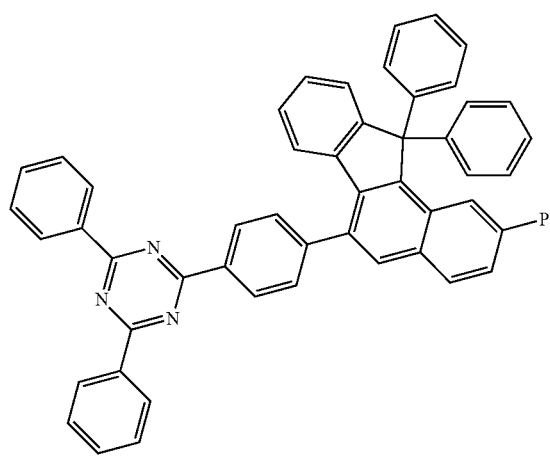
408
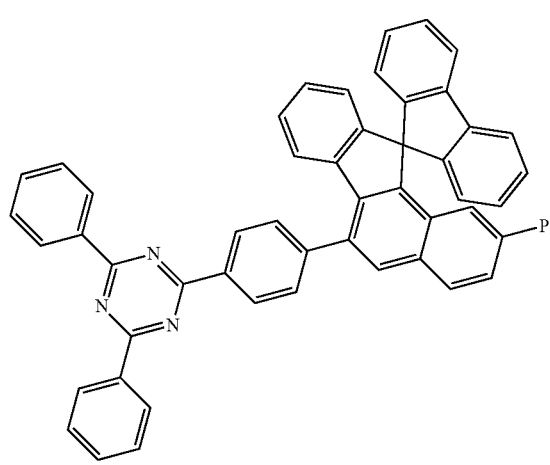
409
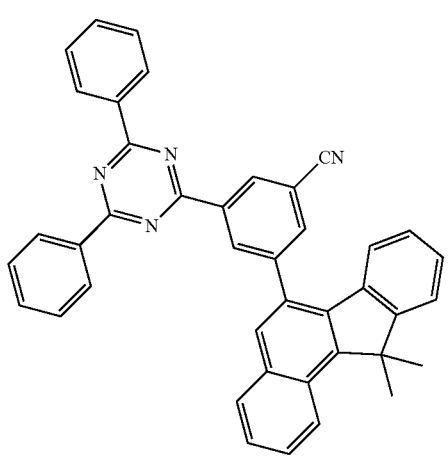
410
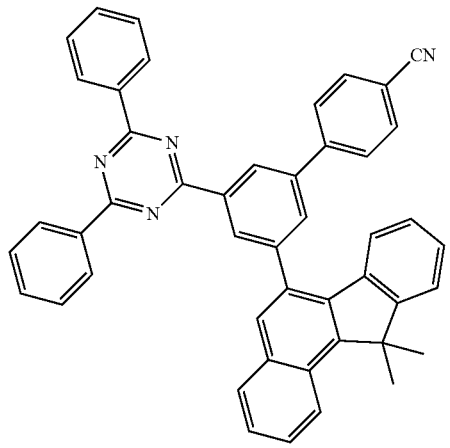
411
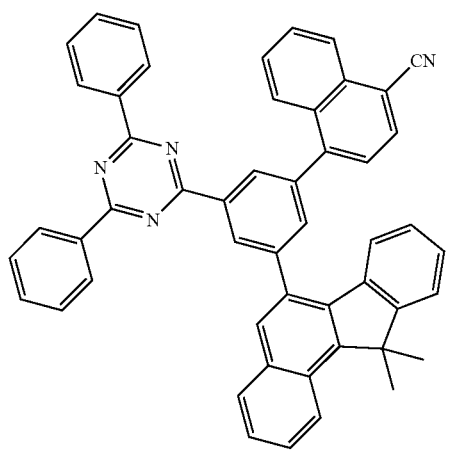
412
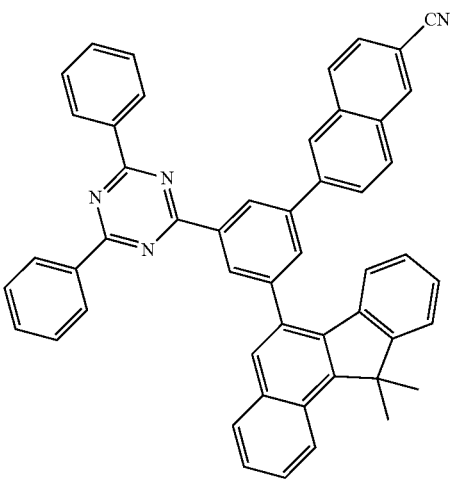

-continued

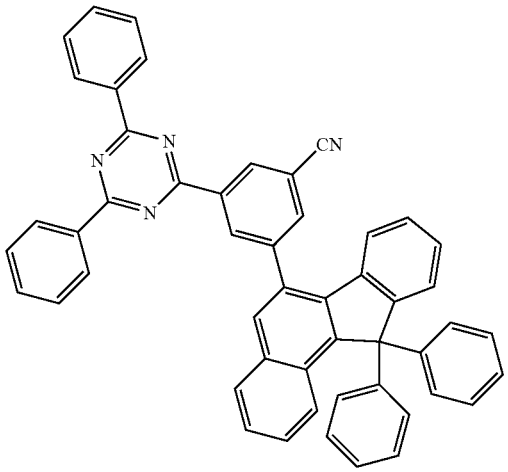
413

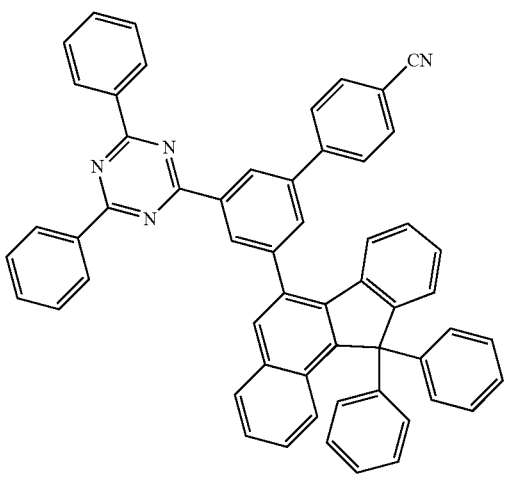
414

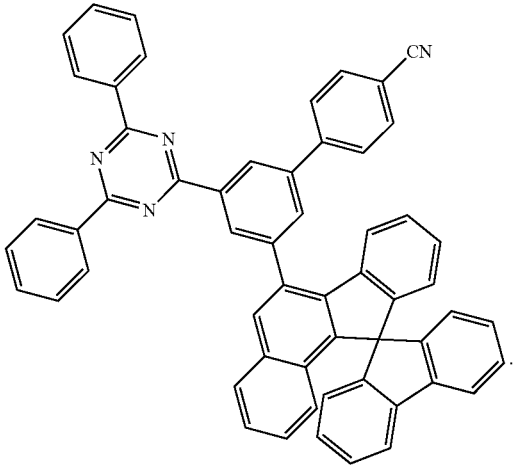
416

415

8. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

9. The organic light emitting device of claim 8, wherein the organic material layer comprises an electron transfer layer, and the electron transfer layer comprises the heterocyclic compound.

10. The organic light emitting device of claim 8, wherein the organic material layer comprises an electron injection layer or a hole transfer layer, and the electron injection layer or the hole transfer layer comprises the heterocyclic compound.

11. The organic light emitting device of claim 8, wherein the organic material layer comprises an electron blocking layer or a hole blocking layer, and the electron blocking layer or the hole blocking layer comprises the heterocyclic compound.

12. The organic light emitting device of claim 8, further comprising one, two or more layers selected from the group consisting of a light emitting layer, a hole injection layer, a hole transfer layer, an electron injection layer, an electron transfer layer, an electron blocking layer and a hole blocking layer.

13. The organic light emitting device of claim 8 comprising:
a first electrode
a first stack provided on the first electrode and comprising a first light emitting layer;
a charge generation layer provided on the first stack;
a second stack provided on the charge generation layer and comprising a second light emitting layer; and
a second electrode provided on the second stack.

14. The organic light emitting device of claim 13, wherein the charge generation layer comprises the heterocyclic compound.

* * * * *